(12) United States Patent
Webster et al.

(10) Patent No.: US 8,299,063 B2
(45) Date of Patent: Oct. 30, 2012

(54) AMIDO-THIOPHENE COMPOUNDS AND THEIR USE

(75) Inventors: Scott Peter Webster, Edinburgh (GB); Jonathan Robert Seckl, Edinburgh (GB); Brian Robert Walker, Edinburgh (GB); Peter Ward, Middlesex (GB); Thomas David Pallin, Harlow (GB); Hazel Joan Dyke, Harlow (GB); Trevor Robert Perrior, Bury St Edmunds (GB)

(73) Assignee: The University of Edinburgh, Edinburgh (GB)

( * ) Notice: Subject to any disclaimer, the term of this patent is extended or adjusted under 35 U.S.C. 154(b) by 0 days.

(21) Appl. No.: 12/920,774

(22) PCT Filed: Mar. 13, 2009

(86) PCT No.: PCT/GB2009/000686
§ 371 (c)(1),
(2), (4) Date: Sep. 2, 2010

(87) PCT Pub. No.: WO2009/112845
PCT Pub. Date: Sep. 17, 2009

(65) Prior Publication Data
US 2011/0015178 A1    Jan. 20, 2011

Related U.S. Application Data

(60) Provisional application No. 61/036,111, filed on Mar. 13, 2008.

(30) Foreign Application Priority Data

Mar. 13, 2008 (GB) .................... 0804685.6

(51) Int. Cl.
| | | |
|---|---|---|
| A61K 31/55 | (2006.01) |
| A61K 31/551 | (2006.01) |
| A61K 31/541 | (2006.01) |
| A61K 31/5355 | (2006.01) |
| A61K 31/536 | (2006.01) |
| A61K 31/496 | (2006.01) |
| A61K 31/498 | (2006.01) |
| A61K 31/4709 | (2006.01) |
| A61K 31/451 | (2006.01) |
| A61K 31/4535 | (2006.01) |
| A61K 31/4402 | (2006.01) |
| A61K 31/4155 | (2006.01) |
| C07D 243/08 | (2006.01) |
| C07D 401/14 | (2006.01) |
| C07D 403/14 | (2006.01) |
| C07D 265/36 | (2006.01) |
| C07D 265/30 | (2006.01) |
| C07D 279/12 | (2006.01) |
| C07D 231/12 | (2006.01) |
| C07D 239/04 | (2006.01) |

(52) U.S. Cl. .............. 514/217.04; 514/217.09; 514/218; 514/227.8; 514/230.5; 514/236.5; 514/249; 514/254.07; 514/314; 514/326; 514/336; 514/406; 540/575; 540/603; 544/58.4; 544/105; 544/140; 544/349; 544/353; 544/371; 546/164; 546/248; 546/275.4; 548/365.7

(58) Field of Classification Search ........................ None
See application file for complete search history.

(56) References Cited

U.S. PATENT DOCUMENTS

| 5,087,631 A | 2/1992 | Shaffer et al. |
| 6,340,678 B1 | 1/2002 | Matsuhisa |
| 2006/0111366 A1 | 5/2006 | Andersen et al. |
| 2007/0117800 A1* | 5/2007 | Arnold et al. .............. 514/235.5 |
| 2010/0197662 A1 | 8/2010 | Ogawa |
| 2010/0267696 A1 | 10/2010 | Webster et al. |
| 2011/0015178 A1 | 1/2011 | Webster et al. |
| 2012/0095046 A1 | 4/2012 | Webster et al. |

FOREIGN PATENT DOCUMENTS

| EP | 1894919 A1 | 3/2008 |
| WO | WO 98/39325 A1 | 9/1998 |
| WO | WO 00/51608 A1 | 9/2000 |
| WO | WO 03/044009 A1 | 5/2003 |
| WO | WO 2004/016617 A1 | 2/2004 |

(Continued)

OTHER PUBLICATIONS

Andrews, R.C., et al., 2003, "Effects of the 11β-hydroxysteroid dehydrogenase inhibitor carbenoxolone on insulin sensitivity in men with type 2 diabetes," *J. Clin. Endocrinol. Metab.*, vol. 88, pp. 285-291.

Christy, C., et al., 2003, "11β-hydroxysteroid dehydrogenase type 2 in mouse aorta; Localization and influence on response to glucocorticoids," *Hypertension*, vol. 42, pp. 580-587.

(Continued)

*Primary Examiner* — Joseph K. McKane
*Assistant Examiner* — Alicia L Otton
(74) *Attorney, Agent, or Firm* — Swanson & Bratschun, L.L.C.

(57) ABSTRACT

The present invention pertains generally to the field of therapeutic compounds. More specifically the present invention pertains to certain amido-thiophene compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

29 Claims, No Drawings

FOREIGN PATENT DOCUMENTS

| | | |
|---|---|---|
| WO | WO 2005/046685 A1 | 5/2005 |
| WO | WO 2005/047250 A1 | 5/2005 |
| WO | WO 2005/121145 A2 | 12/2005 |
| WO | WO 2006/132197 A1 | 12/2006 |
| WO | WO 2007/053776 A1 | 5/2007 |
| WO | WO 2007/082808 A2 | 7/2007 |
| WO | WO 2008/011453 A2 | 1/2008 |
| WO | WO 2009/074789 A1 | 6/2009 |
| WO | WO 2009/090239 A1 | 7/2009 |
| WO | WO 2009/112845 A1 | 9/2009 |
| WO | WO 2010/023161 A1 | 3/2010 |
| WO | WO 2010/146338 A1 | 12/2010 |
| WO | WO 2011/033255 A1 | 3/2011 |
| WO | WO 2011/135276 A1 | 11/2011 |

OTHER PUBLICATIONS

Cooper, M.S., et al., Sep. 2000, "Expression and functional consequences of 11β-hydroxysteroid dehydrogenase activity in human bone," *Bone*, vol. 27(3), pp. 375-381.

Gotthardt, H., 1971, "1.3-Dipolare Cycloadditionen Mit 1.3.2-Oxathiazolium-5-oxiden. Ein Neuer Weg in Die 5-Aryl-Isothiazol-Reihe", *Tetrahedron Letters*, No. 17, pp. 1281-1284.

Hadoke, P.W.F., et al., 2001, "Endothelial cell dysfunction in mice after transgenic knockout of type 2, but not type 1, 11β-hydroxysteroid dehydrogenase," *Circulation*, vol. 104, pp. 2832-2837.

Hwang et al., 2001, "4-Hydroxy-6-oxo-6,7-dihydro-thieno[2,3-b]pyrimidine derivatives: synthesis and their biological evaluation for the glycine site acting on the N-methyl-D-aspartate (NMDA) receptor", *Archives of Pharmacol. Research*, vol. 24, No. 4, pp. 270-275.

Kotelevtsev, Y.V., et al., Dec. 1997, "11β-Hydroxysteroid dehydrogenase type 1 knockout mice show attenuated glucocorticoid inducible responses and resist hyperglycaemia on obesity and stress," *Proc. Natl. Acad. Sci.*, vol. 94, pp. 14924-14929.

Masuzaki, H., et al., 2001, "A Transgenic Model of Visceral Obesity and the Metabolic Syndrome," *Science*, vol. 294, pp. 2166-2170.

Moisan, M. P., et al., 1990, "11β-hydroxysteroid dehydrogenase bioactivity and messenger RNA expression in rat forebrain: localization in hypothalamus, hippocampus, and cortex," *Endocrinology*, vol. 127(3), pp. 1450-1455.

Morton, N.M., et al., Nov. 2, 2001, "Improved lipid and lipoprotein profile, hepatic insulin sensitivity, and glucose tolerance in 11β-hydroxysteroid dehydrogenase type 1 null mice," *J. Biol. Chem.*, vol. 276(44), pp. 41293-41300.

Morton, N.M., et al., Apr. 2004, "Novel adipose tissue-mediated resistance to diet-induced visceral obesity in 11β-hydroxysteroid dehydrogenase type 1 deficient mice," *Diabetes*, vol. 53, pp. 931-938.

Patani, G.A., et al., 1996, "Bioisosterism: A rational approach in drug design", *American Chemical Society*, vol. 96, pp. 3147-3176.

Paterson, J.M., et al., May 4, 2004, "Metabolic syndrome without obesity: hepatic overexpression of 11β-hydroxysteroid dehydrogenase type 1 in transgenic mice," *Proc. Natl. Acad. Sci.*, vol. 101(18), pp. 7088-7093).

Rask, E., et al., 2001, "Tissue-specific dysregulation of cortisol metabolism in human obesity," *J. Clin. Endocrinol. Metab.*, vol. 86(3), pp. 1418-1421.

Rauz, S., et al., 2001, "Expression and putative role of 11β-hydroxysteroid dehydrogenase isozymes within the human eye," *Investigative Opthalmology & Visual Science*, vol. 42(9), pp. 2037-2042.

Sandeep, T.C., et al., Apr. 27, 2004, "11β-hydroxysteroid dehydrogenase inhibition improves cognitive function in healthy elderly men and type 2 diabetics," *Proc. Natl. Acad. Sci.*, vol. 101(17), pp. 6734-6739.

Seckl, J.R., Walker, B.R., 2001, "11β-Hydroxysteroid dehydrogenase type 1—a tissue-specific amplifier of glucocorticoid action," *Endocrinology*, vol. 142(4), pp. 1371-1376.

Small, G.R., et al., Aug. 23, 2005, "Preventing local regeneration of glucocorticoids by 11β-hydroxysteroid dehydrogenase type 1 enhances angiogenesis," *Proc. Natl. Acad. Sci.*, vol. 102(34), pp. 12165-12170.

Stimson, R.H., et al., 2010, "Extra-adrenal cortisol production in obese men with type two diabetes mellitus—how big is the therapeutic target for 11βHSD1 inhibitors?" $92^{nd}$ Annual Meeting of the Endocrine Society, San Diego, USA.

Walker, B.R., et al., 1991, "11β-Hydroxysteroid dehydrogenase in vascular smooth muscle and heart: implications for cardiovascular responses to glucocorticoids," *Endocrinology*, vol. 129(6), pp. 3305-3312.

Walker, B.R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, vol. 80(11), pp. 3155-3139.

Yau, J.L.W., et al., Apr. 10, 2001, "Lack of tissue glucocorticoid reactivation in 11β-hydroxysteroid dehydrogenase type 1 knockout mice ameliorates age-related learning impairments," *Proc. Natl. Acad. Sci.*, vol. 98(8), pp. 4716-4721.

Registry No. 727385-01-5, entered STN Aug. 16, 2004.
Registry No. 717867-85-1, entered STN Jul. 28, 2004.
Registry No. 717867-57-7, entered STN Jul. 28, 2004.
IPRP for PCT/GB2010/001155, issued Dec. 16, 2011.
IPRP for PCT/GB2010/001732, issued Mar. 20, 2012.
ISR and WOISA for PCT/GB2010/001732, issued Mar. 20, 2012.

\* cited by examiner

AMIDO-THIOPHENE COMPOUNDS AND THEIR USE

RELATED APPLICATIONS

This application is a 35 U.S.C. §371 national phase application of PCT/GB2009/000686, filed Mar. 13, 2009 (WO 2009/112845), entitled "Amido-Thiophene Compounds and Their Use". PCT/GB2009/000686 is a non-provisional application of U.S. provisional patent application No. 61/036,111 filed Mar. 13, 2008 and United Kingdom patent application number 0804685.6 filed Mar. 13, 2008, the contents of both of which are incorporated herein by reference in their entirety.

TECHNICAL FIELD

The present invention pertains generally to the field of therapeutic compounds. More specifically the present invention pertains to certain amido-thiophene compounds that, inter alia, inhibit 11β-hydroxysteroid dehydrogenase type 1 (11β-HSD1). The present invention also pertains to pharmaceutical compositions comprising such compounds, and the use of such compounds and compositions, both in vitro and in vivo, to inhibit 11β-hydroxysteroid dehydrogenase type 1; to treat disorders that are ameliorated by the inhibition of 11β-hydroxysteroid dehydrogenase type 1; to treat the metabolic syndrome, which includes disorders such as type 2 diabetes and obesity, and associated disorders including insulin resistance, hypertension, lipid disorders and cardiovascular disorders such as ischaemic (coronary) heart disease; to treat CNS disorders such as mild cognitive impairment and early dementia, including Alzheimer's disease; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Glucocorticoids (cortisol in man, corticosterone in rodents) are hormones that regulate a range of pathways involved in stress and metabolic signalling. They are antagonists of insulin action and impair insulin-dependent glucose uptake, increase lipolysis, and enhance hepatic gluconeogenesis. These effects are evident in Cushing's syndrome, which is caused by elevated circulating levels of glucocorticoids. The features of Cushing's syndrome are diverse and reflect the tissue distribution of glucocorticoid receptors in the body. They include a cluster of metabolic (central/visceral obesity, insulin resistance, hyperglycaemia, dyslipidaemia) and cardiovascular (hypertension) abnormalities which, when observed in patients without Cushing's syndrome, constitute the metabolic syndrome. These abnormalities confer a substantial risk of cardiovascular disease. In addition, Cushing's syndrome is associated with neuropsychiatric manifestations including depression and cognitive impairment. The features of Cushing's syndrome are reversible upon removal of the cause of glucocorticoid excess.

It is recognised that glucocorticoid activity is controlled at the tissue level by the intracellular conversion of active cortisol and inactive cortisone by 11β-hydroxysteroid dehydrogenases (see, e.g., Seckl et al., 2001). These enzymes exist in two distinct isoforms. 11β-HSD1, which catalyses the reaction that activates cortisone, is expressed in liver, adipose tissue, brain, skeletal muscle, vascular smooth muscle and other organs, while, 11β-HSD2, which inactivates cortisol, is predominantly expressed in the kidney. Pharmacological inhibition of 11β-HSD1 in rat and man with carbenoxolone (see, e.g., Walker et al., 1995), and transgenic knockout in mice (see, e.g., Kotelevtsev et al., 1997), results in enhanced hepatic insulin sensitivity and reduced gluconeogenesis and glycogenolysis, suggesting that 11β-HSD1 inhibition will be a useful treatment in type 2 diabetes and other insulin resistance syndromes. Furthermore, mice lacking 11β-HSD1 possess low triglycerides, increased HDL cholesterol, and increased apo-lipoprotein A-I levels (see, e.g., Morton et al., 2001), suggesting that inhibitors of 11β-HSD1 may be of utility in the treatment of atherosclerosis.

The link between 11β-HSD1 and the metabolic syndrome has been strengthened by studies in transgenic mice and man. 11β-HSD1 knockout mice on two different genetic backgrounds are protected from dietary obesity (see, e.g., Morton et al., 2004), while administration of carbenoxolone to patients with type 2 diabetes enhances insulin sensitivity (see, e.g., Andrews et al., 2003). However, it has become apparent that the key tissue in which 11β-HSD1 exerts the greatest influence upon metabolic disease is the adipose tissue rather than the liver. Mice with transgenic overexpression of 11β-HSD1 in adipose tissue (see, e.g. Masuzaki et al., 2001) have a more profound metabolic syndrome and obesity than mice with overexpression in liver (see, e.g., Paterson et al., 2004). In obese humans, 11β-HSD1 activity is increased in adipose tissue, but enzyme activity is decreased in the liver (see, e.g., Rask et al., 2001).

In the CNS, 11β-HSD1 is highly expressed in regions important for cognition such as hippocampus, frontal cortex, and cerebellum (see, e.g., Moisan et al., 1990). Elevated cortisol is associated with cognitive dysfunction, and glucocorticoids have a range of neurotoxic effects. 11β-HSD1 knockout mice are protected against age-related cognitive dysfunction (see, e.g., Yau et al., 2001), while administration of the 11β-HSD inhibitor carbenoxolone has been shown to enhance cognitive function in elderly men and type 2 diabetics who have a selective impairment in verbal memory (see, e.g., Sandeep et al., 2004). Thus, 11β-HSD1 inhibitors are of potential therapeutic utility in the treatment of diseases such as Alzheimer's Disease, which are characterised by cognitive impairment.

The isozymes of 11β-HSD are also expressed in the blood vessel wall (see, e.g., Walker et al., 1991; Christy et al., 2003). 11β-HSD1 is expressed in vascular smooth muscle, while 11β-HSD2 is expressed in endothelial cells where it modulates endothelial-dependent vasodilation (see, e.g., Hadoke et al., 2001). 11β-HSD1 knockout mice have normal vascular function, but they exhibit enhanced angiogenesis in response to inflammation or ischaemia (see, e.g., Small et al., 2005). This offers therapeutic potential in the treatment of myocardial infarction, since inhibition of 11β-HSD1 may enhance revascularisation of ischaemic tissues.

Studies have shown that 11β-HSD1 affects intraocular pressure in man (see, e.g., Rauz et al., 2001). Inhibition of 11β-HSD1 may be useful in reducing intraocular pressure in the treatment of glaucoma.

Glucocorticoids are involved in the regulation of bone formation and skeletal development. Treatment of healthy volunteers with carbenoxolone led to a decrease in bone resorption markers suggesting that 11β-HSD1 plays a role in bone resorption (see, e.g., Cooper et al., 2000). 11β-HSD1 inhibitors could be used as protective agents in the treatment of osteoporosis.

The inventors have discovered compounds that inhibit 11β-hydroxysteroid dehydrogenase type 1 (11β-HSD1) that are useful in the treatment, control, and/or prevention of disorders (e.g., diseases) that are responsive to the inhibition of 11β-HSD1.

SUMMARY OF THE INVENTION

One aspect of the invention pertains to certain amidothiophenes (referred to herein as AMTP compounds), as described herein.

Another aspect of the invention pertains to a composition (e.g., a pharmaceutical composition) comprising an AMTP compound, as described herein, and a pharmaceutically acceptable carrier or diluent.

Another aspect of the invention pertains to a method of preparing a composition (e.g., a pharmaceutical composition) comprising the step of admixing an AMTP compound, as described herein, and a pharmaceutically acceptable carrier or diluent.

Another aspect of the present invention pertains to a method of inhibiting 11β-hydroxysteroid dehydrogenase type 1 (11β-HSD1) function (e.g., in a cell), in vitro or in vivo, comprising contacting the cell with an effective amount of an AMTP compound, as described herein.

Another aspect of the present invention pertains to a method of treatment comprising administering to a subject in need of treatment a therapeutically-effective amount of an AMTP compound, as described herein, preferably in the form of a pharmaceutical composition.

Another aspect of the present invention pertains to an AMTP compound as described herein for use in a method of treatment of the human or animal body by therapy.

Another aspect of the present invention pertains to use of an AMTP compound, as described herein, in the manufacture of a medicament for use in treatment.

In one embodiment, the treatment is treatment or prevention of a disorder (e.g., a disease) that is ameliorated by the inhibition of 11β-hydroxysteroid dehydrogenase type 1 (11β-HSD1).

In one embodiment, the treatment is treatment or prevention of metabolic syndrome, which includes conditions such as type 2 diabetes and obesity, and associated disorders including insulin resistance, hypertension, lipid disorders and cardiovascular disorders such as ischaemic (coronary) heart disease.

In one embodiment, the treatment is treatment or prevention of a CNS disorder (e.g., a CNS disease) such as mild cognitive impairment and early dementia, including Alzheimer's disease.

Another aspect of the present invention pertains to a kit comprising (a) an AMTP compound, as described herein, preferably provided as a pharmaceutical composition and in a suitable container and/or with suitable packaging; and (b) instructions for use, for example, written instructions on how to administer the compound.

Another aspect of the present invention pertains to an AMTP compound obtainable by a method of synthesis as described herein, or a method comprising a method of synthesis as described herein.

Another aspect of the present invention pertains to an AMTP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain amido-thiophenes (for convenience, collectively referred to herein as "amido-thiophene compounds" or "AMTP compounds").

In one embodiment, the compounds are selected from compounds of the following formula, and pharmaceutically acceptable salts, hydrates, and solvates thereof:

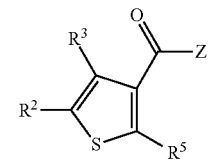

wherein:
—$R^2$ is independently —$R^{2A}$ or —$R^{2B}$;
—$R^3$ is independently —H, —$R^{3A}$, —$R^{3B}$, or —$R^{3C}$;
—$R^5$ is independently —H, —$R^{5A}$, —$R^{5B}$, or —$R^{5C}$; and
-Z is independently -$J^1$, -$J^2$, -$J^3$, or -$J^4$;
wherein:
—$R^{2A}$ is independently phenyl or naphthyl, and is optionally substituted;
—$R^{2B}$ is independently $C_{5-10}$heteroaryl, and is optionally substituted;
—$R^{3A}$ is independently saturated aliphatic $C_{1-4}$alkyl;
—$R^{3B}$ is independently —F, —Cl or —Br;
—$R^{3C}$ is independently —CN;
—$R^{5A}$ is independently saturated aliphatic $C_{1-4}$alkyl;

—$R^{5B}$ is independently —F, —Cl or —Br;
—$R^{5C}$ is independently —CN;
-$J^1$ is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted;
-$J^2$ is independently a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said fused bicyclic non-aromatic heterocyclyl group is optionally substituted;
-$J^3$ is independently a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said bridged non-aromatic heterocyclyl group is optionally substituted;
with the proviso that -$J^3$ is not:

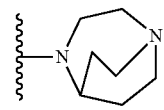

-$J^4$ is independently a spiro non-aromatic heterocyclyl group having from 8 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said spiro non-aromatic heterocyclyl group is optionally substituted.

For the avoidance of doubt, it is not intended that —$R^2$, —$R^3$, and —$R^5$ are attached to one another other than as shown in the above formula. For example, it is not intended that —$R^2$ and —$R^3$ together form a ring fused to the central thiophene ring. Similarly, it is not intended that —$R^2$ and —$R^5$ together form a ring fused to the central thiophene ring. Similarly, it is not intended that —$R^3$ and —$R^5$ together form a ring fused to the central thiophene ring.

Also for the avoidance of doubt, it is not intended that —$R^2$, —$R^3$, and —$R^5$ are attached to -Z other than as shown in the above formula. For example, it is not intended that —$R^2$ and -Z together form a ring fused to the central thiophene ring. Similarly, it is not intended that —$R^3$ and -Z together form a ring fused to the central thiophene ring. Similarly, it is not intended that —$R^5$ and -Z together form a ring fused to the central thiophene ring.

Optional Provisos

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

In one embodiment, the proviso is that the compound is not a compound selected from: compounds (PP-01) through (PP-09), and salts, hydrates, and solvates thereof.

| # | Structure | Name | Registry No. |
|---|-----------|------|--------------|
| PP-01 | 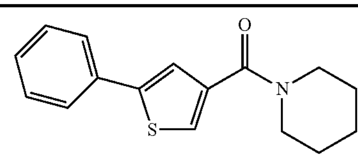 | (5-Phenyl-thiophen-3-yl)-piperidin-1-yl-methanone | 930054-08-3 |
| PP-02 | 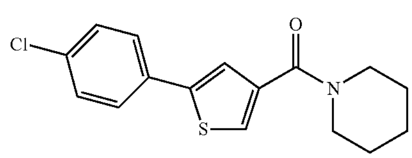 | [5-(4-Chloro-phenyl)-thiophen-3-yl]-piperidin-1-yl-methanone | 883018-92-6 |
| PP-03 | 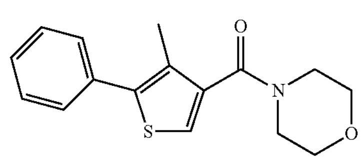 | (4-Methyl-5-phenyl-thiophen-3-yl)-morpholin-4-yl-methanone | 433964-84-2 |
| PP-04 | 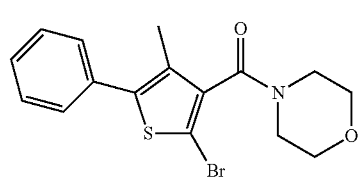 | (2-Bromo-4-methyl-5-phenyl-thiophen-3-yl)-morpholin-4-yl-methanone | 313661-14-2 |

-continued

| # | Structure | Name | Registry No. |
|---|---|---|---|
| PP-05 | 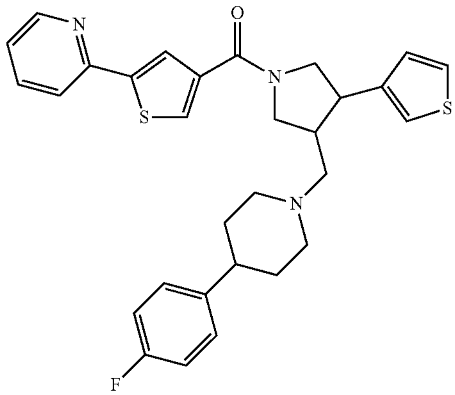 | {3-[4-(4-Fluoro-phenyl)-piperidin-1-ylmethyl]-4-thiophen-3-yl-pyrrolidin-1-yl}-(5-pyridin-2-yl-thiophen-3-yl)-methanone | 291285-76-2 |
| PP-06 | 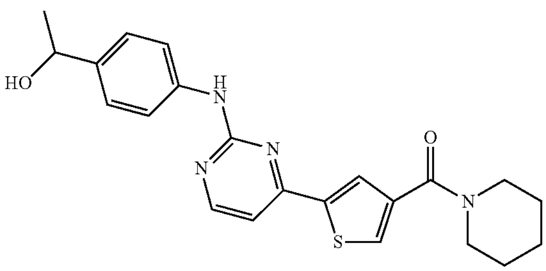 | (5-{2-[4-(1-Hydroxy-ethyl)-phenylamino]-pyrimidin-4-yl}-thiophen-3-yl)-piperidin-1-yl-methanone | 936138-06-6 |
| PP-07 | 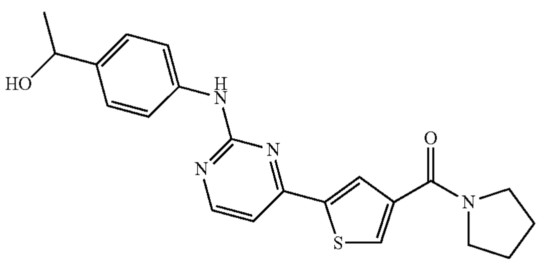 | (5-{2-[4-(1-Hydroxy-ethyl)-phenylamino]-pyrimidin-4-yl}-thiophen-3-yl)-pyrrolidin-1-yl-methanone | 936138-01-1 |
| PP-08 | 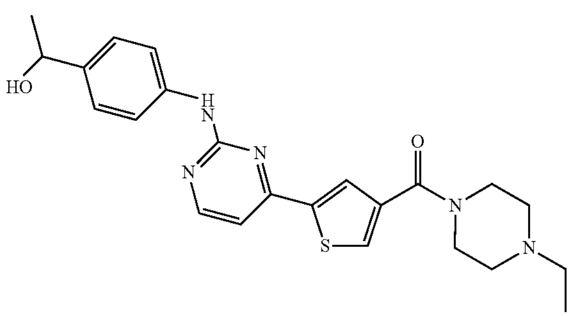 | (4-Ethyl-piperazin-1-yl)-(5-{2-[4-(1-hydroxy-ethyl)-phenylamino]-pyrimidin-4-yl}-thiophen-3-yl)-methanone | 936138-08-8 |
| PP-09 | 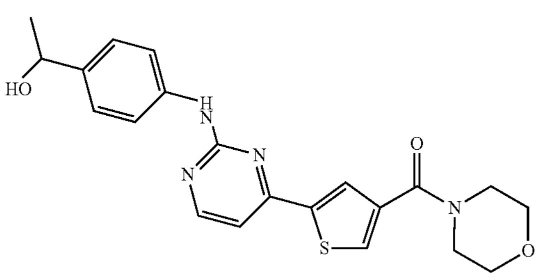 | (5-{2-[4-(1-Hydroxy-ethyl)-phenylamino]-pyrimidin-4-yl}-thiophen-3-yl)-morpholin-4-yl-methanone | 936138-00-0 |

In one or more aspects of the present invention (e.g., compounds for use in therapy, use of compounds in the manufacture of a medicament, methods of treatment, etc.), the compounds are optionally as defined herein, but without the proviso regarding compounds (PP-01) through (PP-09).

For example, a reference to a particular group of compounds "without the recited proviso regarding compounds (PP-01) through (PP-09)" (e.g., for use in therapy) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

In one or more aspects of the present invention (e.g., compounds for use in therapy, use of compounds in the manufacture of a medicament, methods of treatment, etc.), the compounds are optionally as defined herein, with the proviso regarding compounds (PP-01) through (PP-09).

The Group —$R^2$

In one embodiment, —$R^2$ is independently —$R^{2A}$ or —$R^{2B}$.

In one embodiment, —$R^2$ is independently —$R^{2A}$.

In one embodiment, —$R^2$ is independently —$R^{2B}$.

The Group -Z

In one embodiment, -Z is independently -$J^1$, -$J^2$, -$J^3$, or -$J^4$.

In one embodiment, -Z is independently -$J^2$, -$J^3$, or -$J^4$.

In one embodiment, -Z is independently -$J^1$.

In one embodiment, -Z is independently -$J^2$.

In one embodiment, -Z is independently -$J^3$.

In one embodiment, -Z is independently -$J^4$.

The Group —$R^3$

In one embodiment, —$R^3$ is independently —H, —$R^{3A}$, —$R^{3B}$, or —$R^{3C}$.

In one embodiment, —$R^3$ is independently —$R^{3A}$, —$R^{3B}$, or —$R^{3C}$.

In one embodiment, —$R^3$ is independently —H, —$R^{3B}$, or —$R^{3C}$.

In one embodiment, —$R^3$ is independently —$R^{3B}$ or —$R^{3C}$.

In one embodiment, —$R^3$ is independently —H.

In one embodiment, —$R^3$ is independently —$R^{3A}$.

In one embodiment, —$R^3$ is independently —$R^{3B}$.

In one embodiment, —$R^3$ is independently —$R^{3C}$.

The Group —$R^5$

In one embodiment, —$R^5$ is independently —H, —$R^{5A}$, —$R^{5B}$, or —$R^{5C}$.

In one embodiment, —$R^5$ is independently —$R^{5A}$, —$R^{5B}$, or —$R^{5C}$.

In one embodiment, —$R^5$ is independently —H, —$R^{5B}$, or —$R^{5C}$.

In one embodiment, —$R^5$ is independently —$R^{5B}$ or —$R^{5C}$.

In one embodiment, —$R^5$ is independently —H.

In one embodiment, —$R^5$ is independently —$R^{5A}$.

In one embodiment, —$R^5$ is independently —$R^{5B}$.

In one embodiment, —$R^5$ is independently —$R^{5C}$.

The Group —$R^{2A}$

In one embodiment, —$R^{2A}$, if present, is independently phenyl or naphthyl, and is optionally substituted.

In one embodiment, —$R^{2A}$, if present, is independently phenyl, and is optionally substituted.

In one embodiment, —$R^{2A}$, if present, is independently selected from the groups —$R^{2A}$ shown in the compounds described under the heading "Examples of Specific Embodiments".

The Group —$R^{2B}$

In one embodiment, —$R^{2B}$, if present, is independently $C_{5-10}$heteroaryl, and is optionally substituted.

In one embodiment, —$R^{2B}$, if present, is independently $C_{5-6}$heteroaryl, and is optionally substituted.

In one embodiment, —$R^{2B}$, if present, is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, indolyl, isoindolyl, benzofuranyl, isobenzofuranyl, benzothienyl, isobenzothienyl, indazolyl, benzimidazolyl, benzothiazolyl, benzoxazolyl, quinolinyl, isoquinolinyl, cinnolinyl, or quinazolinyl, and is optionally substituted.

In one embodiment, —$R^{2B}$, if present, is independently furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, pyridazinyl, and is optionally substituted.

In one embodiment, —$R^{2B}$, if present, is independently imidazolyl, pyrazolyl, oxazolyl, isoxazolyl, pyridyl, pyrimidinyl, or quinolinyl, and is optionally substituted.

In one embodiment, —$R^{2B}$, if present, is independently imidazolyl, pyrazolyl, pyridyl, pyrimidinyl, or quinolinyl, and is optionally substituted.

In one embodiment, —$R^{2B}$, if present, is independently imidazolyl, and is optionally substituted.

In one embodiment, —$R^{2B}$, if present, is independently imidazol-1-yl, and is optionally substituted.

In one embodiment, —$R^{2B}$, if present, is independently imidazol-4-yl, and is optionally substituted.

In one embodiment, —$R^{2B}$, if present, is independently pyrazolyl, and is optionally substituted.

In one embodiment, —$R^{2B}$, if present, is independently pyrazol-1-yl, and is optionally substituted.

In one embodiment, —$R^{2B}$, if present, is independently pyrazol-3-yl, and is optionally substituted.

In one embodiment, —$R^{2B}$, if present, is independently pyrazol-4-yl, and is optionally substituted.

In one embodiment, —$R^{2B}$, if present, is independently oxazolyl, and is optionally substituted.

In one embodiment, —$R^{2B}$, if present, is independently oxazol-2-yl, and is optionally substituted.

In one embodiment, —$R^{2B}$, if present, is independently oxazol-4-yl, and is optionally substituted.

In one embodiment, —$R^{2B}$, if present, is independently isoxazolyl, and is optionally substituted.

In one embodiment, —$R^{2B}$, if present, is independently isoxazol-4-yl, and is optionally substituted.

In one embodiment, —$R^{2B}$, if present, is independently pyridyl, and is optionally substituted.

In one embodiment, —$R^{2B}$, if present, is independently pyrid-2-yl, and is optionally substituted.

In one embodiment, —$R^{2B}$, if present, is independently pyrid-3-yl, and is optionally substituted.

In one embodiment, —$R^{2B}$, if present, is independently pyrid-4-yl, and is optionally substituted.

In one embodiment, —$R^{2B}$, if present, is independently pyrimidinyl, and is optionally substituted.

In one embodiment, —$R^{2B}$, if present, is independently pyrimidin-5-yl, and is optionally substituted.

In one embodiment, —$R^{2B}$, if present, is independently quinolinyl, and is optionally substituted.

In one embodiment, —$R^{2B}$, if present, is independently quinolin-6-yl, and is optionally substituted.

In one embodiment, —$R^{2B}$, if present, is independently furanyl, and is optionally substituted.

In one embodiment, —$R^{2B}$, if present, is independently thienyl, and is optionally substituted.

In one embodiment, —$R^{2B}$, if present, is independently pyrrolyl, and is optionally substituted.

In one embodiment, —$R^{2B}$, if present, is independently triazolyl, and is optionally substituted.

In one embodiment, —$R^{2B}$, if present, is independently tetrazolyl, and is optionally substituted.

In one embodiment, —$R^{2B}$, if present, is independently thiazolyl, and is optionally substituted.

In one embodiment, —$R^{2B}$, if present, is independently isothiazolyl, and is optionally substituted.

In one embodiment, —$R^{2B}$, if present, is independently pyridazinyl, and is optionally substituted.

In one embodiment, —$R^{2B}$, if present, is independently indolyl, and is optionally substituted.

In one embodiment, —$R^{2B}$, if present, is independently isoindolyl, and is optionally substituted.

In one embodiment, —$R^{2B}$, if present, is independently benzofuranyl, and is optionally substituted.

In one embodiment, —$R^{2B}$, if present, is independently isobenzofuranyl, and is optionally substituted.

In one embodiment, —$R^{2B}$, if present, is independently benzothienyl, and is optionally substituted.

In one embodiment, —$R^{2B}$, if present, is independently isobenzothienyl, and is optionally substituted.

In one embodiment, —$R^{2B}$, if present, is independently indazolyl, and is optionally substituted.

In one embodiment, —$R^{2B}$, if present, is independently benzimidazolyl, and is optionally substituted.

In one embodiment, —$R^{2B}$, if present, is independently benzothiazolyl, and is optionally substituted.

In one embodiment, —$R^{2B}$, if present, is independently benzoxazolyl, and is optionally substituted.

In one embodiment, —$R^{2B}$, if present, is independently isoquinolinyl, and is optionally substituted.

In one embodiment, —$R^{2B}$, if present, is independently cinnolinyl, and is optionally substituted.

In one embodiment, —$R^{2B}$, if present, is independently quinazolinyl, and is optionally substituted.

In one embodiment, —$R^{2B}$, if present, is independently selected from the groups —$R^{2B}$ shown in the compounds described under the heading "Examples of Specific Embodiments".

The Group —$R^{3A}$

In one embodiment, —$R^{3A}$, if present, is independently saturated aliphatic $C_{1-4}$alkyl.

In one embodiment, —$R^{3A}$, if present, is independently -Me, -Et, -nPr, or -iPr.

In one embodiment, —$R^{3A}$, if present, is independently -Me.

The Group —$R^{3B}$

In one embodiment, —$R^{3B}$, if present, is independently —F, —Cl, or —Br.

In one embodiment, —$R^{3B}$, if present, is independently —Cl or —Br.

In one embodiment, —$R^{3B}$, if present, is independently —Cl.

In one embodiment, —$R^{3B}$, if present, is independently —Br.

The Group —$R^{3C}$

In one embodiment, —$R^{3C}$, if present, is independently —CN.

The Group —$R^{5A}$

In one embodiment, —$R^{5A}$, if present, is independently saturated aliphatic $C_{1-4}$alkyl.

In one embodiment, —$R^{5A}$, if present, is independently -Me, -Et, -nPr, or -iPr.

In one embodiment, —$R^{5A}$, if present, is independently -Me.

The Group —$R^{5B}$

In one embodiment, —$R^{5B}$, if present, is independently —F, —Cl, or —Br.

In one embodiment, —$R^{5B}$, if present, is independently —Cl or —Br.

In one embodiment, —$R^{5B}$, if present, is independently —Cl.

In one embodiment, —$R^{5B}$, if present, is independently —Br.

The Group —$R^{5C}$

In one embodiment, —$R^{5C}$, if present, is independently —CN.

The Group -$J^1$

In one embodiment, -$J^1$, if present, is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted, for example, with one or more substituents as discussed below under the heading "Optional Substituents on -$J^1$, -$J^2$, -$J^3$, and -$J^{4n}$".

In one embodiment, exactly 1 of said -$J^1$ ring atoms is a ring heteroatom, and is N.

In one embodiment, exactly 2 of said -$J^1$ ring atoms are ring heteroatoms, and are both N.

In one embodiment, exactly 2 of said -$J^1$ ring atoms are ring heteroatoms, and are N and O.

In one embodiment, exactly 2 of said -$J^1$ ring atoms are ring heteroatoms, and are N and S.

In one embodiment, said -$J^1$ monocyclic non-aromatic heterocyclyl group has from 4 to 7 ring atoms.

In one embodiment, said -$J^1$ monocyclic non-aromatic heterocyclyl group has from 5 to 7 ring atoms.

In one embodiment, said -$J^1$ monocyclic non-aromatic heterocyclyl group has 6 or 7 ring atoms.

In one embodiment, -$J^1$, if present, is independently selected from the following groups and is optionally substituted, for example, with one or more substituents as discussed below under the heading "Optional Substituents on -$J^1$, -$J^2$, -$J^3$, and -$J^4$", for example, one or more substituents selected from saturated aliphatic $C_{1-4}$alkyl:

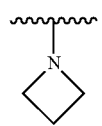 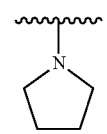 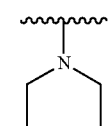

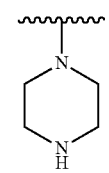 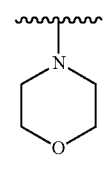 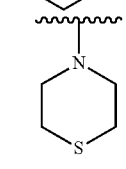

-continued

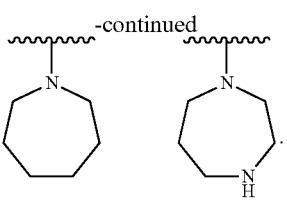

In one embodiment, -J¹, if present, is independently selected from the following groups and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

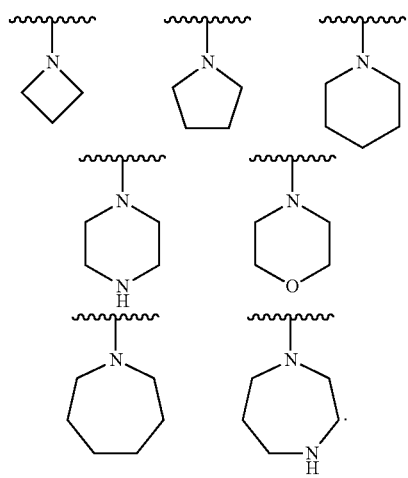

In one embodiment, -J¹, if present, is independently selected from the following groups and is optionally substituted, for example, with one or more substituents as discussed below under the heading "Optional Substituents on -J¹, -J², -J³, and -J⁴'", for example, with one or more substituents selected from saturated aliphatic $C_{1-4}$alkyl:

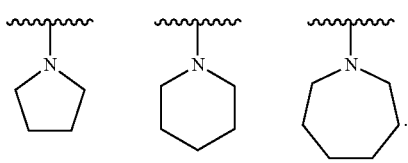

In one embodiment, -J¹, if present, is independently the following group and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

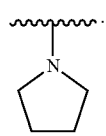

In one embodiment, -J¹, if present, is independently:

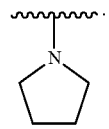

In one embodiment, -J¹, if present, is independently selected from the following group and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

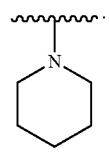

In one embodiment, -J¹, if present, is independently:

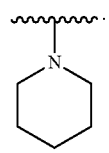

In one embodiment, -J¹, if present, is independently the following group and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

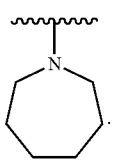

In one embodiment, -J¹, if present, is independently:

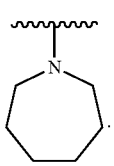

In one embodiment, -J¹, if present, is independently selected from the following groups and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

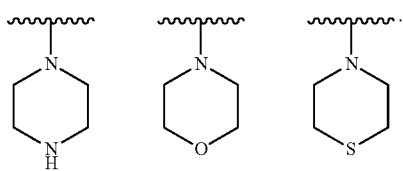
Examples of -J¹ groups (e.g., wherein exactly 1 of said ring atoms is a ring heteroatom, and is N) which additionally bear one or more substituents include the following:
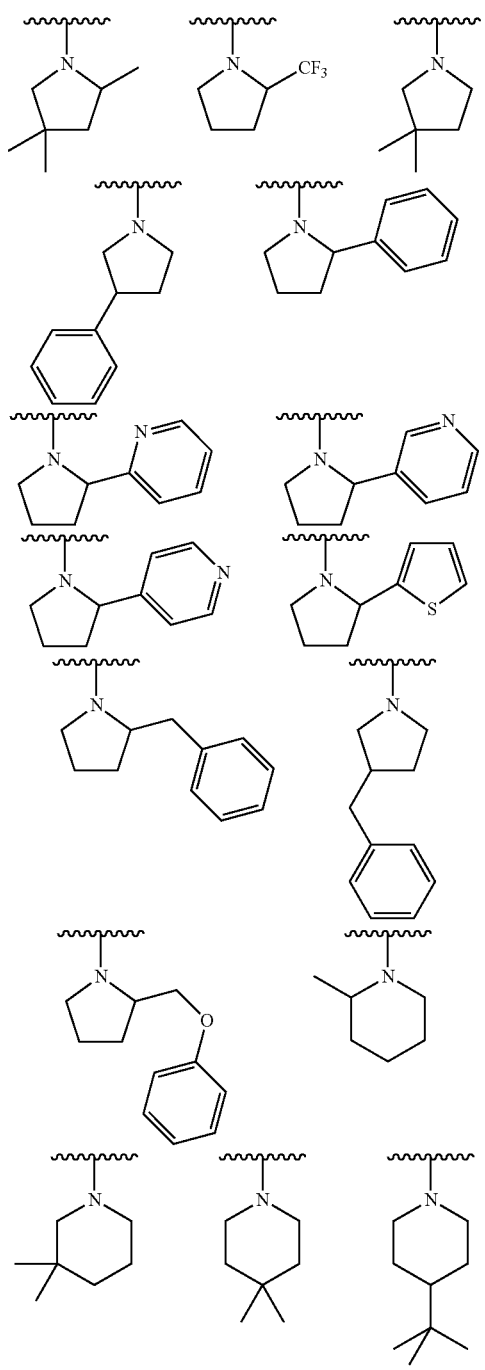
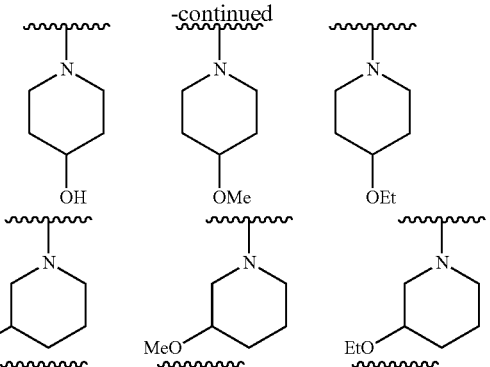
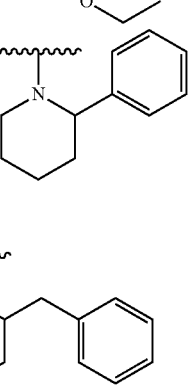
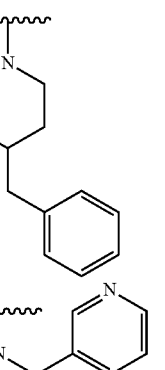
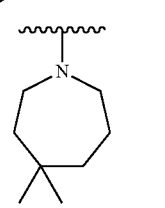

-continued

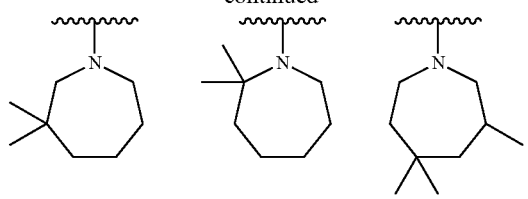
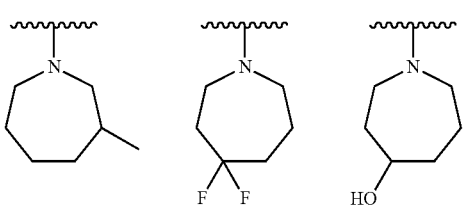
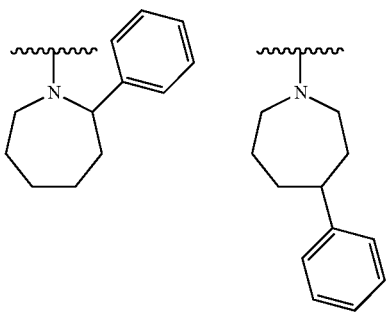
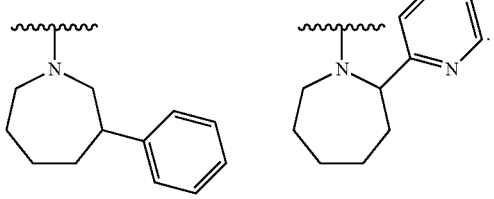

Examples of -J¹ groups (wherein exactly 2 of said ring atoms are ring heteroatoms, and are both N; or wherein exactly 2 of said ring atoms are ring heteroatoms, and are N and O; or wherein exactly 2 of said ring atoms are ring heteroatoms, and are N and S) which additionally bear one or more substituents include the following:

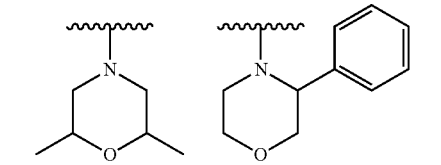
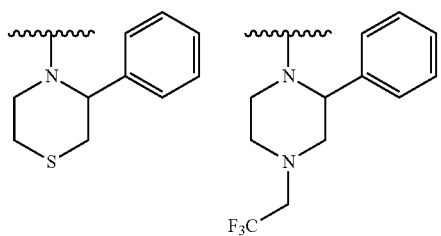

-continued

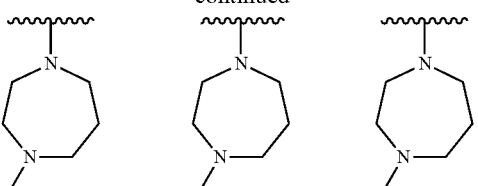
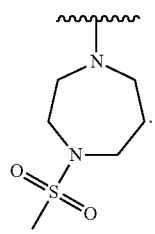

Examples of -J¹ groups which additionally bear at least one substituent that is phenyl include the following:

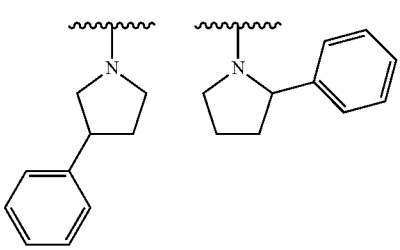
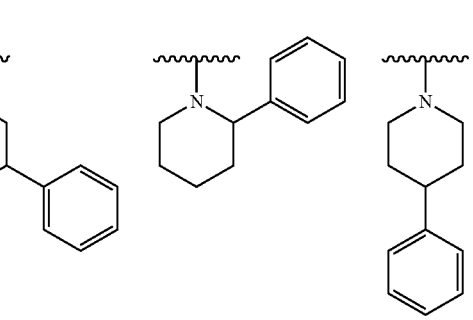
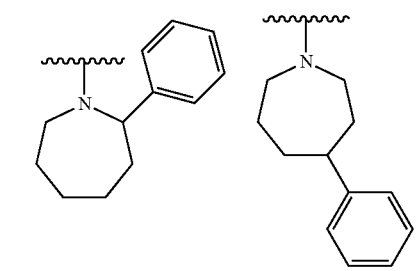
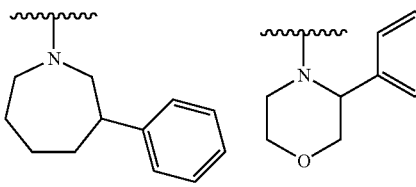

-continued

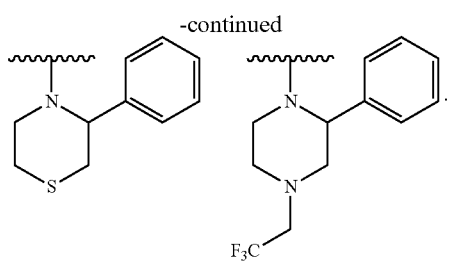

In one embodiment, -J$^1$, if present, is independently selected from the groups -J$^1$ shown in the compounds described under the heading "Examples of Specific Embodiments".

The Group -J$^2$

In one embodiment, -J$^2$, if present, is independently a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said fused bicyclic non-aromatic heterocyclyl group is optionally substituted, for example, with one or more substituents as discussed below under the heading "Optional Substituents on -J$^1$, -J$^2$, -J$^3$, and -J$^4$".

In one embodiment, -J$^2$, if present, is independently a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said fused bicyclic non-aromatic heterocyclyl group is optionally substituted, for example, with one or more substituents as discussed below under the heading "Optional Substituents on -J$^1$, -J$^2$, -J$^3$, and -J$^4$".

In one embodiment, exactly 1 of said -J$^2$ ring atoms is a ring heteroatom, and is N.

In one embodiment, exactly 2 of said -J$^2$ ring atoms are ring heteroatoms, and are both N.

In one embodiment, exactly 2 of said -J$^2$ ring atoms are ring heteroatoms, and are N and O.

In one embodiment, exactly 2 of said -J$^2$ ring atoms are ring heteroatoms, and are N and S.

In one embodiment, exactly 3 of said -J$^2$ ring atoms are ring heteroatoms, and are N, O, and O.

In one embodiment, exactly 3 of said -J$^2$ ring atoms are ring heteroatoms, and are N,N, and O.

In one embodiment, exactly 3 of said -J$^2$ ring atoms are ring heteroatoms, and are N,N, and S.

In one embodiment, exactly 3 of said -J$^2$ ring atoms are ring heteroatoms, and are N, O, and S.

In one embodiment, said -J$^2$ fused bicyclic non-aromatic heterocyclyl group has 9 to 10 ring atoms.

In one embodiment, said -J$^2$ fused bicyclic non-aromatic heterocyclyl group has 9 ring atoms.

In one embodiment, said -J$^2$ fused bicyclic non-aromatic heterocyclyl group has 10 ring atoms.

In one embodiment, -J$^2$, if present, is independently selected from the following groups and is optionally substituted, for example, with one or more substituents as discussed below under the heading "Optional Substituents on -J$^1$, -J$^2$, -J$^3$, and -J$^4$", for example, one or more substituents selected from saturated aliphatic C$_{1-4}$alkyl:

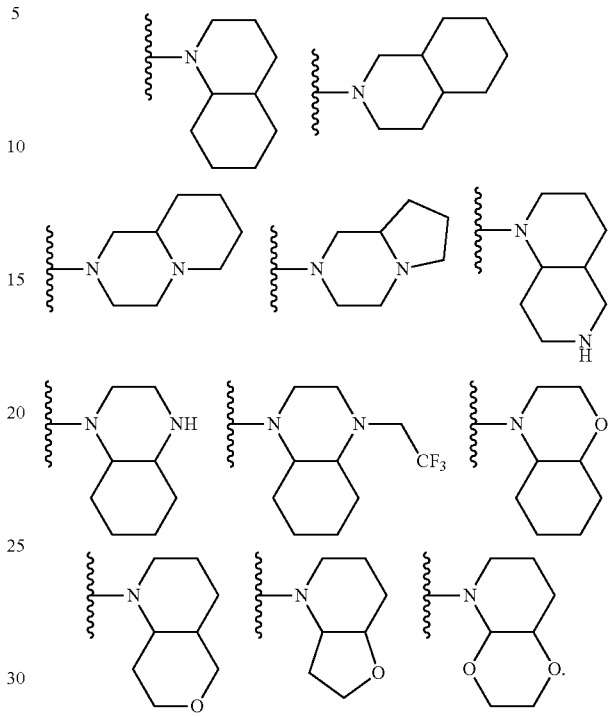

In one embodiment, -J$^2$, if present, is independently selected from the following groups and is optionally substituted, for example, with one or more substituents as discussed below under the heading "Optional Substituents on -J$^1$, -J$^2$, -J$^3$, and -J$^4$", for example, one or more substituents selected from saturated aliphatic C$_{1-4}$alkyl:

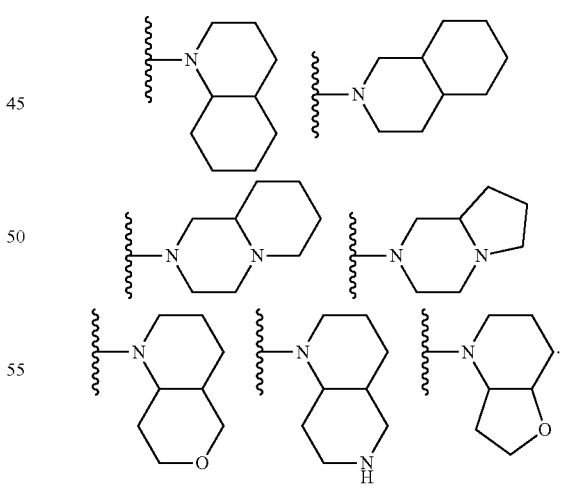

In one embodiment, -J$^2$, if present, is independently selected from the following groups and is optionally substituted, for example, with one or more substituents as discussed below under the heading "Optional Substituents on -J$^1$, -J$^2$, -J$^3$, and -J$^4$", for example, one or more substituents selected from saturated aliphatic C$_{1-4}$alkyl:

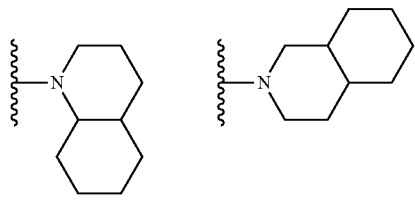

In one embodiment, -J², if present, is independently selected from the following groups and is optionally substituted, for example, with one or more substituents as discussed below under the heading "Optional Substituents on -J¹, -J², -J³, and -J⁴", for example, one or more substituents selected from saturated aliphatic $C_{1-4}$alkyl:

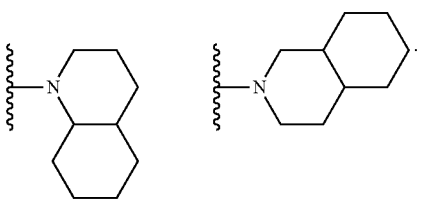

In one embodiment, -J², if present, is independently the following group and is optionally substituted, for example, with one or more substituents as discussed below under the heading "Optional Substituents on -J¹, -J², -J³, and -J⁴", for example, one or more substituents selected from saturated aliphatic $C_{1-4}$alkyl:

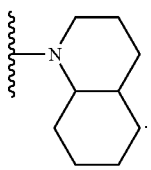

In one embodiment, -J², if present, is independently:

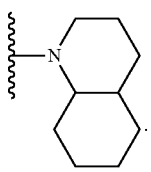

In one embodiment, -J², if present, is independently selected from:

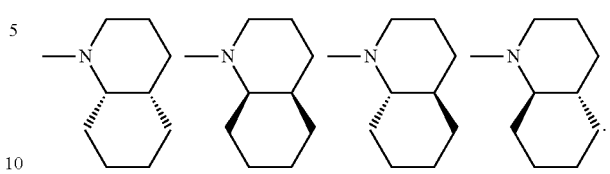

In one embodiment, -J², if present, is independently selected from:

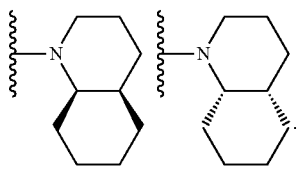

In one embodiment, -J², if present, is independently selected from the groups -J² shown in the compounds described under the heading "Examples of Specific Embodiments".

The Group -J³

In one embodiment, -J³, if present, is independently a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said bridged non-aromatic heterocyclyl group is optionally substituted, for example, with one or more substituents as discussed below under the heading "Optional Substituents on -J¹, -J², -J³, and -J⁴"; with the proviso that -J³ is not:

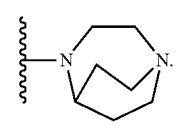

In one embodiment, exactly 1 of said -J³ ring atoms is a ring heteroatom, and is N.

In one embodiment, exactly 2 of said -J³ ring atoms are ring heteroatoms, and are both N.

In one embodiment, exactly 2 of said -J³ ring atoms are ring heteroatoms, and are N and O.

In one embodiment, exactly 2 of said -J³ ring atoms are ring heteroatoms, and are N and S.

In one embodiment, said -J³ bridged non-aromatic heterocyclyl group has 7 ring atoms.

In one embodiment, said -J³ bridged non-aromatic heterocyclyl group has 8 ring atoms.

In one embodiment, said -J³ bridged non-aromatic heterocyclyl group has 9 ring atoms.

In one embodiment, said -J³ bridged non-aromatic heterocyclyl group has 11 ring atoms.

In one embodiment, -J³, if present, is independently selected from the following groups and is optionally substituted, for example, with one or more substituents as discussed below under the heading "Optional Substituents on -J¹, -J², -J³, and -J⁴", for example, one or more substituents selected from saturated aliphatic $C_{1-4}$alkyl, —F:

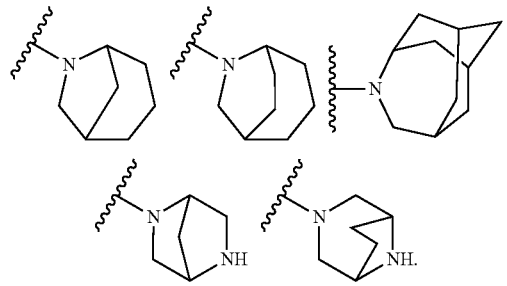

Examples of -J³ groups (e.g., wherein exactly 1 of said ring atoms is a ring heteroatom, and is N) which additionally bear one or more substituents (e.g., -Me) include the following:

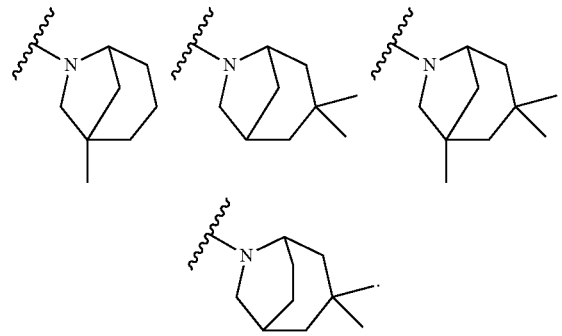

Examples of -J³ groups (e.g., wherein exactly 2 of said ring atoms is a ring heteroatom, and are both N) which additionally bear one or more substituents (e.g., -Me) include the following:

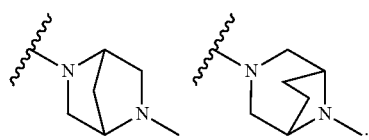

In one embodiment, -J³, if present, is independently selected from the following groups and is optionally substituted, for example, with one or more substituents as discussed below under the heading "Optional Substituents on -J¹, -J², -J³, and -J⁴'", for example, one or more substituents selected from saturated aliphatic $C_{1-4}$alkyl:

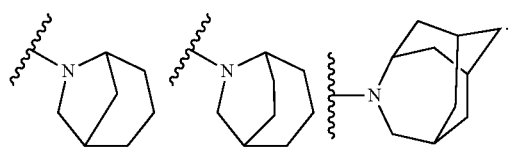

In one embodiment, -J³, if present, is independently selected from:

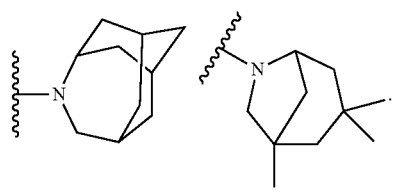

In one embodiment, -J³, if present, is independently:

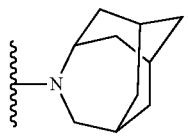

In one embodiment, -J³, if present, is independently:

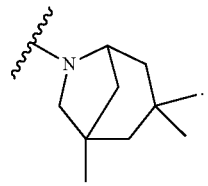

In one embodiment, -J³, if present, is independently selected from:

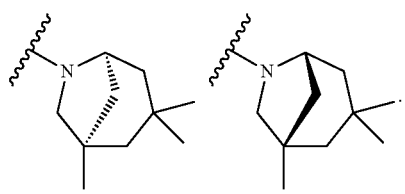

In one embodiment, -J³, if present, is independently selected from the groups -J³ shown in the compounds described under the heading "Examples of Specific Embodiments".

The Group -J⁴

In one embodiment, -J⁴, if present, is independently a spiro non-aromatic heterocyclyl group having from 8 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said spiro non-aromatic heterocyclyl group is optionally substituted, for example, with one or more substituents as discussed below under the heading "Optional Substituents on -J¹, -J², -J³, and -J⁴'".

In one embodiment, exactly 1 of said -J⁴ ring atoms is a ring heteroatom, and is N.

In one embodiment, exactly 2 of said -J⁴ ring atoms are ring heteroatoms, and are both N.

In one embodiment, exactly 2 of said -J⁴ ring atoms are ring heteroatoms, and are N and O.

In one embodiment, exactly 2 of said -J$^4$ ring atoms are ring heteroatoms, and are N and S.

In one embodiment, exactly 3 of said -J$^4$ ring atoms are ring heteroatoms, and are N,N, and O.

In one embodiment, exactly 3 of said -J$^4$ ring atoms are ring heteroatoms, and are N, O, and O.

In one embodiment, exactly 3 of said -J$^4$ ring atoms are ring heteroatoms, and are N,N, and S.

In one embodiment, exactly 3 of said -J$^4$ ring atoms are ring heteroatoms, and are N, O, and S.

In one embodiment, said -J$^4$ spiro non-aromatic heterocyclyl group has 8 ring atoms.

In one embodiment, said -J$^4$ spiro non-aromatic heterocyclyl group has 10 ring atoms.

In one embodiment, said -J$^4$ spiro non-aromatic heterocyclyl group has 11 ring atoms.

In one embodiment, said -J$^4$ spiro non-aromatic heterocyclyl group has 12 ring atoms.

In one embodiment, -J$^4$, if present, is independently selected from the following groups and is optionally substituted, for example, with one or more substituents as discussed below under the heading "Optional Substituents on -J$^1$, -J$^2$, -J$^3$, and -J$^4$", for example, one or more substituents selected from saturated aliphatic C$_{1-4}$alkyl:

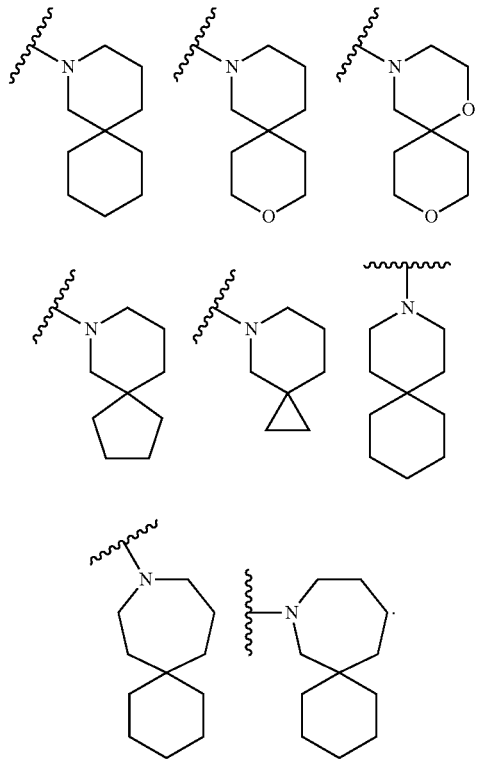

In one embodiment, -J$^4$, if present, is independently selected from the following groups and is optionally substituted, for example, with one or more substituents as discussed below under the heading "Optional Substituents on -J$^1$, -J$^2$, -J$^3$, and -J$^4$", for example, one or more substituents selected from saturated aliphatic C$_{1-4}$alkyl:

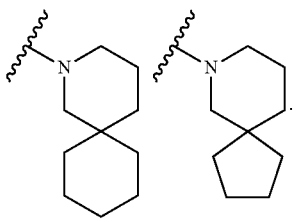

In one embodiment, -J$^4$, if present, is independently selected from:

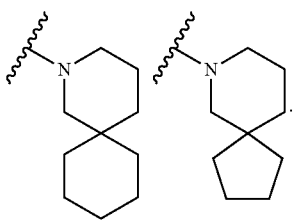

In one embodiment, -J$^4$, if present, is independently:

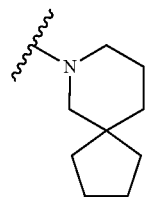

In one embodiment, -J$^4$, if present, is independently selected from the groups -J$^4$ shown in the compounds described under the heading "Examples of Specific Embodiments".

Optional Substituents on the Groups —R$^{2A}$ and —R$^{2B}$

In one embodiment, —R$^{2A}$ is independently optionally substituted.

In one embodiment, —R$^{2A}$ is independently unsubstituted.

In one embodiment, —R$^{2B}$ is independently optionally substituted.

In one embodiment, —R$^{2B}$ is independently unsubstituted.

In one embodiment, optional substituents on —R$^{2A}$, if present, and optional substituents on —R$^{2B}$, if present, are independently selected from:

—R$^Q$, —R$^R$, —R$^L$—R$^R$,
—F, —Cl, —Br,
—CN,
—NO$_2$,
—CF$_3$, —OCF$_3$,
—SR$^P$,
—OH, —OR$^P$,
—R$^L$—OH, —R$^L$—OR$^P$,
—O—R$^L$—OH, —O—R$^L$—OR$^P$,
—NH—R$^L$—OH, —NH—R$^L$—OR$^P$,
—NR$^Q$—R$^L$—OH, —NR$^Q$—R$^L$—OR$^P$,
—NH$_2$, —NHR$^P$, —NR$^P$$_2$, —R$^M$,
—R$^L$—NH$_2$, —R$^L$—NHR$^P$, —R$^L$—NR$^P$$_2$, —R$^L$—R$^M$,
—O—R$^L$—NH$_2$, —O—R$^L$—NHR$^P$, —O—R$^L$—NR$^P$$_2$, —O—R$^L$—R$^M$,
—NH—R$^L$—NH$_2$, —NH—R$^L$—NHR$^P$, —NH—R$^L$—NR$^P$$_2$, —NH—R$^L$—R$^M$,

—NR$^Q$—R$^L$—NH$_2$, —NR$^Q$—R$^L$—NHR$^P$, —NR$^Q$—R$^L$—NR$^P_2$, —NR$^Q$—R$^L$—R$^M$,

—S(=O)$_2$NH$_2$, —S(=O)$_2$NHR$^P$, —S(=O)$_2$NR$^P_2$, —S(=O)$_2$R$^M$,

—R$^L$—S(=O)$_2$NH$_2$, —R$^L$—S(=O)$_2$NHR$^P$, —R$^L$—S(=O)$_2$NR$^P_2$, —R$^L$—S(=O)$_2$R$^M$,

—O—R$^L$—S(=O)$_2$NH$_2$, —O—R$^L$—S(=O)$_2$NHR$^P$, —O—R$^L$—S(=O)$_2$NR$^P_2$, —O—R$^L$—S(=O)$_2$R$^M$,

—NH—R$^L$—S(=O)$_2$NH$_2$, —NH—R$^L$—S(=O)$_2$NHR$^P$, —NH—R$^L$—S(=O)$_2$NR$^P_2$, —NH—R$^L$—S(=O)$_2$R$^M$,

—NR$^Q$—R$^L$—S(=O)$_2$NH$_2$, —NR$^Q$—R$^L$—S(=O)$_2$NHR$^P$,

—NR$^Q$—R$^L$—S(=O)$_2$NR$^P_2$, —NR$^Q$—R$^L$—S(=O)$_2$R$^M$,

—NHS(=O)$_2$R$^P$, —NHS(=O)$_2$R$^M$,

—NR$^Q$S(=O)$_2$R$^P$, —NR$^Q$S(=O)$_2$R$^M$,

—R$^L$—NHS(=O)$_2$R$^P$, —R$^L$—NHS(=O)$_2$R$^M$,

—R$^L$—NR$^Q$S(=O)$_2$R$^P$, —R$^L$—NR$^Q$S(=O)$_2$R$^M$,

—O—R$^L$—NHS(=O)$_2$R$^P$, —O—R$^L$—NHS(=O)$_2$R$^M$,

—O—R$^L$—NR$^Q$S(=O)$_2$R$^P$, —O—R$^L$—NR$^Q$S(=O)$_2$R$^M$,

—NH—R$^L$—NHS(=O)$_2$R$^P$, —NH—R$^L$—NHS(=O)$_2$R$^M$,

—NH—R$^L$—NR$^Q$S(=O)$_2$R$^P$, —NH—R$^L$—NR$^Q$S(=O)$_2$R$^M$,

—NR$^Q$—R$^L$—NHS(=O)$_2$R$^P$, —NR$^Q$—R$^L$—NHS(=O)$_2$R$^M$,

—NR$^Q$—R$^L$—NR$^Q$S(=O)$_2$R$^P$, —NR$^Q$—R$^L$—NR$^Q$S(=O)$_2$R$^M$,

—S(=O)$_2$R$^P$, —S(=O)$_2$R$^M$,

—R$^L$—S(=O)$_2$R$^P$, —R$^L$—S(=O)$_2$R$^M$,

—O—R$^L$—S(=O)$_2$R$^P$, —O—R$^L$—S(=O)$_2$R$^M$,

—NH—R$^L$—S(=O)$_2$R$^P$, —NH—R$^1$—S(=O)$_2$R$^M$,

—NR$^Q$—R$^L$—S(=O)$_2$R$^P$, —NR$^Q$—R$^L$—S(=O)$_2$R$^M$,

—C(=O)R$^P$,

—C(=O)OH, —C(=O)OR$^P$,

—R$^L$—C(=O)OH, —R$^L$—C(=O)OR$^P$,

—O—R$^L$—C(=O)OH, —O—R$^L$—C(=O)OR$^P$,

—NH—R$^L$—C(=O)OH, —NH—R$^L$—C(=O)OR$^P$,

—NR$^Q$—R$^L$—C(=O)OH, —NR$^Q$—R$^L$—C(=O)OR$^P$,

—C(=O)NH$_2$, —C(=O)NHR$^P$, —C(=O)NR$^P_2$, —C(=O)R$^M$,

—R$^L$—C(=O)NH$_2$, —R$^L$—C(=O)NHR$^P$, —R$^L$—C(=O)NR$^P_2$, —R$^L$—C(=O)R$^M$,

—O—R$^L$—C(=O)NH$_2$, —O—R$^L$—C(=O)NHR$^P$, —O—R$^L$—C(=R$^P_2$, —O—R$^L$—C(=O)R$^M$,

—NH—R$^1$—C(=O)NH$_2$, —NH—R$^L$—C(=O)NHR$^P$,

—NH—R$^L$—C(=O)NR$^P_2$, —NH—R$^1$—C(=O)R$^M$,

—NR$^Q$—R$^L$—C(=O)NH$_2$, —NR$^Q$—R$^L$—C(=O)NHR$^P$,

—NR$^Q$—R$^L$—C(=O)NR$^P_2$, —NR$^Q$—R$^L$—C(=O)R$^M$,

—NHC(=O)R$^P$, —NR$^Q$C(=O)R$^P$,

—R$^L$—NHC(=O)R$^P$, —R$^L$—NR$^Q$C(=O)R$^P$,

—O—R$^L$—NHC(=O)R$^P$, —O—R$^L$—NR$^Q$C(=O)R$^P$,

—NH—R$^L$—NHC(=O)R$^P$, —NH—R$^L$—NR$^Q$C(=O)R$^P$,

—NR$^Q$—R$^L$—NHC(=O)R$^P$, —NR$^Q$—R$^L$—NR$^Q$C(=O)R$^P$,

—O—C(=O)NH$_2$, —O—C(=O)NHR$^P$,

—O—C(=O)NR$^P_2$, —O—C(=O)R$^M$,

—R$^L$—O—C(=O)NH$_2$, —R$^L$—O—C(=O)NHR$^P$,

—R$^L$—O—C(=O)NR$^P_2$, —R$^L$—O—C(=O)R$^M$,

—O—R$^L$—O—C(=O)NH$_2$, —O—R$^L$—O—C(=O)NHR$^P$,

—O—R$^L$—O—C(=O)NR$^P_2$,

—NH—R$^L$—O—C(=O)NH$_2$, —NH—R$^L$—O—C(=O)NHR$^P$,

—NH—R$^L$—O—C(=O)NR$^P_2$, —NH—R$^1$—O—C(=O)R$^M$, —NR$^Q$—R$^L$—O—C(=O)NH$_2$, —NR$^Q$—R$^L$—O—C(=O)NHR$^P$,

—NR$^Q$—R$^L$—O—C(=O)NR$^P_2$, —NR$^Q$—R$^L$—O—C(=O)R$^M$,

—NH—C(=O)OR$^P$, —NR$^Q$—C(=O)OR$^P$,

—R$^1$—NH—C(=O)OR$^P$, —R$^L$—NR$^Q$—C(=O)OR$^P$,

—O—R$^1$—NH—C(=O)OR$^P$, —O—R$^L$—NR$^Q$—C(=O)OR$^P$,

—NH—R$^L$—NH—C(=O)OR$^P$, —NH—R$^L$—NR$^Q$—C(=O)OR$^P$,

—NR$^Q$—R$^L$—NH—C(=O)OR$^P$, —NR$^Q$—R$^L$—NR$^Q$—C(=O)OR$^P$,

—NH—C(=O)NH$_2$, —NH—C(=O)NHR$^P$,

—NH—C(=O)NR$^P_2$, —NH—C(=O)R$^M$,

—NR$^Q$—C(=O)NH$_2$, —NR$^Q$—C(=O)NHR$^P$,

—NR$^Q$—C(=O)NR$^P_2$, —NR$^Q$—C(=O)R$^M$,

—R$^L$—NH—C(=O)NH$_2$, —R$^1$—NH—C(=O)NHR$^P$,

—R$^L$—NH—C(=O)NR$^P_2$, —R$^L$—NH—C(=O)R$^M$,

—R$^L$—NR$^Q$—C(=O)NH$_2$, —R$^L$—NR$^Q$—C(=O)NHR$^P$,

—R$^L$—NR$^Q$—C(=O)NR$^P_2$, —R$^L$—NR$^Q$—C(=O)R$^M$,

—O—R$^L$—NH—C(=O)NH$_2$, H—C(=O)NHR$^P$,

—O—R$^L$—NH—C(=O)NR$^P_2$, —O—R$^L$—NH—C(=O)R$^M$,

—O—R$^L$—NR$^Q$—C(=O)NH$_2$, —O—R$^L$—NR$^Q$—C(=O)NHR$^P$,

—O—R$^L$—NR$^Q$—C(=O)NR$^P_2$, —O—R$^L$—NR$^Q$—C(=O)R$^M$,

—NH—R$^L$—NH—C(=O)NH$_2$, —NH—R$^L$—NH—C(=O)NHR$^P$,

—NH—R$^L$—NH—C(=O)NR$^P_2$, —NH—R$^L$—NH—C(=O)R$^M$,

R$^Q$—C(=O)NH$_2$, —NH—R$^L$—NR$^Q$—C(=O)NHR$^P$, —NH—R$^L$—NR$^Q$—C(=O)NR$^P_2$, —NH—R$^L$—NR$^Q$—C(=O)R$^M$,

—NR$^Q$—R$^L$—NH—C(=O)NH$_2$, —NR$^Q$—R$^L$—NH—C(=O)NHR$^P$,

—NR$^Q$—R$^L$—NH—C(=O)NR$^P_2$, —NR$^Q$—R$^L$—NH—C(=O)R$^M$,

—NR$^Q$—R$^L$—NR$^Q$—C(=O)NH$_2$, —NR$^Q$—R$^L$—NR$^Q$—C(=O)NHR$^P$,

—NR$^Q$—R$^L$—NR$^Q$—C(=O)NR$^P_2$, and —NR$^Q$—R$^L$—NR$^Q$—C(=O)R$^M$;

or two adjacent substituents, if present, together form —O—CH$_2$—O— or —O—CH$_2$CH$_2$—O—;

or two adjacent substituents, if present, together form —O—C(=O)—NH—, —O—C(=O)—NR$^Q$—, —NR$^Q$—C(=O)—NH—, —NH—C(=O)—NR$^Q$—, or —NR$^Q$—C(=O)—NR$^Q$—.

In one embodiment, optional substituents on —R$^{2A}$, if present, and optional substituents on —R$^{2B}$, if present, are independently selected from:

—R$^Q$, —R$^L$—R$^R$,

—F, —Cl, —Br,

—CN,

—NO$_2$,

—CF$_3$, —OCF$_3$,

—OH, —OR$^P$,

—R$^L$—OH, —R$^L$—OR$^P$,

—O—R$^L$—OH, —O—R$^L$—OR$^P$,

—NH—R$^L$—OH, —NH—R$^L$—OR$^P$,

—NH$_2$, —NHR$^P$, —NR$^P_2$, —R$^M$,

—R$^L$—NH$_2$, —R$^L$—NHR$^P$, —R$^L$—NR$^P_2$, —R$^L$—R$^M$,

—O—R$^L$—NH$_2$, —O—R$^L$—NHR$^P$, —O—R$^L$—NR$^P_2$, —O—R$^L$—R$^M$,

—NH—$R^L$—$NH_2$, —NH—$R^L$—$NHR^P$, —NH—$R^L$—$NR^P_2$, —NH—$R^L$—$R^M$,
—S(=O)$_2$$NH_2$, —S(=O)$_2$$NHR^P$, —S(=O)$_2$$NR^P_2$, —S(=O)$_2$$R^M$,
—$R^L$—S(=O)$_2$$NH_2$, —$R^L$—S(=O)$_2$$NHR^P$, —$R^L$—S(=O)$_2$$NR^P_2$, —$R^L$—S(=O)$_2$$R^M$,
—O—$R^L$—S(=O)$_2$$NH_2$, —O—$R^L$—S(=O)$_2$$NHR^P$, —O—$R^L$—S(=O)$_2$$NR^P_2$, —O—$R^L$—S(=O)$_2$$R^M$,
—NH—$R^L$—S(=O)$_2$$NH_2$, —NH—$R^L$—S(=O)$_2$$NHR^P$, —NH—$R^L$—S(=O)$_2$$NR^P_2$, —NH—$R^L$—S(=O)$_2$$R^M$,
—NHS(=O)$_2$$R^P$, —NHS(=O)$_2$$R^M$,
—$NR^Q$S(=O)$_2$$R^P$, —$NR^Q$S(=O)$_2$$R^M$,
—$R^L$—NHS(=O)$_2$$R^P$, —$R^L$—NHS(=O)$_2$$R^M$,
—$R^L$—$NR^Q$S(=O)$_2$$R^P$, —$R^L$—$NR^Q$S(=O)$_2$$R^M$,
—O—$R^L$—NHS(=O)$_2$$R^P$, —O—$R^L$—NHS(=O)$_2$$R^M$,
—O—$R^L$—$NR^Q$S(=O)$_2$$R^P$, —O—$R^L$—$NR^Q$S(=O)$_2$$R^M$,
—NH—$R^L$—NHS(=O)$_2$$R^P$, —NH—$R^L$—NHS(=O)$_2$$R^M$,
—NH—$R^L$—$NR^Q$S(=O)$_2$$R^P$, —NH—$R^L$—$NR^Q$S(=O)$_2$$R^M$,
—S(=O)$_2$$R^P$, —S(=O)$_2$$R^M$,
—$R^L$—S(=O)$_2$$R^P$, —$R^L$—S(=O)$_2$$R^M$,
—O—$R^L$—S(=O)$_2$$R^P$, —O—$R^L$—S(=O)$_2$$R^M$,
—NH—$R^L$—S(=O)$_2$$R^P$, —NH—$R^L$—S(=O)$_2$$R^M$,
—C(=O)OH, —C(=O)$OR^P$,
—$R^L$—C(=O)OH, —$R^L$—C(=O)$OR^P$,
—O—$R^L$—C(=O)OH, —O—$R^L$—C(=O)$OR^P$,
—NH—$R^L$—C(=O)OH, —NH—$R^L$—C(=O)$OR^P$,
—C(=O)$NH_2$, —C(=O)$NHR^P$, —C(=O)$NR^P_2$, —C(=O)$R^M$,
—$R^L$—C(=O)$NH_2$, —$R^L$—C(=O)$NHR^P$, —$R^L$—C(=O)$NR^P_2$, —$R^L$—C(=O)$R^M$,
—O—$R^L$—C(=O)$NH_2$, —O—$R^L$—C(=O)$NHR^P$, —O—$R^L$—C(=O)$NR^P_2$, —O—$R^L$—C(=O)$R^M$,
—NH—$R^L$—C(=O)$NH_2$, —NH—$R^1$—C(=O)$NHR^P$, —NH—$R^L$—C(=O)$NR^P_2$, —NH—$R^L$—C(=O)$R^M$,
—NHC(=O)$R^P$, —$NR^Q$C(=O)$R^P$,
—$R^L$—NHC(=O)$R^P$, —$R^L$—$NR^Q$C(=O)$R^P$,
—O—$R^L$—NHC(=O)$R^P$, —O—$R^L$—$NR^Q$C(=O)$R^P$,
—NH—$R^L$—NHC(=O)$R^P$, —NH—$R^1$—$NR^Q$C(=O)$R^P$,
—O—C(=O)$NH_2$, —O—C(=O)$NHR^P$,
—O—C(=O)$NR^P_2$, —O—C(=O)$R^M$,
—$R^L$—O—C(=O)$NH_2$, —$R^L$—O—C(=O)$NHR^P$,
—$R^L$—O—C(=O)$NR^P_2$, —$R^L$—O—C(=O)$R^M$,
—O—$R^L$—O—C(=O)$NH_2$, —O—$R^L$—O—C(=O)$NHR^P$,
—O—$R^L$—O—C(=O)$NR^P_2$, —O—$R^L$—O—C(=O)$R^M$,
—NH—$R^L$—O—C(=O)$NH_2$, —NH—$R^L$—O—C(=O)$NHR^P$,
—NH—$R^L$—O—C(=O)$NR^P_2$, —NH—$R^L$—O—C(=O)$R^M$,
—NH—C(=O)$OR^P$, —$NR^Q$—C(=O)$OR^P$,
—$R^L$—NH—C(=O)$OR^P$, —$R^L$—$NR^Q$—C(=O)$OR^P$,
—O—$R^1$—NH—C(=O)$OR^P$, —O—$R^1$—$NR^Q$—C(=O)$OR^P$,
—NH—$R^L$—NH—C(=O)$OR^P$, —NH—$R^L$—$NR^Q$—C(=O)$OR^P$,
—NH—C(=O)$NH_2$, —NH—C(=O)$NHR^P$,
—NH—C(=O)$NR^P_2$, —NH—C(=O)$R^M$,
—$R^L$—NH—C(=O)$NH_2$, —$R^L$—NH—C(=O)$NHR^P$,
—$R^L$—NH—C(=O)$NR^P_2$, —$R^L$—NH—C(=O)$R^M$,
—$R^L$—$NR^Q$—C(=O)$NH_2$, —$R^L$—$NR^Q$—C(=O)$NHR^P$,
—$R^L$—$NR^Q$—C(=O)$NR^P_2$, —$R^L$—$NR^Q$—C(=O)$R^M$,
—O—$R^L$—NH—C(=O)$NH_2$, —O—$R^L$—NH—C(=O)$NHR^P$,
—O—$R^L$—NH—C(=O)$NR^P_2$, —O—$R^L$—NH—C(=O)$R^M$,
—O—$R^L$—$NR^Q$—C(=O)$NH_2$, —O—$R^L$—$NR^Q$—C(=O)$NHR^P$,
—O—$R^L$—$NR^Q$—C(=O)$NR^P_2$, —O—$R^L$—$NR^Q$—C(=O)$R^M$,
—NH—$R^L$—NH—C(=O)$NH_2$, —NH—$R^L$—NH—C(=O)$NHR^P$,
—NH—$R^1$—NH—C(=O)$NR^P_2$, —NH—$R^L$—NH—C(=O)$R^M$,
—NH—$R^L$—$NR^Q$—C(=O)$NH_2$, —NH—$R^L$—$NR^Q$—C(=O)$NHR^P$,
—NH—$R^L$—$NR^Q$—C(=O)$NR^P_2$, and —NH—$R^L$—$NR^Q$—C(=O)$R^M$, or two adjacent substituents, if present, together form —O—$CH_2$—O— or —O—$CH_2$$CH_2$—O—;

or two adjacent substituents, if present, together form —O—C(=O)—NH—, —O—C(=O)—$NR^Q$—, —$NR^Q$—C(=O)—NH—, —NH—C(=O)—$NR^Q$—, or —$NR^Q$—C(=O)—$NR^Q$—.

In one embodiment, optional substituents on —$R^{2A}$, if present, and optional substituents on —$R^{2B}$, if present, are independently selected from:
—$R^Q$, —$R^L$—$R^R$,
—F, —Cl, —Br,
—CN,
—$NO_2$,
—$CF_3$, —$OCF_3$,
—OH, —$OR^P$,
—$R^L$—OH, —$R^L$—$OR^P$,
—O—$R^L$—OH, —O—$R^L$—$OR^P$,
—$NH_2$, —$NHR^P$, —$NR^P_2$, —$R^M$,
—$R^L$—$NH_2$, —$R^L$—$NHR^P$, —$R^L$—$NR^P_2$, —$R^L$—$R^M$,
—O—$R^L$—$NH_2$, —O—$R^L$—$NHR^P$, —O—$R^L$—$NR^P_2$, —O—$R^L$—$R^M$,
—S(=O)$_2$$NH_2$, —S(=O)$_2$$NHR^P$, —S(=O)$_2$$NR^P_2$, —S(=O)$_2$$R^M$,
—$R^L$—S(=O)$_2$$NH_2$, —$R^L$—S(=O)$_2$$NHR^P$, —$R^L$—S(=O)$_2$$NR^P_2$, —$R^L$—S(=O)$_2$$R^M$,
—O—$R^L$—S(=O)$_2$$NH_2$, —O—$R^L$—S(=O)$_2$$NHR^P$, —O—$R^L$—S(=O)$_2$$NR^P_2$, —O—$R^L$—S(=O)$_2$$R^M$,
—NHS(=O)$_2$$R^P$, —NHS(=O)$_2$$R^M$,
—$NR^Q$S(=O)$_2$$R^P$, —$NR^Q$S(=O)$_2$$R^M$,
—$R^L$—NHS(=O)$_2$$R^P$, —$R^L$—NHS(=O)$_2$$R^M$,
—$R^L$—$NR^Q$S(=O)$_2$$R^P$, —$R^L$—$NR^Q$S(=O)$_2$$R^M$,
—O—$R^L$—NHS(=O)$_2$$R^P$, —O—$R^L$—NHS(=O)$_2$$R^M$,
—O—$R^L$—$NR^Q$S(=O)$_2$$R^P$, —O—$R^L$—$NR^Q$S(=O)$_2$$R^M$,
—S(=O)$_2$$R^P$, —S(=O)$_2$$R^M$,
—$R^L$—S(=O)$_2$$R^P$, —$R^L$—S(=O)$_2$$R^M$,
—O—$R^L$—S(=O)$_2$$R^P$, —O—$R^L$—S(=O)$_2$$R^M$,
—C(=O)OH, —C(=O)$OR^P$,
—$R^L$—C(=O)OH, —$R^L$—C(=O)$OR^P$,
—O—$R^L$—C(=O)OH, —O—$R^L$—C(=O)$OR^P$,
—C(=O)$NH_2$, —C(=O)$NHR^P$, —C(=O)$NR^P_2$, —C(=O)$R^M$,
—$R^L$—C(=O)$NH_2$, —$R^L$—C(=O)$NHR^P$, —$R^L$—C(=O)$NR^P_2$, —$R^L$—C(=O)$R^M$,
—O—$R^L$—C(=O)$NH_2$, —O—$R^L$—C(=O)$NHR^P$, —O—$R^L$—C(=O)$NR^P_2$, —O—$R^L$—C(=O)$R^M$,
—NHC(=O)$R^P$, —$NR^Q$C(=O)$R^P$,
—$R^L$—NHC(=O)$R^P$, —$R^L$—$NR^Q$C(=O)$R^P$,
—O—$R^L$—NHC(=O)$R^P$, —O—$R^L$—$NR^Q$C(=O)$R^P$,
—O—C(=O)$NH_2$, —O—C(=O)$NHR^P$,
—O—C(=O)$NR^P_2$, —O—C(=O)$R^M$, —$R^L$—O—C(=O)$NH_2$, —$R^L$—O—C(=O)$NHR^P$,
—$R^L$—O—C(=O)$NR^P_2$, —$R^L$—O—C(=O)$R^M$,
—O—$R^L$—O—C(=O)$NH_2$, —O—$R^L$—O—C(=O)$NHR^P$,
—O—$R^L$—O—C(=O)$NR^P_2$, —O—$R^L$—O—C(=O)$R^M$,
—$R^L$—NH—C(=O)$OR^P$, —$R^L$—$NR^Q$—C(=O)$OR^P$,
—O—$R^L$—NH—C(=O)$OR^P$, —O—$R^L$—$NR^Q$—C(=O)$OR^P$,
—NH—C(=O)$NH_2$, —NH—C(=O)$NHR^P$,
—NH—C(=O)$NR^P_2$, —NH—C(=O)$R^M$,
—$R^L$—NH—C(=O)$NH_2$, —$R^L$—NH—C(=O)$NHR^P$,
—$R^L$—NH—C(=O)$NR^P_2$, —$R^L$—NH—C(=O)$R^M$,
—$R^L$—$NR^Q$—C(=O)$NH_2$, —$R^L$—$NR^Q$—C(=O)$NHR^P$,
—$R^L$—$NR^Q$—C(=O)$NR^P_2$, —$R^L$—$NR^Q$—C(=O)$R^M$,
—O—$R^L$—NH—C(=O)$NH_2$, —O—$R^1$—NH—C(=O)$NHR^P$,
—O—$R^L$—NH—C(=O)$NR^P_2$, —O—$R^L$—NH—C(=O)$R^M$,
—O—$R^L$—$NR^Q$—C(=O)$NH_2$, —O—$R^L$—$NR^Q$—C(=O)$NHR^P$,
—O—$R^L$—$NR^Q$—C(=O)$NR^P_2$, and —O—$R^L$—$NR^Q$—C(=O)$R^M$;

or two adjacent substituents, if present, together form —O—$CH_2$—O— or —O—$CH_2CH_2$—O—;

or two adjacent substituents, if present, together form —O—C(=O)—NH—, —O—C(=O)—$NR^Q$—, —$NR^Q$—C(=O)—NH—, —NH—C(=O)—$NR^Q$—, or —$NR^Q$—C(=O)—$NR^Q$—.

In one embodiment, optional substituents on —$R^{2A}$, if present, and optional substituents on —$R^{2B}$, if present, are independently selected from:
—$R^Q$, —$R^L$—$R^R$,
—F, —Cl, —Br,
—CN,
—$NO_2$,
—$CF_3$, —$OCF_3$,
—OH, —$OR^P$,
—$R^L$—OH, —$R^L$—$OR^P$,
—$NH_2$, —$NHR^P$, —$NR^P_2$, —$R^M$,
—$R^L$—$NH_2$, —$R^L$—$NHR^P$, —$R^L$—$NR^P_2$, —$R^L$—$R^M$,
—S(=O)$_2NH_2$, —S(=O)$_2NHR^P$, —S(=O)$_2NR^P_2$,
—S(=O)$_2R^M$,
—$R^L$—S(=O)$_2NH_2$, —$R^L$—S(=O)$_2NHR^P$, —$R^L$—S(=O)$_2NR^P_2$, —$R^L$—S(=O)$_2R^M$,
—NHS(=O)$_2R^P$, —NHS(=O)$_2R^M$,
—$NR^Q$S(=O)$_2R^P$, —$NR^Q$S(=O)$_2R^M$,
—$R^L$—NHS(=O)$_2R^P$, —$R^L$—NHS(=O)$_2R^M$,
—$R^L$—$NR^Q$S(=O)$_2R^P$, —$R^L$—$NR^Q$S(=O)$_2R^M$,
—S(=O)$_2R^P$, —S(=O)$_2R^M$,
—$R^L$—S(=O)$_2R^P$, —$R^L$—S(=O)$_2R^M$,
—C(=O)OH, —C(=O)$OR^P$,
—$R^L$—C(=O)OH, —$R^L$—C(=O)$OR^P$,
—C(=O)$NH_2$, —C(=O)$NHR^P$, —C(=O)$NR^P_2$,
—C(=O)$R^M$,
—$R^L$—C(=O)$NH_2$, —$R^L$—C(=O)$NHR^P$, —$R^L$—C(=O)$NR^P_2$, —$R^L$—C(=O)$R^M$,
—NHC(=O)$R^P$, —$NR^Q$C(=O)$R^P$,
—$R^L$—NHC(=O)$R^P$, —$R^L$—$NR^Q$C(=O)$R^P$,
—O—C(=O)$NH_2$, —O—C(=O)$NHR^P$,
—O—C(=O)$NR^P_2$, —O—C(=O)$R^M$,
—$R^L$—O—C(=O)$NH_2$, —$R^L$—O—C(=O)$NHR^P$,
—$R^L$—O—C(=O)$NR^P_2$, —$R^L$—O—C(=O)$R^M$,
—$R^1$—NH—C(=O)$OR^P$, —$R^L$—$NR^Q$—C(=O)$OR^P$,
—NH—C(=O)$NH_2$, —NH—C(=O)$NHR^P$,
—NH—C(=O)$NR^P_2$, —NH—C(=O)$R^M$,
—$R^L$—NH—C(=O)$NH_2$, —$R^1$—NH—C(=O)$NHR^P$,
—$R^L$—NH—C(=O)$NR^P_2$, —$R^L$—NH—C(=O)$R^M$,
—$R^L$—$NR^Q$—C(=O)$NH_2$, —$R^L$—$NR^Q$—C(=O)$NHR^P$,
—$R^L$—$NR^Q$—C(=O)$NR^P_2$, and —$R^L$—$NR^Q$—C(=O)$R^M$;

or two adjacent substituents, if present, together form —O—$CH_2$—O— or —O—$CH_2CH_2$—O—;

or two adjacent substituents, if present, together form —O—C(=O)—NH—, —O—C(=O)—$NR^Q$—, —$NR^Q$—C(=O)—NH—, —NH—C(=O)—$NR^Q$—, or —$NR^Q$—C(=O)—$NR^Q$—.

In one embodiment, optional substituents on —$R^{2A}$, if present, and optional substituents on —$R^{2B}$, if present, are independently selected from:
—$R^{X1}$,
—F, —Cl, —Br,
—OH, —$OR^{X1}$,
—$R^{XL}$—$OR^{X1}$,
—CN,
—$NO_2$,
—$NH_2$, —$NHR^{X1}$, —$NR^{X1}_2$, -M,
—$R^{XL}$—$NH_2$, —$R^{X1}$—$NHR^{X1}$, —$R^{XL}$—$NR^{X1}_2$, —$R^{XL}$-M,
—NHC(=O)$R^{X1}$, —$NR^{X1}$C(=O)$R^{X1}$,
—$R^{XL}$—NHC(=O)$R^{X1}$, —$R^{XL}$—$NR^{X1}$C(=O)$R^{X1}$,
—C(=O)OH, —C(=O)$OR^{X1}$,
—$R^{XL}$—C(=O)OH, —$R^{X1}$—C(=O)$OR^{X1}$,
—C(=O)$NH_2$, —C(=O)$NHR^{X1}$, —C(=O)$NR^{X1}_2$,
—C(=O)M,
—$R^{X1}$—C(=O)$NH_2$, —$R^{XL}$—C(=O)$NHR^{X1}$, —$R^{XL}$—C(=O)$NR^{X1}_2$, —$R^{XL}$—C(=O)M,
—S(=O)$_2NH_2$, —S(=O)$_2NH_2$, —S(=O)$_2NR^{X1}_2$, —S(=O)$_2M$,
—NHS(=O)$_2R^{X1}$, —$NR^{X1}$S(=O)$_2R^{X1}$,
—NHC(=O)$NH_2$, —NHC(=O)$NHR^{X1}$, —NHC(=O)$NR^{X1}_2$, —NHC(=O)M,
—$NR^{X1}$C(=O)$NH_2$, —$NR^{X1}$C(=O)$NHR^{X1}$, —$NR^{X1}$C(=O)$NR^{X1}_2$, and —$NR^{X1}$C(=O)M;

or two adjacent substituents, if present, together form —O—$CH_2$—O— or —O—$CH_2CH_2$—O—;

wherein:
each —$R^{X1}$ is independently saturated aliphatic $C_{1-4}$alkyl or phenyl;
each —$R^{XL}$— is independently saturated aliphatic $C_{1-4}$alkylene; and
each -M is pyrrolidino, piperidino, piperazino, or morpholino, and is optionally substituted, for example, with one or more groups selected from saturated aliphatic $C_{1-4}$alkyl.

In one embodiment, optional substituents on —$R^{2A}$, if present, and optional substituents on —$R^{2B}$, if present, are independently selected from:
—$R^{X1}$, —F, —Cl, —Br, —OH, —$OR^{X1}$, —CN, —$NO_2$, —$NH_2$, —$NHR^{X1}$, —$NR^{X1}_2$, —NHC(=O)$R^{X1}$, —$NR^{X1}$C(=O)$R^{X1}$, —C(=O)$NH_2$, —C(=O)$NHR^{X1}$, —C(=O)$NR^{X1}_2$, —S(=O)$_2NH_2$, —S(=O)$_2NHR^{X1}$, —S(=O)$_2NR^{X1}_2$, —NHS(=O)$_2R^{X1}$, —$NR^{X1}$S(=O)$_2R^{X1}$, —NHC(=O)$NH_2$, —NHC(=O)$NHR^M$, —NHC(=O)$NR^{X1}_2$, —$NR^{X1}$C(=O)$NH_2$, —$NR^{X1}$C(=O)$NHR^{X1}$, and —$NR^{X1}$C(=O)$NR^{X1}_2$;

wherein each —$R^{X1}$ is independently saturated aliphatic $C_{1-4}$alkyl or phenyl.

In one embodiment, optional substituents on —$R^{2A}$, if present, and optional substituents on —$R^{2B}$, if present, are independently selected from:

—$R^{X1}$, —F, —Cl, —Br, —OH, —$OR^{X1}$, —$NH_2$, —$NHR^{X1}$, —$NR^{X1}_2$, —$NHC(=O)R^{X1}$, and —$NR^{X1}C(=O)R^{X1}$;

wherein each —$R^{X1}$ is independently saturated aliphatic $C_{1-4}$alkyl or phenyl.

In one embodiment, optional substituents on —$R^{2A}$, if present, and optional substituents on —$R^{2B}$, if present, are independently selected from the substituents on —$R^{2A}$ and —$R^{2B}$ shown in the compounds described under the heading "Examples of Specific Embodiments".

In one embodiment, optional substituents on —$R^{2A}$, if present, are independently selected from the substituents on —$R^{2A}$ shown in the compounds described under the heading "Examples of Specific Embodiments".

In one embodiment, optional substituents on —$R^{2B}$, if present, are independently selected from the substituents on —$R^{2A}$ shown in the compounds described under the heading "Examples of Specific Embodiments".

Optional Substituents on $-J^1$, $-J^2$, $-J^3$, and $-J^4$

In one embodiment, each of $-J^1$, $-J^2$, $-J^3$, and $-J^4$ is independently optionally substituted.

In one embodiment, each of $-J^1$, $-J^2$, $-J^3$, and $-J^4$ is independently unsubstituted.

In one embodiment, $-J^1$ is independently unsubstituted.
In one embodiment, $-J^2$ is independently unsubstituted.
In one embodiment, $-J^3$ is independently unsubstituted.
In one embodiment, $-J^4$ is independently unsubstituted.

In one embodiment, optional substituents on each of $-J^1$, $-J^2$, $-J^3$, and $-J^4$, if present, are independently selected from:
substituents on carbon, independently selected from:
—$R^Q$, —$R^R$, —$R^L$—$R^R$,
—F, —Cl, —Br,
—OH, —$R^L$—OH, —O—$R^L$—OH,
—$OR^P$, —$R^L$—$OR^P$, —O—$R^L$—$OR^P$,
—$SR^P$,
—$NH_2$, —$NHR^P$, —$NR^P_2$, —$R^M$,
—$NHC(=O)R^P$, —$NR^QC(=O)R^P$,
—NH—C(=O)$NH_2$, —NH—C(=O)$NHR^P$, —NH—C(=O)$NR^P_2$, —NH—C(=O)$R^M$,
—$NR^Q$—C(=O)$NH_2$, —$NR^Q$—C(=O)$NHR^P$, —$NR^Q$—C(=O)$NR^P_2$, —$NR^Q$—C(=O)$R^M$,
—C(=O)$NH_2$, —C(=O)$NHR^P$, —C(=O)$NR^P_2$, —C(=O)$R^M$,
—C(=O)OH, —C(=O)$OR^P$,
—S(=O)$_2NH_2$, —S(=O)$_2NHR^P$, —S(=O)$_2NR^P_2$, —S(=O)$_2R^M$,
—NHS(=O)$_2R^P$, —$NR^QS(=O)_2R^P$, —NHS(=O)$_2R^M$, —$NR^QS(=O)_2R^M$,
—CN,
—$R^L$—S(=O)$_2NH_2$, —$R^L$—S(=O)$_2NHR^P$, —$R^L$—S(=O)$_2NR^P_2$, —$R^L$—S(=O)$_2R^M$,
—$R^L$—$NH_2$, —$R^L$—$NHR^P$, —$R^L$—$NR^P_2$, —$R^L$—$R^M$,
—$R^L$—$NHC(=O)R^P$, —$R^L$—$NR^QC(=O)R^P$,
—$R^L$—NHS(=O)$_2R^P$, —$R^1$—$NR^QS(=O)_2R^P$,
—$R^L$—NHS(=O)$_2R^M$, —$R^L$—$NR^QS(=O)_2R^M$,
—$R^1$—C(=O)OH, —$R^L$—C(=O)$OR^P$,
—$R^L$—C(=O)$NH_2$, —$R^L$—C(=O)$NHR^P$, —$R^L$—C(=O)$NR^P_2$, and —$R^L$—C(=O)$R^M$,
—$R^L$—NH—C(=O)$NH_2$, —$R^L$—NH—C(=O)$NHR^P$, —$R^L$—NH—C(=O)$NR^P_2$,
—$R^L$—$NR^Q$—C(=O)$NH_2$, —$R^L$—$NR^Q$—C(=O)$NHR^P$, —$R^L$—$NR^Q$—C(=O)$NR^P_2$; and substituents on nitrogen, if present, independently selected from:
—$R^Q$, —$R^R$, —$R^L$—$R^R$,
—C(=O)$OR^P$,
—C(=O)$R^P$,
—C(=O)—$R^L$—OH, —C(=O)—$R^L$—$OR^P$,
—C(=O)$NH_2$, —C(=O)$NHR^P$, —C(=O)$NR^P_2$, —C(=O)$R^M$,
—C(=O)—$R^L$—$NH_2$, —C(=O)—$R^L$—$NHR^P$,
—C(=O)—$R^L$—$NR^P_2$, —C(=O)—$R^L$—$R^M$,
—C(=O)—$R^L$—NHS(=O)$_2R^P$, —C(=O)—$R^L$—$NR^QS(=O)_2R^P$,
—C(=O)—$R^L$—NHS(=O)$_2R^M$, —C(=O)—$R^L$—$NR^QS(=O)_2R^M$,
—C(=O)—$R^L$—S(=O)$_2NH_2$, —C(=O)—$R^L$—S(=O)$_2NHR^P$,
—C(=O)—$R^L$—S(=O)$_2NR^P_2$, —C(=O)—$R^L$—S(=O)$_2R^M$,
—S(=O)$_2NH_2$, —S(=O)$_2NHR^P$, —S(=O)$_2NR^P_2$, —S(=O)$_2R^M$,
—S(=O)$_2R^P$,
—$R^L$—OH, —$R^L$—$OR^P$,
—$R^L$—$NH_2$, —$R^L$—$NHR^P$, —$R^L$—$NR^P_2$, —$R^L$—$R^M$,
—$R^L$—NHS(=O)$_2R^P$, —$R^L$—$NR^QS(=O)_2R^P$,
—$R^L$—S(=O)$_2NH_2$, —$R^L$—S(=O)$_2NHR^P$, —$R^L$—S(=O)$_2NR^P_2$, —$R^L$—S(=O)$_2R^M$, and
—$R^L$—S(=O)$_2R^P$.

In one embodiment, for the optional substituents on $-J^1$, if present, substituents on carbon, if present, are independently selected from:
—$R^Q$, —$R^R$, —$R^L$—$R^R$,
—F,
—OH, —$R^L$—OH,
—$OR^P$, —$R^L$—$OR^P$,
—$NHC(=O)R^P$, —$NR^QC(=O)R^P$,
—C(=O)$NH_2$, —C(=O)$NHR^P$, —C(=O)$NR^P_2$, —C(=O)$R^M$,
—CN,
—$R^L$—S(=O)$_2NH_2$, —$R^L$—S(=O)$_2NHR^P$, —$R^L$—S(=O)$_2NR^P_2$, —$R^L$—S(=O)$_2R^M$,
—$R^L$—$NHC(=O)R^P$, —$R^L$—$NR^QC(=O)R^P$,
—$R^L$—NHS(=O)$_2R^P$, —$R^L$—$NR^QS(=O)_2R^P$, —$R^L$—NHS(=O)$_2R^M$, —$R^1$—$NR^QS(=O)_2R^M$,
—$R^L$—C(=O)OH, —$R^L$—C(=O)$OR^P$,
—$R^L$—C(=O)$NH_2$, —$R^L$—C(=O)$NHR^P$, —$R^L$—C(=O)$NR^P_2$, and —$R^L$—C(=O)$R^M$.

In one embodiment, optional substituents on each of $-J^1$, $-J^2$, $-J^3$, and $-J^4$, if present, are independently selected from:
substituents on carbon, independently selected from:
—F, —OH, —$OR^{X2}$, —$R^{X2}$, —$CH_2C(=O)OR^{X2}$, —$CF_3$, —CN, phenyl, benzyl, thienyl, and pyridyl; and
substituents on nitrogen, if present, independently selected from:
—$R^{X2}$, —$CH_2CF_3$, —S(=O)$_2R^{X2}$ and —C(=O)$R^{X2}$;
wherein:
each —$R^{X2}$ is independently saturated aliphatic $C_{1-4}$alkyl; and wherein:
each phenyl, benzyl, thienyl, and pyridyl is optionally substituted with one or more groups selected from: —F, —Cl, —$R^{X22}$, —OH, and —$OR^{X22}$, wherein each —$R^{X22}$ is independently saturated aliphatic $C_{1-4}$alkyl.

In one embodiment, optional substituents on $-J^1$, if present, are independently selected from:
substituents on carbon, independently selected from:
phenyl, benzyl, thienyl, and pyridyl; and
substituents on nitrogen, if present, independently selected from:
—$R^{X2}$, —$CH_2CF_3$, —S(=O)$_2R^{X2}$ and —C(=O)$R^{X2}$;
wherein:
each phenyl, benzyl, thienyl, and pyridyl is optionally substituted with one or more groups selected from: —F, —Cl, —R$^{X22}$, —OH, and —OR$^{X22}$ wherein each —R$^{X22}$ is independently saturated aliphatic C$_{1-4}$alkyl; and each —R$^{X2}$ is independently saturated aliphatic C$_{1-4}$alkyl.

In one embodiment, optional substituents on if present, are independently selected from:
substituents on carbon, independently selected from:
phenyl; and
substituents on nitrogen, if present, independently selected from:
—R$^{X2}$.
wherein:
each phenyl is optionally substituted with one or more groups selected from: —F, —Cl, —R$^{X22}$, —OH, and —OR$^{X22}$, wherein each —R$^{X22}$ is independently saturated aliphatic C$_{1-4}$alkyl; and
each —R$^{X2}$ is independently saturated aliphatic C$_{1-4}$alkyl.

In one embodiment, optional substituents on each of -J$^1$, -J$^2$, -J$^3$, and -J$^4$, if present, are independently selected from:
substituents on carbon, independently selected from:
—F, —OH, —OR$^{X2}$, —R$^{X2}$, —CF$_3$, —CN, phenyl, and pyridyl; and
substituents on nitrogen, if present, independently selected from:
—R$^{X2}$, —S(=O)$_2$R$^{X2}$ and —C(=O)R$^{X2}$;
wherein each —R$^{X2}$ is independently saturated aliphatic C$_{1-4}$alkyl.

In one embodiment, optional substituents on each of -J$^1$, -J$^2$, -J$^3$, and -J$^4$, if present, are independently selected from:
substituents on carbon, independently selected from:
—F, —OH, —OR$^{X2}$, and —R$^{X2}$; and
substituents on nitrogen, if present, independently selected from:
—R$^{X2}$, —S(=O)$_2$R$^{X2}$ and —C(=O)R$^{X2}$;
wherein each —R$^{X2}$ is independently saturated aliphatic C$_{1-4}$alkyl.

In one embodiment, optional substituents on each of -J$^1$, -J$^2$, -J$^3$, and -J$^4$, if present, are independently selected from:
substituents on carbon, independently selected from:
—F and —R$^{X2}$; and
substituents on nitrogen, if present, independently selected from:
—R$^{X2}$;
wherein each —R$^{X2}$ is independently saturated aliphatic C$_{1-4}$alkyl.

In one embodiment, optional substituents on each of -J$^1$, -J$^2$, -J$^3$, and -J$^4$, if present, are independently selected from: saturated aliphatic C$_{1-4}$alkyl.

In one embodiment, optional substituents on each of 4, -J$^2$, -J$^3$, and -J$^4$, if present, are independently selected from the substitutents on -J$^2$, -J$^3$, and -J$^4$ shown in the compounds described under the heading "Examples of Specific Embodiments".

In one embodiment, optional substituents on -J$^1$, if present, are independently selected from the substitutents on -J$^1$ shown in the compounds described under the heading "Examples of Specific Embodiments".

The Group —R$^P$

In one embodiment, each —R$^P$ is independently —R$^Q$, —R$^R$, or —R$^L$—R$^R$.
In one embodiment, each —R$^P$ is independently —R$^Q$.
In one embodiment, each —R$^P$ is independently —R$^R$ or —R$^L$—R$^R$.
In one embodiment, each —R$^P$ is independently —R$^R$.

The Group —R$^Q$

In one embodiment, each —R$^Q$ is independently saturated aliphatic C$_{1-4}$alkyl, and is optionally substituted, for example, with one or more fluorine atoms.
In one embodiment, each —R$^Q$ is independently saturated aliphatic C$_{1-4}$alkyl.

The Group —R$^R$

In one embodiment, each —R$^R$ is independently phenyl or C$_{5-6}$heteroaryl (e.g., furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, or pyridazinyl), and is optionally substituted, for example, with one or more substitutents independently selected from:
—F, —Cl, —Br,
—R$^{K1}$, —CF$_3$,
—OH, —OR$^{K1}$, —OCF$_3$,
—NH$_2$, —NHR$^{K1}$, —NR$^{K1}$$_2$,
—NHC(=O)R$^M$, —NR$^{K1}$C(=O)R$^{K1}$,
—C(=O)OH, —C(=O)OR$^{K1}$,
—C(=O)NH$_2$, —C(=O)NHR$^{K1}$, —C(=O)NR$^{K1}$$_2$,
—NO$_2$, and
—CN;
wherein each —R$^{K1}$ is independently saturated aliphatic C$_{1-4}$alkyl.

The Group —R$^L$—

In one embodiment, each —R$^L$— is independently saturated aliphatic C$_{1-4}$alkylene.
In one embodiment, each —R$^L$— is independently saturated aliphatic C$_{1-3}$alkylene.
In one embodiment, each —R$^L$— is independently —CH$_2$—, —CH$_2$CH$_2$—, —CH$_2$CH$_2$CH$_2$— or —CH$_2$CH$_2$CH$_2$CH$_2$—.
In one embodiment, each —R$^L$— is independently —CH$_2$— or —CH$_2$CH$_2$—.
In one embodiment, each —R$^L$— is independently —CH$_2$—.

The Group —R$^M$

In one embodiment, each —R$^M$ is independently azetidino, pyrrolidino, piperidino, piperazino, morpholino, azepino, or diazepino, and is optionally substituted, for example, on carbon, with one or more substitutents independently selected from:
—F, —R$^{K2}$, —OH, —OR$^{K2}$, —OCF$_3$, and —CN; and
on nitrogen, if present, with one or more substitutents independently selected from:
—C(=O)R$^{K2}$, —R$^{K2}$, —C(=O)Ph, —S(=O)$_2$R$^{K2}$, —S(=O)$_2$Ph, —S(=O)$_2$NH$_2$,
—S(=O)$_2$NHR$^{K2}$, —S(=O)$_2$NR$^{K2}$$_2$, and —S(=O)$_2$NHPh;
wherein each —R$^{K2}$ is independently saturated aliphatic C$_{1-4}$alkyl.

Molecular Weight

In one embodiment, the AMTP compound has a molecular weight of from 232 to 1200.
In one embodiment, the bottom of range is from 235, 240, 250, 275, 300, or 350.
In one embodiment, the top of range is 1100, 1000, 900, 800, 700, or 600.
In one embodiment, the range is 240 to 600.

Combinations

Each and every compatible combination of the embodiments described above is explicitly disclosed herein, as if each and every combination was individually and explicitly recited.

Examples of Specific Embodiments

In one embodiment, the compounds are selected from compounds of the following formulae and pharmaceutically acceptable salts, hydrates, and solvates thereof:

| Code No. | Synthesis | Structure |
|---|---|---|
| AA-01 | 14 | 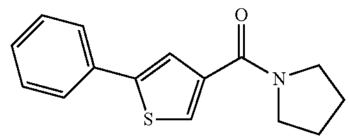 |
| AA-02 | 16 | 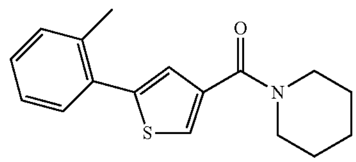 |
| AA-03 | 16 | 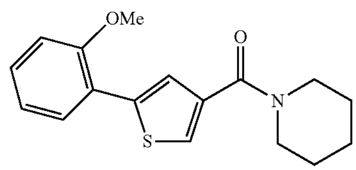 |
| AA-04 | 16 | 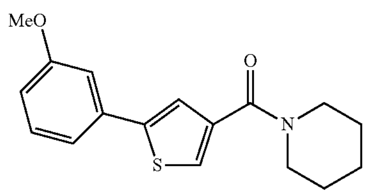 |
| AA-05 | 16 | 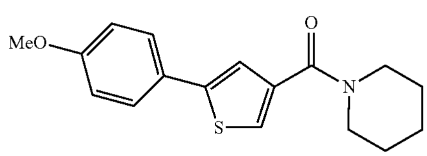 |
| AA-06 | 16 | 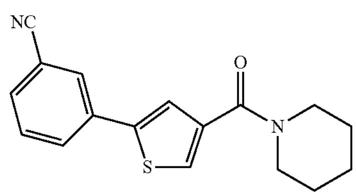 |
| AA-07 | 16 | 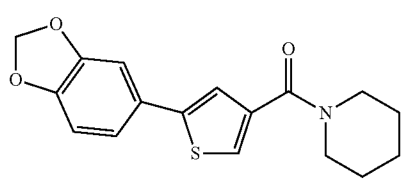 |
| AA-08 | 16 | 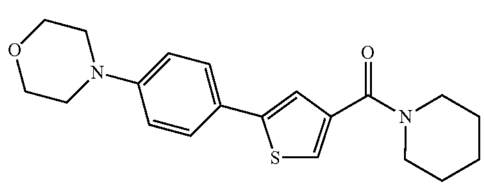 |

-continued

| Code No. | Synthesis | Structure |
|---|---|---|
| AA-09 | 16 | 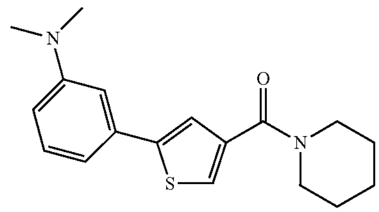 |
| AA-10 | 16 | 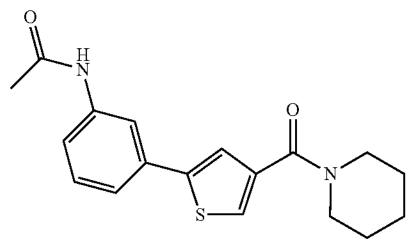 |
| AA-11 | 17 | 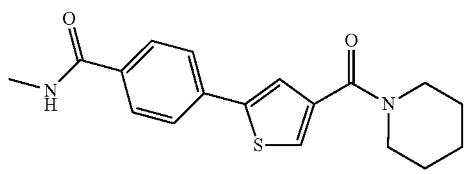 |
| AA-12 | 16 | 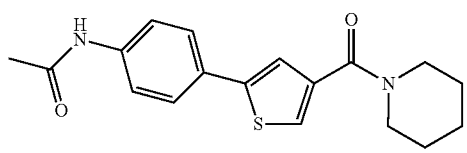 |
| AA-13 | 16 | 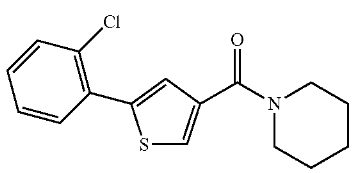 |
| AA-14 | 13 | 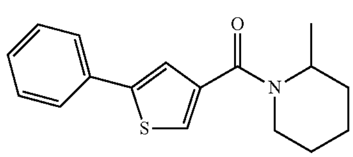 |
| AA-15 | 12 | 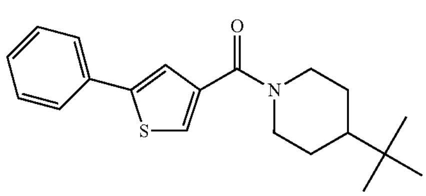 |
| AA-16 | 13 | 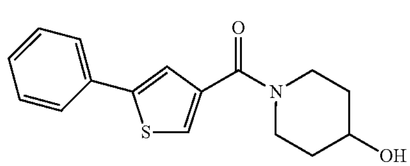 |

-continued
| Code No. | Synthesis | Structure |
|---|---|---|
| AA-17 | 13 | 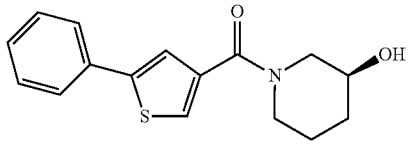 |
| AA-18 | 13 | 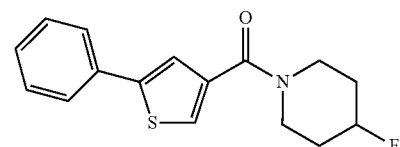 |
| AA-19 | 12 | 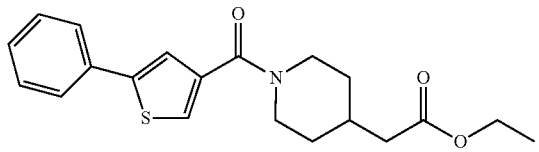 |
| AA-20 | 14 | 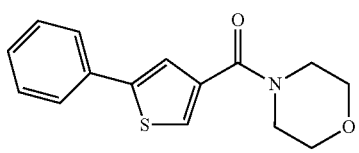 |
| AA-21 | 14 | 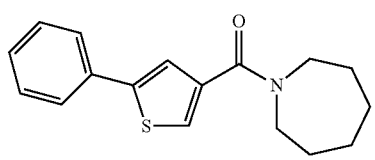 |
| AA-22 | 16 | 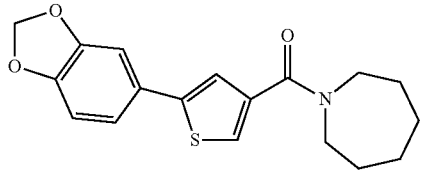 |
| AA-23 | 16 | 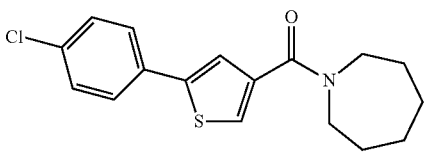 |
| AA-24 | 16 | 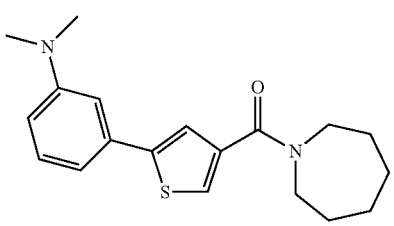 |
| AA-25 | 13 | 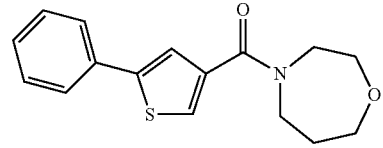 |

-continued
| Code No. | Synthesis | Structure |
|---|---|---|
| AA-26 | 75 | 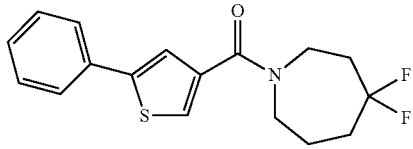 |
| AA-27 | 12 | 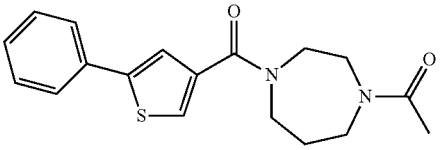 |
| AA-28 | 9 | 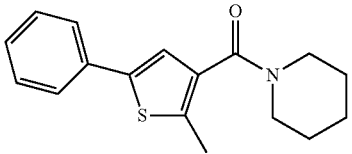 |
| AA-29 | 9 | 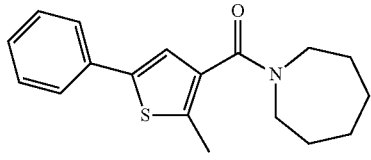 |
| AA-30 | 4 | 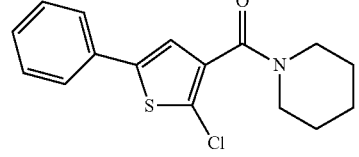 |
| AA-31 | 19 | 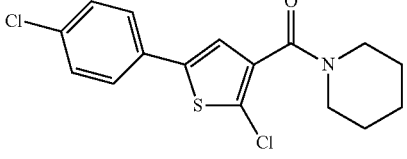 |
| AA-32 | 19 | 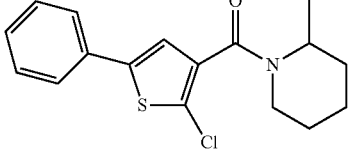 |
| AA-33 | 19 | 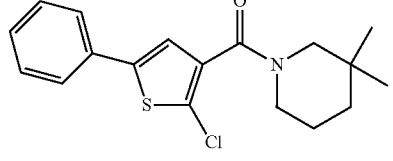 |
| AA-34 | 5 | 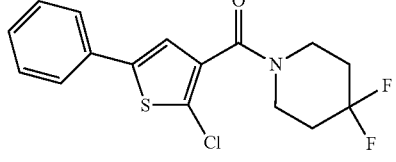 |

-continued
| Code No. | Synthesis | Structure |
|---|---|---|
| AA-35 | 5 | 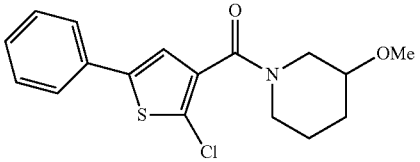 |
| AA-36 | 5 | 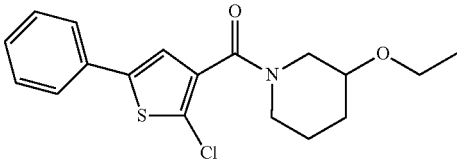 |
| AA-37 | 19 | 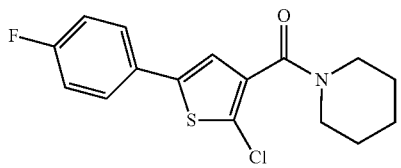 |
| AA-38 | 4 | 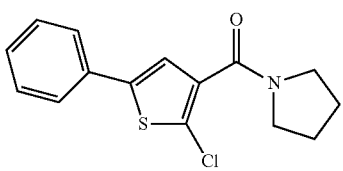 |
| AA-39 | 4 | 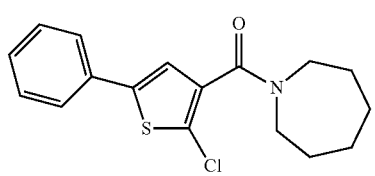 |
| AA-40 | 19 | 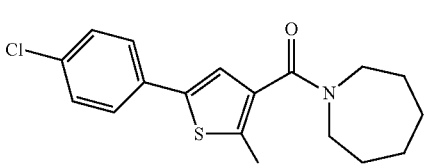 |
| AA-41 | 19 | 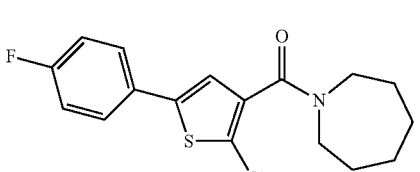 |
| AA-42 | 5 | 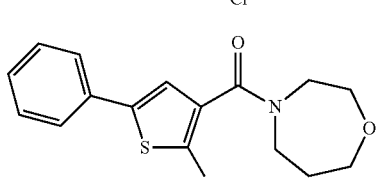 |
| AA-43 | 76 | 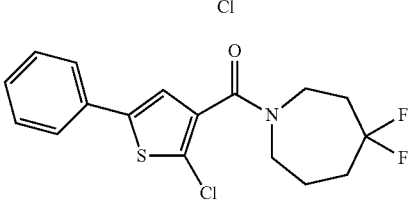 |

-continued
| Code No. | Synthesis | Structure |
|---|---|---|
| AA-44 | 5 | 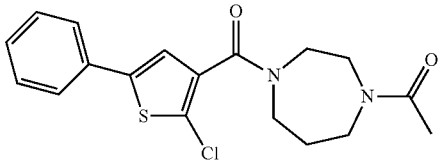 |
| AA-45 | 5 | 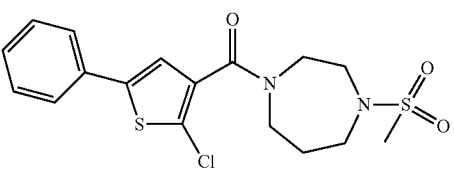 |
| AA-46 | 5 | 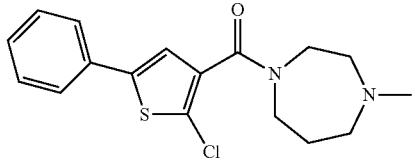 |
| AA-47 | 8 | 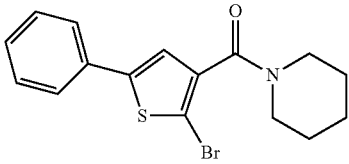 |
| AA-48 | 8 | 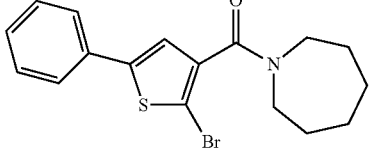 |
| AA-49 | 19 | 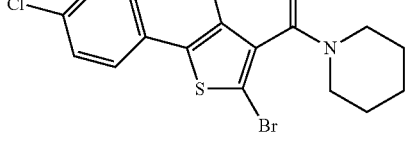 |
| AA-50 | 19 | 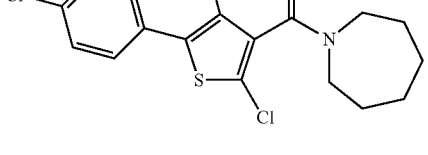 |
| AA-51 | 10 | 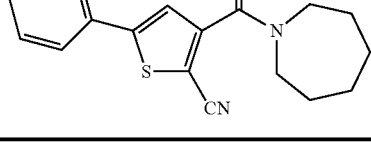 |

In one embodiment, the compounds are selected from compounds of the following formulae and pharmaceutically acceptable salts, hydrates, and solvates thereof:

| Code No. | Synthesis | Structure |
|---|---|---|
| BB-01 | 12 | 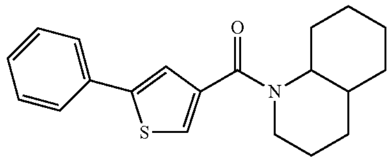 |
| BB-02 | 66 | CIS ISOMERS |
| BB-03 | 66 | CIS ISOMERS |
| BB-04 | 19 | 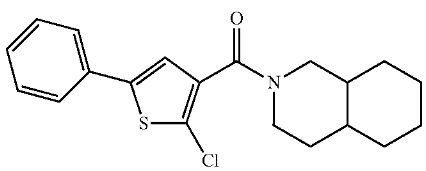 |
| BB-05 | 5 | 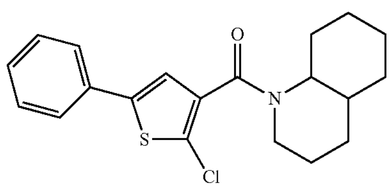 |
| BB-06 | 5 | 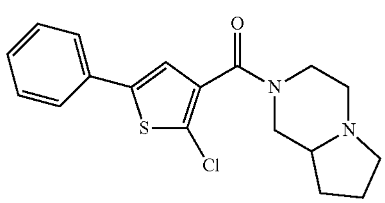 |
| BB-07 | 5 | 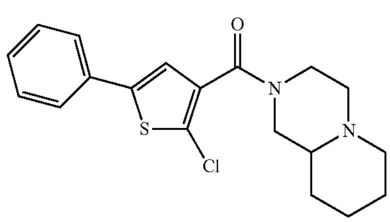 |

In one embodiment, the compounds are selected from compounds of the following formulae and pharmaceutically acceptable salts, hydrates, and solvates thereof:

| Code No. | Synthesis | Structure |
|---|---|---|
| CC-01 | 13 | 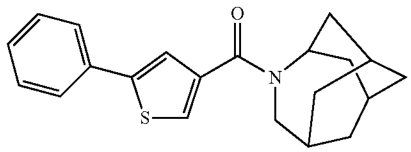 |
| CC-02 | 19 | 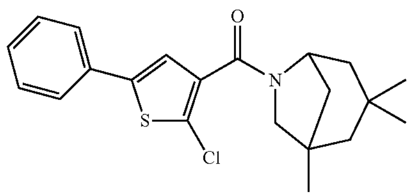 |

In one embodiment, the compounds are selected from compounds of the following formulae and pharmaceutically acceptable salts, hydrates, and solvates thereof:

| Code No. | Synthesis | Structure |
|---|---|---|
| DD-01 | 5 | 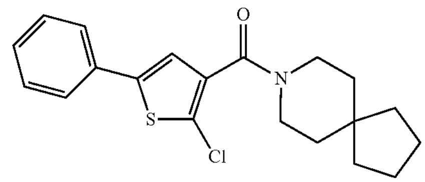 |

In one embodiment, the compounds are selected from compounds of the following formulae and pharmaceutically acceptable salts, hydrates, and solvates thereof:

| Code No. | Synthesis | Structure |
|---|---|---|
| EE-01 | 18 | 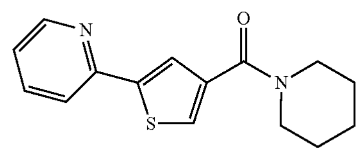 |
| EE-02 | 16 | 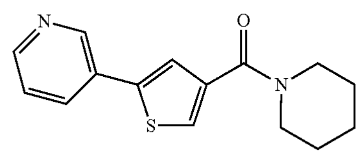 |
| EE-03 | 16 | 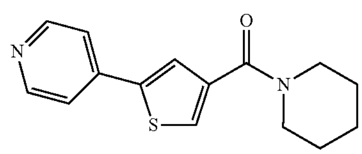 |
| EE-04 | 16 | 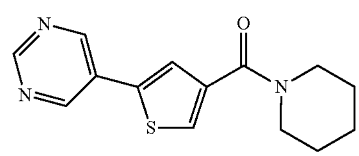 |
| EE-05 | 16 | 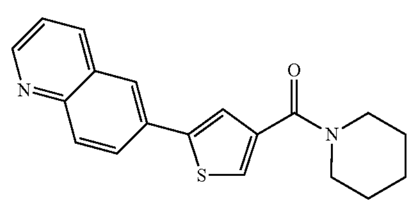 |
| EE-06 | 25 | 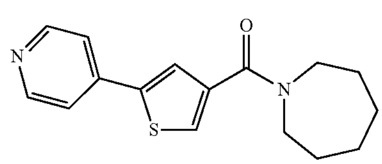 |

-continued

| Code No. | Synthesis | Structure |
|---|---|---|
| EE-07 | 25 | 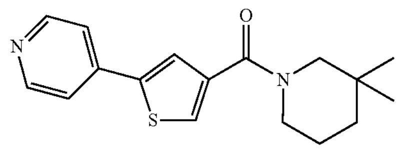 |
| EE-08 | 16 | 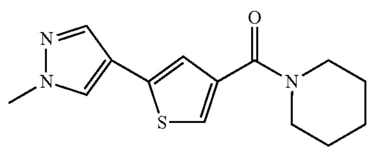 |
| EE-09 | 19 | 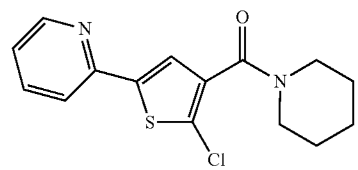 |
| EE-10 | 19 | 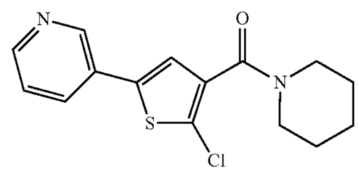 |
| EE-11 | 19 | 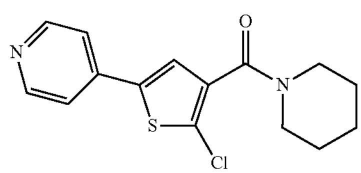 |
| EE-12 | 19 | 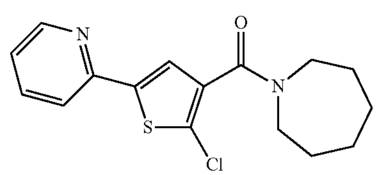 |
| EE-13 | 19 | 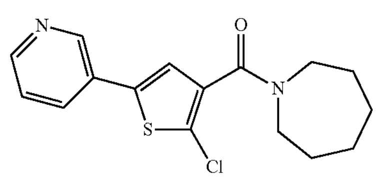 |
| EE-14 | 19 | 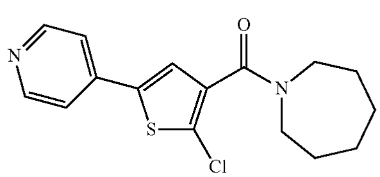 |
| EE-15 | 19 | 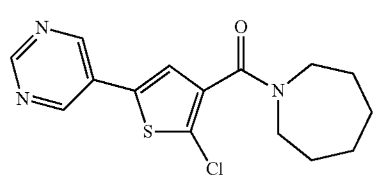 |

-continued

| Code No. | Synthesis | Structure |
|---|---|---|
| EE-16 | 26 | 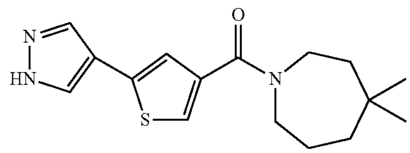 |
| EE-17 | 59 | 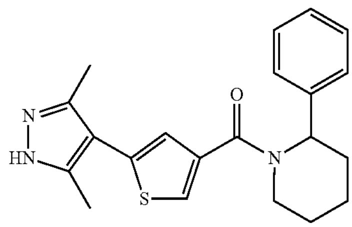 |
| EE-18 | 60 | 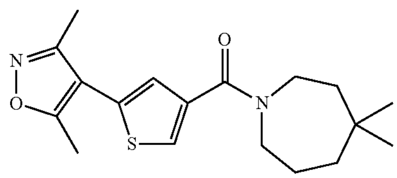 |
| EE-19 | 59 | 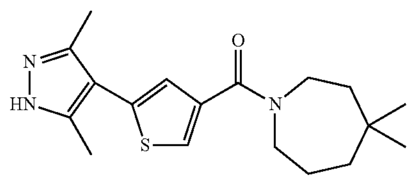 |
| EE-20 | 60 | 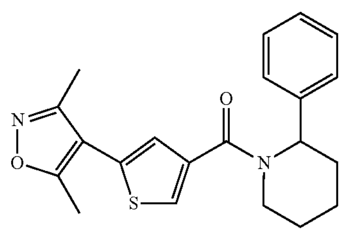 |
| EE-21 | 27 | 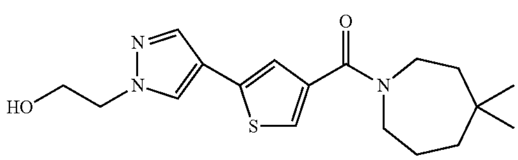 |
| EE-22 | 29 | 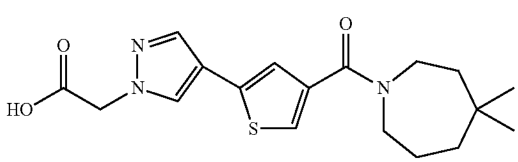 |
| EE-23 | 31 | 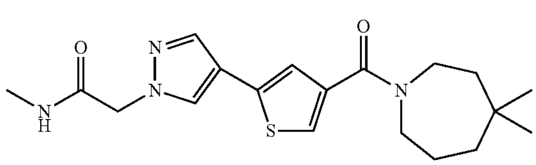 |

-continued

| Code No. | Synthesis | Structure |
|---|---|---|
| EE-24 | 33 | 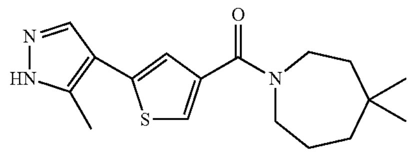 |
| EE-25 | 46 | 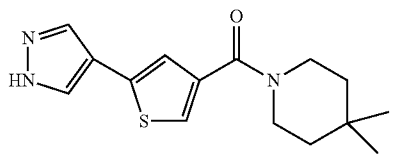 |
| EE-26 | 46 | 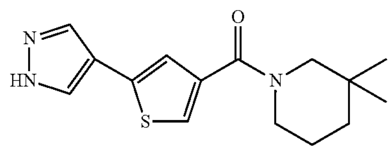 |
| EE-27 | 46 | 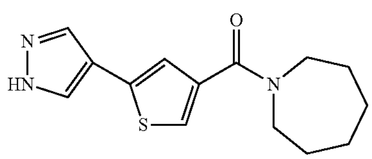 |
| EE-28 | 49 | 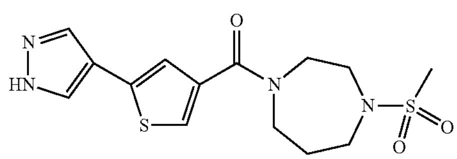 |
| EE-29 | 46 | 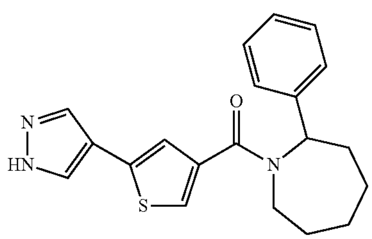 |
| EE-30 | 46 | 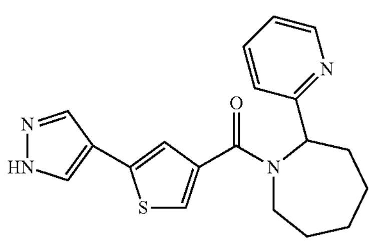 |
| EE-31 | 46 | 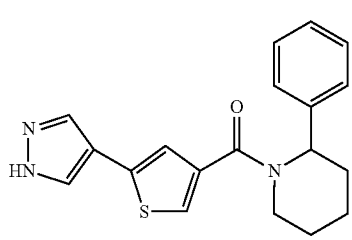 |

-continued
| Code No. | Synthesis | Structure |
|---|---|---|
| EE-32 | 46 | 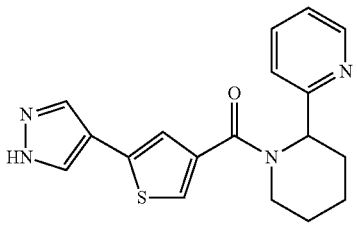 |
| EE-33 | 46 | 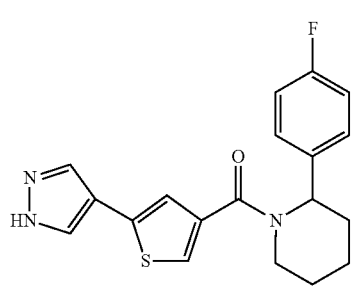 |
| EE-34 | 46 | 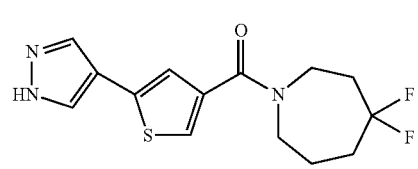 |
| EE-35 | 46 | 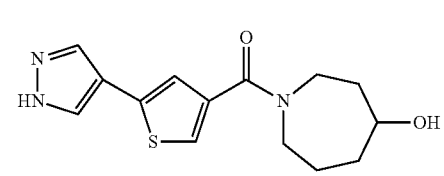 |
| EE-36 | 46 | 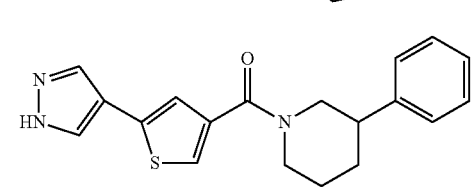 |
| EE-37 | 46 | 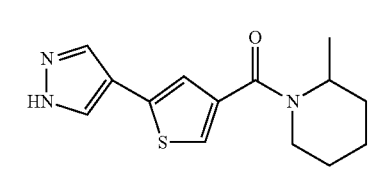 |
| EE-38 | 46 | 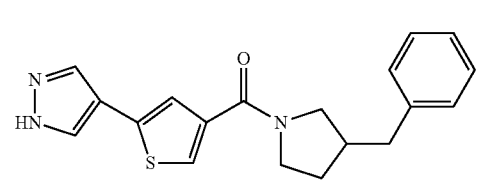 |
| EE-39 | 46 | 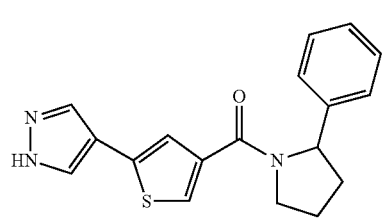 |

-continued
| Code No. | Synthesis | Structure |
|---|---|---|
| EE-40 | 46 | 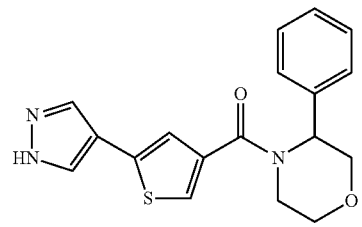 |
| EE-41 | 46 | 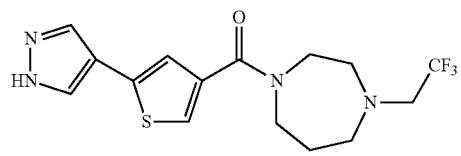 |
| EE-42 | 46 | 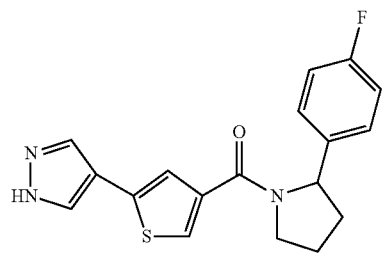 |
| EE-43 | 46 | 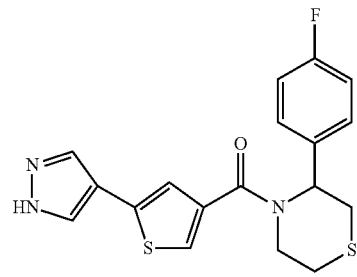 |
| EE-44 | 71 | 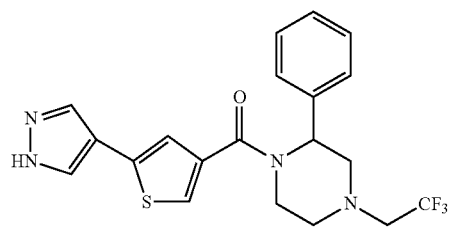 |
| EE-45 | 72 | 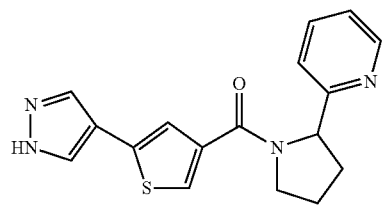 |

-continued
| Code No. | Synthesis | Structure |
|---|---|---|
| EE-46 | 46 | 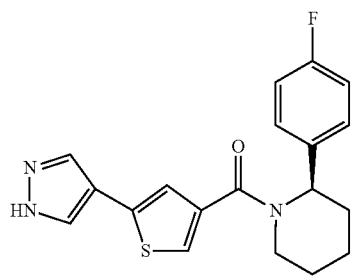<br>from S-phenyglycinol |
| EE-47 | 46 | 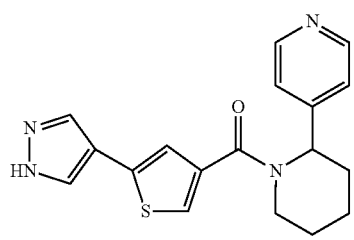 |
| EE-48 | 46 | 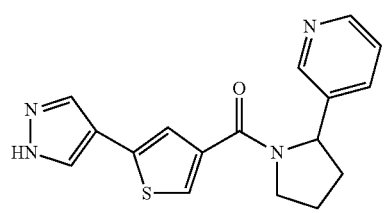 |
| EE-49 | 46 | 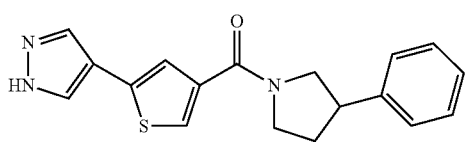 |
| EE-50 | 46 | 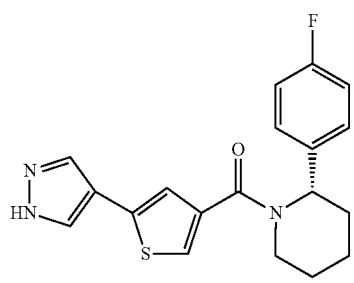<br>from R-phenylglycinol |
| EE-51 | 46 | 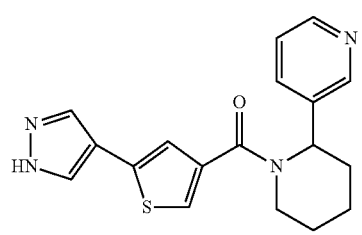 |

-continued

| Code No. | Synthesis | Structure |
|---|---|---|
| EE-52 | 46 | 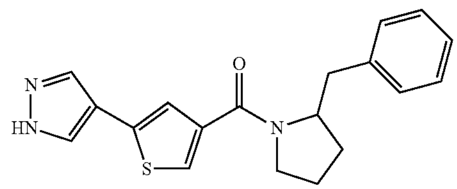 |
| EE-53 | 46 | 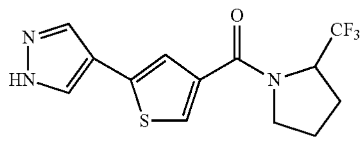 |
| EE-54 | 46 | 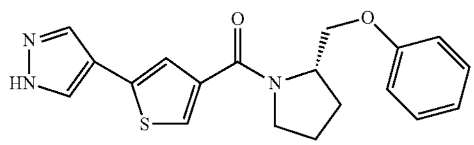 |
| EE-55 | 46 | 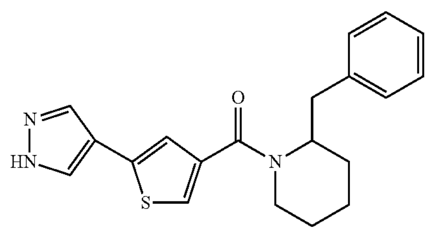 |
| EE-56 | 46 | 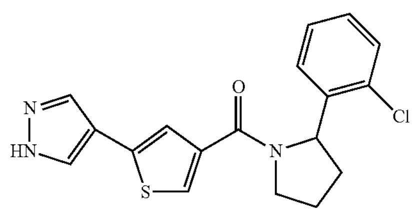 |
| EE-57 | 46 | 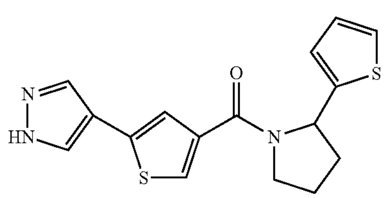 |
| EE-58 | 46 | 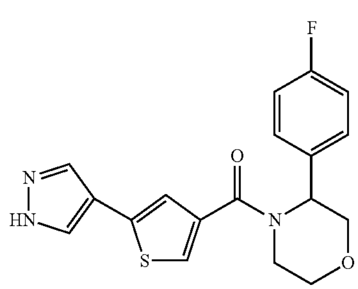 |

-continued
| Code No. | Synthesis | Structure |
|---|---|---|
| EE-59 | 46 | 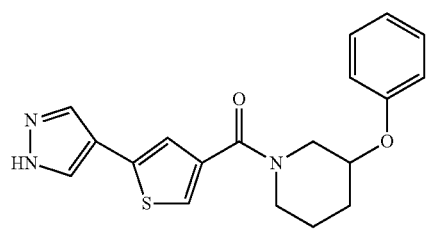 |
| EE-60 | 46 | 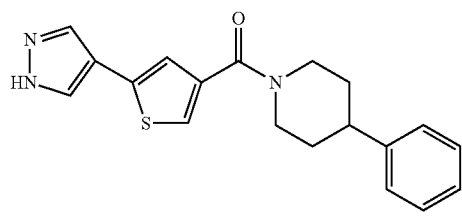 |
| EE-61 | 78 | 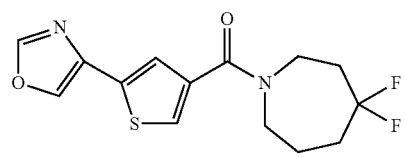 |
| EE-62 | 78 | 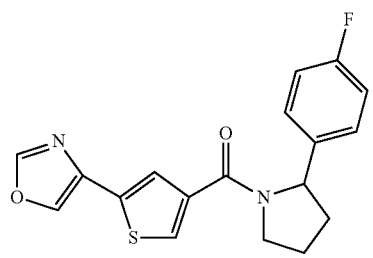 |
| EE-63 | 78 | 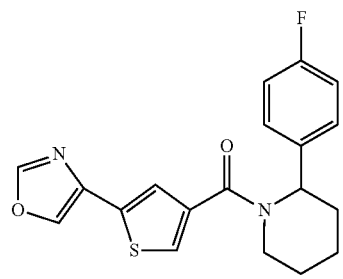 |
| EE-64 | 46 | 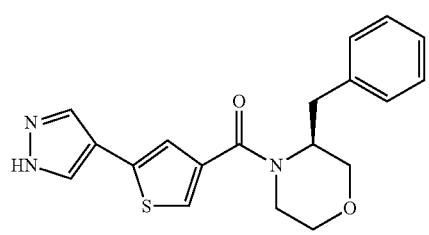 |

In one embodiment, the compounds are selected from compounds of the following formulae and pharmaceutically acceptable salts, hydrates, and solvates thereof:
| Code No. | Synthesis | Structure |
|---|---|---|
| FF-01 | 25 | 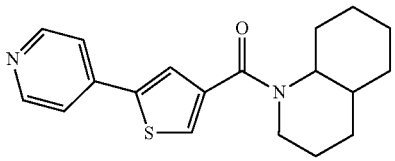<br>CIS ISOMERS |
| FF-02 | 63 | 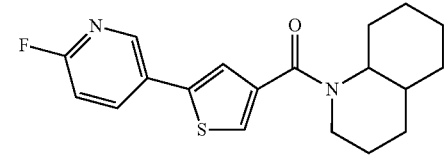<br>CIS ISOMERS |
| FF-03 | 65 | 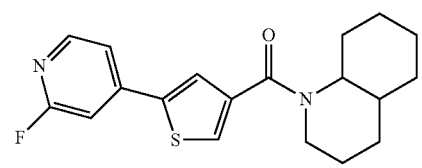<br>CIS ISOMERS |
| FF-04 | 66 | 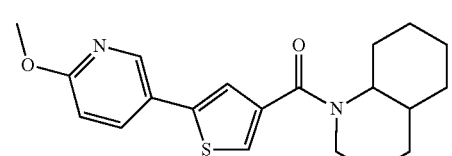<br>CIS ISOMERS |
| FF-05 | 66 | 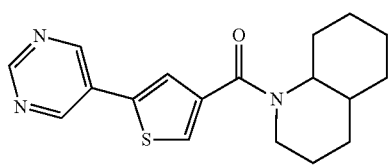<br>CIS ISOMERS |
| FF-06 | 21 | 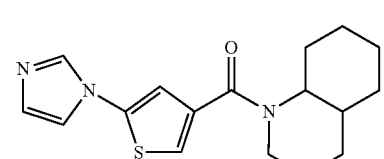<br>CIS ISOMERS |
| FF-07 | 61 | 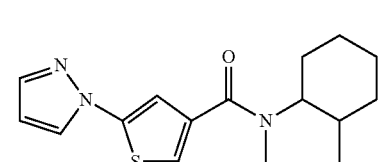<br>CIS ISOMERS |

-continued
| Code No. | Synthesis | Structure |
|---|---|---|
| FF-08 | 66 | 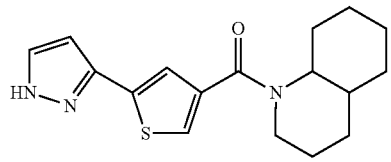<br>CIS ISOMERS |
| FF-09 | 22 | 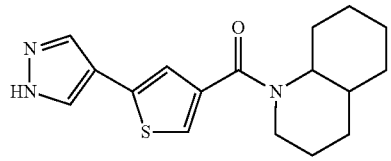<br>CIS ISOMERS |
| FF-10 | 66 | 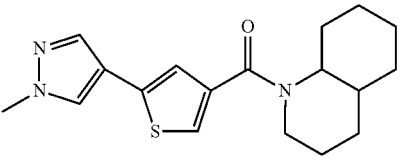<br>CIS ISOMERS |
| FF-11 | 59 | 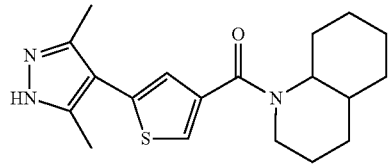<br>CIS ISOMERS |
| FF-12 | 60 | 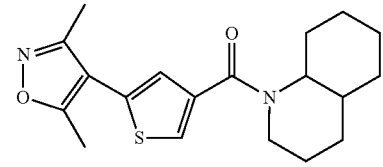<br>CIS ISOMERS |
| FF-13 | 28 | 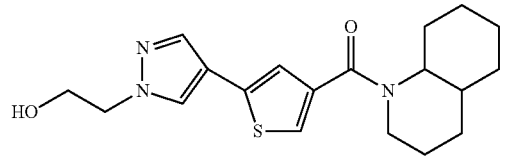<br>CIS ISOMERS |
| FF-14 | 30 | 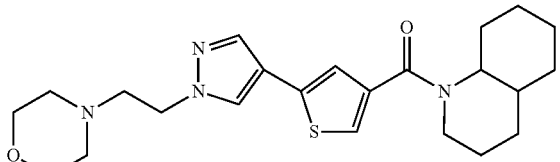<br>CIS ISOMERS |

| Code No. | Synthesis | Structure |
|---|---|---|
| FF-15 | 32 | 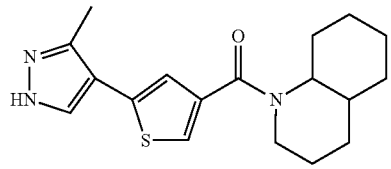<br>CIS ISOMERS |
| FF-16 | 46 | 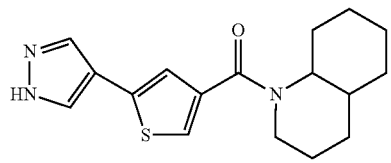<br>DHQ [CIS-S] |
| FF-17 | 46 | 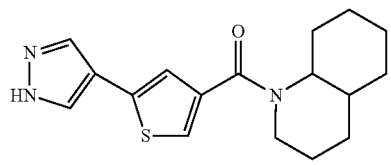<br>DHQ [CIS-R] |
| FF-18 | 35 | 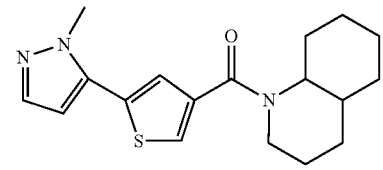<br>DHQ [CIS-S] |
| FF-19 | 37 | 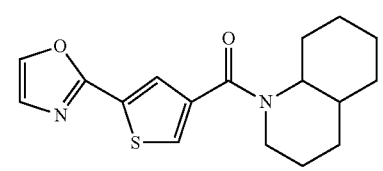<br>DHQ [CIS-S] |
| FF-20 | 39 | 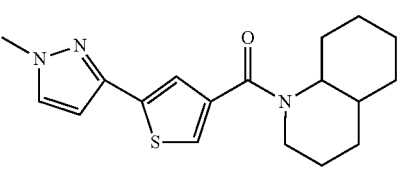<br>DHQ [CIS-S] |
| FF-21 | 41 | 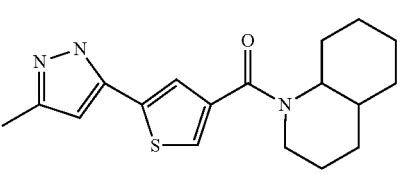<br>DHQ [CIS-S] |

-continued

| Code No. | Synthesis | Structure |
|---|---|---|
| FF-22 | 43 | DHQ [CIS-S] |
| FF-23 | 44 | DHQ [CIS-S] |
| FF-24 | 50 | CIS ISOMERS |
| FF-25 | 52 | CIS ISOMERS |
| FF-26 | 53 | CIS ISOMERS |
| FF-27 | 54 | 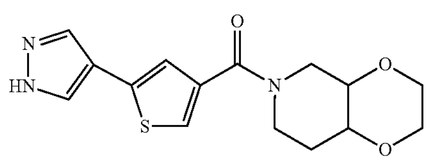 |
| FF-28 | 46 | FORMATE SALT |
| FF-29 | 56 | 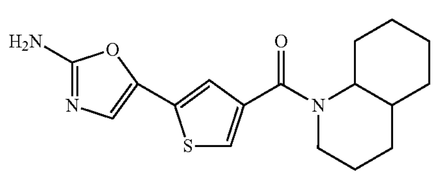 |

| Code No. | Synthesis | Structure |
|---|---|---|
| FF-30 | 46 | 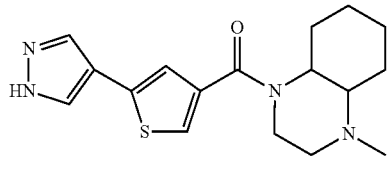 |
| | | CIS ISOMERS |

In one embodiment, the compounds are selected from compounds of the following formulae and pharmaceutically acceptable salts, hydrates, and solvates thereof:

| Code No. | Synthesis | Structure |
|---|---|---|
| GG-01 | 25 | 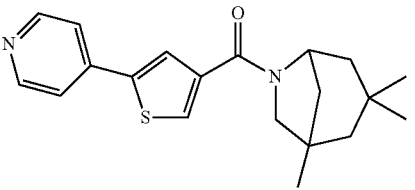 |
| GG-02 | 58 | 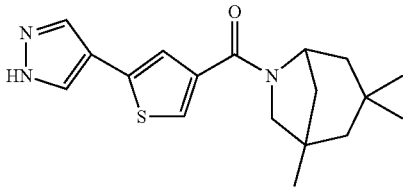 |
| GG-03 | 60 | 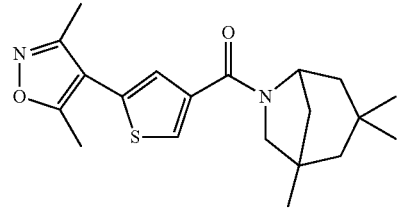 |
| GG-04 | 59 | 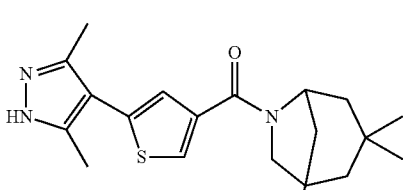 |

Substantially Purified Forms

One aspect of the present invention pertains to AMTP compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

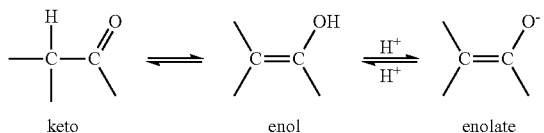

keto          enol          enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of AMTP compounds of the present invention are described herein. These and/or other well known methods may be modified and/or adapted in known ways in order to facilitate the synthesis of additional compounds within the scope of the present invention.

Compositions

One aspect of the present invention pertains to a composition (e.g., a pharmaceutical composition) comprising an AMTP compound, as described herein, and a pharmaceutically acceptable carrier, diluent, or excipient.

Another aspect of the present invention pertains to a method of preparing a composition (e.g., a pharmaceutical composition) comprising admixing an AMTP compound, as described herein, and a pharmaceutically acceptable carrier, diluent, or excipient.

Uses

The AMTP compounds, as described herein, are useful, for example, in the treatment of disorders (e.g., diseases) that are ameliorated by the inhibition of 11β-hydroxysteroid dehydrogenase type 1 (11β-HSD1), as described herein.

Use in Methods of Inhibiting 11β-Hydroxysteroid Dehydrogenase Type 1 (11β-HSD1)

One aspect of the present invention pertains to a method of inhibiting 11β-hydroxysteroid dehydrogenase type 1 in a cell, in vitro or in vivo, comprising contacting the cell with an effective amount of an AMTP compound, as described herein.

Suitable assays for determining 11β-hydroxysteroid dehydrogenase type 1 inhibition are described herein and/or are known in the art.

In one embodiment, the method is performed in vitro.
In one embodiment, the method is performed in vivo.
In one embodiment, the AMTP compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound inhibits 11β-hydroxysteroid dehydrogenase type 1. For example, suitable assays are described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an AMTP compound, as described herein, for use in a method of treatment of the human or animal body by therapy.

Use in the Manufacture of Medicaments

Another aspect of the present invention pertains to use of an AMTP compound, as described herein, in the manufacture of a medicament for use in treatment.

In one embodiment, the medicament comprises the AMTP compound.

Methods of Treatment

Another aspect of the present invention pertains to a method of treatment comprising administering to a patient in need of treatment a therapeutically effective amount of an AMTP compound, as described herein, preferably in the form of a pharmaceutical composition.

Disorders Treated—Disorders Ameliorated by the Inhibition of 11β-Hydroxysteroid Dehydrogenase Type 1

In one embodiment (e.g., of use in methods of therapy, of use in the manufacture of medicaments, of methods of treatment), the treatment is treatment or prevention of a disorder (e.g., a disease) that is ameliorated by the inhibition of 11β-hydroxysteroid dehydrogenase type 1.

Disorders Treated—Disorders Characterised by Up-Regulation of 11β-HSD1 etc.

In one embodiment (e.g., of use in methods of therapy, of use in the manufacture of medicaments, of methods of treatment), the treatment is treatment or prevention of a disorder (e.g., a disease) that is characterised by one or more of: up-regulation of 11β-HSD1; up-regulation of glucocorticoid receptor mediated pathways; elevated PEPCK levels; other biochemical markers pertaining to glucocorticoid excess and insulin resistance.

Disorders Treated

In one embodiment (e.g., of use in methods of therapy, of use in the manufacture of medicaments, of methods of treatment), the treatment is treatment or prevention of one or more of the following:
(1) Cushing's syndrome;
(2) type 2 diabetes and impaired glucose tolerance;
(3) insulin resistance syndromes such as myotonic dystrophy, Prader Willi, lipodystrophies, gastrointestinal diabetes, etc.;
(4) obesity and being overweight;
(5) lipid disorders;
(6) atherosclerosis and its sequelae, including myocardial infarction and peripheral vascular disease;
(7) Metabolic Syndrome;
(8) steatohepatitis/fatty liver;
(9) cognitive impairment in type 2 diabetes, glucose intolerance and ageing, and in psychotic disorders and pre-schizophrenia;
(10) dementias such as Alheimer's disease, multi-infarct dementia, dementia with Lewy bodies, fronto-temporal dementia (including Pick's disease), progressive supranuclear palsy, Korsakoffs syndrome, Binswanger's disease, HIV-associated dementia, Creutzfeldt-Jakob disease (CJD), multiple sclerosis, motor neurone disease, Parkinson's disease, Huntington's disease, Niemann-Pick disease type C, normal pressure hydrocephalus, and Down's syndrome;
(11) mild cognitive impairment (cognitive impairment, no dementia);
(12) β-cell dysfunction in pancreatic disease;
(13) glaucoma;
(14) anxiety;
(15) depression and other affective disorders; typical (melancholic) and atypical depression; dysthymia; post-partum depression; bipolar affective disorder; drug-induced affective disorders; anxiety; posttraumatic stress disorder; panic; phobias;
(16) delirium and acute confusional state;
(17) inflammatory disease;
(18) osteoporosis;
(19) myocardial infarction, for example, to prevent left ventricular dysfunction after myocardial infarction; and
(20) stroke, for example, to limit ischaemic neuronal loss after cardiovascular accident.

In one embodiment (e.g., of use in methods of therapy, of use in the manufacture of medicaments, of methods of treatment), the treatment is treatment or prevention of one or more of the following:
(1) hyperglycaemia;
(2) glucose intolerance and impaired glucose tolerance;
(3) insulin resistance;
(4) hyperlipidaemia;
(5) hypertriglyceridaemia;
(6) hypercholesterolaemia;
(7) low HDL levels;
(8) high LDL levels;
(9) vascular restenosis;
(10) abdominal obesity;
(11) neurodegenerative disease;
(12) retinopathy;
(13) neuropathy; and
(14) hypertension; and
(15) other diseases where insulin resistance is a component.

In one embodiment (e.g., of use in methods of therapy, of use in the manufacture of medicaments, of methods of treatment), the treatment is treatment or prevention of an adverse effect of glucocorticoids used to treat inflammatory diseases, such as asthma, chronic obstructive pulmonary disease, skin diseases, rheumatoid arthritis and other arthropathies, inflammatory bowel disease, and giant cell arthritis/polymyalgia rheumatica.

In one embodiment (e.g., of use in methods of therapy, of use in the manufacture of medicaments, of methods of treatment), the treatment is treatment or prevention of metabolic syndrome, which includes disorders such as type 2 diabetes and obesity, and associated disorders including insulin resistance, hypertension, lipid disorders and cardiovascular disorders such as ischaemic (coronary) heart disease.

In one embodiment (e.g., of use in methods of therapy, of use in the manufacture of medicaments, of methods of treatment), the treatment is treatment or prevention of a CNS disorder (e.g., a CNS disease) such as mild cognitive impairment and early dementia, including Alzheimer's disease.

Treatment

The term "treatment," as used herein in the context of treating a disorder, pertains generally to treatment and therapy, whether of a human or an animal (e.g., in veterinary applications), in which some desired therapeutic effect is achieved, for example, the inhibition of the progress of the disorder, and includes a reduction in the rate of progress, a halt in the rate of progress, alleviatiation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of metabolic syndrome, reducing the incidence of metabolic syndrome, alleviating the symptoms of metabolic syndrome, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the AMTP compounds described herein include the following:

(1) insulin and insulin analogues;
(2) insulin sensitising agents, for example: PPAR-γ agonists; PPAR-α agonists; PPAR-α/γ dual agonists; biguanides;
(3) incretin and incretin mimetics;
(4) sulfonylureas and other insulin secretogogues;
(5) α-glucosidase inhibitors;
(6) glucagon receptor antagonists;
(7) GLP-1, GLP-1 analogues, and GLP-receptor agonists;
(8) GIP, GIP mimetics, and GIP receptor agonists;
(9) PACAP, PACAP mimetics, and PACAP receptor δ agonists;
(10) agents that suppress hepatic glucose output, such as metformin;
(11) agents designed to reduce the absorption of glucose from the intestine, such as acarbose;
(12) phosphotyrosine phosphatase 1B inhibitors;
(13) glucose 6-phosphatase inhibitors;
(14) glucokinase activators;
(15) glycogen phosphorylase inhibitors;
(16) fructose 1,6-biphosphatase inhibitors;
(17) glutamine:fructose-6-phosphate amidotransferase inhibitors;
(18) anti-obesity agents, including: orilistat, sibutramine, fenfluramine, phentermine, dexfenfluramine, cannabinoid CB1 receptor antagonists or inverse agonists such as rimonobant, ghrelin antagonists, oxyntomodulin, neuropeptide Y1 or Y5 antagonists, 5-$HT_{1B}$ receptor agonists, 5-$HT_{2C}$ receptor agonists, 5-$HT_{1B/2C}$ receptor dual agonists, melanocortin receptor agonists, and melanin-concentrating hormone receptor antagonists;
(19) anti-dyslipidaemia agents, including: HMG-CoA reductase inhibitors, PPAR-α agonists, PPAR-α/γ dual agonists, bile acid sequestrants, ileal bile acid absorption inhibitors, acyl CoA:cholesterol acyltransferase inhibitors, cholesterol absorption inhibitors, cholesterol ester transfer protein inhibitors, nicotinyl alcohol and its analogues, and anti-oxidants;
(20) anti-inflammatory agents, including: non-steroidal anti-inflammatory drugs such as aspirin; and steroidal anti-inflammatory agents such as hydrocortisone and dexamethasone;
(21) anti-hypertensive agents, including: β-blockers such as atenolol and inderal; calcium antagonists such as nifedipine; ACE inhibitors such as lisinopril, aptopril and captopril; angiotensin receptor antagonists such as candesartan, losartan and cilexetil; diuretic agents such as furosemide and benzthiazide; α-antagonists; centrally acting agents such as clonidine, methyl dopa, and indapamide; and vasodilators such as hydralazine;
(22) dipeptidyl peptidase IV (DPP-IV) inhibitors such as sitagliptin and saxagliptin;
(23) acetylcholinesterase inhibitors, including: donezepil hydrochloride, rivastigmine and galanthamine;
(24) NMDA receptor blockers, including memantine hydrochloride;
(25) Histamine H3 antagonists;
(26) 5-$HT_6$ receptor antagonists;
(27) α7 receptor agonists; and
(28) γ-secretase modulators, including tarenflurbil.

Other Uses

The AMTP compounds described herein may also be used as cell culture additives to inhibit 11β-hydroxysteroid dehydrogenase type 1 (11β-HSD1), etc.

The AMTP compounds described herein may also be used as part of an in vitro assay, for example, in order to determine whether a candidate host is likely to benefit from treatment with the compound in question.

The AMTP compounds described herein may also be used as a standard, for example, in an assay, in order to identify other active compounds, other 11β-hydroxysteroid dehydrogenase type 1 (11β-HSD1) inhibitors, etc.

Kits

One aspect of the invention pertains to a kit comprising (a) an AMTP compound as described herein, or a composition comprising an AMTP compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The AMTP compound or pharmaceutical composition comprising the AMTP compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the AMTP compound to be administered alone, it is preferable to present it as a pharmaceutical formulation (e.g., composition, preparation, medicament) comprising at least one AMTP compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one AMTP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the AMTP compounds, and compositions comprising the AMTP compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular AMTP compound, the route of administration, the time of administration, the rate of excretion of the AMTP compound, the duration of the treatment, other drugs, compounds, and/or materials used in combination, the severity of the disorder, and the species, sex, age, weight, condition, general health, and prior medical history of the patient. The amount of AMTP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the AMTP compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Analytical Method 1:

The system consisted of a Waters LC system with a 1525 LC pump and a Higgins Clipeus 5 µm C18 100×3.0 mm column. Detection was achieved using a Micromass Platform LCT time of flight mass spectrometer (electrospray, positive ion), a Waters UV2488 dual wavelength UV detector at 254 nm and a Sedex ELS 85 evaporative light scattering detector. Mobile Phase A: 0.1% aqueous formic acid, Mobile Phase B: 0.1% formic acid in MeCN. Flow rate 1 mL/min: Gradient: 0-1 min 5% B; 1-15 min 5-95% B; 15-20 min 95% B; 20-22 min 95-5% B; 22-25 min 95% B.

Analytical Method 2:

The system consisted of a Hewlett Packard HP1100 LC system and a Higgins Clipeus 5 μm C18 100×3.0 mm column. Detection was achieved using a Micromass ZQ quadrupole electrospray (positive and negative ion), a UV detector at 254 nm and a Sedex ELS 85 evaporative light scattering detector. Mobile Phase A: 0.1% aqueous formic acid, Mobile Phase B: 0.1% formic acid in MeCN. Flow rate 1 mL/min: Gradient: 0-1 min 5% B; 1-15 min 5-95% B; 15-20 min 95% B; 20-22 min 95-5% B; 22-25 min 95% B.

Analytical Method 3:

The system consisted of a Waters HPLC and mass spectrometer system and an Agilent Scalar 5 μm C18 50×4.6 mm column. Detection was achieved using an electrospray ionization source (positive or negative ion), a UV detector at 254 nm and 215 nm. Mobile Phase A: 0.1% aqueous formic acid, Mobile Phase B: 0.1% formic acid in MeCN. Flow rate 2.5 mL/min: Gradient: 0-0.1 min 5% B; 0.1-5 min 5-95% B; 5-5.5 min 95% B; 5.5-5.6 min 95% B, flow increased to 3.5 mL/min; 5.6-6.6 95% B; 6.6-6.75 min 95-5% B; 6.75-6.9 min 5% B; 6.9-7 min 5% B, flow reduced to 2.5 mL/min.

Analytical Method 4:

The system consisted of Hewlett Packard HP1100 LC system and a Phenomenex Luna 3 μm C18 30×4.6 mm column. Detection was achieved using a Waters Platform LC quadrupole mass spectrometer (positive and negative ion), a UV diode array detector and a Sedex ELS 85 evaporative light scattering detector. Mobile Phase A: 0.1% aqueous formic acid, Mobile Phase B: 0.1% formic acid in MeCN. Flow rate 2 mL/min: Gradient: 0-0.5 min 5% B; 0.5-4.5 min 5-95% B; 4.5-5.5 min 95% B; 5.5-6 min 95-5% B.

Analytical Method 5:

The system consisted of an HPLC system and a ChiralPak IA 5 μm 250×21.2 mm column. Detection was achieved using a UV detector at 254 nm. The isocratic mobile phase used is stated in the text below. Flow rate 1 mL/min.

Analytical Method 6:

The system consisted of a Finnigan AQA single quadrupole mass spectrometer linked to a Hewlett Packard 1050 LC system with UV diode array detector and autosampler and using a Luna 3 μm C18(2) 30×4.6 mm column or equivalent. The spectrometer had an electrospray source operating in positive ion mode. Additional detection was achieved using a Sedex 65 evaporative light scattering detector. Mobile Phase A: 0.1% aqueous formic acid, Mobile Phase B: 0.1% formic acid in MeCN. Flow rate 2 mL/min: Gradient 0-0.5 min 5% B; 0.5-4.5 min 5-95% B; 4.5-5.5 95% B; 5.5-6.0 min 95-5% B.

Analytical Method 7:

The system consisted of a Waters Platform LC quadrupole mass spectrometer linked to a Hewlett Packard HP1100 LC system with diode array detector and 100 position autosampler with an Phenomenex Luna 3 μm C18(2) 30×4.6 mm column or equivalent. The spectrometer had an electrospray source operating in positive and negative ion mode. Additional detection was achieved using a Sedex 85 evaporative light scattering detector. Mobile Phase A: 0.1% aqueous formic acid, Mobile Phase B: 0.1% formic acid in MeCN. Flow rate 2 mL/min: Gradient 0-0.5 min 5% B; 0.5-4.5 min 5-95% B; 4.5-5.5 95% B; 5.5-6.0 min 95-5% B.

Analytical Method 8:

The system consisted of a Waters Platform ZMD quadrupole mass spectrometer linked to a Waters 1525 LC system with Waters 996 diode array detector. Sample injection is done by a Waters 2700 autosampler with a Luna 3 micron C18(2) 30×4.6 mm column or equivalent. The spectrometer had an electrospray source operating in positive and negative ion mode. Additional detection was achieved using a Sedex 85 evaporative light scattering detector. Mobile Phase A: 0.1% aqueous formic acid, Mobile Phase B: 0.1% formic acid in MeCN. Flow rate 2 mL/min: Gradient 0-0.5 min 5% B; 0.5-4.5 min 5-95% B; 4.5-5.5 95% B; 5.5-6.0 min 95-5% B.

Analytical Method 9:

The system consisted of a Finnigan AQA single quadrupole mass spectrometer linked to a Hewlett Packard 1050 LC system with UV diode array detector and autosampler and using a Luna 3 micron C18(2) 30×4.6 mm column or equivalent. The spectrometer had an electrospray source operating in positive ion mode. Additional detection was achieved using a Sedex 65 evaporative light scattering detector. Mobile Phase A: 0.1% aqueous formic acid, Mobile Phase B: 0.1% formic acid in methanol. Flow rate 2 mL/min: Gradient 0-0.5 min 5% B; 0.5-4.5 min 5-95% B; 4.5-5.5 95% B; 5.5-6.0 min 95-5% B.

Analytical Method 10:

The system consisted of a Hewlett Packard HP1100 LC system and a Higgins Clipeus 5 μm C18 100×3.0 mm column. Detection was achieved using a Micromass ZQ quadrupole electrospray (positive and negative ion), a UV detector at 254 nm and a Sedex ELS 85 evaporative light scattering detector. Mobile Phase A: 0.1% aqueous formic acid, Mobile Phase B: 0.1% formic acid in methanol. Flow rate 1 mL/min: Gradient: 0-1 min 15% B; 1-13 min 15-95% B; 13-20 min 95% B; 20-22 min 95-15% B; 22-25 min 15% B.

Abbreviations:

| Abbreviations: | |
|---|---|
| HATU = | (O-(7-Azabenzotriazol-1-yl)-N,N,N',N'-tetramethyluroniumhexafluoro-phosphate). |
| DCM = | Dichloromethane. |
| IMS = | Industrial methylated spirit. |
| THF = | Tetrahydrofuran. |
| DIPEA = | Diisopropylethylamine. |
| DMF = | Dimethylformamide. |
| HCl = | Hydrochloric acid. |
| TFA = | Trifluoroacetic acid. |
| Herrmann's catalyst = | trans-Di-μ-acetobis[2-(di-o-tolylphosphino)-benzyl]-dipalladium (II). |
| tBuONO = | t-Butylnitrite. |
| DEAD = | Diethyl azodicarboxylate. |
| NCS = | N-Chlorosuccinimide. |
| NBS = | N-Bromosuccinimide. |
| TBAF = | Tetrabutylammonium fluoride. |
| TBDMSCl = | t-Butyldimethylsilyl chloride. |
| DME = | 1,2-Dimethoxyethane. |
| DEA = | Diethylamine. |
| EDC = | 1-Ethyl-3-(3-dimethylaminopropyl)-carbodiimide.hydrochloride. |
| DAST = | (Diethylamino)sulfur trifluoride. |
| DIAD = | Diisopropyl azodicarboxylate. |
| TBAB = | Tetrabutyl ammonium bromide. |
| R.T. = | retention time. |
| SM = | starting material. |
| s = | singlet. |
| d = | doublet. |
| t = | triplet. |
| m = | multiplet. |
| q = | quartet. |

Compounds were named using Autonom.

Compounds containing chiral centres were prepared as racemic mixtures, unless stated otherwise.

Materials

Decahydroquinoline (a mixture containing both of the cis- and both of the trans-enantiomers) was obtained from the Sigma-Aldrich Corporation.

Single cis-decahydroquinoline enantiomers were prepared from 3-(2-oxo-cyclohexyl)-propionic acid and (R)-(−)-2-phenylglycinol or from 3-(2-oxo-cyclohexyl)-propionic acid and (S)-(+)-2-phenylglycinol, using the method described in Amat et al., 2006, Chem. Eur. J., Vol. 12, No. 30, pp. 7872-7881.

Compounds containing decahydroquinolyl amides were prepared as:

(a) a mixture of the cis-diastereomers (referred to as CIS ISOMERS) or (b) a single enantiomer of the cis-decahydroquinoline, prepared using (S)-(+)-2-phenylglycinol as a chiral auxiliary utilising the method outlined above (referred to as DHQ [CIS-S]), or (c) a single enantiomer of the cis-decahydroquinoline, prepared using (R)-(−)-2-phenylglycinol as a chiral auxiliary utilising the method outlined above (referred to as DHQ [CIS-R]).

It is predicted that the single enantiomer of cis-decahydroquinoline (DHQ [CIS-S]) prepared using (S)-(+)-2-phenylglycinol as a chiral auxiliary is, or is predominantly, (4aS,8aS)-decahydroquinoline.

It is predicted that the single enantiomer of cis-decahydroquinoline (DHQ [CIS-R]) prepared using (R)-(−)-2-phenylgiycinol as a chiral auxiliary is, or is predominantly, (4aR,8aR)-decahydroquinoline.

When thiophene-3-carboxylic acids are coupled using HATU to a mixture containing an excess of both of the cis- and both of the trans-isomers of decahydroquinoline, it was observed that the amide formed with the cis-decahydroquinoline is the major product. Decahydroquinolyi amides consisting of a mixture of cis-diastereomers (referred to as CIS ISOMERS) were prepared using this method.

Certain compounds containing a 2-phenyl piperidine amide were prepared as single enantiomers from either (S)-(+)-2-phenylglycinol or (R)-(−)-2-phenylglycinol.

It is predicted that the single enantiomer prepared using (S)-(+)-2-phenylglycinol as a chiral auxiliary is, or is predominantly, (R)-2-phenyl piperidine.

It is predicted that the single enantiomer prepared using (R)-(−)-2-phenylglycinol as a chiral auxiliary is, or is predominantly, (S)-2-phenyl piperidine.

Synthesis 1

5-Phenyl-thiophene-3-carboxylic acid ethyl ester

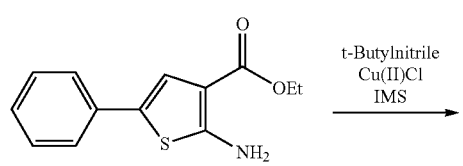

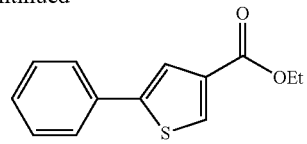

2-Amino-5-phenyl thiophene-3-carboxylic ethyl ester was prepared according to the method described by Hwang et al., 2001. t-Butylnitrite (1.6 mL, 13.3 mmol) and anhydrous copper (II) chloride (25 mmol) were dissolved in IMS (100 mL). To this was added 2-amino-5-phenyl-thiophene-3-carboxylic acid ethyl ester (6.9 mmol) in one portion and the reaction was stirred for 1 hour. The reaction was quenched with saturated aqueous ammonium chloride (2 mL) and the solvent evaporated. The resulting slurry was partitioned between DCM and water. The organic solution was separated and dried over magnesium sulfate, filtered and the solvent evaporated to give the title compound as a brown oil (1.7 g, 98%). $^1$H NMR (400 MHz, CHCl$_3$-d): δ 8.0 (s, 1H), 7.75 (s, 1H), 7.65 (d, 2H), 7.4 (t, 2H), 7.3 (m, 1H), 4.35 (q, 2H), 1.4 (t, 3H).

Synthesis 2

2-Chloro-5-phenyl-thiophene-3-carboxylic acid ethyl ester

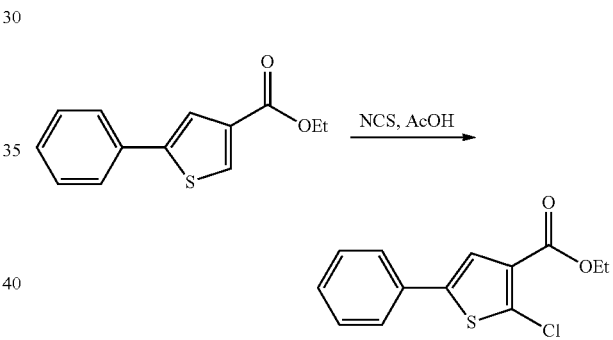

Ethyl-2-phenylthiophen-4-carboxylate (0.5 g, 2.15 mmol) was dissolved in acetic acid (5 mL). N-chlorosuccinimide (2.17 mmol) was added and the reaction stirred overnight. The reaction was concentrated under vacuum and purified by flash chromatography on silica, eluting with 0%-50% ethyl acetate in cyclohexane. The fractions containing the desired product were concentrated under vacuum to give the title compound (0.44 g). $^1$H NMR (400 MHz, CHCl$_3$-d): δ 7.5 (d, 2H), 7.4-7.25 (m, 4H), 4.4 (q, 2H), 1.4 (t, 3H).

Synthesis 3

2-Chloro-5-phenyl-thiophene-3-carboxylic acid

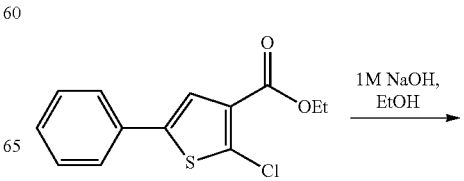

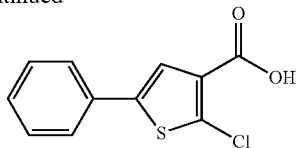

2-Chloro-5-phenyl-thiophene-3-carboxylic acid ethyl ester (0.44 g, 1.65 mmol) was dissolved in a solution of 1 M NaOH (3 mL) and ethanol (2 mL). The reaction mixture was heated to 100° C. using microwave irradiation for 10 minutes. After cooling, the reaction mixture was partitioned between diethyl ether and water. The aqueous solution was acidified with 1 M HCl and further extracted with diethyl ether. The combined organic solutions were dried over magnesium sulfate, filtered and the solvent evaporated. The residue was triturated in diethyl ether and filtered to give the title compound (0.17 g). $^1$H NMR (400 MHz, CHCl$_3$-d): δ 7.6 (s, 1H), 7.55 (d, 2H), 7.4-7.3 (m, 3H).

Synthesis 4

(2-Chloro-5-phenyl-thiophen-3-yl)-(pyrrolidin-1-yl)-methanone (AA-38)

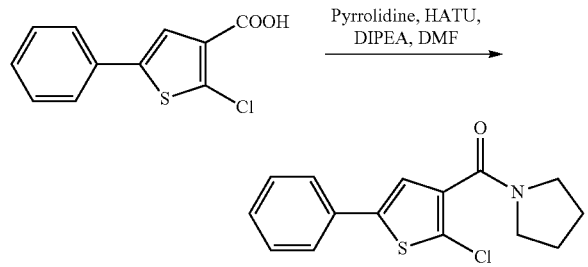

2-Chloro-5-phenyl-thiophene-3-carboxylic acid (28 mg, 0.11 mmol) was dissolved in DMF (1 mL). DIPEA (0.22 mmol), HATU (0.11 mmol) and pyrrolidine (0.11 mmol) were added and the reaction mixture stirred at room temperature. The reaction mixture was partitioned between ethyl acetate and 1 N hydrochloric acid. The organic solution was separated and dried over magnesium sulfate, filtered and the solvent evaporated. The residue was purified by preparative HPLC, eluting with 50%-90% acetonitrile in water (0.1% formic acid) over 30 minutes. The fractions containing the desired product were concentrated under vacuum to give the title compound (81 mg). LCMS m/z 292.10 [M+H]$^+$ R.T.=11.27 mins (Analytical Method 1)

$^1$H NMR (400 MHz, CHCl$_3$-d): δ 7.5 (d, 2H), 7.4 (t, 2H), 7.3 (m, 1H), 7.2 (s, 1H), 3.7 (t, 2H), 3.45 (t, 2H), 1.9 (m, 4H).

The following compounds were prepared using analogous methods.

| Code No. | Structure | $^1$H NMR | Analytical Method | R.T. (min) | MS [m/z] |
|---|---|---|---|---|---|
| AA-30 | 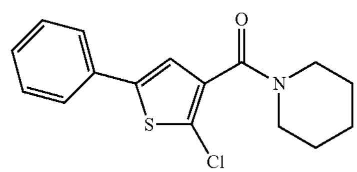 | 7.5 (d, 2H), 7.4 (t, 2H), 7.3 (m, 1H), 7.1 (s, 1H), 3.7 (m, 2H), 3.4 (m, 2H), 1.7 (m, 4H), 1.6 (m, 2H). | 2 | 12.15 | [M + H]$^+$ 306.08 |
| AA-39 | 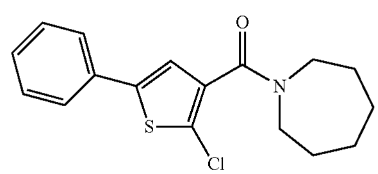 | 7.5 (d, 2H), 7.4 (t, 2H), 7.3 (m, 1H), 7.1 (s, 1H), 3.7 (t, 2H), 3.45 (t, 2H), 1.9 (m, 2H), 1.7-1.6 (m, 6H) | 2 | 12.62 | [M + H]$^+$ 320.09 |

Synthesis 5

(2-Chloro-5-phenyl-thiophen-3-yl)-[1,4]oxazepan-4-yl-methanone (AA-42)

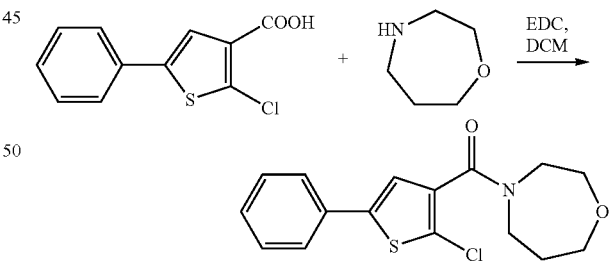

To a solution of 2-chloro-5-phenyl-thiophene-3-carboxylic acid (1 eq.) in DCM (1 mL/100 mg SM) was added EDC (1.5 eq.). This mixture was stirred at room temperature for 5 minutes and then [1,4]oxazepane (1.2 eq.) was added and the mixture was allowed to stir for 18 hours. Water (1 mL/100 mg SM) was then added and the organic layer separated, dried and evaporated to give the crude product which was purified by column chromatography (EtOAc/iso-hexane). LCMS m/z 322 [M+H]$^+$ R.T.=3.34 mins (Analytical Method 3).

The following compounds were prepared using analogous methods.

| Code No. | Structure | Analytical Method | R.T. (min) | MS [m/z] |
|---|---|---|---|---|
| AA-34 | 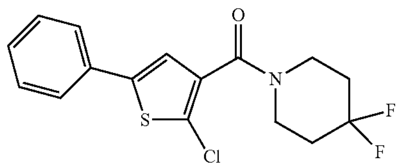 | 3 | 4.00 | [M + H]⁺ 342 |
| DD-01 | 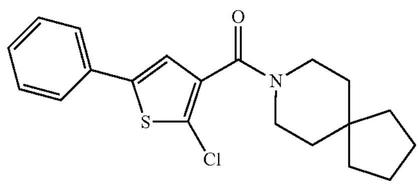 | 3 | 5.05 | [M + H]⁺ 360 |
| BB-06 | 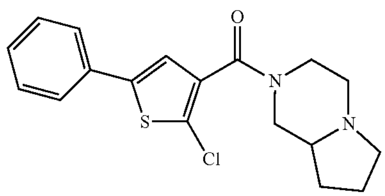 | 3 | 1.84 | [M + H]⁺ 347 |
| BB-07 | 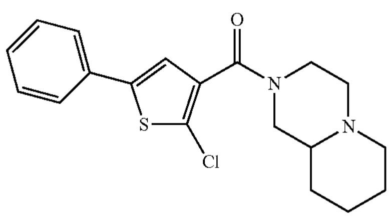 | 3 | 1.90 | [M + H]⁺ 361 |
| BB-05 | 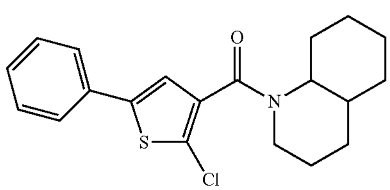 | 3 | 4.97 | [M + H]⁺ 360 |
| AA-35 | 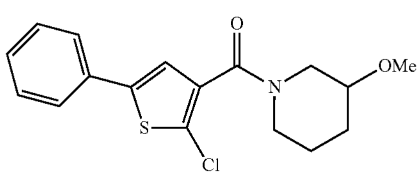 | 3 | 3.72 | [M + H]⁺ 336 |
| AA-44 | 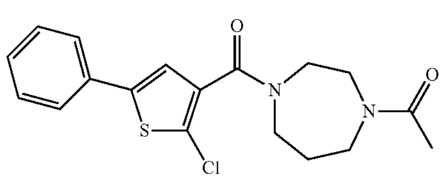 | 3 | 2.77 | [M + H]⁺ 363 |
| AA-45 | 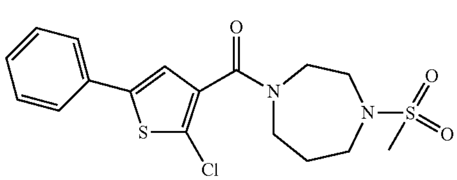 | 3 | 3.23 | [M + H]⁺ 399 |

-continued

| Code No. | Structure | Analytical Method | R.T. (min) | MS [m/z] |
|---|---|---|---|---|
| AA-46 | 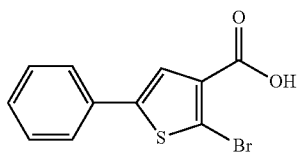 | 3 | 1.84 | [M + H]+ 335 |
| AA-36 | 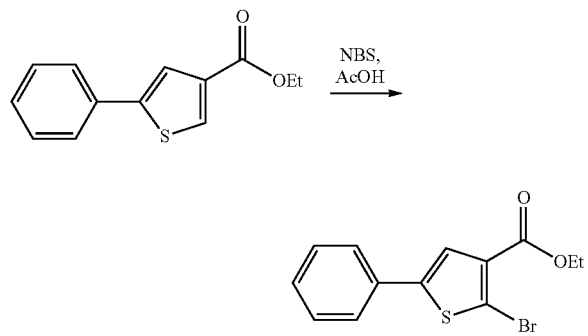 | 3 | 4.02 | [M + H]+ 350 |

Synthesis 6

2-Bromo-5-phenyl-thiophene-3-carboxylic acid ethyl ester

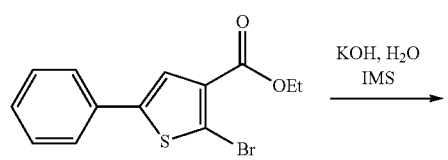

N-Bromosuccinimide (1.22 g, 6.83 mmol) was added to a solution of ethyl-2-phenylthiophen-4-carboxylate (6.83 mmol) in acetic acid (10 mL) and stirred overnight. Toluene was added and the solvent was removed under vacuum. The product was purified by flash chromatography on silica, eluting with 0%-10% ethyl acetate in cyclohexane. The fractions containing the desired product were concentrated under vacuum to give the title compound (1.2 g). LCMS m/z 312.52 [M+H]+ R.T.=4.55 mins (Analytical Method 5).

Synthesis 7

2-Bromo-5-phenyl-thiophene-3-carboxylic acid

Potassium hydroxide (0.65 g, 11.6 mmol) in water (2 mL) was added to a solution of 2-bromo-5-phenyl-thiophene-3-carboxylic acid ethyl ester (3.9 mmol) in IMS (6 mL). The reaction was stirred for 1 hour and then partitioned between diethyl ether and water. The aqueous layer was acidified to pH 7 with 1 N hydrochloric acid and further extracted with diethyl ether. The organic solution was dried over magnesium sulfate, filtered and the solvent evaporated to give the title compound (0.96 g, 87%). LCMS m/z 281.97 [M−H]− R.T.=3.64 min. (Analytical Method 5).

Synthesis 8

(2-Bromo-5-phenyl-thiophen-3-yl)-piperidin-1-yl-methanone (AA-47)

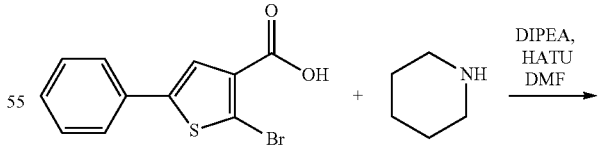

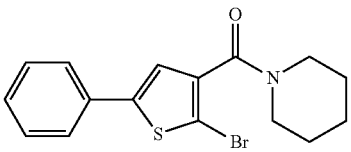

2-Bromo-5-phenyl-thiophene-3-carboxylic acid (0.99 g, 3.5 mmol) was dissolved in DMF (20 mL). DIPEA (7.0 mmol), HATU (3.5 mmol) and piperidine (3.5 mmol) were added and the solution stirred at room temperature. The reaction mixture was partitioned between ethyl acetate and 1 N hydrochloric acid. The organic solution was dried over magnesium sulfate, filtered and the solvent evaporated. The residue was purified by flash chromatography on silica, eluting with 0%-50% ethyl acetate in cyclohexane. The fractions containing the desired product were concentrated under vacuum to give a solid which was further purified by HPLC, eluting with 50%-90% acetonitrile in water (0.1% formic acid) over 30 minutes. The fractions containing the desired product were concentrated under vacuum then freeze-dried to give the title compound (95 mg). LCMS m/z 350.07 [M+H]+ R.T.=12.57 min (Analytical Method 1). 1H NMR (400 MHz, CHCl3-d): δ 7.50 (d, 1H), 7.40 (t, 2H), 7.3 (m, 1H), 7.1 (s, 1H), 3.7 (m, 2H), 3.4 (t, 2H), 1.7 (m, 4H), 1.6 (m, 2H).

The following compounds were prepared using analogous methods.

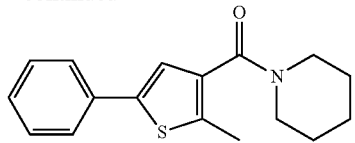

2-Bromo-5-phenyl-thiophen-3-yl)-piperidin-1-yl-methanone (110 mg, 0.31 mmol) was added into a stirred suspension of trimethylboroxine (0.93 mmol), [1,1'-bis(diphenylphosphino)ferrocine]dichloropalladium (II) (0.03 mmol) and caesium carbonate (0.93 mmol) in dimethoxyethane (1 mL) and IMS (1 mL). The reaction mixture was heated to 150° C. using microwave irradiation for 1 hour and then partitioned between ethyl acetate and 1 N hydrochloric acid. The organic solution was dried over magnesium sulfate, filtered and the solvent evaporated. The residue was purified by

| Code No. | Structure | 1H NMR | Analytical Method | R.T. (min) | MS [m/z] |
|---|---|---|---|---|---|
| AA-48 | 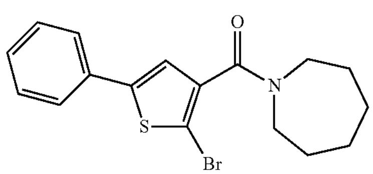 | 7.5 (d, 2H), 7.4 (m, 2H), 7.3 (m, 1H), 7.1 (s, 1H), 3.7 (m, 2H), 3.4 (m, 2H), 1.9 (m, 2H), 1.7 (m, 6H) | 1 | 13.09 | [M + H]+ 364.09 |

Synthesis 9

(2-Methyl-5-phenyl-thiophen-3-yl)-piperidin-1-yl-methanone (AA-28)

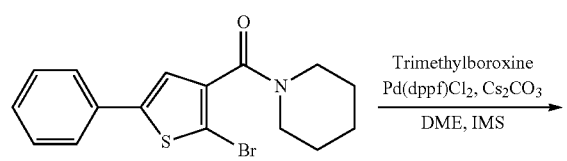

HPLC, eluting with 50%-90% acetonitrile in water (0.1% formic acid) over 30 minutes. The fractions containing the desired product were concentrated under vacuum and freeze-dried to give the title compound (5 mg). LCMS m/z 286.16 [M+H]+ R.T.=11.82 mins (Analytical Method 1). 1H NMR (400 MHz, CHCl3-d): δ 7.50 (d, 2H), 7.4 (t, 2H), 7.3 (m, 1H), 7.1 (s, 1H), 3.7 (m, 2H), 3.4 (m, 2H), 2.5 (s, 3H), 1.7 (m, 4H), 1.5 (m, 2H).

The following compounds were prepared using analogous methods.

| Code No. | Structure | 1H NMR | Analytical Method | R.T. (min) | MS [m/z] |
|---|---|---|---|---|---|
| AA-29 | 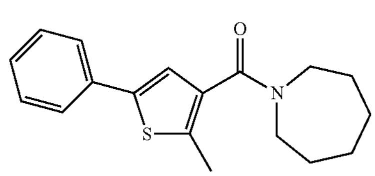 | 7.50 (m, 2H), 7.4 (t, 2H), 7.3 (m, 1H), 7.1 (s, 1H), 3.7 (t, 2H), 3.4 (t, 2H), 2.5 (s, 3H), 1.9 (m, 2H), 1.7-1.55 (m, 6H) | 1 | 12.32 | [M + H]+ 300.21 |

Synthesis 10

3-(Azepane-1-carbonyl)-5-phenyl-thiophene-2-carbonitrile (AA-51)

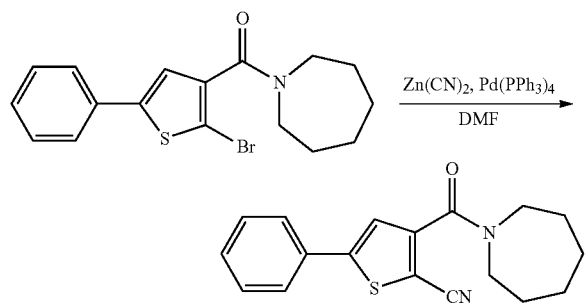

Azepan-1-yl-(2-bromo-5-phenyl-thiophen-3-yl)-methanone (109 mg, 0.30 mmol) was dissolved in DMF (2 mL). Zinc cyanide (0.30 mmol) and tetrakis(triphenylphosphine)palladium (0) (0.15 mmol) were added and the reaction heated at 100° C. for 5 hours. The reaction mixture was cooled to ambient temperature, quenched with a 1:1 mixture of 5% aqueous sodium thiosulfate and 10% aqueous potassium carbonate. The resulting mixture was extracted with ethyl acetate, and the organic solvent separated and then evaporated. The residue was purified by HPLC, eluting with 50%-90% acetonitrile in water (0.1% formic acid) over 30 minutes. The fractions containing the desired product were concentrated under vacuum and freeze-dried to give the title compound (16 mg). LCMS m/z 311.10 [M+H]$^+$ R.T.=11.43 min (Analytical Method 2). $^1$H NMR (400 MHz, CHCl$_3$-d): δ 7.60 (m, 2H), 7.5 (m, 3H), 7.2 (s, 1H), 3.75 (t, 2H), 3.5 (t, 2H), 1.9 (m, 2H), 1.75-1.6 (m, 6H).

Synthesis 11

5-Phenyl-thiophene-3-carboxylic acid

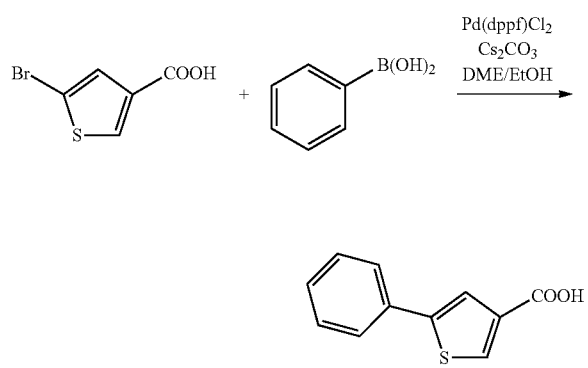

5-Bromo-thiophene-3-carboxylic acid (2.07 g, 10 mmol) was dissolved in dimethoxyethane (15 mL) and ethanol (15 mL). Phenyl boronic acid (14 mmol), [1,1'-bis(diphenylphosphino)ferrocine]dichloropalladium (II) (0.5 mmol) and caesium carbonate (14 mmol) were added and the reaction mixture refluxed under nitrogen overnight. The solvent was evaporated under vacuum, and the residue dissolved in ethyl acetate. The organic solution was washed with 1 N hydrochloric acid, dried over magnesium sulfate, filtered and the solvent evaporated. The residue was dissolved in hot ethyl acetate, filtered and the solvent evaporated to give the title compound as a pale brown solid. LCMS m/z 203.20 [M−H]$^-$ R.T.=3.23 min (Analytical Method 5).

Synthesis 12

1-[4-(5-Phenyl-thiophene-3-carbonyl)-[1,4]diazepan-1-yl]-ethanone (AA-27)

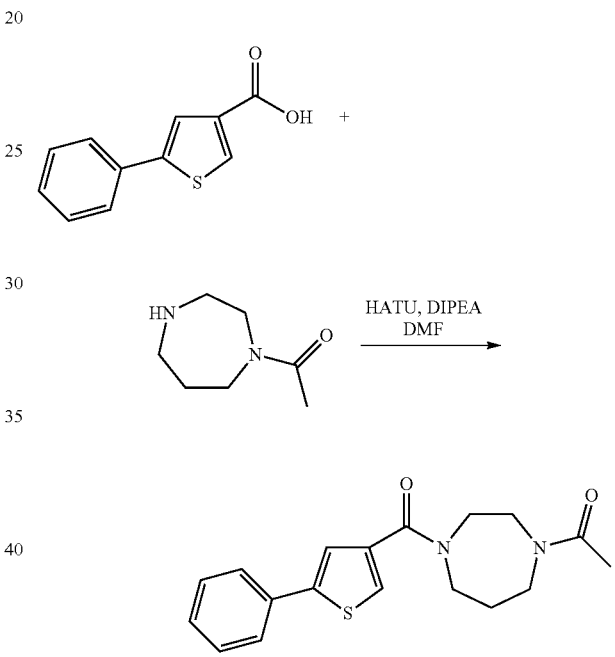

5-Phenyl-thiophene-3-carboxylic acid (0.1 g, 0.5 mmol) was dissolved in DMF (3 mL).

1-[1,4]Diazepan-1-yl-ethanone (0.5 mmol), DIPEA (1.5 mmol) and HATU (0.5 mmol) were added and the reaction mixture stirred for 0.5 hours. Ethyl acetate (20 mL) was added and the organic solution was washed with 1 N hydrochloric acid, dried with magnesium sulfate, filtered and the solvent removed by evaporation. The residue was purified by HPLC, eluting with 70%-90% acetonitrile in water (0.1% formic acid) over 30 minutes. The fractions containing the desired product were concentrated under vacuum and freeze-dried to give the title compound (28 mg). LCMS m/z 329.20 [M+H]$^+$ R.T.=8.20 min (Analytical Method 1). $^1$H NMR (400 MHz, CHCl$_3$-d): δ 7.6 (m, 2H), 7.55-7.3 (m, 5H), 3.9-3.5 (m, 8H), 2.1 (s, 3H), 2.0-1.3.2 (m, 2H).

The following compounds were prepared using analogous methods.

| Code No. | Structure | ¹H NMR | Analytical Method | R.T. (min) | MS [m/z] |
|---|---|---|---|---|---|
| AA-19 | 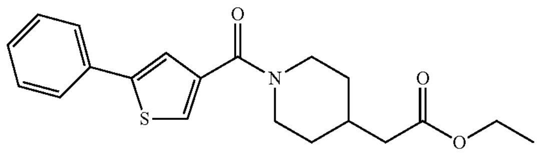 | 7.60 (d, 2H), 7.4-7.3 (m, 5H), 4.6 (m, 2H), 4.2 (q, 2H), 3.2-2.8 (m, 2H), 2.3 (d, 2H), 2.1 (m, 1H), 1.8 (m, 2H), 1.30 (m, 5H) | 2 | 11.20 | [M + H]⁺ 358.12 |
| AA-15 | 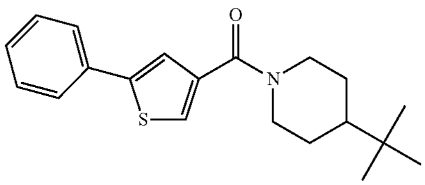 | — | 1 | 13.89 | [M + H]⁺ 328.25 |
| BB-01 | 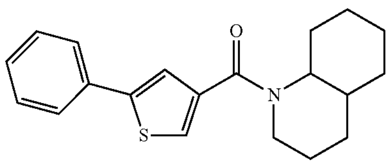 | — | 1 | 13.47 | [M + H]⁺ 326.25 |

Synthesis 13

(2-Methyl-piperidin-1-yl)-(5-phenyl-thiophen-3-yl)-methanone (AA-14)

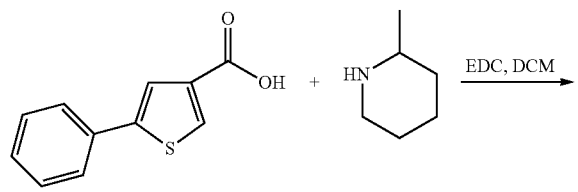

-continued

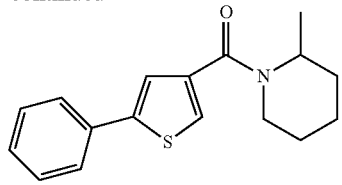

To a solution of 5-phenyl-thiophene-3-carboxylic acid (1 eq.) in DCM (1 mL/100 mg SM) was added EDC (1.5 eq.). This mixture was stirred at room temperature for 5 minutes and then 2-methyl piperidine (1.2 eq.) was added and the mixture stirred for 18 hours. Water (1 mL/100 mg SM) was then added and the organic layer separated, dried and evaporated to give the crude product which was purified by column chromatography (EtOAc/iso-hexane). LCMS m/z 286 [M+H]⁺ R.T.=3.85 min (Analytical Method 3).

The following compounds were prepared using analogous methods.

| Code No. | Structure | Analytical Method | R.T. (min) | MS [m/z] |
|---|---|---|---|---|
| AA-16 | 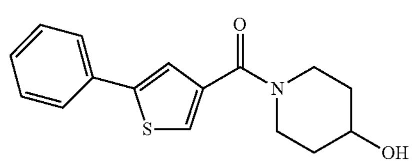 | 3 | 2.47 | [M + H]⁺ 288 |
| AA-17 | 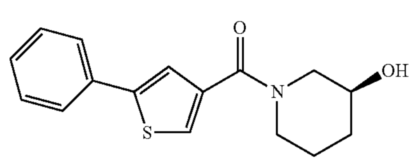 | 3 | 2.63 | [M + H]⁺ 288 |

-continued

| Code No. | Structure | Analytical Method | R.T. (min) | MS [m/z] |
|---|---|---|---|---|
| AA-18 | 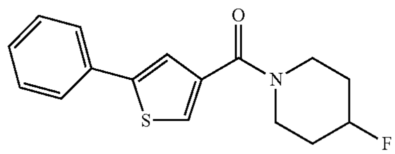 | 3 | 3.38 | [M + H]⁺ 290 |
| AA-25 | 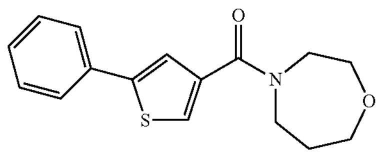 | 3 | 2.92 | [M + H]⁺ 288 |
| CC-01 | 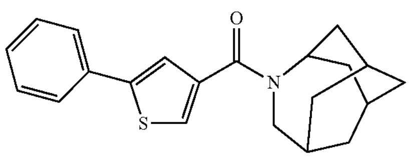 | 3 | 4.50 | [M + H]⁺ 338 |

Synthesis 14

(5-Phenyl-thiophen-3-yl)-pyrrolidin-1-yl-methanone (AA-01)

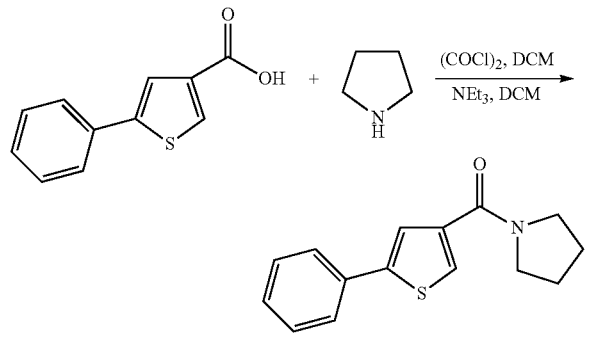

To a solution of 5-phenyl-thiophene-3-carboxylic acid (1 eq.) in DCM (1 mL/100 mg) was added oxalyl chloride (1.5 eq.) and DMF (1 drop). This mixture was stirred at room temperature for 3 hours and then the solvent was removed in vacuo to give the crude acid chloride. The crude acid chloride was dissolved in DCM (1 mL/100 mg) and a solution of amine (1.2 eq.) and triethylamine (1.5 eq) in DCM added. The mixture was stirred at room temperature for 18 hours after which time the solvent was removed in vacuo and the crude product purified by column chromatography (EtOAc/isohexane). LCMS m/z 258 [M+H]⁺ R.T.=2.97 min (Analytical Method 3).

The following compounds were prepared using analogous methods.

| Code No. | Structure | Analytical Method | R.T. (min) | MS [m/z] |
|---|---|---|---|---|
| AA-20 | 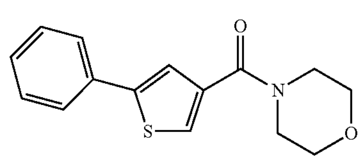 | 3 | 2.65 | [M + H]⁺ 274 |
| AA-21 | 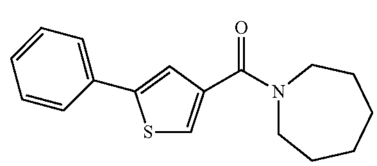 | 3 | 3.48 | [M + H]⁺ 286 |

Synthesis 15

(5-Bromo-thiophen-3-yl)-piperidin-1-yl-methanone

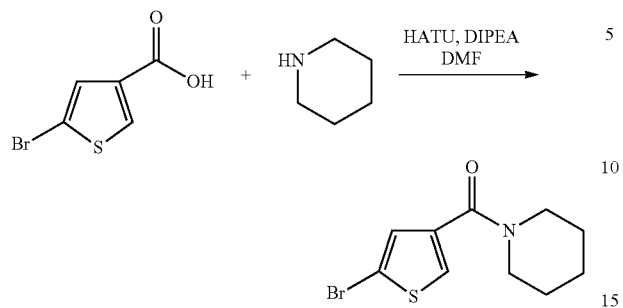

5-Bromo-thiophene-3-carboxylic acid (150 mg, 0.72 mmol) was dissolved in DMF (3 mL). DIPEA (2.16 mmol), HATU (0.72 mmol) and piperidine (0.72 mmol) were added and the reaction mixture stirred at room temperature for 1 hour. The mixture was partitioned between ethyl acetate and water and the organic solution separated, washed with 1 N hydrochloric acid, dried over magnesium sulfate, filtered and the solvent evaporated. The residue was purified by flash chromatography on silica, eluting with 0%-50% ethyl acetate in cyclohexane. The fractions containing the desired product were concentrated under vacuum to give the title compound (86 mg). LCMS m/z 273.97 [M+H]$^+$ R.T.=3.19 min (Analytical Method 5).

Synthesis 16

[5-(2-chloro-phenyl)thiophen-3-yl]piperidin-1-yl-methanone (AA-13)

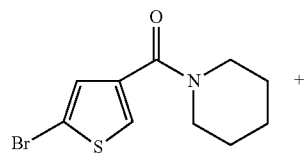

+

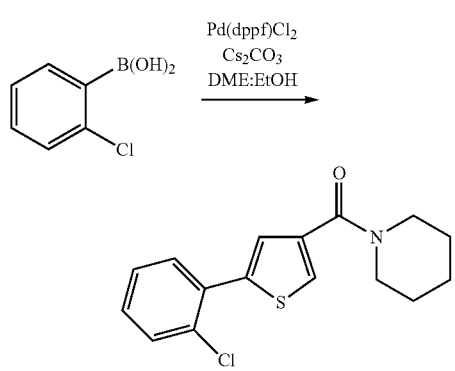

(5-Bromo-thiophen-3-yl)-piperidin-1-yl-methanone (75 mg, 0.27 mmol) was dissolved in dimethoxyethane (1 mL) and ethanol (1 mL). 2-Chlorophenylboronic acid (0.54 mmol), [1,1'-bis(diphenylphosphino)ferrocine]dichloropalladium (II) (0.014 mmol) and caesium carbonate (0.41 mmol) were added and the reaction mixture heated to 140° C. using microwave irradiation for 1 hour. The solvent was removed under vacuum and the residue dissolved in ethyl acetate. The organic solution was washed with water, dried over magnesium sulfate, filtered and the solvent evaporated. The residue was purified by column chromatography on silica, eluting with 0%-25% ethyl acetate in petroleum ether. The fractions containing the desired product were concentrated under vacuum to give the title compound (48 mg). LCMS m/z 306.02 [M+H]$^+$ R.T.=11.48 min (Analytical Method 2). $^1$H NMR (400 MHz, CHCl$_3$-d): δ 7.5 (m, 3H), 7.4 (s, 1H), 7.3-7.4 (m, 2H), 3.6 (m, 4H), 1.7-1.5 (m, 6H).

The following compounds were prepared using analogous methods.

| Code No. | Structure | Analytical Method | R.T. (min) | MS [m/z] |
|---|---|---|---|---|
| AA-02 | 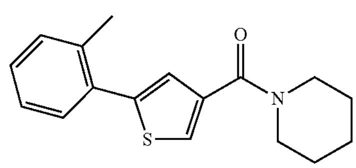 | 3 | 3.84 | [M + H]$^+$ 286 |
| AA-03 | 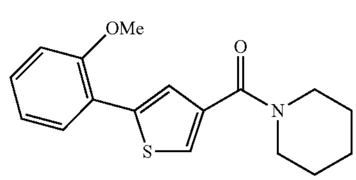 | 3 | 3.60 | [M + H]$^+$ 302 |

-continued
| Code No. | Structure | Analytical Method | R.T. (min) | MS [m/z] |
|---|---|---|---|---|
| AA-04 | 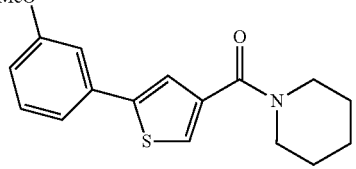 | 3 | 3.60 | [M + H]+ 302 |
| AA-05 | 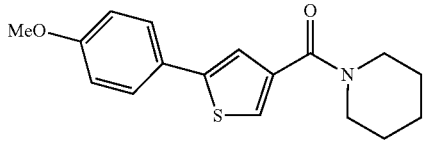 | 3 | 3.57 | [M + H]+ 302 |
| AA-06 | 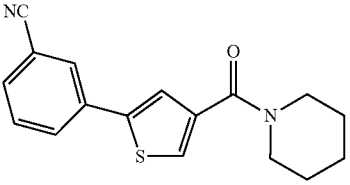 | 3 | 3.32 | [M + H]+ 297 |
| EE-03 | 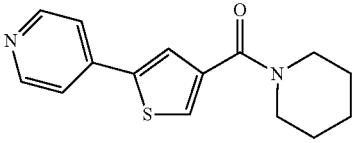 | 3 | 2.48 | [M + H]+ 273 |
| EE-02 | 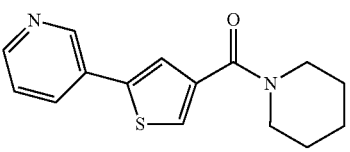 | 3 | 2.50 | [M + H]+ 273 |
| EE-04 | 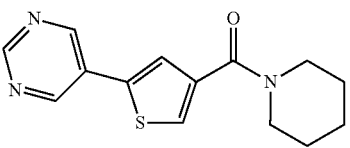 | 3 | 2.15 | [M + H]+ 274 |
| EE-05 | 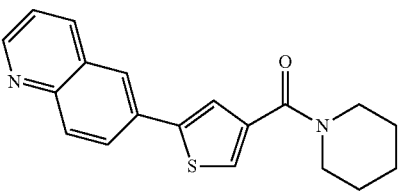 | 3 | 3.02 | [M + H]+ 323 |
| EE-08 | 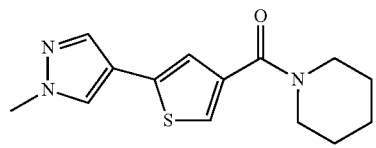 | 3 | 2.42 | [M + H]+ 276 |
| AA-07 | 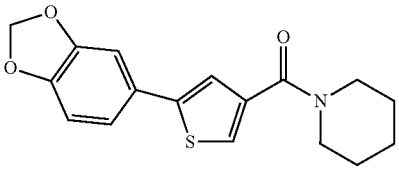 | 3 | 3.50 | [M + H]+ 316 |

-continued

| Code No. | Structure | Analytical Method | R.T. (min) | MS [m/z] |
|---|---|---|---|---|
| AA-08 | 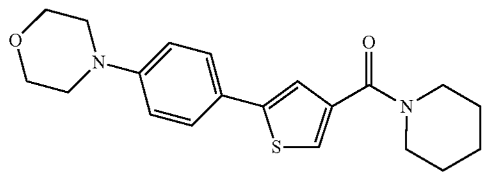 | 3 | 3.37 | [M + H]+ 357 |
| AA-09 | 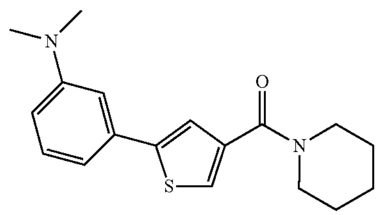 | 3 | 3.92 | [M + H]+ 315 |
| AA-10 | 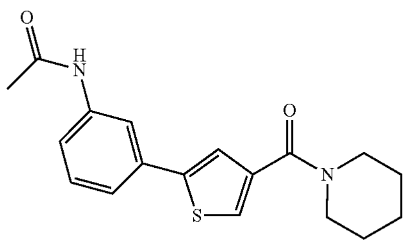 | 3 | 2.68 | [M + H]+ 329 |
| AA-12 | 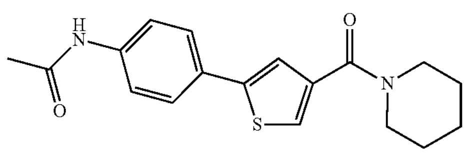 | 3 | 2.63 | [M + H]+ 329 |
| AA-23 | 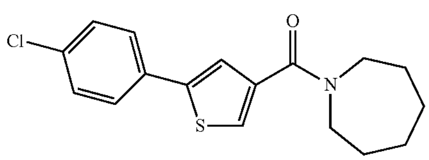 | 3 | 4.20 | [M + H]+ 319 |
| AA-24 | 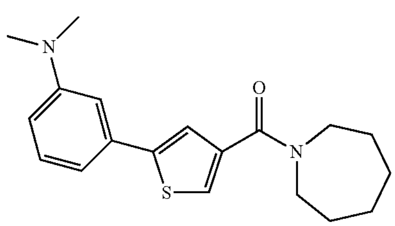 | 3 | 4.07 | [M + H]+ 329 |
| AA-22 | 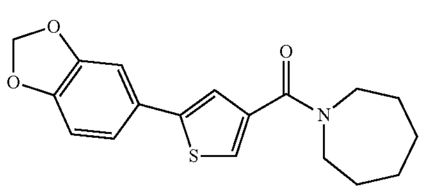 | 3 | 3.67 | [M + H]+ 330 |

The following intermediate was prepared using analogous methods.

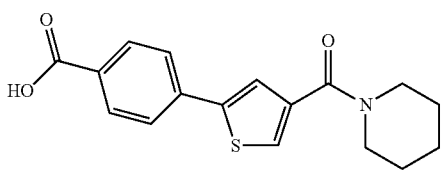

Synthesis 17

N-Methyl-4-[4-(piperidine-1-carbonyl)-thiophen-2-yl]-benzamide (AA-11)

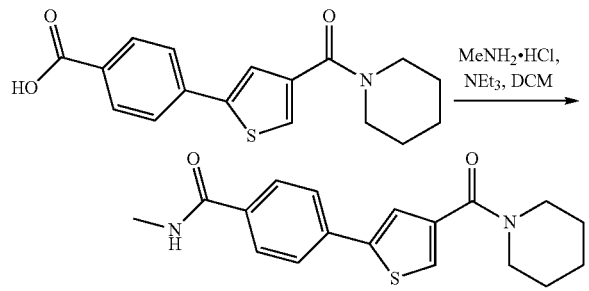

4-[4-(Piperidine-1-carbonyl)-thiophen-2-yl]-benzoic acid was taken up in DCM (5 mL) and oxalyl chloride (0.099 mL, 3 eq.) added with a drop of DMF. The mixture was then stirred for 1 hour and then evaporated and the residue taken up in DCM (5 mL). Triethylamine (0.106 mL, 2 eq.) was added followed by methylamine.HCl (28 mg, 1.1 eq). The mixture was stirred for 2 hours and then evaporated and the residue purified by column chromatography (EtOAc/iso-hexane) to give the desired product (21.9 mg, 17%). LCMS m/z 329 [M+H]+ R.T.=2.47 min (Analytical Method 3).

Synthesis 18

Piperidin-1-yl-(5-pyridin-2-yl-thiophen-3-yl)-methanone (EE-01)

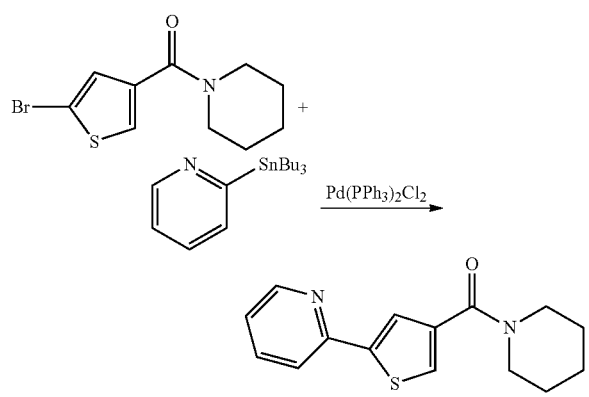

A mixture of piperidin-1-yl-(5-bromo-thiophen-3-yl)-methanone (76 mg, 1 eq.), tributyl(2-pyridyl)tin (0.102 mL, 1 eq.) and PdCl$_2$(PPh$_3$)$_2$ (0.011 g, 0.1 eq) were heated at 100° C. in toluene (1 mL) for 6 hours. The solvent was evaporated and the residue purified by column chromatography (EtOAc/iso-hexane) to give the desired product (9.2 mg, 12%). LCMS m/z 273 [M+H]+ R.T.=2.73 min (Analytical Method 3).

Synthesis 19

[2-Chloro-5-(4-chloro-phenyl)-thiophen-3-yl]-piperidin-1-yl-methanone (AA-31) and [2,4-Dichloro-5-(4-chloro-phenyl)-thiophen-3-yl]-piperidin-1-yl-methanone (AA-49)

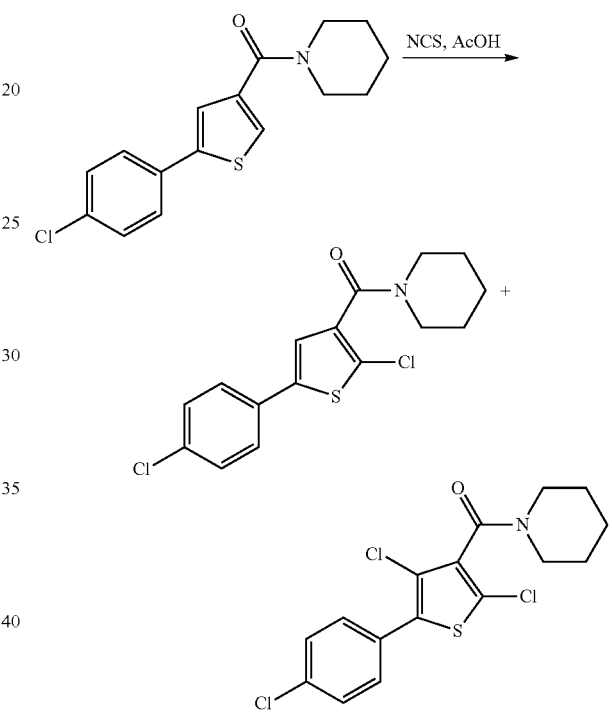

[5-(4-Chloro-phenyl)-thiophen-3-yl]-piperidin-1-yl-methanone (164 mg, 0.54 mmol) was dissolved in acetic acid (3 mL). N-Chlorosuccinimide (0.54 mmol) was added and the reaction heated to 100° C. using microwave irradiation for 10 minutes. The reaction products were separated by HPLC, eluting with 20%-95% acetonitrile in water (0.1% formic acid). The fractions containing the desired products were concentrated under vacuum to give the title compounds as white solids.

[2-chloro-5-(4-chloro-phenyl)-thiophen-3-yl]-piperidin-1-yl-methanone (32 mg): LCMS m/z 339.99 [M+H]+ RT=13.17 min. (Analytical Method 2). $^1$H NMR (400 MHz, CHCl$_3$-d): δ 7.45 (d, 2H), 7.35 (d, 2H), 7.1 (s, 1H), 3.75 (m, 2H), 3.4 (m, 2H), 1.7-1.5 (m, 6H).

[2,4-dichloro-5-(4-chloro-phenyl)-thiophen-3-yl]-piperidin-1-yl-methanone (35 mg): LCMS m/z 375.95 [M+H]+ RT=13.70 min. (Analytical Method 2). $^1$H NMR (400 MHz, CHCl$_3$-d): δ 7.5 (d, 2H), 7.4 (d, 2H), 3.8 (m, 2H), 3.3 (m, 2H), 1.8-1.5 (m, 6H).

The following compounds were prepared using analogous methods.

| Code No. | Structure | ¹H NMR | Analytical Method | R.T. (min) | MS [m/z] |
|---|---|---|---|---|---|
| AA-40 | 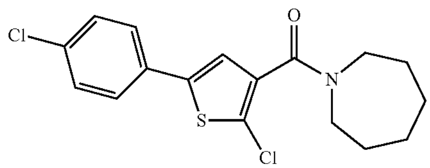 | 7.45 (d, 2H), 7.35 (d, 2H), 7.1 (s, 1H), 3.7 (m, 2H), 3.4 (m, 2H), 1.9 (m, 2H), 1.7-1.5 (m, 6H) | 2 | 13.65 | [M + H]⁺ 353.99 |
| AA-50 | 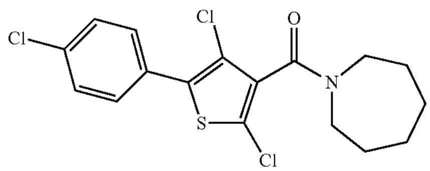 | 7.6 (d, 2H), 7.4 (d, 2H), 3.75 (t, 2H), 3.4 (m, 2H), 1.9 (m, 2H), 1.75-1.5 (m, 6H) | 2 | 14.20 | [M + H]⁺ 389.97 |
| AA-32 | 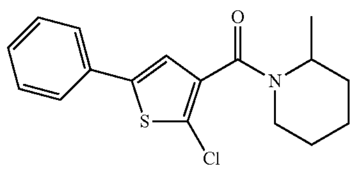 | — | 3 | 4.34 | [M + H]⁺ 320 |
| BB-04 | 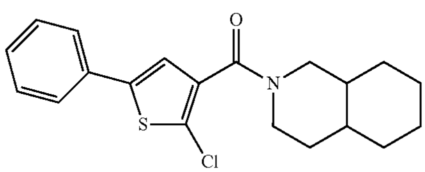 | — | 3 | 5.09 | [M + H]⁺ 360 |
| CC-02 | 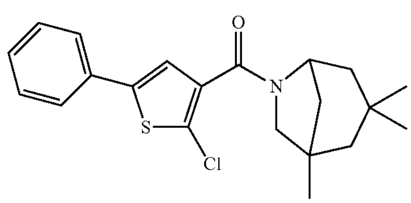 | — | 3 | 5.00 | [M + H]⁺ 374 |
| AA-33 | 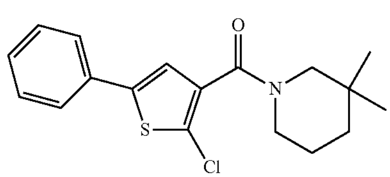 | — | 3 | 4.57 | [M + H]⁺ 334 |
| AA-41 | 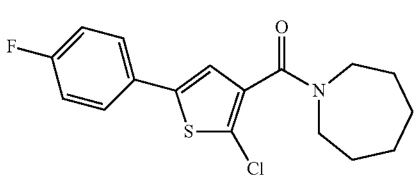 | — | 3 | 4.27 | [M + H]⁺ 338 |
| AA-37 | 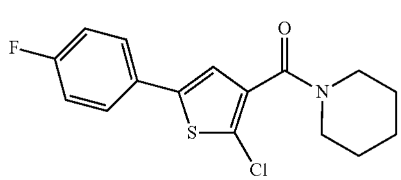 | — | 3 | 4.10 | [M + H]⁺ 324 |

-continued

| Code No. | Structure | ¹H NMR | Analytical Method | R.T. (min) | MS [m/z] |
|---|---|---|---|---|---|
| EE-10 | 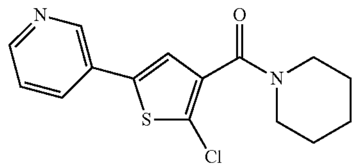 | — | 3 | 2.40 | [M + H]⁺ 307 |
| EE-09 | 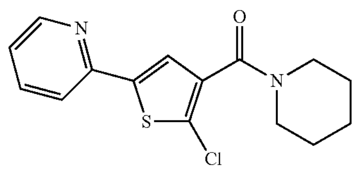 | — | 3 | 3.30 | [M + H]⁺ 307 |
| EE-11 | 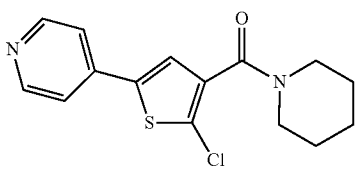 | — | 3 | 1.70 | [M + H]⁺ 307 |
| EE-14 | 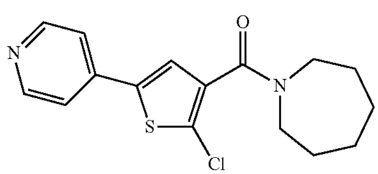 | — | 3 | 1.87 | [M + H]⁺ 321 |
| EE-13 | 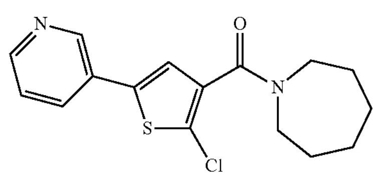 | — | 3 | 2.60 | [M + H]⁺ 321 |
| EE-15 | 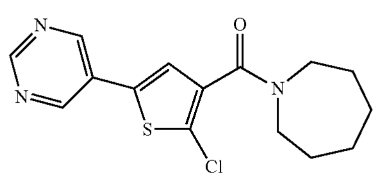 | — | 3 | 2.72 | [M + H]⁺ 322 |
| EE-12 | 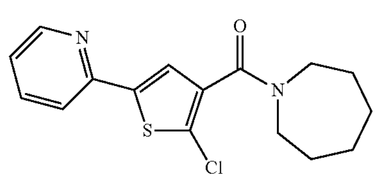 | — | 3 | 3.50 | [M + H]⁺ 321 |

Synthesis 20 cis-(5-Bromo-thiophen-3-yl)-(octahydro-quinolin-1-yl)-methanone

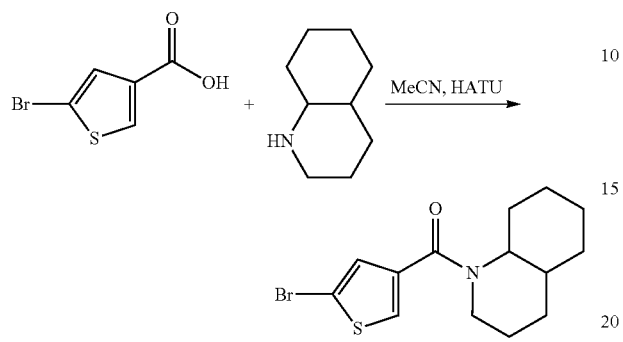

5-Bromo-thiophene-3-carboxylic acid (0.44 g, 2.18 mmol) was dissolved in acetonitrile (3 mL) and decahydroquinoline (a 3:2 mixture of cis- to trans-isomers; 2 mL) then HATU (2.18 mmol) was added. The reaction mixture was stirred overnight, and then the solvent evaporated and the residue purified by flash chromatography on silica eluting with 0-50% ethyl acetate in cyclohexane. The fractions containing the desired cis-product were concentrated under vacuum to give the title compound (0.63 g) as a colourless gum. LCMS m/z 330.36 [M+H]$^+$ R.T.=4.09 min. (Analytical Method 5).

Synthesis 21

(5-Imidazol-1-yl-thiophen-3-yl)-(octahydro-quinolin-1-yl)-methanone (FF-06) (CIS ISOMERS)

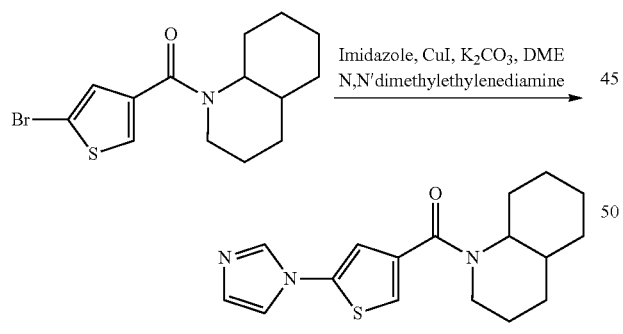

cis-(5-Bromo-thiophen-3-yl)-(octahydro-quinolin-1-yl)-methanone (0.15 mmol) was added to a solution of potassium carbonate (0.15 mmol), N,N'-dimethylethylene-diamine (0.03 mmol), imidazole (0.3 mmol) and copper (I) iodide (0.03 mmol) in DME (1 mL). The reaction mixture was heated under nitrogen to 120° C. for 90 hours and then diluted with DCM (5 mL) and washed with water. The organic solution was dried and filtered and the solvent evaporated. The residue was purified by HPLC, eluting with 10%-98% acetonitrile in water (0.1% formic acid) over 30 minutes. The fractions containing the desired product were concentrated under vacuum to give the title compound as a pale brown solid (26 mg). LCMS m/z 316.06 [M+H]$^+$ RT=6.44 min. (Analytical Method 2).

Synthesis 22

[5-(4H-Pyrazol-4-yl)-thiophen-3-yl]-(octahydro-quinolin-1-yl)-methanone (FF-09) (CIS ISOMERS)

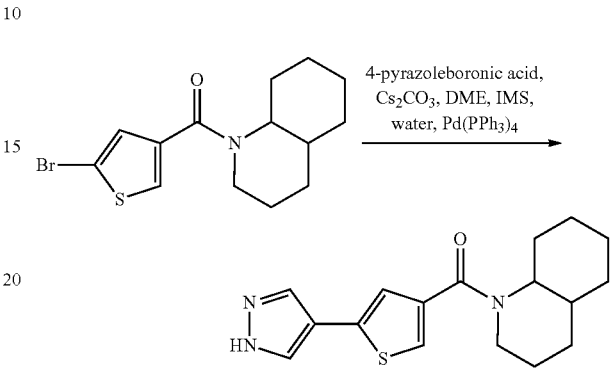

cis-(5-Bromo-thiophen-3-yl)-(octahydro-quinolin-1-yl)-methanone (0.15 mmol) was added to a solution of caesium carbonate (0.15 mmol), 4-pyrazoleboronic acid (0.3 mmol) and palladium tetrakis(triphenylphosphine) (0.03 mmol) in DME (6 mL), IMS (2 mL) and water (0.001 mL). The reaction mixture was heated by microwave irradiation to 140° C. for 20 minutes and then diluted with ethyl acetate (5 mL) and washed with water. The organic solution was dried and filtered and the solvent evaporated. The residue was purified by HPLC, eluting with 10%-98% acetonitrile in water (0.1% formic acid) over 30 minutes. The fractions containing the desired product were concentrated under vacuum to give the title compound as a pale yellow oil (10 mg). LCMS m/z 316.27 [M+H]$^+$ RT=9.34 min. (Analytical Method 2).

Synthesis 23

5-Pyridin-4-yl-thiophene-3-carboxylic acid ethyl ester

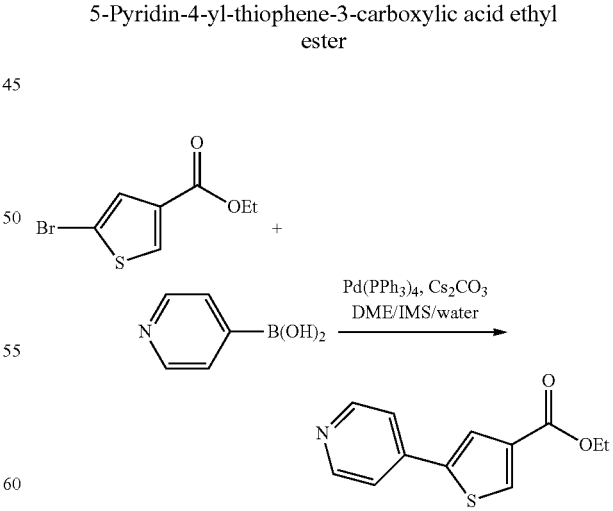

5-Bromo-thiophene-3-carboxylic acid ethyl ester (5.26 mmol), 4-pyridylboronic acid (5.26 mmol), caesium carbonate (7.9 mmol) and palladium (0) tetrakis-triphenylphosphine (0.53 mmol) were dissolved in a mixture of water (10 mL), IMS (20 mL) and DME (50 mL). The reaction mixture was Synthesis 25

Azepan-1-yl-(5-pyridin-4-yl-thiophen-3-yl)-methanone (EE-06)

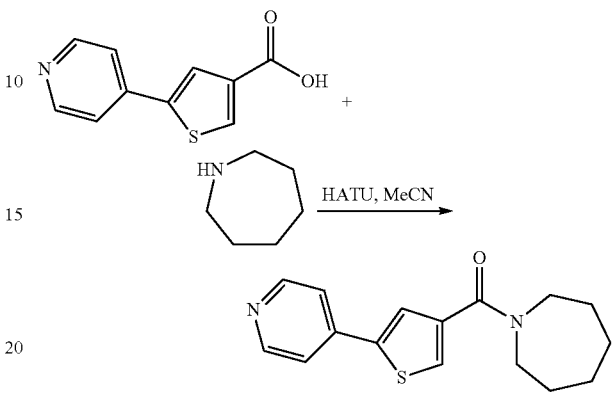

heated by microwave irradiation to 140° C. for 10 minutes, and then ether (100 mL) and water (20 mL) were added. The organic solution was washed with water, dried with anhydrous magnesium sulfate, filtered and the solvent evaporated to give brown oil. The residue was purified by flash chromatography on silica. The fractions containing the desired product were concentrated under vacuum to give the title compound (0.035 g) as an off-white solid. LCMS m/z 234.04 [M+H]$^+$ R.T.=2.10 min. (Analytical Method 5).

Synthesis 24

5-Pyridin-4-yl-thiophene-3-carboxylic acid

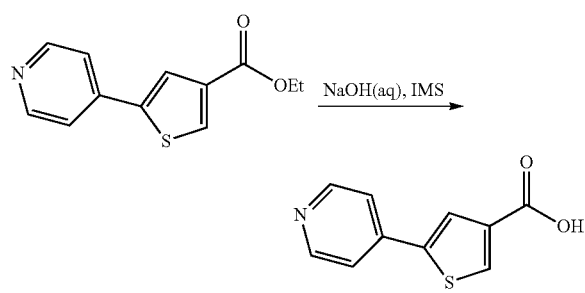

5-Pyridin-4-yl-thiophene-3-carboxylic acid ethyl ester (1.4 mmol) was dissolved in 1 M aqueous sodium hydroxide (4 mL) and IMS (5 mL). The mixture was heated by microwave irradiation at 130° C. for 10 minutes, and then filtered. 1 N Hydrochloric acid was added and the resulting precipitate was isolated by filtration washed with water and dried to give the title compound as a white solid (0.15 g). LCMS m/z 205.96 [M+H]$^+$ R.T.=1.51 min. (Analytical Method 5).

5-Pyridin-4-yl-thiophene-3-carboxylic acid (0.4 mmol) was dissolved in MeCN (2 mL). 1-[1,4]Diazepan-1-yl-ethanone (1.8 mmol), and HATU (0.4 mmol) were added and the reaction mixture stirred for 72 hours. DCM (20 mL) was added and the organic solution was separated and the solvent removed by evaporation. The residue was purified by HPLC, eluting with 10%-90% acetonitrile in water (0.1% formic acid) over 30 minutes. The fractions containing the desired product were concentrated under vacuum and freeze-dried to give the title compound as a white solid (33 mg). LCMS m/z 287.09 [M+H]$^+$ RT=5.20 min. (Analytical Method 2). $^1$H NMR (400 MHz, MeCN-d): δ 8.6 (d, 2H), 7.95 (d, 2H), 7.9 (s, 1H), 7.8 (s, 1H), 3.6 (t, 2H), 3.5 (t, 2H), 1.8-1.6 (m, 6H).

The following compounds were prepared using analogous methods.

| Code No. | Structure | $^1$H NMR | Analytical Method | R.T. (min) | MS [m/z] |
|---|---|---|---|---|---|
| EE-07 | 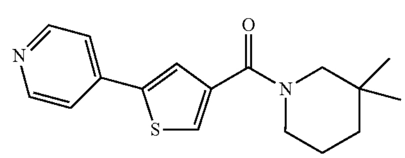 | DMSO-d: δ 8.6 (d, 2H), 7.75 (s, 1H), 7.7 (s, 1H), 7.6 (d, 2H), 3.5 (t, 2H), 3.2 (s, 2H), 1.6 (m, 2H), 1.4 (m, 2H), 0.9 (s, 6H) | 2 | 5.92 | 301.11 |
| FF-01 | 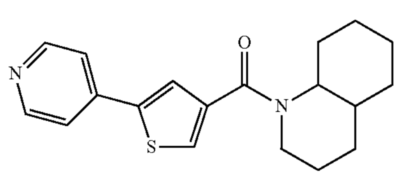 | — | 2 | 6.80 | 327.13 |
| GG-01 | 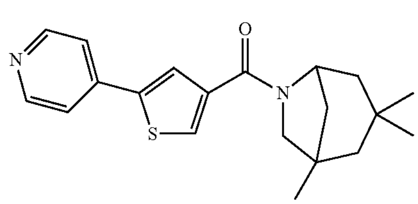 | — | 2 | 7.15 | 341.18 |

Synthesis 26

(5-Bromo-thiophen-3-yl)-(4,4-dimethyl-azepan-1-yl)methanone (EE-16)

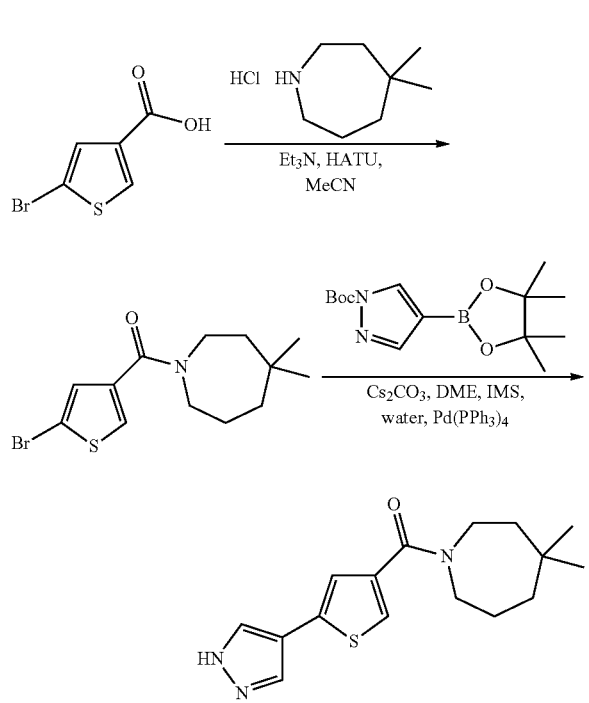

5-Bromo-thiophene-3-carboxylic acid (0.5 g, 2.42 mmol), 4,4-dimethyl-azepane hydrochloride (0.475 g, 2.91 mmol), triethylamine (1.01 mL, 7.25 mmol) and HATU (1.20 g, 3.16 mmol) were dissolved in acetonitrile (10 mL) and the resulting mixture stirred overnight. The mixture was diluted with water and extracted with DCM (×2). The organics were dried over sodium sulfate, filtered and evaporated. The crude material was purified by chromatography on a silica II cartridge, eluting with 10-25% ethyl acetate in cyclohexane. The fractions containing the desired product were concentrated under vacuum to give (5-bromo-thiophen-3-yl)-(4,4-dimethyl-azepan-1-yl)methanone (0.55 g).

This material (0.27 g, 0.85 mmol) was added to a solution of caesium carbonate (0.414 g, 1.27 mmol), 4-(4,4,5,5-tetramethyl-[1,3,2]dioxaborolan-2-yl)-pyrazole-1-carboxylic acid tert-butyl ester (0.275 g, 0.94 mmol) and palladium tetrakis(triphenylphosphine) (0.098 g, 0.085 mmol) in DME (6 mL), IMS (2 mL) and water (1 mL). The reaction mixture was heated by microwave irradiation to 140° C. for 20 minutes and then diluted with water and extracted with DCM (×2). The organic solution was dried over sodium sulfate, filtered and the solvent evaporated. The residue was purified by chromatography on a 5 g silica II cartridge, eluting with 10, 20, 33, 50, 75 and 100% ethyl acetate in cyclohexane. The fractions containing the desired product were concentrated under vacuum to give the title compound as a colourless oil (0.15 g). LCMS m/z 304.29 [M+H]+ R. T.=9.05 min (Analytical Method 2).

Synthesis 27

(4,4-Dimethyl-azepan-1-yl)-{5-[1-(2-hydroxy-ethyl)-1H-pyrazol-4-yl]-thiophen-3-yl}-methanone (EE-21)

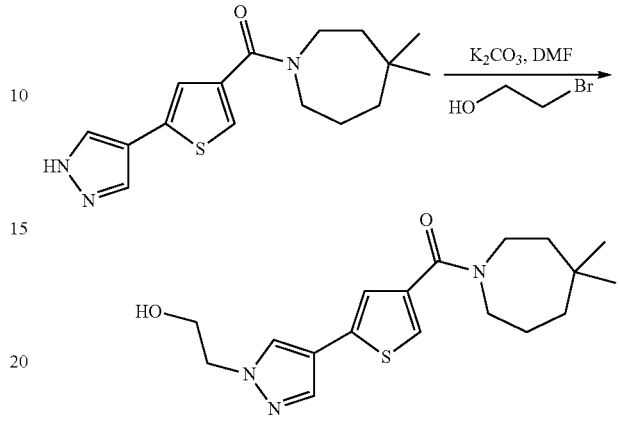

(4,4-Dimethyl-azepan-1-yl)-[5-(1H-pyrazol-4-yl)-thiophen-3-yl]-methanone (0.075 g, 0.25 mmol) was dissolved in DMF (1 mL) and potassium carbonate (44 mg, 0.32 mmol) was added followed by 2-bromoethanol (27 µL, 0.38 mmol). The reaction mixture was heated at 100° C. overnight then quenched by addition of ammonium chloride. The mixture was extracted with ethyl acetate (×2) then the organics were washed with lithium chloride (15% aqueous solution) and evaporated. The crude material was purified by chromatography on a silica II cartridge, eluting with 10-66% ethyl acetate in cyclohexane. The residue was purified by HPLC, eluting with 10%-98% acetonitrile in water (0.1% formic acid) over 20 minutes. The fractions containing the desired product were concentrated under vacuum and freeze-dried to give the title compound as a colourless oil (0.020 g). LCMS m/z 348.29 [M+H]+ R.T.=8.62 min (Analytical Method 2).

Synthesis 28

{5-[1-(2-Hydroxy-ethyl)-1H-pyrazol-4-yl]-thiophen-3-yl}-octahydro-quinolin-1-yl)-methanone (FF-13) (CIS ISOMERS)

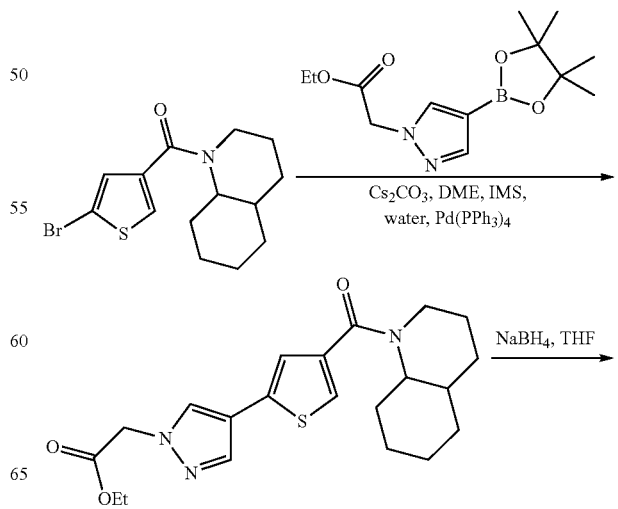

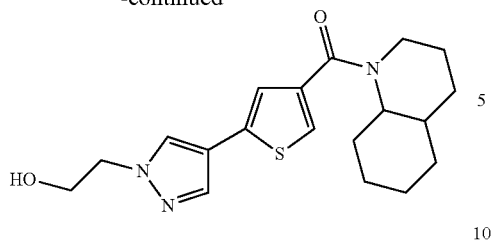

cis-(5-Bromo-thiophen-3-yl)-(octahydro-quinolin-1-yl)-methanone (0.217 g, 0.66 mmol) was added to a solution of caesium carbonate (0.32 g, 0.99 mmol), [4-(4,4,5,5-tetramethyl-[1,3,2]dioxaborolan-2-yl)-pyrazol-1-yl]acetic acid ethyl ester (0.203 g, 0.725 mmol) and palladium tetrakis (triphenylphosphine) (76 mg, 0.07 mmol) in DME (6 mL), IMS (2 mL) and water (1 mL). The reaction mixture was purged with nitrogen and heated by microwave irradiation to 140° C. for 20 minutes then diluted with water and extracted with DCM (×2). The organic solution was dried over sodium sulfate, filtered and the solvent evaporated. The crude material was purified by chromatography on a 5 g silica II cartridge, eluting with 10-50% ethyl acetate in cyclohexane then columned using 0-25% diethyl ether in DCM to afford {4-[4-(octahydro-quinoline-1-carbonyl)-thiophen-2-yl]-pyrazol-1-yl}-acetic acid ethyl ester (164 mg). LCMS m/z 402.41 [M+H]$^+$ R.T.=3.91 min (Analytical Method 6).

A portion of this material (0.054 g, 0.14 mmol) was dissolved in THF (1 mL) and sodium borohydride (0.008 g, 0.21 mmol) was added. The mixture was stirred for 72 hours then was treated with HCl (1 M, pH adjusted to 4). The solution was extracted with DCM (×3) then the organics were dried over sodium sulfate, filtered and evaporated. The residue was purified by HPLC, eluting with 10%-98% acetonitrile in water (0.1% formic acid) over 20 minutes and the fractions containing the desired product were freeze-dried to give the title compound as a white solid (0.018 g). LCMS m/z 360.27 [M+H]$^+$ R.T.=8.95 min (Analytical Method 2).

Synthesis 29

(4,4-Dimethyl-azepan-1-yl)-[5-(1H-pyrazol-4-yl)-thiophen-3-yl]-methanone (EE-22)

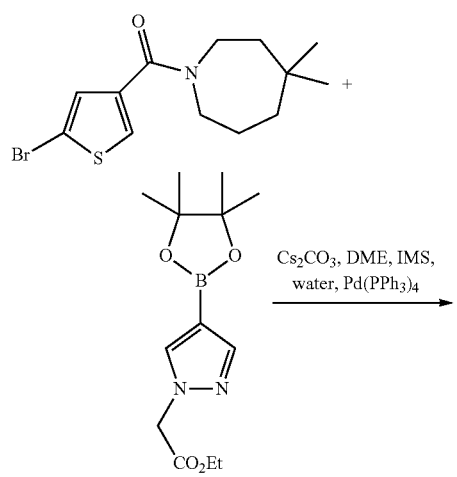

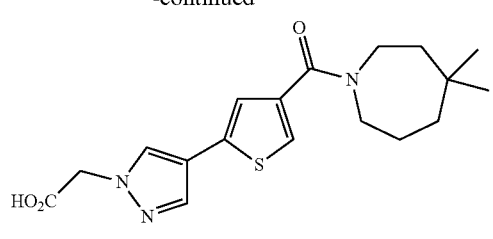

(5-Bromo-thiophen-3-yl)-(4,4-dimethyl-azepan-1-yl)-methanone (0.31 g, 0.99 mmol), together with caesium carbonate (0.483 g, 1.49 mmol),), [4-(4,4,5,5-tetramethyl-[1,3,2]dioxaborolan-2-yl)-pyrazol-1-yl]-acetic acid ethyl ester (0.28 g, 1.0 mmol) and palladium tetrakis(triphenylphosphine) (114 mg, 0.1 mmol) were taken up in DME (9 mL), IMS (2 mL) and water (1 mL) and the vessel was purged with argon. The reaction mixture was heated by microwave irradiation to 140° C. for 20 minutes and then diluted with water then treated with dilute HCl (pH adjusted to 4) and extracted with DCM (×3). The organic solution was dried over sodium sulfate, filtered and the solvent evaporated. The residue was purified by chromatography on a silica II cartridge, eluting with 50 then 100% ethyl acetate in cyclohexane then 5% acetic acid in ethyl acetate. The residue was further purified by HPLC, eluting with 10%-98% acetonitrile in water (0.1% formic acid) and the fractions containing desired product were freeze-dried to give the title compound (0.015 g). LCMS m/z 362.24 [M+H]$^+$ R.T.=8.84 min (Analytical Method 2).

Synthesis 30

{5-[1-(2-Morpholin-4-yl-ethyl)-1H-pyrazol-4-yl]-thiophen-3-yl}-(octahydro-quinolin-1yl)-methanone formate (FF-14) (CIS ISOMERS)

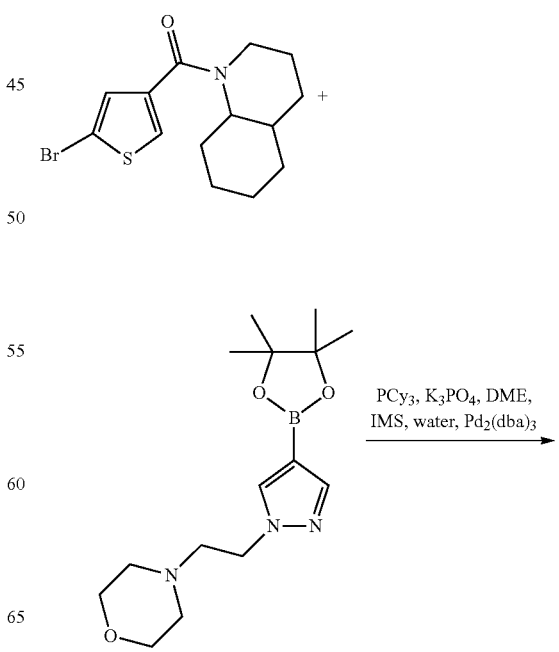

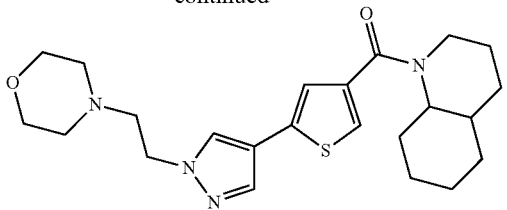

cis-(5-Bromo-thiophen-3-yl)-(octahydro-quinolin-1-yl)-methanone (0.06 g, 0.18 mmol) was mixed with 4-{2-[4-(4,4,5,5-tetramethyl-[1,3,2]dioxaborolan-2-yl)-pyrazol-1-yl]-ethyl}-morpholine (0.062 g, 0.2 mmol), tricyclohexylphosphine (0.004 g, 0.01 mmol), potassium phosphate (0.047 g, 0.22 mmol) and tris(dibenzylideneacetone)dipalladium (0) (0.007 g, 0.008 mmol) in DME (2 mL), IMS (0.5 mL) and water (0.25 mL). The reaction mixture was purged with argon then heated by microwave irradiation to 140° C. for 20 minutes.

The resultant mixture was diluted with water and extracted with DCM (×2) then the organic phase was dried over sodium sulfate, filtered and the solvent evaporated. The residue was purified by HPLC, eluting with 10%-98% acetonitrile in water (0.1% formic acid) over 20 minutes. The fractions containing the desired product were freeze-dried to give the title compound (0.029 g). LCMS m/z 429.25 [M+H]+ R.T.=7.03 min (Analytical Method 2).

Synthesis 31

2-{4-[4-(4,4-Dimethyl-azepane-1-carbonyl)-thiophen-2-yl]-pyrazol-1-yl}-N-methyl-acetamide (EE-23)

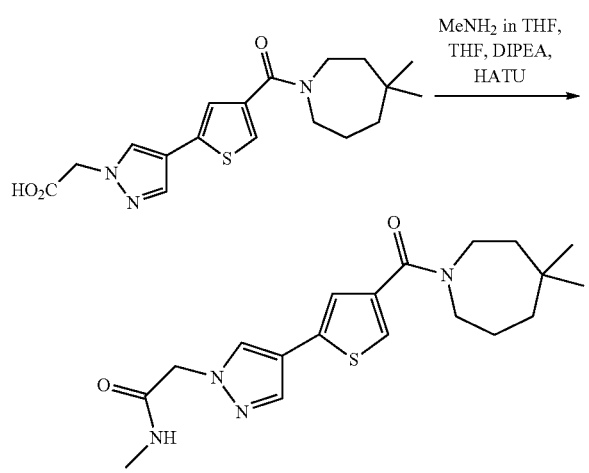

(4,4-Dimethyl-azepan-1-yl)-[5-(1H-pyrazol-4-yl)-thiophen-3-yl]-methanone (0.052 g, 0.14 mmol) was dissolved in THF (1 mL) and DIPEA (32 µL, 0.19 mmol) and methylamine (2 M in THF, 94 µL, 0.19 mmol) were added followed by HATU (0.066 g, 0.17 mmol). The reaction mixture was stirred at room temperature for 2 hours and then diluted with water and extracted with DCM (×3). The organic solution was dried over sodium sulfate, filtered and the solvent evaporated. The residue was purified by HPLC, eluting with 10%-98% acetonitrile in water (0.1% formic acid) over 20 minutes. The fractions containing the desired product were freeze-dried to give the title compound as a white solid (0.029 g). LCMS m/z 375.29 [M+H]+ R.T.=8.49 min (Analytical Method 2).

Synthesis 32

[5-(3-Methyl-1H-pyrazol-4-yl)-thiophen-3-yl]-(octahydro-quinolin-1-yl)-methanone (FF-15) (CIS ISOMERS)

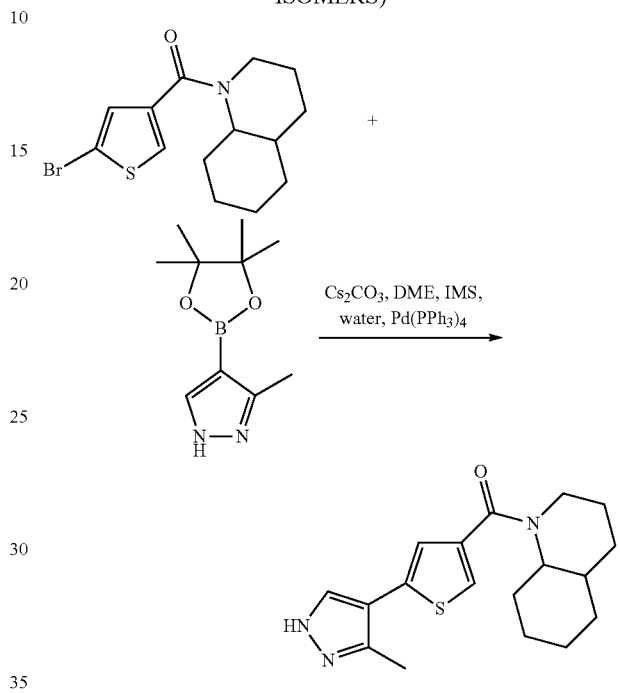

cis-(5-Bromo-thiophen-3-yl)-(octahydro-quinolin-1-yl)-methanone (0.09 g, 0.27 mmol) was combined with 3-methyl-4-(4,4,5,5-tetramethyl-[1,3,2]dioxaborolan-2-yl)-1H-pyrazole (62 mg, 0.3 mmol), caesium carbonate (0.134 g, 0.41 mmol), and palladium tetrakis(triphenylphosphine) (0.031 g, 0.03 mmol) in DME (3 mL), IMS 0.6 mL) and water (0.3 mL). The reaction mixture was degassed then heated by microwave irradiation to 140° C. for 20 minutes then further quantities of 3-methyl-4-(4,4,5,5-tetramethyl-[1,3,2]dioxaborolan-2-yl)-1H-pyrazole (0.062 g), caesium carbonate (0.067 g), and palladium tetrakis(triphenylphosphine) (0.031 g) were added. The mixture was heated by microwave irradiation to 140° C. for 20 minutes followed by addition of 3-methyl-4-(4,4,5,5-tetramethyl-[1,3,2]dioxaborolan-2-yl)-1H-pyrazole (0.062 g) and further heating at 140° C. for 20 minutes. Further quantities of 3-methyl-4-(4,4,5,5-tetramethyl-[1,3,2]dioxaborolan-2-yl)-1H-pyrazole (0.062 g), caesium carbonate (0.097 g), and palladium tetrakis(triphenylphosphine) (0.031 g) were added and the mixture heated by microwave irradiation to 140° C. for a final 20 minutes before diluting with water and extraction with DCM (×3). The organic solution was dried over sodium sulfate, filtered and the solvent removed by evaporation. The residue was purified by chromatography on a silica II cartridge, eluting with 10-50% ethyl acetate in cyclohexane and then was further purified by HPLC, eluting with 5%-98% acetonitrile in water (0.1% formic acid) over 20 minutes. The fractions containing the desired product were freeze-dried to give the title compound as a white solid (0.027 g). LCMS m/z 330.30 [M+H]+ R.T.=9.62 min (Analytical Method 2).

Synthesis 33

(4,4-Dimethyl-azepan-1-yl)-[5-(3-methyl-1H-pyrazol-4-yl)-thiophen-3-yl]-methanone (EE-24)

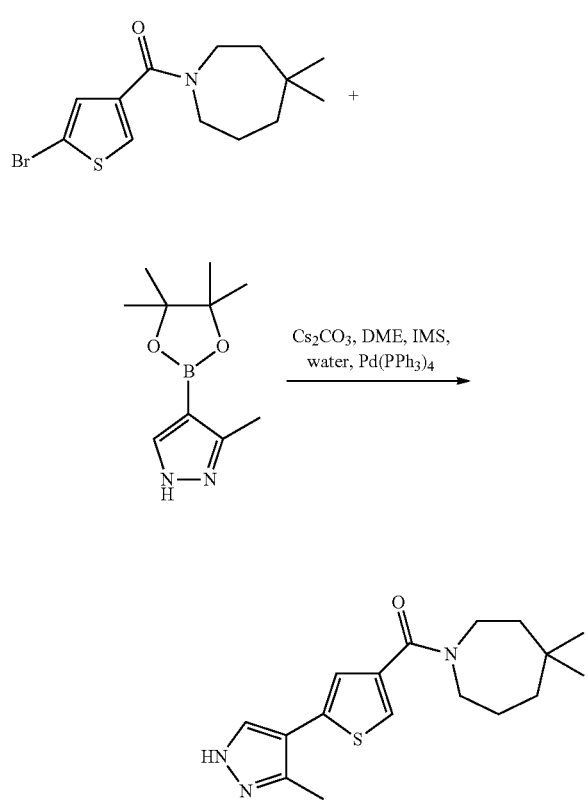

(5-Bromo-thiophen-3-yl)-(4,4-dimethyl-azepan-1-yl)-methanone (0.105 g, 0.33 mmol) together with 3-methyl-4-(4,4,5,5-tetramethyl-[1,3,2]dioxaborolan-2-yl)-1H-pyrazole (83 mg, 0.4 mmol), caesium carbonate (0.150 g, 0.46 mmol), and palladium tetrakis(triphenylphosphine) (0.057 g, 0.05 mmol) in DME (3 mL), IMS 1 mL) and water (0.5 mL) was degassed then heated by microwave irradiation to 140° C. for 20 minutes. Further quantities of 3-methyl-4-(4,4,5,5-tetramethyl-[1,3,2]dioxaborolan-2-yl)-1H-pyrazole (0.035 g), caesium carbonate (0.054 g), and palladium tetrakis(triphenylphosphine) (19 mg) were added and the mixture was heated by microwave irradiation to 140° C. for 20 minutes before diluting with water and extracting with DCM (×3). The organic solution was dried over sodium sulfate, filtered and the solvent evaporated. The residue was purified by chromatography on a silica II cartridge, eluting with 10-60% ethyl acetate in cyclohexane and then was further purified by HPLC using a phenyl hexyl column, eluting with 15%-95% acetonitrile in water (0.1% formic acid) over 20 minutes. The fractions containing the desired product were freeze-dried then taken up as a solution in methanol and dried to give the title compound as a colourless semi-solid (0.016 g). LCMS m/z 318.28 [M+H]$^+$ R.T.=9.29 min (Analytical Method 2).

Synthesis 34

5-(2-Methyl-2H-pyrazol-3-yl)-thiophene-3-carboxylic acid

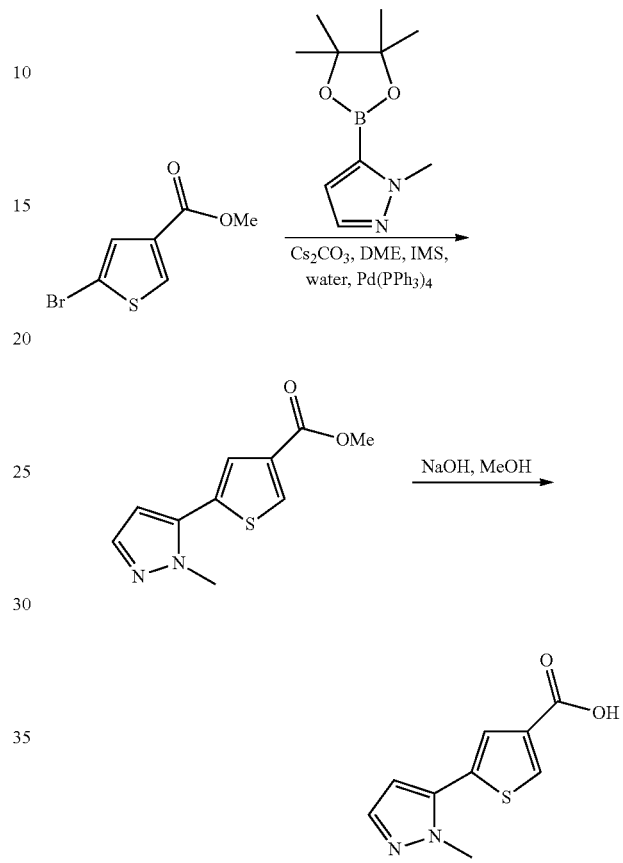

5-Bromo-thiophene-3-carboxylic acid methyl ester (0.193 g, 0.87 mmol) was combined with 1-methyl-5-(4,4,5,5-tetramethyl-[1,3,2]dioxaborolan-2-yl)-1H-pyrazole (0.2 g, 0.96 mmol), caesium carbonate (0.424 g, 1.3 mmol), and palladium tetrakis(triphenylphosphine) (0.1 g, 0.09 mmol) in DME (10 mL), IMS 2 mL) and water (1 mL). The reaction mixture was degassed then heated by microwave irradiation to 140° C. for 20 minutes. The mixture was diluted with water then extracted with DCM (×3) then the organic solution was dried over sodium sulfate, filtered and the solvent evaporated. The residue was purified by chromatography on a 5 g silica II cartridge, eluting with 5-30% ethyl acetate in cyclohexane to give 5-(2-methyl-2H-pyrazol-3-yl)-thiophene-3-carboxylic acid methyl ester as a brown oil (0.163 g). LCMS m/z 223.24 [M+H]$^+$ R.T.=3.24 min (Analytical Method 6).

5-(2-Methyl-2H-pyrazol-3-yl)-thiophene-3-carboxylic acid methyl ester (0.163 g, 073 mmol) was suspended in methanol (1 mL) then sodium hydroxide (1 M, 0.95 mL) was added and the mixture stirred for 2 hours. The solution was evaporated, the residue was taken up in HCl (1 N, 1.5 mL) and the resultant precipitate was collected by filtration and dried in vacuo to afford the title compound as a white solid (0.084 g). LCMS m/z 209.15 [M+H]$^+$ R.T.=2.76 min (Analytical Method 6).

Synthesis 35

[5-(2-Methyl-2H-pyrazol-3-yl)-thiophen-3-yl]-octahydro-quinolin-1-yl-methanone (FF-18) (DHQ [CIS-S])

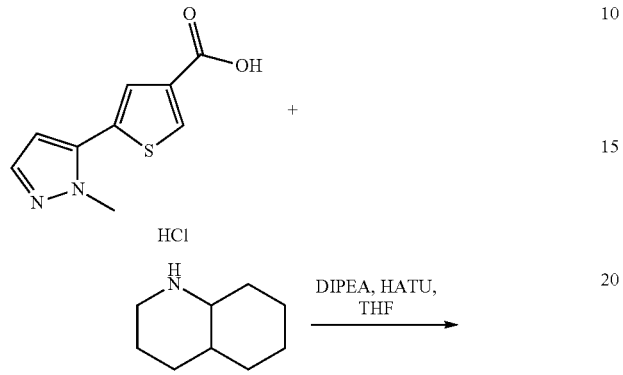

5-(2-Methyl-2H-pyrazol-3-yl)-thiophene-3-carboxylic acid (0.084 g, 0.40 mmol) was dissolved in THF (2 mL) then DIPEA (0.22 mL, 1.3 mmol) and cis-decahydro-quinoline hydrochloride (DHQ [CIS-S]) (0.084 g, 0.48 mmol) were added followed by HATU (0.182 g, 0.48 mmol). The resulting mixture was stirred overnight then the mixture was diluted with water and extracted with DCM (×2). The organics were dried over sodium sulfate, filtered and evaporated. The crude material was purified by chromatography on a silica II cartridge, eluting with 50-100% ethyl acetate in cyclohexane. The fractions containing the desired product were concentrated under vacuum to give the title compound as a colourless oil (0.101 g). LCMS m/z 330.19 [M+H]$^+$ R.T.=10.43 min (Analytical Method 2).

Synthesis 36

5-Oxazol-2-yl-thiophene-3-carboxylic acid methyl ester

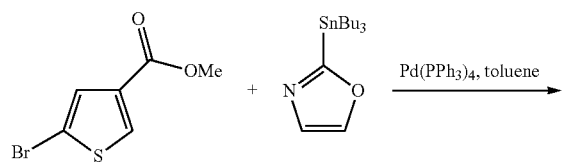

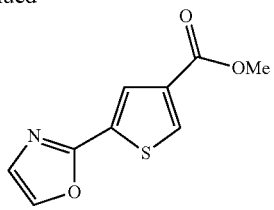

5-Bromo-thiophene-3-carboxylic acid methyl ester (0.3 g, 1.35 mmol) was dissolved in toluene (5 mL), 2-tributylstannyl oxazole (0.311 mL, 1.48 mmol) was added then the reaction mixture was purged with nitrogen before addition of palladium tetrakis(triphenylphosphine) (0.14 g, 0.12 mmol). The reaction mixture was heated at 100° C. over the weekend. The mixture was filtered then evaporated and the residue was purified by chromatography on a silica II cartridge, eluting with 10-20% DCM in pentane to give the title compound as a yellow solid (0.105 g). LCMS m/z 210 [M+H]$^+$ and 251.23 [M+MeCN+H]$^+$ R.T.=3.03 min (Analytical Method 6).

Synthesis 37 cis-Octahydro-quinolin-1-yl-(5-oxazol-2-yl-thiophen-3-yl)-methanone (FF-19) (DHQ [CIS-S])

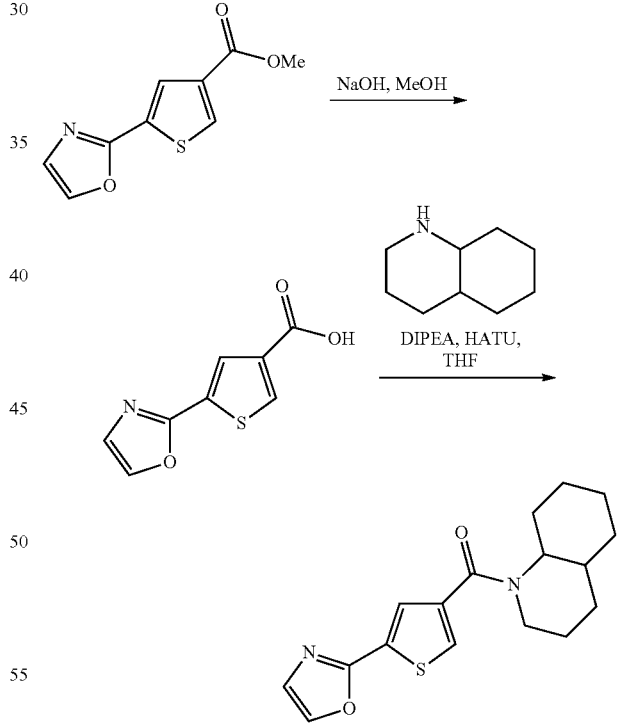

5-Oxazol-2-yl-thiophene-3-carboxylic acid methyl ester (0.105 g, 0.50 mmol) was suspended in methanol (1 mL) then sodium hydroxide (1 M, 0.603 mL) was added and the mixture stirred for 2 hours. A further portion of sodium hydroxide (1 M, 0.60 mL) was added and the mixture stirred overnight. The solution was evaporated, the residue was taken up in HCl (1 N, 1.5 mL) and the resultant precipitate was collected by filtration, washed with water and dried to afford 5-oxazol-2-yl-thiophene-3-carboxylic acid as a tan solid (0.072 g).

This material (0.072 g, 0.37 mmol) was suspended in THF (1 mL) then DIPEA (0.202 mL, 1.18 mmol) and cis-decahydro-quinoline hydrochloride (DHQ [CIS-S]) (0.078 g, 0.44 mmol) were added followed by HATU (0.169 g, 0.44 mmol). The resulting mixture was stirred for 3 hours and then was diluted with water and extracted with DCM (×2). The organics were dried over sodium sulfate, filtered and evaporated. The crude material was purified by chromatography on a 2 g silica II cartridge, eluting with 10-20% ethyl acetate in cyclohexane to afford the title compound as a colourless oil (0.071 g). LCMS m/z 317.18 [M+H]+ R.T.=10.48 min (Analytical Method 2).

Synthesis 38

5-(1-Methyl-1H-pyrazol-3-yl)-thiophene-3-carboxylic acid methyl ester

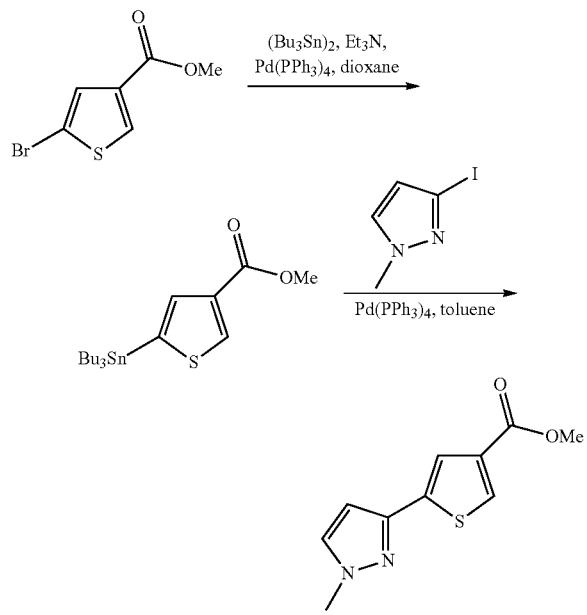

5-Bromo-thiophene-3-carboxylic acid methyl ester (0.484 g, 2.19 mmol), hexabutylditin (1.99 mL, 3.95 mmol) and triethylamine (7 mL) were dissolved in dioxane (15 mL) then the solution was degassed with nitrogen before the addition of palladium tetrakis(triphenylphosphine) (0.152 g, 0.13 mmol). The reaction mixture was heated to reflux overnight then filtered and evaporated. The crude material was purified by chromatography on a silica II cartridge, eluting with 2-10% DCM in pentane to afford 5-tributylstannanyl-thiophene-3-carboxylic acid methyl ester as a colourless oil (0.228 g).

This material (0.225 g, 0.52 mmol) was dissolved in toluene (5 mL), 3-iodo-1-methyl-1H-pyrazole (0.119 g, 0.57 mmol) was added then the reaction mixture was purged with nitrogen before addition of palladium tetrakis(triphenylphosphine) (0.06 g, 0.05 mmol). The reaction mixture was heated at 115° C. for two days then filtered and evaporated. The residue was purified by chromatography on a silica II cartridge, eluting with 5-20% ethyl acetate in cyclohexane to give the title compound as a yellow-brown oil which solidified on standing (0.076 g). LCMS m/z 223.01 [M+H]+ and R.T.=3.04 min (Analytical Method 7).

Synthesis 39

[5-(2-Methyl-2H-pyrazol-3-yl)-thiophen-3-yl]-octahydro-quinolin-1-yl-methanone (FF-20) (DHQ [CIS-S])

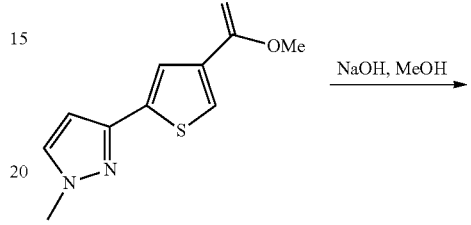

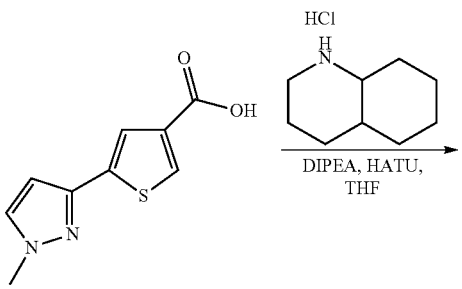

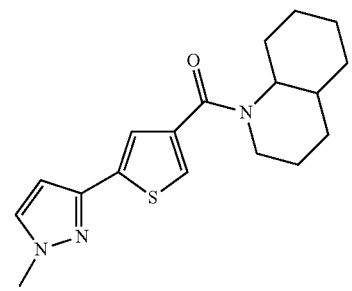

5-(2-Methyl-2H-pyrazol-3-yl)-thiophene-3-carboxylic acid methyl ester (0.076 g, 0.34 mmol) was suspended in methanol (0.75 mL) then sodium hydroxide (1 M, 0.41 mL) was added and the mixture stirred for 1.5 hours. A further amount of sodium hydroxide (1 M, 0.41 mL) was added and the mixture stirred overnight. The solution was evaporated, the residue was taken up in HCl (1 N, 1.0 mL) and the resultant precipitate was collected by filtration, washed with water and dried to afford 5-(1-methyl-1H-pyrazol-3-yl)-thiophene-3-carboxylic acid as a grey solid (0.042 g).

This material (0.042 g, 0.20 mmol) was suspended in THF (1 mL) then DIPEA (0.11 mL, 0.64 mmol) and cis-decahydro-quinoline hydrochloride (DHQ [CIS-S]) (0.043 g, 0.24 mmol) were added followed by HATU (91 mg, 0.24 mmol). The resulting mixture was stirred for 3 hours and then diluted with water and extracted with DCM (×3). The organics were dried over sodium sulfate, filtered and evaporated. The crude material was purified by chromatography on a silica II cartridge, eluting with 10-33% ethyl acetate in cyclohexane to give the title compound as an off-white oil (0.048 g). LCMS m/z 330.20 [M+H]+ R.T.=10.40 min (Analytical Method 2).

Synthesis 40

5-(5-Methyl-1H-pyrazol-3-yl)-thiophene-3-carboxylic acid methyl ester

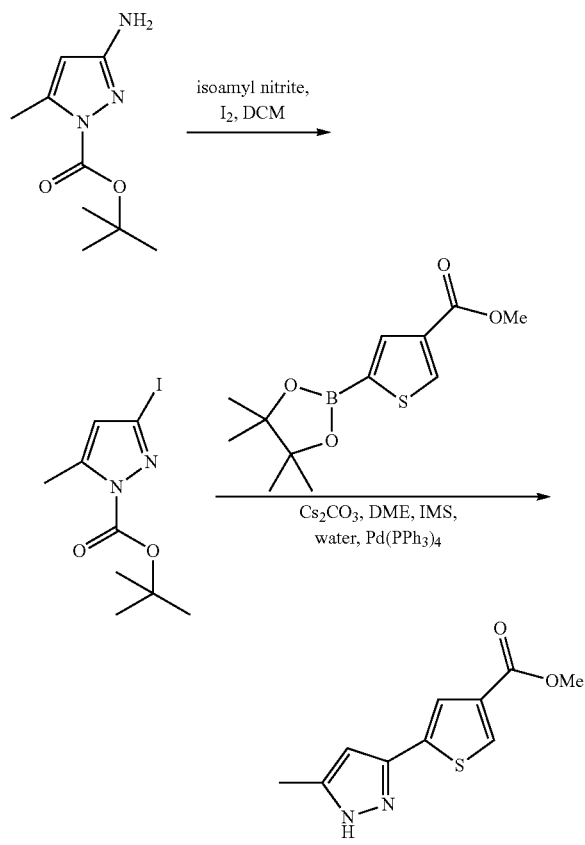

Iodine (0.774 g, 3.0 mmol) was dissolved in DCM (5 mL) then isoamyl nitrite (0.682 mL, 5.1 mmol) was added followed by the slow addition of 3-amino-5-methyl-pyrazole-1-carboxylic acid tert-butyl ester (0.50 g, 2.54 mmol) as a solution in DCM (4 mL). The reaction mixture was stirred at room temperature for 1.5 hours and then poured onto saturated sodium thiosulfate solution. The phases were separated and the aqueous layer was extracted with DCM (×3). The organics were washed with brine then dried over sodium sulfate, filtered and evaporated. The crude material was purified by chromatography on a silica II cartridge, eluting with 2-6% ethyl acetate in pentane to give 3-iodo-5-methyl-pyrazole-1-carboxylic acid tert-butyl ester as a solid (0.13 g).

5-(4,4,5,5-Tetramethyl-[1,3,2]dioxaborolan-2-yl)-thiophene-3-carboxylic acid methyl ester (0.10 g, 0.37 mmol) was dissolved in DME (3 mL), IMS 1 mL) and water (0.5 mL) and 3-iodo-5-methyl-pyrazole-1-carboxylic acid tert-butyl ester (0.125 g, 0.41 mmol) was added followed by caesium carbonate (0.18 g, 0.56 mmol). The mixture was degassed and purged with nitrogen then palladium tetrakis(triphenylphosphine) (0.043 g, 0.04 mmol) was added. The reaction mixture was purged with nitrogen then heated by microwave irradiation to 140° C. for 20 minutes. The mixture was diluted with water then extracted with DCM (×3) then the organic solution was dried over sodium sulfate, filtered and the solvent evaporated. The residue was purified by chromatography on a 5 g silica II cartridge, eluting with 10-33% ethyl acetate in cyclohexane to give the title compound as a tan semi-solid material (0.052 g). LCMS m/z 223.02 [M+H]$^+$ R.T.=2.93 min (Analytical Method 6).

Synthesis 41

[5-(5-Methyl-1H-pyrazol-3-yl)-thiophen-3-yl]-octahydro-quinolin-1-yl-methanone (FF-21) (DHQ [CIS-S])

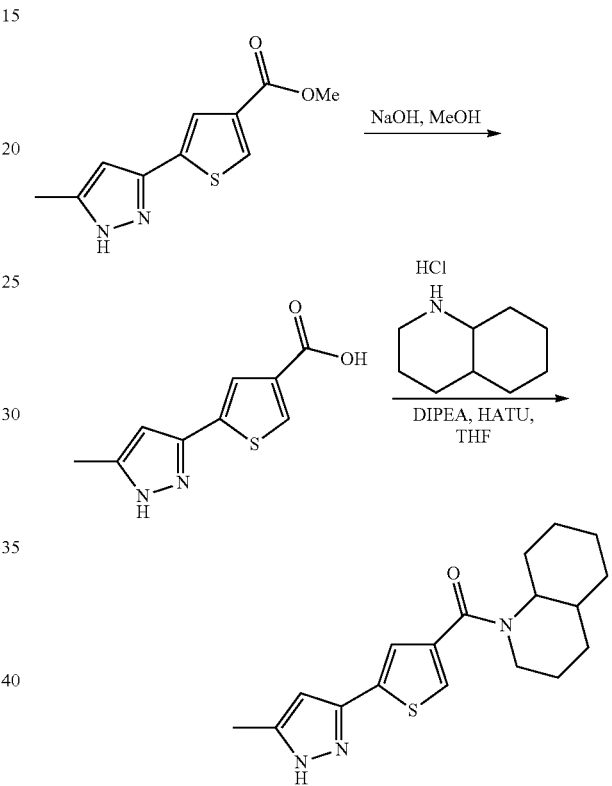

5-(5-Methyl-1H-pyrazol-3-yl)-thiophene-3-carboxylic acid methyl ester (0.052 g, 0.23 mmol) was suspended in methanol (0.75 mL) then sodium hydroxide (1 M, 0.70 mL) was added and the mixture stirred overnight. The solution was evaporated and the residue was taken up in HCl (1 N, 1.0 mL). The resultant fine precipitate, 5-(5-methyl-1H-pyrazol-3-yl)-thiophene-3-carboxylic acid, was collected by evaporation (0.048 g).

This material (0.048 g, 0.23 mmol) was suspended in THF (1 mL) then DIPEA (0.126 mL, 0.74 mmol) and cis-decahydro-quinoline hydrochloride (DHQ [CIS-S]) (0.049 g, 0.28 mmol) were added followed by HATU (0.105 g, 0.28 mmol). The resulting mixture was stirred for 3 hours and then diluted with water and extracted with DCM (×2). The organics were dried over sodium sulfate, filtered and evaporated. The residue was purified by HPLC, eluting with 5%-95% acetonitrile in water (0.1% formic acid) over 20 minutes. The fractions containing the desired product were freeze-dried to give the title compound as a white solid (0.023 g). LCMS m/z 330.19 [M+H]$^+$ R.T.=10.01 min (Analytical Method 2).

Synthesis 42

5-(2-Bromo-acetyl)-thiophene-3-carboxylic acid methyl ester

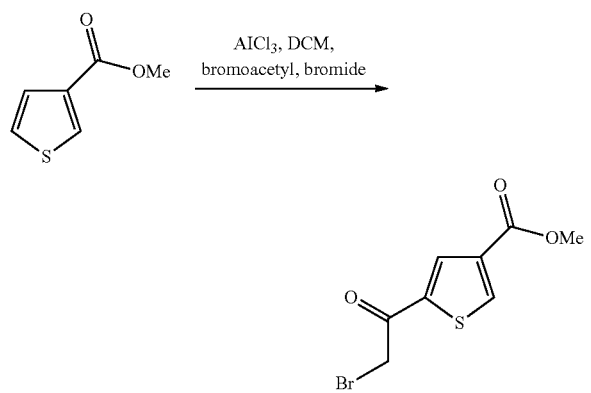

Aluminium trichloride (4.26 g, 32.0 mmol) was dissolved in DCM (15 mL) and cooled to 0° C. Bromoacetyl bromide (1.78 mL, 20.4 mmol) was added slowly as a solution in DCM (7 mL) and stirred at 0° C. for 1 hour. Thiophene-3-carboxylic acid methyl ester (2.89 g, 20.4 mmol) was then added slowly as a solution in DCM (15 mL) and the mixture stirred overnight warming to room temperature. The mixture was poured into ice/water and extracted with DCM (×2) then the organics were washed with water, dried over sodium sulfate, filtered and evaporated. The residue was purified by chromatography on a 50 g silica II cartridge, eluting with 2:1 pentane:DCM to neat DCM, to give the title compound as a white solid (2.1 g). $^1$H NMR (400 MHz, CHCl$_3$-d): δ 8.4 (d, 1H), 8.2 (d, 1H), 4.4 (s, 2H), 3.9 (s, 3H).

Synthesis 43

[5-(1H-Imidazol-4-yl)-thiophen-3-yl]-octahydro-quinolin-1-yl-methanone (FF-22) (DHQ [CIS-S])

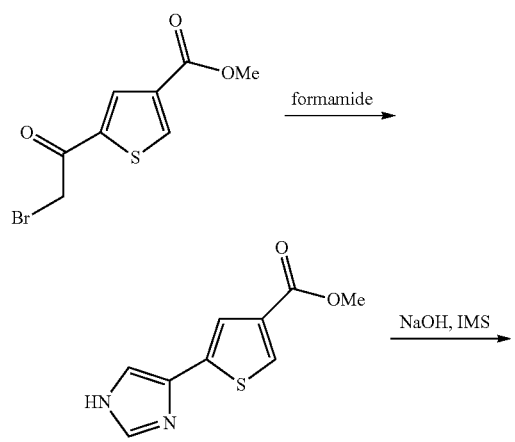

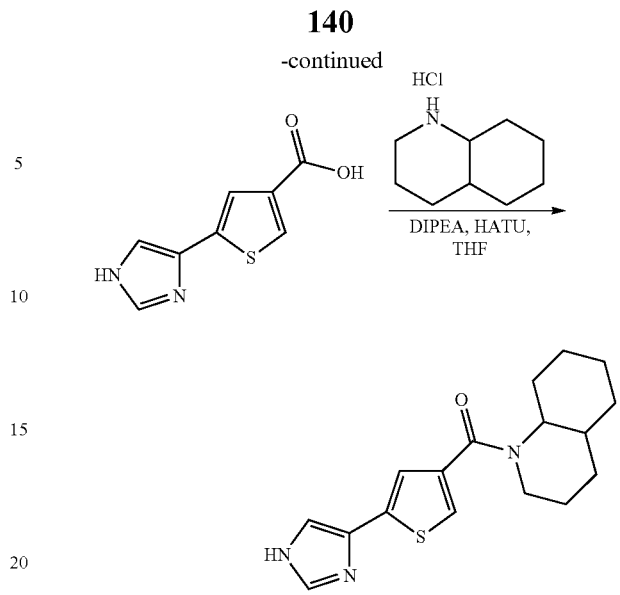

5-(2-Bromo-acetyl)-thiophene-3-carboxylic acid methyl ester (0.4 g, 1.52 mmol) was dissolved in formamide (2 mL) and the tube purged with nitrogen and then sealed. The mixture was heated at 170° C. for 20 minutes. The resultant solution was diluted with HCl (1 M) and water and washed with ethyl acetate. The organic phase was evaporated then purified by chromatography on a silica II cartridge, eluting with 2:1 pentane:DCM to neat DCM, to give the side product, 5-oxazol-4-yl-thiophene-3-carboxylic acid methyl ester as white solid (0.049 g). LCMS m/z 251.35 [M+MeCN+H]$^+$ R.T.=3.07 min (Analytical Method 6).

The aqueous phase was basified to pH 8 (with sodium hydrogen carbonate) and extracted with ethyl acetate (×3). The organics were dried over sodium sulfate, filtered and evaporated. The residue was purified by chromatography on a silica II cartridge, eluting with 2:1 cyclohexane:ethyl acetate to neat ethyl acetate, to give 5-(1H-imidazol-4-yl)-thiophene-3-carboxylic acid methyl ester as an off-white solid (0.115 g). LCMS 1.73 m/z 250.35 (M+MeCN) (Analytical Method 6).

This material (0.115 g) was suspended in IMS (1.5 mL), sodium hydroxide (1 M, 1.66 mL) was added and the mixture stirred overnight at room temperature. The mixture was quenched with HCl (1 N, pH adjusted to 7) and then concentrated to afford 5-(1H-imidazol-4-yl)-thiophene-3-carboxylic acid as a pale tan solid (0.212 g).

This material (0.107 g, 0.55 mmol) was suspended in acetonitrile (2 mL) then DIPEA (0.301 mL, 1.76 mmol) was added followed by cis-decahydro-quinoline hydrochloride (DHQ [CIS-S]) (0.106 g, 0.60 mmol) then HATU (0.251 g, 0.66 mmol). The resulting mixture was stirred over the weekend then diluted with water and extracted with DCM (x 2). The organics were dried over sodium sulfate, filtered and evaporated. The residue was purified by HPLC, eluting with 5%-95% acetonitrile in water (0.1% formic acid) over 20 minutes. The fractions containing the desired product were freeze-dried to give the title compound as a white solid (0.007 g). LCMS m/z 316.15 [M+H]$^+$ R.T.=6.49 min (Analytical Method 2).

Synthesis 44

(4aS,8aS)-Octahydro-quinolin-1-yl-(5-oxazol-4-yl-thiophen-3-yl)-methanone (FF-23) (DHQ [CIS-S])

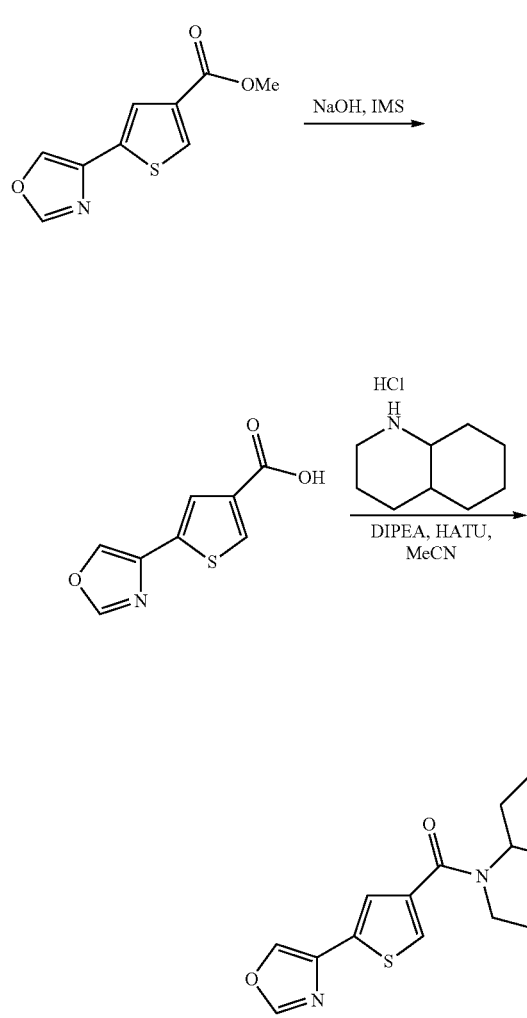

5-Oxazol-4-yl-thiophene-3-carboxylic acid methyl ester (0.049 g, 0.23 mmol) was suspended in IMS (1 mL), sodium hydroxide (1 M, 0.35 mL) was added and the mixture stirred for 60 hours at room temperature. The mixture was quenched with HCl (1 N, 0.35 mL) and then concentrated, azeotroping twice with methanol to afford 5-oxazol-4-yl-thiophene-3-carboxylic acid as a white solid (0.045 g).

This material (0.045 g, 0.23 mmol) was suspended in acetonitrile (1 mL) then DIPEA (0.126 mL, 0.74 mmol) was added followed by cis-decahydro-quinoline hydrochloride (DHQ [CIS-S]) (0.045 g, 0.25 mmol) then HATU (0.105 g, 0.28 mmol). The resulting mixture was stirred under air for 16 hours and then diluted with water and extracted with DCM (×3). The organics were dried over sodium sulfate, filtered and evaporated to give the title compound (0.051 g). LCMS m/z 317.17 [M+H]$^+$ R.T.=10.45 min (Analytical Method 2).

Synthesis 45

5-(1H-Pyrazol-4-yl)-thiophene-3-carboxylic acid

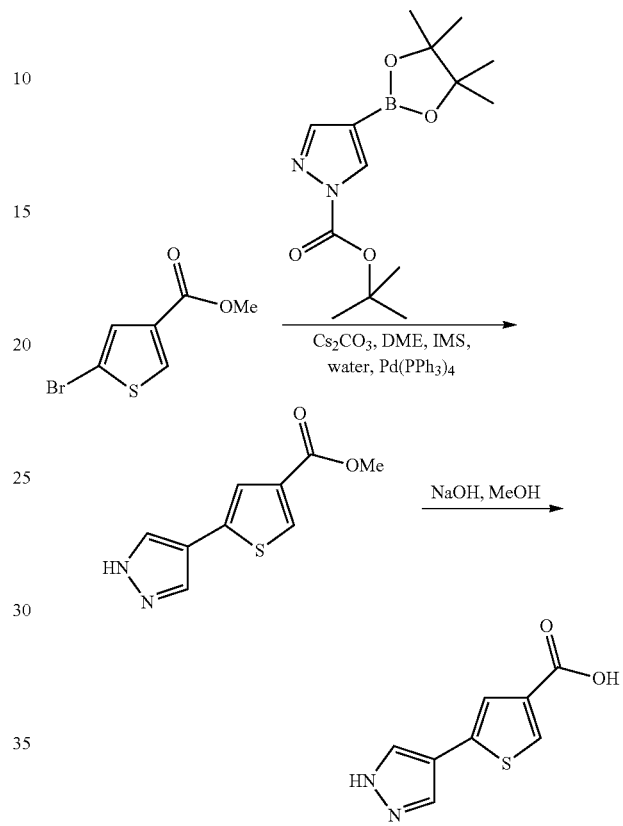

5-Bromo-thiophene-3-carboxylic acid methyl ester (1.29 g, 5.84 mmol) was dissolved in DME (13.5 mL), IMS (4.5 mL) and water (2 mL) and), 4-(4,4,5,5-tetramethyl-[1,3,2]dioxaborolan-2-yl)-pyrazole-1-carboxylic acid tert-butyl ester (1.89 g, 6.43 mmol) and caesium carbonate (2.85 g, 8.77 mmol) were added followed by palladium tetrakis(triphenylphosphine) (0.675 g, 5.84 mmol). The reaction mixture was heated by microwave irradiation at 140° C. for 20 minutes and then diluted with water and extracted with DCM (×3). The organic solution was dried over sodium sulfate, filtered and the solvent evaporated. The residue was purified by chromatography on a silica II cartridge, eluting with 10 to 50% ethyl acetate in cyclohexane. The fractions containing the desired product were concentrated under vacuum to give 5-(1H-pyrazol-4-yl)-thiophene-3-carboxylic acid methyl ester as a white, flocculent solid (0.728 g).

This material (0.725 g, 3.49 mmol) was dissolved in methanol (10 mL) and sodium hydroxide (1 M aqueous, 8.7 mL) was added. The reaction mixture was stirred for 3 hours at room temperature then a further 0.25 eq. of sodium hydroxide was added and the mixture stirred for 20 minutes. HCl (1 N, 7 mL) was added and the mixture was concentrated. The residue was taken up in water and acidified (pH 2) and the resultant white precipitate was collected by filtration to afford the title compound as a white solid (0.5 g). LCMS m/z 236.30 (M+MeCN+H$^+$). R.T.=2.31 min (Analytical Method 6).

Synthesis 46

(4,4-Dimethyl-piperidin-1-yl)-[5-(1H-pyrazol-4-yl)-thiophen-3-yl]-methanone (EE-25)

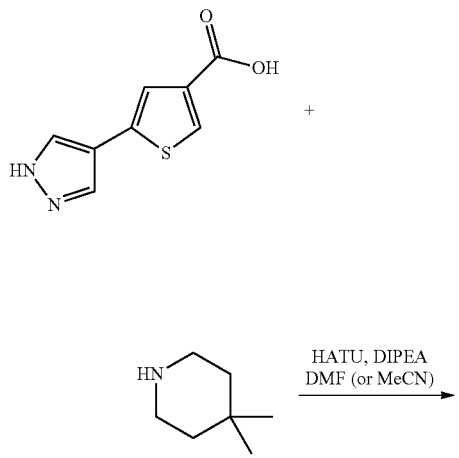

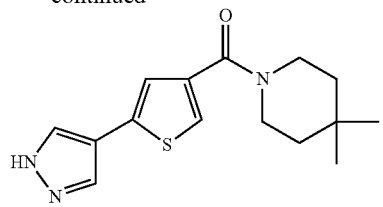

5-(1H-Pyrazol-4-yl)-thiophene-3-carboxylic acid (0.075 g, 0.39 mmol) and 4,4-dimethylpiperidine hydrochloride (0.087 g, 0.58 mmol) were dissolved in DMF (3 mL) then DIPEA (0.2 g, 1.55 mmol) and HATU (0.175 g, 1.55 mmol) were added and the reaction mixture was stirred at room temperature overnight. The solvent was removed by evaporation then the residue was dissolved in DCM and washed with aqueous sodium hydrogen carbonate solution. The organics were dried by evaporation. The crude material was purified by HPLC, eluting with 5%-98% acetonitrile in water (0.1% formic acid) over 20 minutes. The fractions containing the desired product were freeze-dried to give the title compound (0.063 g). LCMS m/z 290.18 [M+H]$^+$ R.T.=8.74 min (Analytical Method 2).

The following compounds were prepared using analogous methods. In some cases the reaction mixture was stirred with 1 N NaOH before extraction with an organic solvent.

| Code No. | Structure | $^1$H NMR | Analytical Method | R.T. (min) | MS [m/z] |
|---|---|---|---|---|---|
| FF-16 | (DHQ [CIS-S]) | — | 2 | 9.38 | 316.29 |
| FF-17 | (DHQ [CIS-R]) | — | 2 | 9.38 | 316.22 |
| EE-26 | 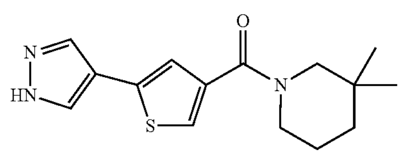 | — | 2 | 8.52 | 290.20 |
| EE-27 | 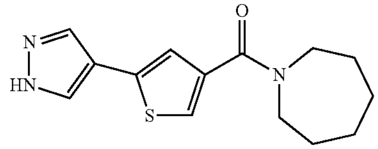 | — | 2 | 7.81 | 276.27 |

-continued

| Code No. | Structure | ¹H NMR | Analytical Method | R.T. (min) | MS [m/z] |
|---|---|---|---|---|---|
| EE-29 | 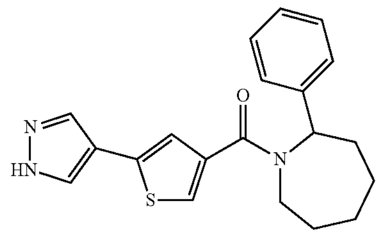 | — | 2 | 10.0 | 352.21 |
| EE-30 | 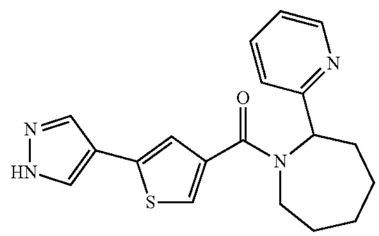 | — | 2 | 6.58 | 353.18 |
| EE-31 | 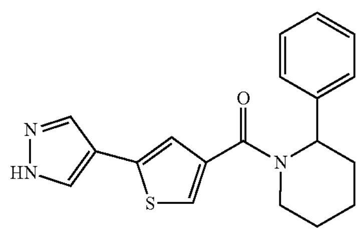 | — | 2 | 9.62 | 338.21 |
| EE-32 | 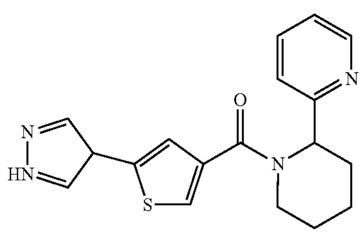 | — | 2 | 6.59 | 339.18 |
| EE-33 | 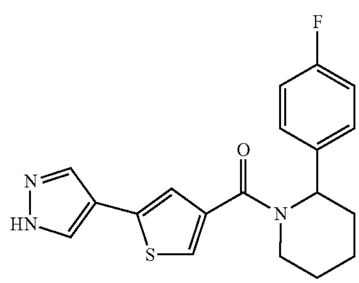 | — | 2 | 9.78 | 356.19 |
| EE-34 | 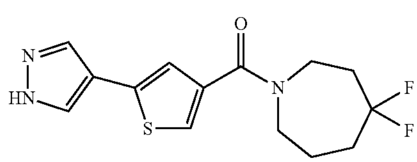 | — | 2 | 7.73 | 312.19 |
| EE-35 | 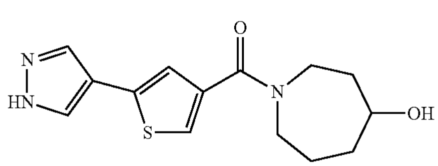 | — | 2 | 5.43 | 292.18 |

-continued

| Code No. | Structure | ¹H NMR | Analytical Method | R.T. (min) | MS [m/z] |
|---|---|---|---|---|---|
| EE-36 | 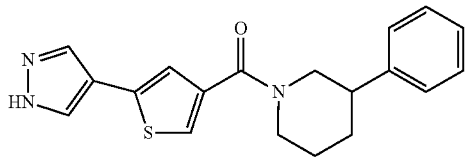 | — | 2 | 9.43 | 338.22 |
| EE-37 | 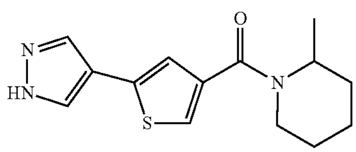 | — | 2 | 7.88 | 276.24 |
| EE-38 | 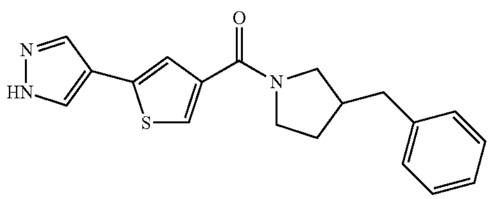 | — | 2 | 9.30 | 338.22 |
| FF-28 | FORMATE SALT | — | 2 | 3.86 | 317.18 |
| EE-39 | 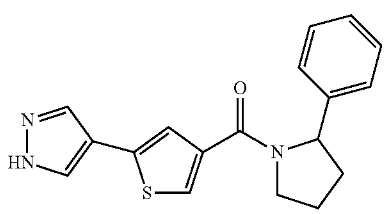 | — | 2 | 8.69 | 324.18 |
| EE-40 | 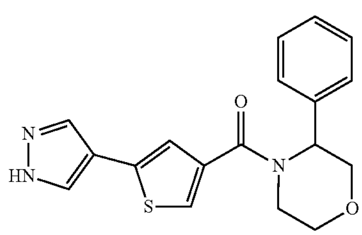 | — | 2 | 8.09 | 340.14 |
| EE-41 | 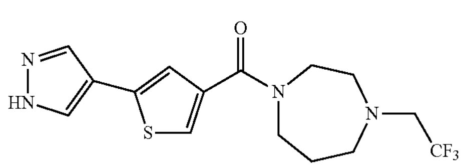 | — | 2 | 7.72 | 359.20 |
| EE-42 | 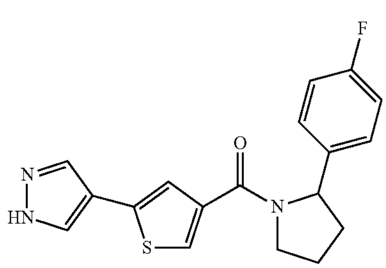 | — | 2 | 8.88 | 342.18 |

-continued
| Code No. | Structure | $^1$H NMR | Analytical Method | R.T. (min) | MS [m/z] |
|---|---|---|---|---|---|
| EE-43 | 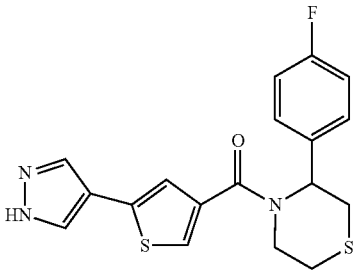 | — | 2 | 9.41 | 374.10 |
| EE-46 | 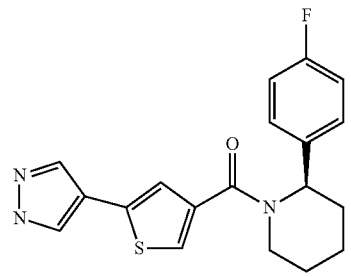    from S-phenylglycinol | — | 2 | 9.82 | 356.23 |
| EE-47 | 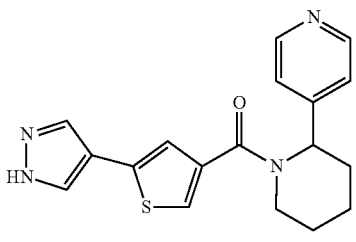 | — | 2 | 5.06 | 339.18 |
| FF-30 | 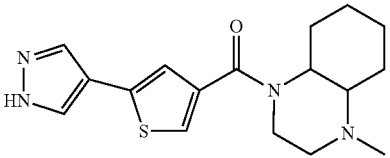    CIS ISOMERS | — | 2 | 4.22 | 331.19 |
| EE-48 | 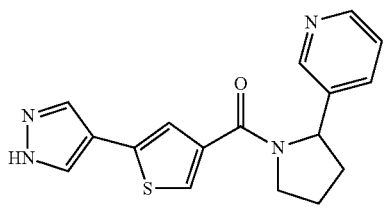 | — | 2 | 4.68 | 325.18 |
| EE-49 | 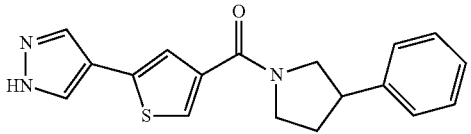 | — | 2 | 8.90 | 324.15 |

-continued

| Code No. | Structure | ¹H NMR | Analytical Method | R.T. (min) | MS [m/z] |
|---|---|---|---|---|---|
| EE-50 | (structure; from R-phenylglycinol) | — | 2 | 9.77 | 356.13 |
| EE-51 | (structure) | — | 2 | 5.18 | 339.16 |
| EE-52 | (structure) | — | 2 | 9.34 | 338.15 |
| EE-53 | (structure) | — | 2 | 8.36 | 316.10 |
| EE-54 | (structure) | — | 2 | 9.45 | 354.14 |
| EE-55 | (structure) | — | 2 | 9.57 | 352.16 |
| EE-56 | (structure) | — | 2 | 9.48 | 358.09 |

-continued
| Code No. | Structure | ¹H NMR | Analytical Method | R.T. (min) | MS [m/z] |
|---|---|---|---|---|---|
| EE-57 | 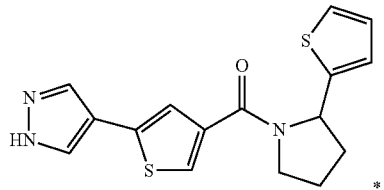 | — | 2 | 8.56 | 330.10 |
| EE-64 | 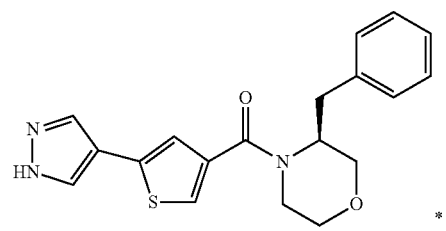 | — | 2 | 8.05 | 354.14 |
| EE-58 | 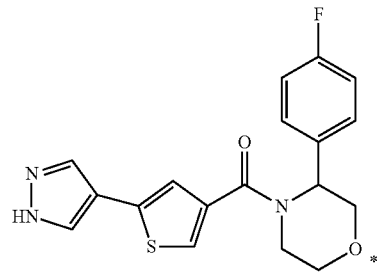 | — | 10 | 9.31 | 358.11 |
| EE-59 | 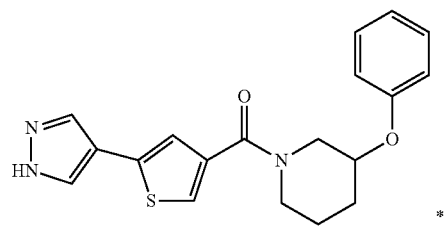 | — | 10 | 9.93 | 354.20 |
| EE-60 | 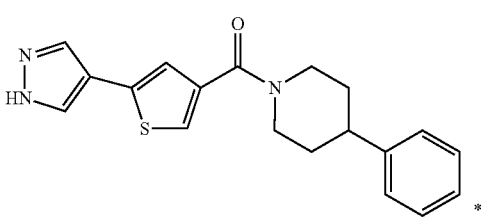 | — | 10 | 10.65 | 338.20 |
(*) purified by HPLC, eluting with 5%-98% methanol in water (0.1% formic acid)

Synthesis 47

4,4-Difluoro-azepane trifluoroacetate

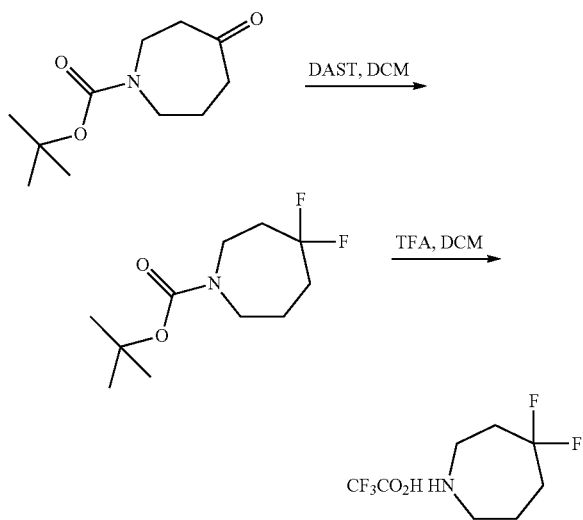

4-Oxo-azepane-1-carboxylic acid tert-butyl ester (0.75 g, 3.52 mmol) was dissolved in DCM (10 mL), cooled in an ice-bath then purged with $N_2$ before addition of DAST (1.14 g, 7.04 mmol). The reaction mixture was stirred overnight warming to room temperature. A further amount of DAST (0.5 mL) was added and stirring continued overnight. The mixture was diluted with DCM and washed with saturated aqueous sodium hydrogen carbonate solution, citric acid (20 mL) then brine before drying and evaporation of solvent. The crude material was purified by chromatography on a 10 g silica II cartridge, eluting with 2.5% ethyl acetate in cyclohexane. The fractions containing the desired product were concentrated under vacuum to give 4,4-difluoro-azepane-1-carboxylic acid tert-butyl ester (0.57 g) as a colourless oil.

This material (0.57 g) was dissolved in DCM (2.5 mL) and TFA (2.5 mL) was added. The reaction mixture was stirred at room temperature for 1 hour and then the solvent was removed by evaporation. The resultant oil was dried at 40° C. in a dessicator to afford the title compound (0.87 g) which was used directly in the synthesis of EE-34.

Synthesis 48

[1,4]Diazepan-1-yl-[5-(1H-pyrazol-4-yl)-thiophen-3-yl]-methanone

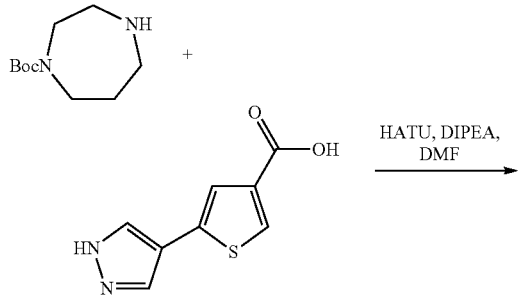

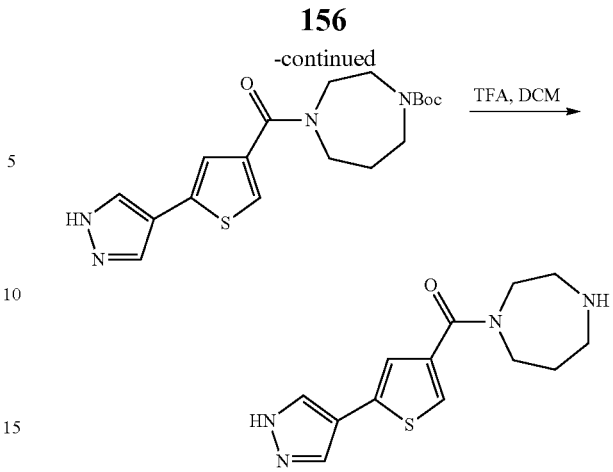

5-(1H-Pyrazol-4-yl)-thiophene-3-carboxylic acid (0.194 g, 1.0 mmol) and [1,4]diazepane-1-carboxylic acid tert-butyl ester (0.25 g, 1.25 mmol) were dissolved in DMF (5 mL) then DIPEA (0.387 g, 3.0 mmol) and HATU (0.46 g, 1.2 mmol) were added and the reaction mixture stirred at room temperature overnight. The solvent was removed by evaporation then the residue was dissolved in DCM and washed with water. The organic phase was washed with 0.5 M HCl then aqueous sodium hydrogen carbonate solution then the organics were evaporated. The crude material was purified by flash chromatography on a 10 g silica II cartridge, eluting with 2% methanol in DCM. The fractions containing the desired product were concentrated under vacuum to give 4-[5-(1H-pyrazol-4-yl)-thiophene-3-carbonyl]-[1,4]diazepane-1-carboxylic acid tert-butyl ester (0.29 g) as a white solid. LCMS m/z 377.32 [M+H]$^+$ R.T.=3.00 min (Analytical Method 6).

This material (0.29 g) was dissolved in DCM (2.5 mL) and TFA (2.5 mL) was added. The reaction mixture was stirred at room temperature for 2 hours and then the solvent was removed by evaporation. The resultant gum was passed through an SCX-2 cartridge (5 g) to afford the free base which was evaporated to remove the solvent and solidified under high vacuum affording the title compound (0.145 g). LCMS m/z 277.27 [M+H]$^+$ R.T.=0.81 min (Analytical Method 6).

Synthesis 49

(4-Methanesulfonyl-[1,4]diazepan-1-yl)-[5-(1H-pyrazol-4-yl)-thiophen-3-yl]-methanone (EE-28)

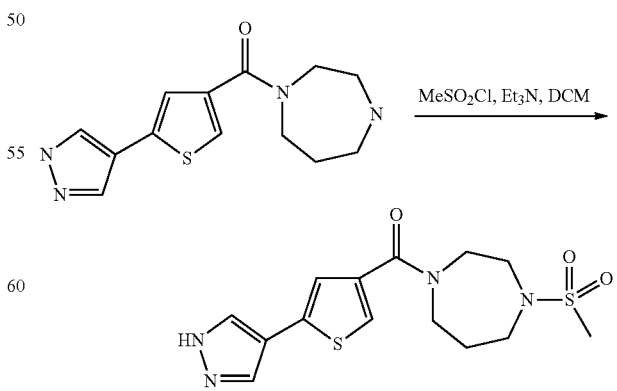

[1,4]Diazepan-1-yl-[5-(1H-pyrazol-4-yl)-thiophen-3-yl]-methanone (0.075 g, 0.27 mmol) was dissolved in DCM (30 mL) and cooled in an ice-bath before addition of triethylamine (0.082 g, 0.82 mmol) and methanesulfonyl chloride (0.038 g, 0.33 mmol). The reaction mixture was stirred at room temperature for 2 hours. The solvent was removed by evaporation and the residue taken up in methanol (2.5 mL) and treated with sodium hydroxide (1 M, 0.3 mL). After 1 hour the solvent was removed and the crude material was purified by HPLC, eluting with 5%-98% acetonitrile in water (0.1% formic acid) over 20 minutes. The fractions containing the desired product were combined and freeze-dried to give the title compound (0.045 g). LCMS m/z 355.14 [M+H]$^+$ R.T.=5.95 min (Analytical Method 2).

Synthesis 50

(Octahydro-quinoxalin-1-yl)-[5-(1H-pyrazol-4-yl)-thiophen-3-yl]-methanone formate (FF-24) (CIS ISOMERS)

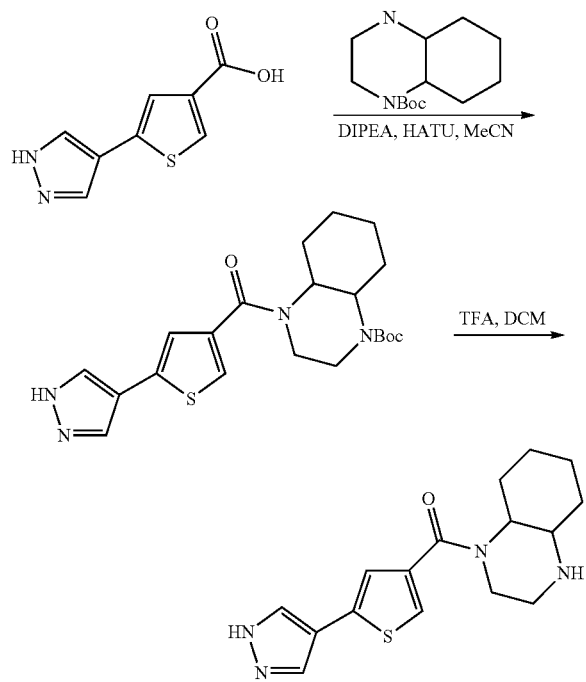

were evaporated. The product was further purified by HPLC, eluting with 5%-95% acetonitrile in water (0.1% formic acid) and the fractions containing the desired product were combined and freeze-dried to give the title compound (0.037 g). LCMS m/z 317.18 [M+H]$^+$ R.T.=4.28 min (Analytical Method 2).

Synthesis 51 cis-Octahydro-benzo[1,4]oxazine

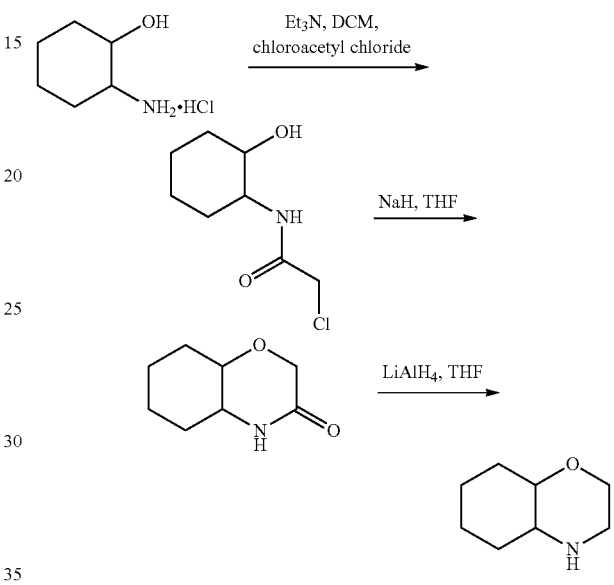

5-(1H-Pyrazol-4-yl)-thiophene-3-carboxylic acid (0.080 g, 0.41 mmol) was suspended in acetonitrile (2 mL) then cis-octahydro-quinoxaline-1-carboxylic acid tert-butyl ester (0.045 g, 0.53 mmol) and DIPEA (0.154 mL, 0.90 mmol) were added followed by HATU (0.187 g, 0.49 mmol). The resulting mixture was stirred over the weekend then evaporated. The residue was taken up in sodium hydroxide (1 N, 2 mL) and stirred for 10 minutes. HCl (1 N, 5 mL) was added and the mixture was stirred for 1 hour and then applied to an SCX-2 cartridge (5 g). The cartridge was washed with methanol then eluted using 2 N ammonia in methanol to afford a mixture of protected and unprotected material, which was used directly.

This material was dissolved in DCM (1.5 mL) and TFA (3 mL) was added. The mixture was stirred at room temperature for 45 minutes then evaporated and the residue taken up in methanol and applied to an SCX-2 cartridge (5 g). The cartridge was washed with methanol then eluted using 2 N ammonia in methanol and the fractions containing product cis-2-Amino-cyclohexanol hydrochloride (0.50 g, 3.30 mmol) was suspended in DCM (5 mL) and triethylamine (0.97 mL, 6.95 mmol) added. The mixture was purged with nitrogen, cooled to −10° C. then chloroacetyl chloride (0.26 mL, 3.30 mmol) was added slowly and the mixture stirred for 10 minutes before removal of the ice bath. Stirring was continued for 45 minutes and then the mixture was diluted with saturated aqueous sodium hydrogen carbonate and extracted with 5% IPA in ethyl acetate. The organics were washed with brine, dried over sodium sulfate, filtered and evaporated to afford cis-2-chloro-N-2-hydroxy-cyclohexyl)-acetamide as a brown oil (0.495 g).

This material (0.495 g, 2.57 mmol) was dissolved in THF (5 mL) and cooled to 0° C. under nitrogen. Sodium hydride (60% in mineral oil, 113 mg, 2.83 mmol) was added carefully and the mixture stirred for 5 minutes before the ice bath was removed. Stirring was continued for 30 minutes then the mixture was diluted with saturated aqueous sodium hydrogen carbonate and extracted with DCM (×3). The organics were dried over sodium sulfate, filtered and evaporated. The crude material was purified by chromatography on a 5 g silica II cartridge, eluting with 1:1 DCM:pentane, pentane, DCM, 2% methanol in DCM then 4% methanol in DCM. The fractions containing the desired product were concentrated to give cis-hexahydro-benzo[1,4]oxazin-3-one (0.224 g) as an off-white foam. LCMS m/z 197.20 [M+H+ MeCN]$^+$R.T.=2.01 min (Analytical Method 6).

Lithium aluminium hydride (0.22 g, 5.79 mmol) was suspended in THF (2 mL) and to this was added a solution of cis-hexahydro-benzo[1,4]oxazin-3-one (0.224 g), 1.45 mmol) in THF (5 mL) under nitrogen. The mixture was heated at 80° C. for 2 hours and then allowed to cool before cautious addition of water. The resultant white suspension was filtered through Celite® then concentrated. The residue was applied to a 5 g SCX-2 cartridge, washed with methanol then eluted using 2 N ammonia in methanol to afford the title compound as a colourless oil (0.142 g). LCMS m/z 183.28 [M+H+MeCN]⁺R.T.=0.37 min (Analytical Method 6).

Synthesis 52

(Octahydro-benzo[1,4]oxazin-4-yl)-[5-(1H-pyrazol-4-yl)-thiophen-3-yl]-methanone (FF-25) (CIS ISOMERS)

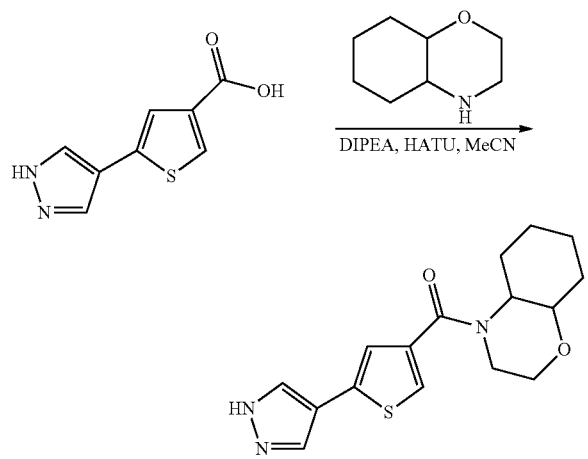

cis-Octahydro-benzo[1,4]oxazine (0.080 g, 0.41 mmol) was suspended in acetonitrile (1.8 mL) then DIPEA (0.156 mL, 0.90 mmol) and octahydro-quinoxaline-1-carboxylic acid tert-butyl ester (0.064 g, 0.45 mmol) were added followed by HATU (0.156 g, 0.41 mmol). The resulting mixture was stirred overnight then evaporated. The residue was taken up in sodium hydroxide (1 N, 2 mL) and stirred for 20 minutes then HCl was added (1 N, pH adjusted to 2). The mixture was extracted with DCM (×3) then the organics were washed with brine, dried over sodium sulfate, filtered and evaporated. The material was purified by HPLC, eluting with 5%-95% acetonitrile in water (0.1% formic acid) and the fractions containing the desired product were combined and freeze-dried to give the title compound (0.02 g). LCMS m/z 318.24 [M+H]⁺ R.T.=7.64 min (Analytical Method 2).

Synthesis 53

[5-(1H-Pyrazol-4-yl)-thiophen-3-yl]-[4-(2,2,2-trifluoro-ethyl)-octahydro-quinoxalin-1-yl]-methanone (FF-26) (CIS ISOMERS)

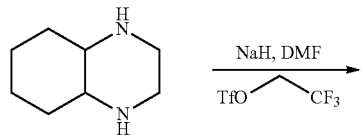

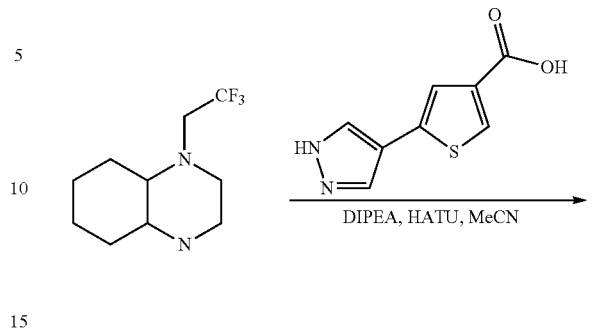

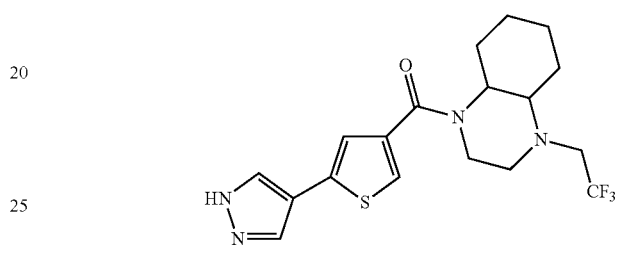

cis-Decahydro-quinoxaline (0.104 g, 0.74 mmol) was dissolved in DMF (1 mL) and sodium hydride (60% in mineral oil, 0.015 g, 0.37 mmol) was added. After 5 minutes, trifluoro-methanesulfonic acid 2,2,2-trifluoro-ethyl ester (0.137 g, 0.37 mmol) was dissolved in a small amount of DMF and added to the mixture. Stirring was continued for 1 hour at room temperature then the material was diluted slightly with methanol and applied to a 10 g SCX-2 cartridge. This was washed with methanol then eluted using 2 N ammonia in methanol to afford 1-(2,2,2-trifluoro-ethyl)-decahydro-quinoxaline as a pale yellow oil (0.119 g).

5-(1H-Pyrazol-4-yl)-thiophene-3-carboxylic acid (0.080 g, 0.41 mmol) was suspended in acetonitrile (2 mL) then DIPEA (0.158 mL, 0.90 mmol) and 1-(2,2,2-trifluoro-ethyl)-decahydro-quinoxaline (0.119 g, 0.54 mmol) were added followed by HATU (0.192 g, 0.50 mmol). The resulting mixture was stirred for about 24 hours and then further amounts of DIPEA (79 μL) and HATU (0.192 g) were added and stirring continued over the weekend. The mixture was evaporated and the residue was taken up in sodium hydroxide (1N) and stirred for 30 minutes. HCl (1 N, 2.5 mL) was added and the solution extracted with ethyl acetate (×3). The organics were dried over sodium sulfate, filtered and evaporated. The material was purified by HPLC, eluting with 5%-95% acetonitrile in water (0.1% formic acid) and the fractions containing the desired product were combined and freeze-dried to give the title compound as a white solid (0.020 g). LCMS m/z 399.17 [M+H]⁺ R.T.=10.05 min (Analytical Method 2).

Synthesis 54

(Hexahydro-[1,4]dioxino[2,3-c]pyridin-6-yl)-[5-(1H-pyrazol-4-yl)-thiophen-3-yl]-methanone (FF-27) (CIS ISOMERS)

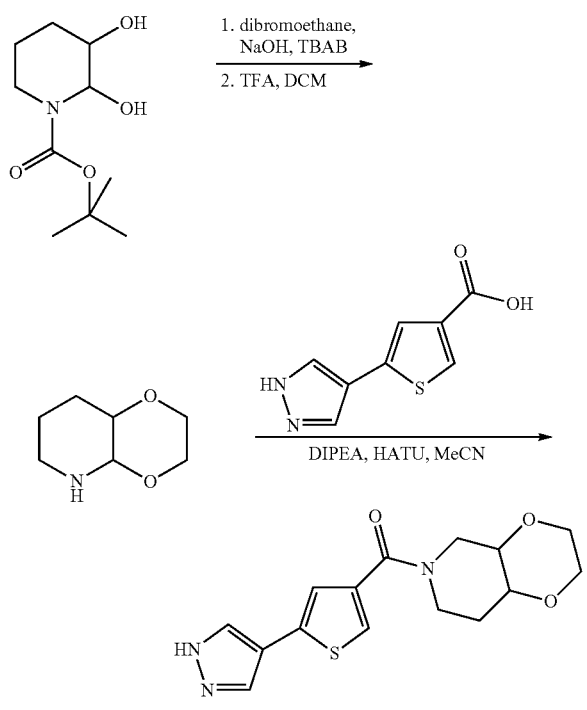

cis-2,3-Dihydroxy-piperidine-1-carboxylic acid tert-butyl ester (0.246 g, 1.13 mmol) was dissolved in dibromoethane (1.7 mL) and tetrabutyl ammonium bromide (71 mg, 2.2 mmol) was added. Sodium hydroxide (50% aqueous solution, 17.8 g) was added slowly over 10 minutes at 50° C. A further amount of dibromoethane (7.4 mL, 105.5 mmol in total) was added and the mixture was heated at 55° C. overnight. Dibromoethane (3 mL) was added and the mixture was heated at 55° C. for a further 4 hours and then diluted with water and extracted with DCM (×2). The organics were washed with brine then dried over sodium sulfate, filtered and evaporated. The crude material was purified by chromatography on a 5 g silica II cartridge, eluting with 10-33% diethyl ether in pentane to afford hexahydro-[1,4]dioxino[2,3-b]pyridine-5-carboxylic acid tert-butyl ester as an off-white oil (0.106 g).

This material (0.093 g, 0.78 mmol) was dissolved in DCM (1 mL) and TFA (1 mL) and the mixture was stirred for 1 hour and then evaporated. The residue was taken up in methanol and applied to an SCX-2 cartridge (5 g). This was washed with methanol then eluted using 2 N ammonia in methanol to afford octahydro-[1,4]dioxino[2,3-b]pyridine as a colourless oil (0.049 g).

Octahydro-[1,4]dioxino[2,3-b]pyridine (0.049 g, 0.34 mmol) was dissolved in acetonitrile (1 mL) then 5-(1H-pyrazol-4-yl)-thiophene-3-carboxylic acid (0.060 g, 0.31 mmol) was added then DIPEA (0.116 mL, 0.68 mmol) followed by HATU (0.141 g, 0.37 mmol). The resulting mixture was stirred overnight then further amounts of DIPEA (0.31 mmol) and HATU (0.31 mmol) were added and stirring continued overnight. The mixture was evaporated and the residue was suspended in sodium hydroxide (1 N, 2.5 mL) and stirred for 20 minutes. The mixture was extracted with DCM (×3) then the organics were dried over sodium sulfate, filtered and evaporated. The material was purified by HPLC, eluting with 5%-95% acetonitrile in water (0.1% formic acid) over 20 minutes and the fractions containing the desired product were combined and freeze-dried to give the title compound as a white foam (0.008 g). LCMS m/z 320.19 [M+H]$^+$ R.T.=5.95 min (Analytical Method 2).

Synthesis 55

5-(2-tert-Butoxycarbonylamino-oxazol-5-yl)-thiophene-3-carboxylic acid methyl ester

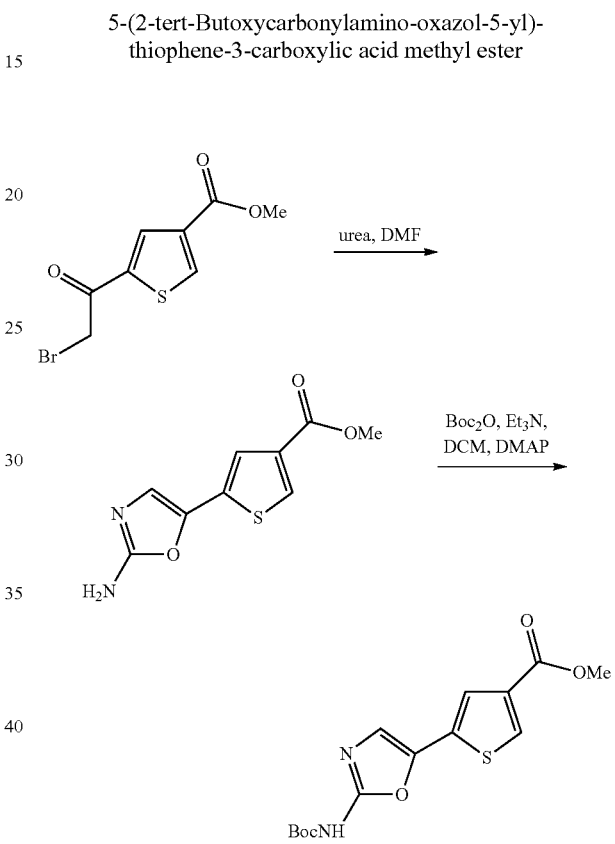

5-(2-Bromo-acetyl)-thiophene-3-carboxylic acid methyl ester (0.261 g, 0.99 mmol) was dissolved in DMF (4 mL) and urea (0.131 g, 2.18 mmol) was added. The vessel was purged with nitrogen then sealed and heated by microwave irradiation at 140° C. for 10 minutes. The resultant mixture was diluted with water and extracted with ethyl acetate (×3). The organic phase was washed with lithium chloride (15% aqueous solution) then dried over sodium sulfate, filtered and evaporated to give crude 5-(2-amino-oxazol-5-yl)-thiophene-3-carboxylic acid methyl ester as an orange-brown solid (0.224 g).

This material (0.222 g, 0.99 mmol) was dissolved in DCM (4 mL) then triethylamine (0.138 mL, 0.99 mmol) was added followed by di-tert-butyl dicarbonate (0.216 g, 0.99 mmol) and the mixture was stirred at room temperature for 3 hours. DMAP (24 mg, 0.20 mmol) was added and the mixture was stirred for 6 days. A further quantity of DMAP (0.181 g) was added and the reaction mixture stirred for 6 hours and then evaporated. The crude material was purified by chromatography on a 5 g silica II cartridge, eluting with 5-33% diethyl

Synthesis 56

[5-(2-Amino-oxazol-5-yl)-thiophen-3-yl]-octahydro-quinolin-1-yl-methanone (FF-29) (DHQ [CIS-S])

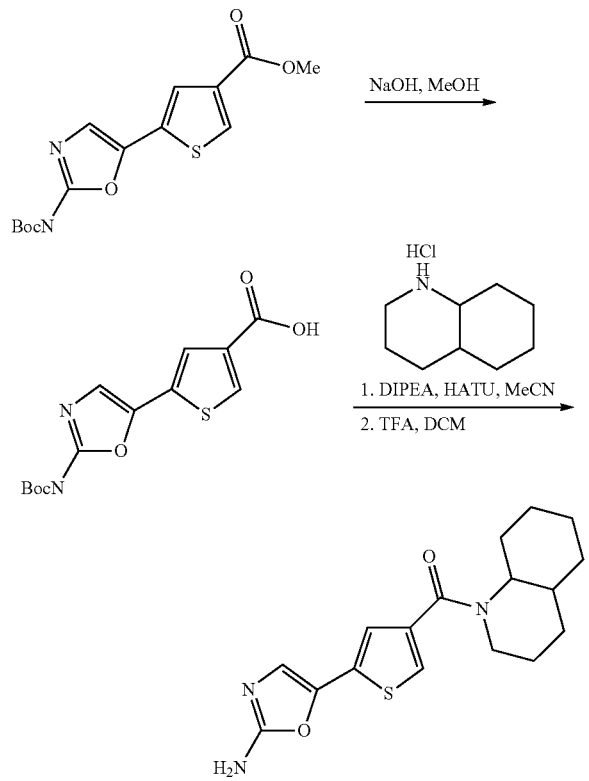

5-(2-tert-Butoxycarbonylamino-oxazol-5-yl)-thiophene-3-carboxylic acid methyl ester (0.152 g, 0.47 mmol) was suspended in methanol (2 mL), sodium hydroxide (1 M, 1.17 mL, 1.18 mmol) was added and the mixture stirred overnight at room temperature. The mixture was evaporated then HCl (1 N, 1.2 mL) and water (1 mL) were added. The resultant white precipitate was collected by filtration then dried under vacuum to afford 5-(2-tert-butoxycarbonylamino-oxazol-5-yl)-thiophene-3-carboxylic acid (0.077 g).

This material (77 mg, 0.25 mmol) was suspended in acetonitrile (1.5 mL) then DIPEA (0.137 mL, 0.80 mmol) was added followed by cis-decahydro-quinoline hydrochloride (DHQ [CIS-S]) (0.48 g, 0.28 mmol) then HATU (0.114 g, 0.30 mmol). The resulting mixture was stirred for 2.5 hours and then concentrated in vacuo. The residue was taken up in DCM (1 mL) and TFA (1 mL) and stirred for 45 minutes then the solvents evaporated. The residue was purified by HPLC, eluting with 5%-95% acetonitrile in water (0.1% formic acid). The fractions containing the desired product were freeze-dried to give the title compound as a white solid (0.035 g). LCMS m/z 332.21 [M+H]$^+$ R.T.=9.04 min (Analytical Method 2).

Synthesis 57

[5-bromo-thiophen-3-yl]-(1,3,3-trimethyl-6-aza-bicyclo[3.2.1]oct-6-yl)-methanone

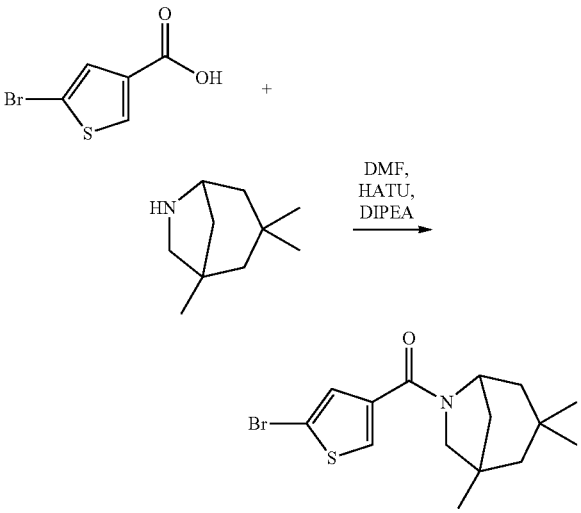

To a solution of 2-bromothiophene carboxylic acid (0.5 g; 1 eq) in DMF (12 mL) was added HATU (1 g; 1.1 eq) and DIPEA (0.633 mL; 1.5 eq). This mixture was stirred at RT for 15 minutes, then a solution of 1,3,3-trimethyl-6-aza-bicyclo [3.2.1]oct-6-ane (0.407 g; 1.1 eq) in DMF (2 mL) was added and the mixture allowed to stir for 3 hours. The mixture was diluted with water (40 mL) and diethyl ether (40 mL) and the organic layer separated, dried and evaporated to give the crude product which was purified by column chromatography (EtOAc/iso-hexane) to give the desired compound (0.667 g). LCMS m/z 342, 344 [M+H]$^+$ R.T.=4.5 min (Analytical Method 3).

The following compounds were prepared using analogous methods:

| Structure | Analytical Method | R.T. (min) | MS [m/z] |
|---|---|---|---|
|  | 3 | 4.3 | 316, 318 |
|  | 3 | 4.4 | 350, 352 |

-continued

| Structure | Analytical Method | R.T. (min) | MS [m/z] |
|---|---|---|---|
| 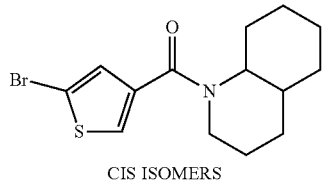 CIS ISOMERS | 3 | 4.4 | 328, 330 |

Synthesis 58

[5-(1H-Pyrazol-4-yl)-thiophen-3-yl]-(1,3,3-trimethyl-6-aza-bicyclo[3.2.1]oct-6-yl)-methanone (GG-02)

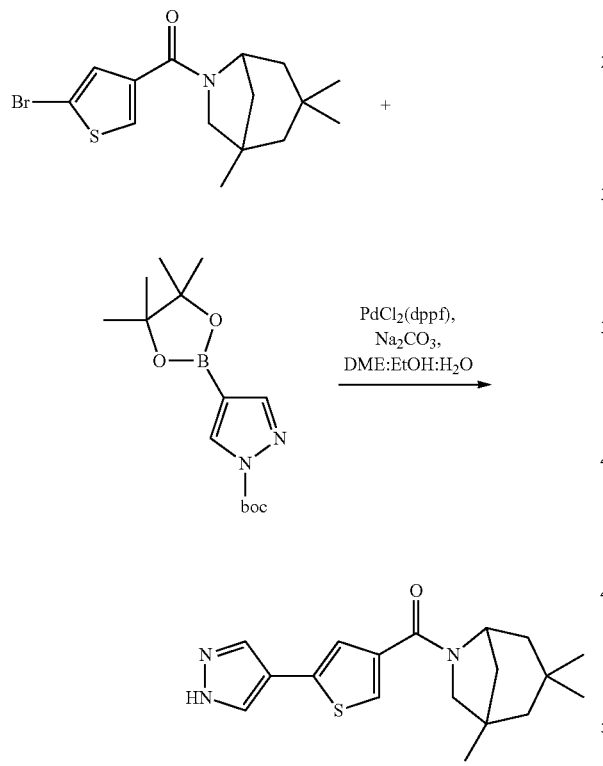

To a suspension of [5-bromo-thiophen-3-yl]-(1,3,3-trimethyl-6-aza-bicyclo[3.2.1]oct-6-yl)-methanone (0.05 g, 1 eq), N-Boc-pyrazole-4-boronic ester pinacol (0.064 g, 1.5 eq), and sodium carbonate (0.020 g, 1.3 eq) was added in a mixture of 4:1 DME:EtOH (2 mL, 1 mL/0.025 g) and water (1 mL/0.05 g). Palladium catalyst (0.003 g, 0.03 eq) was added after de-gassing the solution and then irradiated in the microwave (Smiths Synthesiser) at 140° C. for 20 minutes. The mixture was diluted with NaHCO₃ solution (6 mL) and DCM (6 mL) and the organic layer separated, dried and evaporated to give the crude product which was purified by column chromatography (EtOAc/iso-Hexanes) (0.025 g). LCMS m/z 330 [M+H]⁺ R.T.=3.5 min (Analytical Method 3).

Synthesis 59

[5-(3,5-Dimethyl-1H-pyrazol-4-yl)-thiophen-3-yl]-(2-phenyl-piperidin-1-yl)-methanone (EE-17)

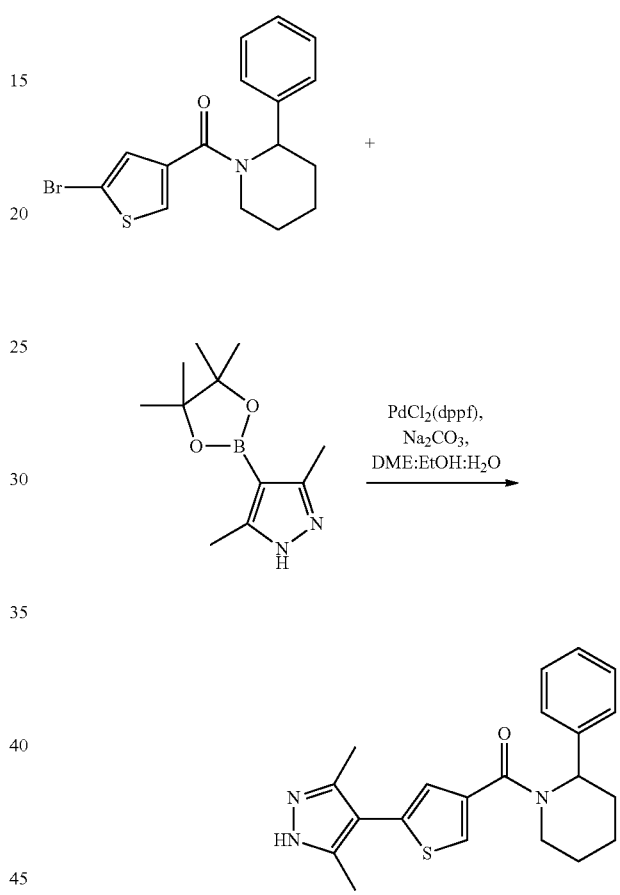

To a suspension of [5-bromo-thiophen-3-yl]-(2-phenyl-piperidin-1-yl)-methanone (0.05 g, 1 eq), 3,5-dimethylpyrazole-4-boronic ester pinacol (0.048 g, 1.3 eq) and sodium carbonate (0.021 g, 1.3 eq) was added in a mixture of 4:1 DME:EtOH (2 mL, 1 mL/0.025 g) and water (1 mL/0.05 g). Palladium catalyst (0.003 g, 0.03 eq) was added after de-gassing the solution and then irradiated in the microwave (Smiths Synthesiser) at 140° C. for 20 minutes. The mixture was diluted with NaHCO₃ solution (6 mL) and DCM (6 mL) and the organic layer separated, dried and evaporated to give the crude product which was purified by column chromatography (EtOAc/iso-Hexane) (0.01 g). LCMS m/z 366 [M+H]⁺ R.T.=3.6 min (Analytical Method 3).

The following compounds were prepared using analogous methods:

| Code No. | Structure | Analytical Method | R.T. (min) | MS [m/z] |
|---|---|---|---|---|
| EE-19 | 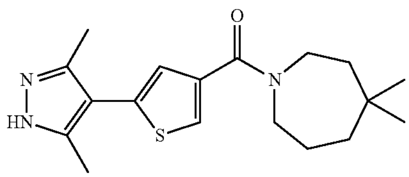 | 3 | 3.4 | 332 |
| FF-11 | CIS ISOMERS | 3 | 3.5 | 344 |
| GG-04 | 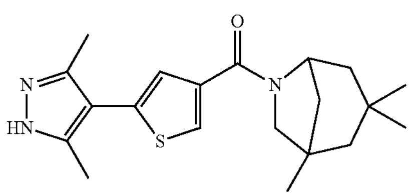 | 3 | 3.7 | 358 |

Synthesis 60

(4,4-Dimethyl-azepan-1-yl)-[5-(3,5-dimethyl-isoxazol-4-yl)-thiophen-3-yl]-methanone (EE-18)

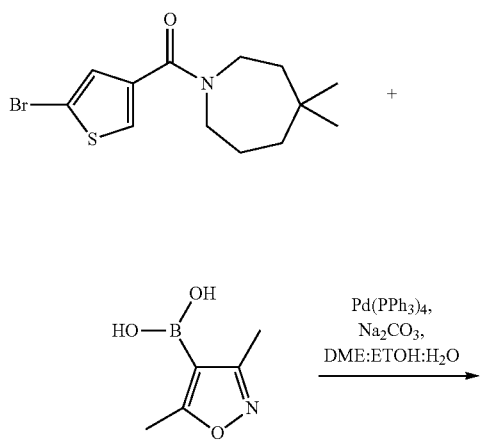

-continued

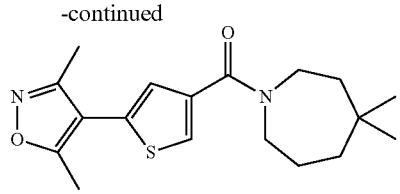

To a suspension of [5-bromo-thiophen-3-yl]-(4,4-Dimethyl-azepan-1-yl)-methanone (0.05 g, 1 eq), 3,5-dimethyl-isoxazoyl-4-boronic acid (0.033 g, 1.5 eq) and sodium carbonate (0.022 g, 1.3 eq) was added in a mixture of 4:1 DME:EtOH (2 mL, 1 mL/0.025 g) and water (1 mL/0.05 g). Palladium catalyst (0.003 g, 0.03 eq) was added after degassing the solution and then irradiated in the microwave (Smiths Synthesiser) at 140° C. for 20 minutes. The mixture was diluted with $NaHCO_3$ solution (6 mL) and DCM (6 mL) and the organic layer separated, dried and evaporated to give the crude product which was purified by column chromatography (EtOAc/iso-Hexane) (0.003 g). LCMS m/z 333 [M+H]$^+$ R.T.=4.1 min (Analytical Method 3).

The following compounds were prepared using analogous methods:

| Code No. | Structure | Analytical Method | R.T. (min) | MS [m/z] |
|---|---|---|---|---|
| EE-20 | 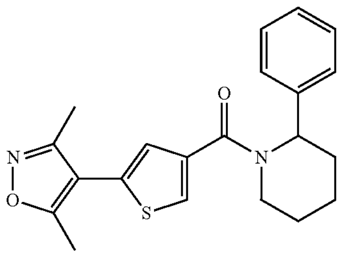 | 3 | 4.1 | 367 |
| FF-12 | CIS ISOMERS | 3 | 4.2 | 345 |
| GG-03 | 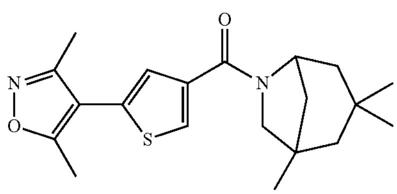 | 3 | 4.3 | 359 |

Synthesis 61

(Octahydro-quinolin-1-yl)-(5-pyrazol-1-yl-thiophen-3-yl)-methanone (FF-07) (CIS ISOMERS)

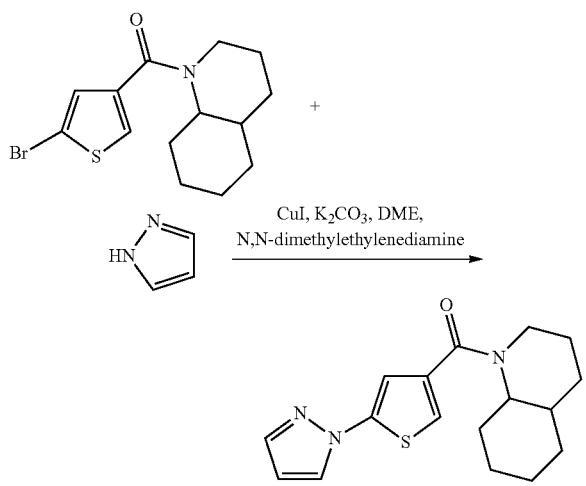

To a solution of cis-(5-bromo-thiophen-3-yl)-(octahydro-quinolin-1-yl)-methanone (0.095 g, 0.29 mmol) in DME (2 mL) was added N'N'-dimethylethylenediamine (0.005 g), pyrazole (0.039 g, 0.58 mmol), copper iodide (0.011 g) and potassium carbonate (0.040 g, 0.29 mmol). The reaction mixture was placed under nitrogen then sealed in a vial and heated at 120° C. for 79 hours. The solution was partitioned between DCM and water and the phases separated using a hydrophobic frit. The organic phase was evaporated and the compound was purified by chromatography on a silica cartridge eluting 0-10% methanol in DCM then re-purified on a larger cartridge using 0-3% methanol in DCM. The compound was further purified by HPLC on a C6 phenyl column, eluting with 50%-98% acetonitrile in water (0.1% formic acid). The fractions containing the desired product were evaporated to give the title compound as a colourless oil (0.02 g). LCMS m/z 316.19 [M+H]$^+$ R.T.=10.74 min (Analytical Method 2).

Synthesis 62

5-(6-Fluoro-pyridin-3-yl)-thiophene-3-carboxylic acid

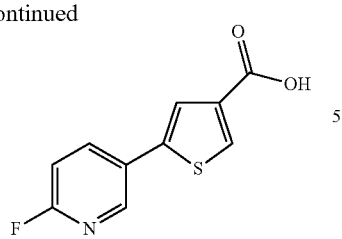

A mixture of 5-bromo-thiophene-3-carboxylic acid (0.71 g, 4.4 mmol), 2-fluoropyridine-5-boronic acid (0.619 g, 4.4 mmol), caesium carbonate (2.9 g, 8.8 mmol), and palladium tetrakis(triphenylphosphine) (0.470 g, 0.44 mmol) in DME (40 mL), IMS 20 mL) and water (10 mL) was divided across three microwave vials and each was heated by microwave irradiation to 120° C. for 20 minutes. The batches were combined and concentrated and the residue was partitioned between saturated aqueous sodium carbonate and DCM. The aqueous phase was isolated and acidified using dilute HCl (pH 2) giving a precipitate which was collected by filtration to afford the title compound as a white solid (0.815 g). LCMS m/z 224.07 [M+H]$^+$ R.T.=2.83 min (Analytical Method 8).

Synthesis 63

[5-(6-Fluoro-pyridin-3-yl)-thiophen-3-yl]-(octahydro-quinolin-1-yl)-methanone (FF-0) (CIS ISOMERS)

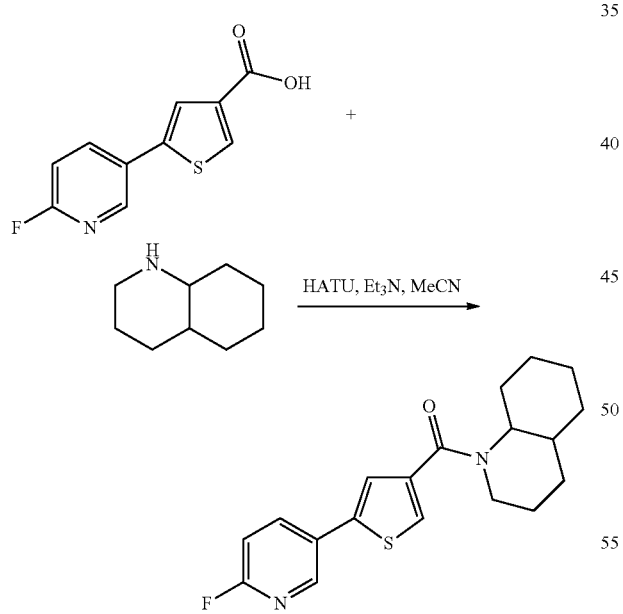

5-(6-Fluoro-pyridin-3-yl)-thiophene-3-carboxylic acid (0.05 g, 0.22 mmol) was dissolved in acetonitrile (1 mL) together with cis, trans-decahydroisoquinoline (0.134 mL, 0.90 mmol), triethylamine (80 μL, 0.60 mmol) and HATU (0.085 g, 0.22 mmol) and the resulting mixture was stirred over the weekend. The crude material was purified by HPLC, eluting with 10%-98% acetonitrile in water (0.1% formic acid). The fractions containing the desired product were evaporated to give the title compound as a pink oil (0.015 g). LCMS m/z 345.23 [M+H]$^+$ R.T.=11.76 min (Analytical Method 2).

Synthesis 64

5-(2-Fluoro-pyridin-4-yl)-thiophene-3-carboxylic acid

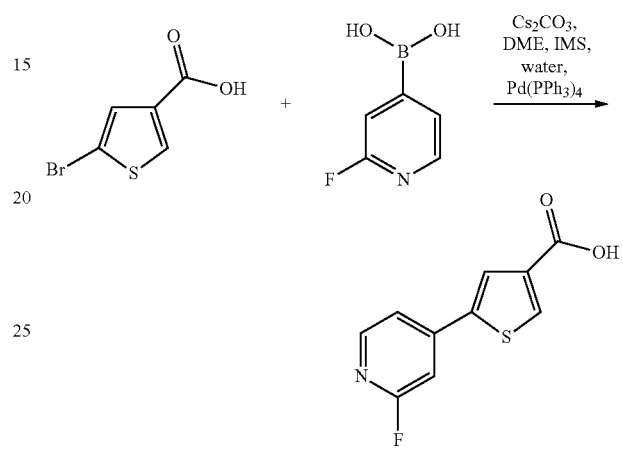

A mixture of 5-bromo-thiophene-3-carboxylic acid (0.71 g, 4.4 mmol), 2-fluoropyridine-4-boronic acid (0.619 g, 4.4 mmol), caesium carbonate (2.9 g, 8.8 mmol), and palladium tetrakis(triphenylphosphine) (0.469 g, 0.44 mmol) in DME (40 mL), IMS 20 mL) and water (10 mL) was divided across three microwave vials and each was heated by microwave irradiation to 120° C. for 20 minutes. The batches were combined and concentrated and the residue was partitioned between saturated aqueous sodium carbonate and DCM. The aqueous phase was isolated and filtered to obtain the title compound as a grey precipitate (0.168 g) and the filtrate was acidified using dilute HCl (pH 2) then re-filtered to obtain a further amount of the title compound as an off-white solid (0.114 g). LCMS m/z 224.06 [M+H]$^+$ R.T.=2.77 min (Analytical Method 8).

Synthesis 65

[5-(2-Fluoro-pyridin-4-yl)-thiophen-3-yl]-(octahydro-quinolin-1-yl)-methanone (FF-03) (CIS ISOMERS)

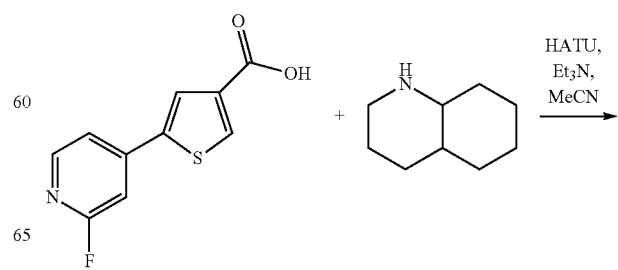

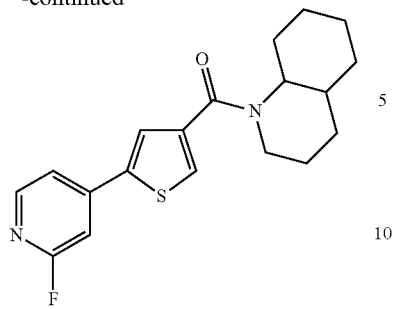

5-(2-Fluoro-pyridin-4-yl)-thiophene-3-carboxylic acid (0.05 g, 0.22 mmol) was dissolved in acetonitrile (2 mL) together with cis, trans-decahydroisoquinoline (0.134 mL, 0.90 mmol), triethylamine (80 µL, 0.60 mmol) and HATU (0.085 g, 0.22 mmol) and the resulting mixture was stirred over the weekend. The crude material was purified by HPLC, eluting with 10%-98% acetonitrile in water (0.1% formic acid). The fractions containing the desired product were evaporated to give the title compound as an oil (0.02 g). LCMS m/z 345.22 [M+H]⁺ R.T.=11.64 min (Analytical Method 2).

Synthesis 66

[5-(6-Methoxy-pyridin-3-yl)-thiophen-3-yl]-(octahydro-quinolin-1-yl)-methanone (FF-04) (CIS ISOMERS)

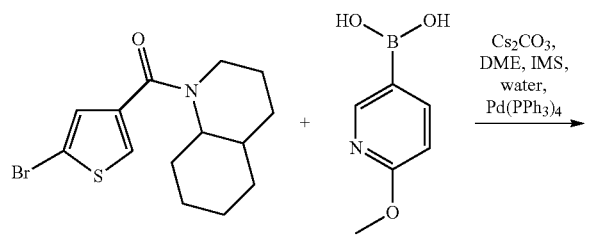

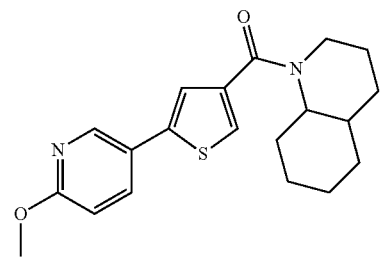

cis-(5-Bromo-thiophen-3-yl)-(octahydro-quinolin-1-yl) methanone (0.1 g, 0.30 mmol) was combined with 2-methoxypyridine-5-boronic acid (0.045 g, 0.3 mmol), caesium carbonate (0.142 g, 0.44 mmol), and palladium tetrakis(triphenylphosphine) (0.031 g, 0.03 mmol) in DME (6 mL), IMS (2 mL) and water (13 mL). The reaction mixture was heated by microwave irradiation to 140° C. for 20 minutes. The solution was partitioned between ethyl acetate and water and the phases separated then the organic phase was dried and evaporated to afford the title compound as a gum. The compound was purified by HPLC, eluting with 10%-98% acetonitrile in water (0.1% formic acid). The fractions containing the desired product were evaporated to give the title compound as an oil (0.077 g). LCMS m/z 357.25 [M+H]⁺ R.T.=12.46 min (Analytical Method 2).

The following compounds were prepared using analogous methods.

| Code No. | Structure | ¹H NMR | Analytical Method | R.T. (min) | MS [m/z] |
|---|---|---|---|---|---|
| FF-05 | 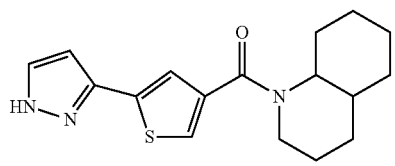<br>CIS ISOMERS | — | 2 | 9.50 | 328.27 |
| FF-08 | <br>CIS ISOMERS | — | 2 | 9.47 | 316.27 |

-continued

| Code No. | Structure | ¹H NMR | Analytical Method | R.T. (min) | MS [m/z] |
|---|---|---|---|---|---|
| BB-02 | (structure) CIS ISOMERS | — | 2 | 13.34 | 369.31 |
| BB-03 | (structure) CIS ISOMERS | — | 2 | 11.15 | 419.17 |
| FF-10 | (structure) CIS ISOMERS | — | 2 | 10.14 | 330.25 |

Synthesis 67

(S)-2-[(R)-2-(4-Fluoro-phenyl)-piperidin-1-yl]-2-phenyl-ethanol hydrochloride

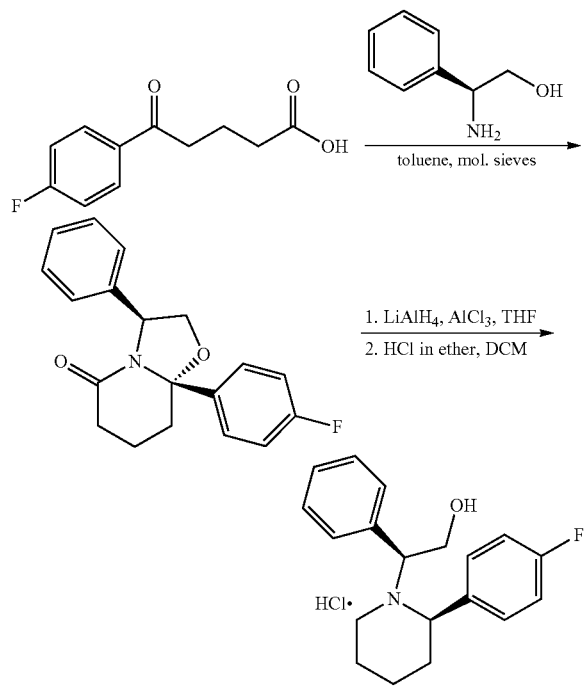

5-(4-Fluoro-phenyl)-5-oxo-pentanoic acid (1 g, 5.10 mmol) and (S)-(+)-2-phenylglycinol (0.839 g, 6.12 mmol) in toluene (15 mL) together with 4 Å molecular sieves was heated at 140° C. under Dean-Stark conditions for 20 hours. The reaction mixture was filtered through Celite®, evaporated and the residue dissolved in ethyl acetate then re-evaporated. The crude material was purified by column chromatography eluting with 20-40% ethyl acetate in cyclohexane to afford (3S,8aS)-8a-(4-fluoro-phenyl)-3-phenyl-hexahydro-oxazolo[3,2-a]pyridin-5-one (1.08 g).

Lithium aluminium hydride (0.395 g, 10.41 mmol) was added to a solution of aluminium trichloride (1.16 g, 8.67 mmol) in THF (40 mL) at 0° C. The mixture was stirred for 30 minutes at room temperature then cooled to −78° C. and a solution of (3S,8aS)-8a-(4-fluoro-phenyl)-3-phenyl-hexahydro-oxazolo[3,2-a]pyridin-5-one (1.08 g, 3.47 mmol) in THF (10 mL) was added dropwise. The reaction mixture was stirred for 1 hour at −78° C. then for 2 hours at room temperature before being cooled to 0° C. and quenched with an aqueous solution of Rochelle salt (potassium sodium tartrate). The material was extracted with DCM, dried over sodium sulfate and then purified by column chromatography, eluting with cyclohexane: DCM:methanol (7:2.5:0.5) to afford the product (0.642 g). This was dissolved in DCM and HCl in ether (2 M, 0.35 mL) was added and the solution evaporated to give the title compound (0.65 g) which was used directly in the next step.

Synthesis 68

(R)-2-(4-Fluoro-phenyl)-piperidine

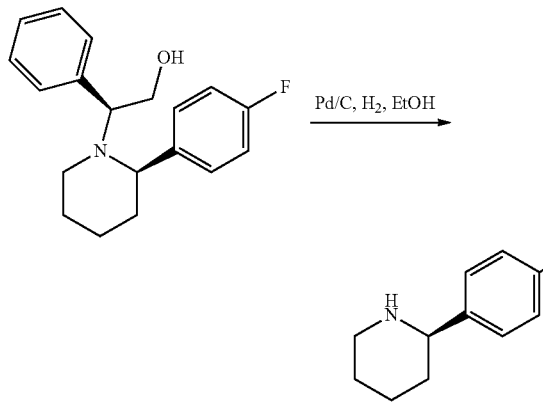

(R)-6-(4-Fluoro-phenyl)-1-((S)-2-hydroxy-1-phenylethyl)-piperidin-2-one (650 mg, 1.94 mmol) and palladium on charcoal (0.2 g) in ethanol (25 mL) were stirred under an atmosphere of hydrogen for 20 hours. The reaction mixture was filtered through Celite® then evaporated and the material dissolved in methanol and purified on a 10 g SCX-2 cartridge, eluting with 2 N ammonium hydroxide in methanol. The ammoniacal fractions were evaporated to yield the title compound (0.321 g), which was used in the synthesis of EE-46. LCMS m/z 180.11 [M+H]+ R.T.=1.3-1.6 min (Analytical Method 6).

(S)-2-(4-Fluoro-phenyl)-piperidine (0.31 g) was prepared by analogous methods to those used in the preparation of (R)-2-(4-fluoro-phenyl)-piperidine but starting from (R)-(−)-2-phenylglycinol. LCMS m/z 180.12 [M+H]+ R.T.=1.75-2.1 min (Analytical Method 6), which was used in the synthesis of EE-50.

Synthesis 69

(S)-2-Phenoxymethyl-pyrrolidine trifluoroacetate

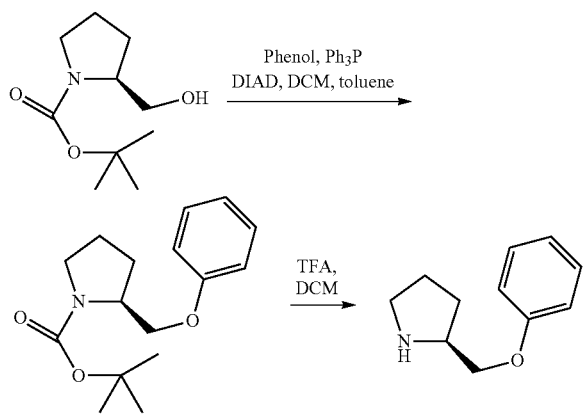

A solution of (S)-(−)-1-Boc-2-pyrrolidine methanol (0.267 g, 1.33 mmol), phenol (0.38 g, 4.02 mmol) and triphenylphosphine (0.71 g, 2.71 mmol) in DCM (5 mL) was cooled in an ice-bath and a solution of diisopropyl azodicarboxylate (0.55 g, 2.71 mmol) in toluene (3 mL) was added. The ice-bath was removed and the reaction mixture was stirred at room temperature over the weekend. The mixture was diluted with ether and washed with sodium hydroxide (3 M), then brine, dried over sodium sulfate and evaporated. The resultant solid was suspended in ethyl acetate and cyclohexane and the resultant white crystalline solid was removed by filtration. The filtrate was evaporated and the crude material was purified by column chromatography using a 10 g Si II cartridge eluting with 10% ethyl acetate in cyclohexane to afford (S)-2-phenoxymethyl-pyrrolidine-1-carboxylic acid tert-butyl ester as a clear oil (0.22 g).

This material (0.21 g, 0.76 mmol) was taken up in DCM (1 mL) and TFA (1 mL) was added. The mixture was stirred at room temperature for 2 hours and then the solvent was removed and the resultant oil was dried at 45° C. under high vacuum to afford the title compound as a colourless oil (0.28 g), which was used in the synthesis of EE-54. LCMS m/z 178.22 [M+H]+ R.T.=1.69 min (Analytical Method 6),

Synthesis 70

3-Phenyl-piperazine-1-carboxylic acid tert-butyl ester

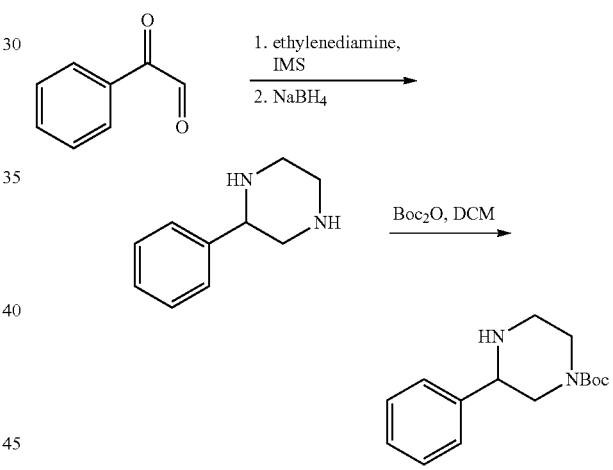

To a stirring solution of ethylenediamine (1.2 g, 20.0 mmol) in IMS (10 mL) was added a solution of phenylglyoxal hydrate (3.0 g, 20.0 mmol) in IMS (20 mL) dropwise. The resultant solution was stirred at room temperature for 3 hours and then sodium borohydride was added and the reaction mixture stirred over the weekend. Water (25 mL) was added and stirring continued for 15 minutes then the ethanol was removed by evaporation. A further amount of water (25 mL) was added and the solution was extracted with DCM (×3) then the combined organics were washed with brine, dried and the solvent evaporated. The material was purified by column chromatography using a silica II cartridge, eluting with 0-20% ammonia in methanol to afford 2-phenyl-piperazine as a pale yellow-orange solid (1.9 g). LCMS m/z 163.36 [M+H]+ R.T.=0.34 min (Analytical Method 6).

2-Phenyl-piperazine (1 g, 6.17 mmol) was dissolved in DCM (15 mL) and cooled to 0° C. before dropwise addition of di-tert-butyl dicarbonate (1.41 g, 6.48 mmol) as a solution in DCM (5 mL). The mixture was stirred at room temperature for 1 hour and then the solvent was removed and the residue purified by column chromatography on a 25 g silica II cartridge, eluting with 0-2% methanol in DCM to afford the title compound as a white crystalline solid (1.3 g). LCMS m/z 263.47 [M+H]+ R.T.=2.21 min (Analytical Method 6).

Synthesis 71

[2-Phenyl-4-(2,2,2-trifluoro-ethyl)-piperazin-1-yl]-[5-(1H-pyrazol-4-yl)-thiophen-3-yl]-methanone (EE-44)

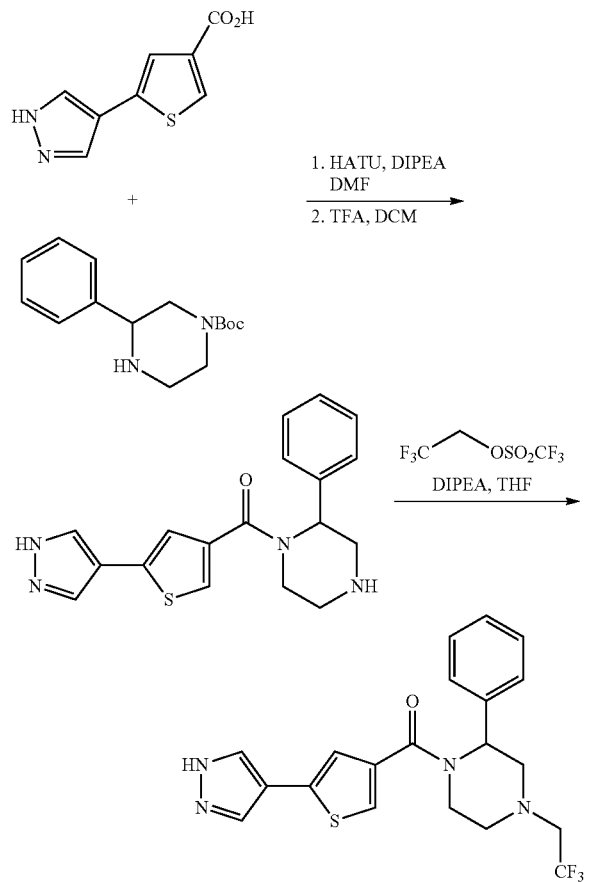

3-Phenyl-4-[5-(1H-pyrazol-4-yl)-thiophene-3-carbonyl]-piperazine-1-carboxylic acid tert-butyl ester (0.095 g) was prepared using analogous methods to Synthesis 46. LCMS m/z 439.2 [M+H]+ R.T.=3.57 min (Analytical Method 6).

This material was dissolved in DCM (2 mL) and TFA (2 mL) was added. After 1.5 hours, the solvent was evaporated and the crude material applied to a 5 g SCX-2 cartridge and eluted using 2 M ammonia in methanol to afford (2-phenyl-piperazin-1-yl)-[5-(1H-pyrazol-4-yl)-thiophen-3-yl]-methanone (0.070 g) as a clear gum.

This material (0.070 g, 0.21 mmol) was dissolved in anhydrous THF (5 mL) and DIPEA (0.08 g, 0.62 mmol) was added. The mixture was cooled in an ice-bath and 2,2,2-trifluoroethyl triflate (0.050 g, 0.22 mmol) was added dropwise as a solution in THF (1.5 mL). After stirring at room temperature for 2 hours, the reaction mixture was heated at reflux overnight. The solvent was removed by evaporation and the resultant gum was partitioned between water and DCM and the organic phase was evaporated then purified by HPLC, eluting with 5%-95% acetonitrile in water (0.1% formic acid) over 20 minutes. The fractions containing the desired product were evaporated to give the title compound as a white solid (0.060 g). LCMS m/z 421.15 [M+H]+ R.T.=10.04 min (Analytical Method 2).

Synthesis 72

[5-(1H-Pyrazol-4-yl)-thiophen-3-yl]-(2-pyridin-2-yl-pyrrolidin-1-yl)-methanone (EE-45)

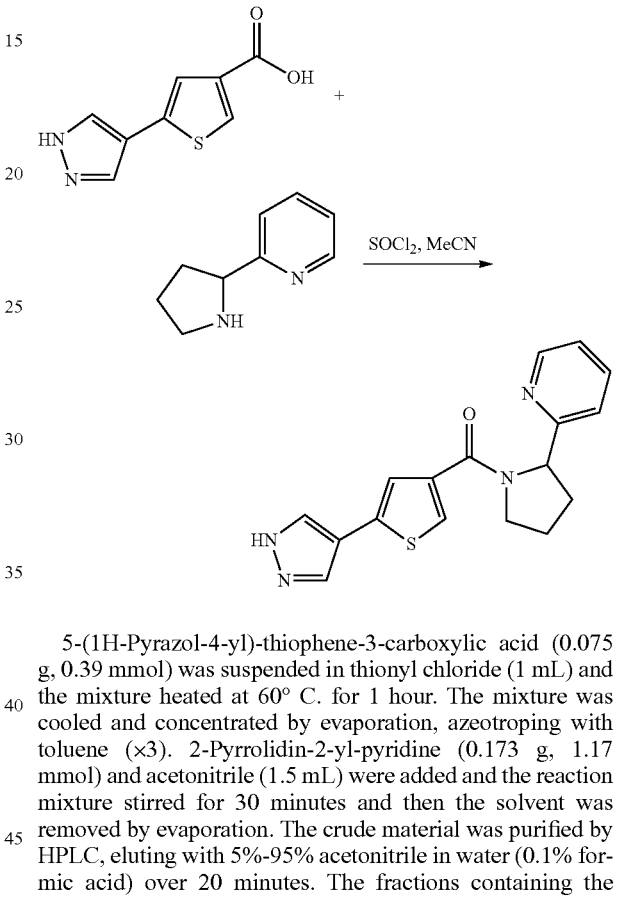

5-(1H-Pyrazol-4-yl)-thiophene-3-carboxylic acid (0.075 g, 0.39 mmol) was suspended in thionyl chloride (1 mL) and the mixture heated at 60° C. for 1 hour. The mixture was cooled and concentrated by evaporation, azeotroping with toluene (×3). 2-Pyrrolidin-2-yl-pyridine (0.173 g, 1.17 mmol) and acetonitrile (1.5 mL) were added and the reaction mixture stirred for 30 minutes and then the solvent was removed by evaporation. The crude material was purified by HPLC, eluting with 5%-95% acetonitrile in water (0.1% formic acid) over 20 minutes. The fractions containing the desired product were evaporated, azeotroping with methanol (×3), to give the title compound as a foam (0.025 g). LCMS m/z 325.18 [M+H]+ R.T.=5.07 min (Analytical Method 2).

Synthesis 73

5-Phenyl-thiophene-3-carboxylic acid

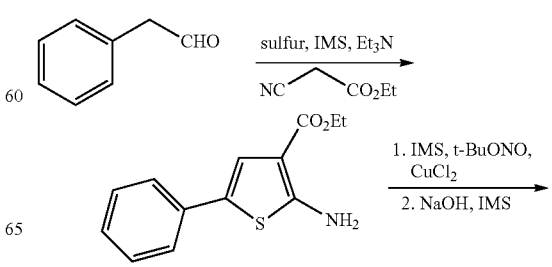

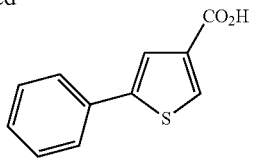

A mixture of phenylacetaldehyde (9.3 mL, 0.083 mol), sulfur (2.64 g, 0.083 mmol), ethyl cyanoacetate (5.73 mL, 0.054 mmol) and triethylamine (15 mL, 0.108 mol) in IMS (80 mL) was heated at 60° C. for 2 hours. The mixture was left to stand at room temperature and the resultant precipitate was collected by filtration and re-crystallised from hot ethanol to afford 2-amino-5-phenyl-thiophene-3-carboxylic acid ethyl ester (7.97 g).

Anhydrous copper (II) chloride (4 g, 0.03 mol) and tert-butyl nitrite (1.9 mL, 0.019 mol) were dissolved in IMS (100 mL) then treated with 2-amino-5-phenyl-thiophene-3-carboxylic acid ethyl ester (2 g, 8.097 mmol). After 30 minutes saturated aqueous ammonium chloride (20 mL) was added and the mixture left for a further 30 minutes. The resultant precipitate was filtered off and the filtrate was concentrated, washed with DCM, dried and concentrated to give a dark oil which was purified by column chromatography, eluting with 0-35% tert-butyl methyl ether in cyclohexane to afford 5-phenyl-thiophene-3-carboxylic acid ethyl ester as a yellow oil (1.38 g).

This material (1.38 g, 5.95 mmol) was placed into a microwave vial together with sodium hydroxide (1 N, 10 mL) and IMS (10 mL) and the mixture was heated by microwave irradiation to 140° C. for 10 minutes. The solution was acidified with 1 M HCl and the resultant white precipitate was collected by filtration, washed with water and suction-dried to yield the title compound as a pale solid (1.01 g). $^1$H NMR 6 (400 MHz, CHCl$_3$-d): 8.2 (d, 1H), 7.8 (d, 1H), 7.6-7.6 (m, 2H), 7.5-7.3 (m, 3H).

Synthesis 74

4,4-Difluoro-azepane hydrochloride

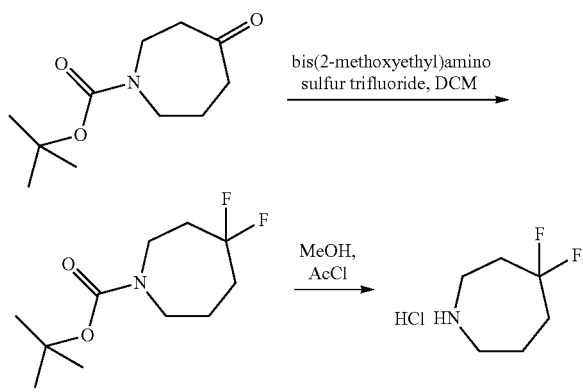

4-Oxo-azepane-1-carboxylic acid tert-butyl ester (5 g, 0.023 mol) was dissolved in DCM (50 mL), and treated with bis(2-methoxyethyl)aminosulfur trifluoride (8 mL, 0.043 mol). The reaction mixture was stirred at room temperature for 48 hours. The mixture was treated carefully with saturated aqueous caesium carbonate solution and the organic phase separated, dried and concentrated. The crude material was purified by chromatography, eluting with 0-30% tert-butyl methyl ether in cyclohexane to give 4,4-difluoro-azepane-1-carboxylic acid tert-butyl ester as an oil (4.3 g).

Acetyl chloride (3.9 mL) was added to methanol (90 mL) at 0° C. and stirred for 20 minutes before addition of 4,4-difluoro-azepane-1-carboxylic acid tert-butyl ester as a solution in methanol (10 mL). After 30 minutes, HCl in dioxane (4 N, 40 mL) was added cautiously and the mixture was stirred at room temperature for 3 hours. The solution was concentrated, triturated with ether, filtered and dried under vacuum overnight to afford the title compound as an off-white solid (2.1 g). $^1$H NMR (400 MHz, DMSO): δ 9.5 (s, 2H), 3.2-3.1 (m, 4H), 2.5-2.4 (m, 2H), 2.3-2.2 (m, 2H), 1.9-1.8 (m, 2H).

Synthesis 75

(4,4-Difluoro-azepan-1-yl)-(5-phenyl-thiophen-3-yl)-methanone (AA-26)

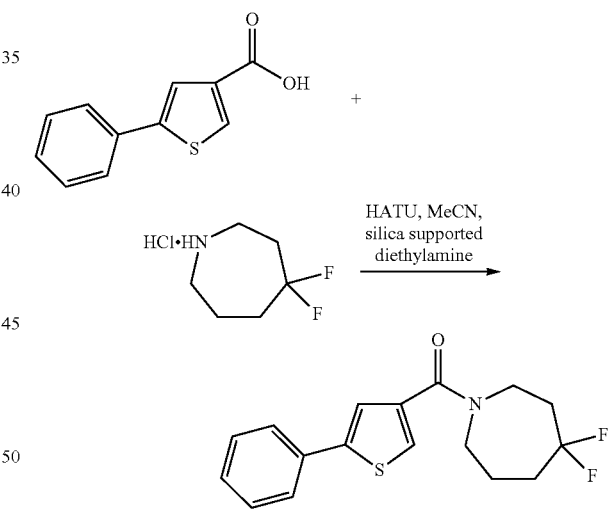

5-Phenyl-thiophene-3-carboxylic acid (0.20 g, 1.11 mmol) and 4,4-difluoro-azepane hydrochloride (0.19 g, 1.11 mmol) were stirred in acetonitrile (10 mL) with silica-supported diethylamine (1.32 mmol/g, 2.5 g) and HATU (0.40 g, 1.11 mmol) for 18 hours. The reaction mixture was filtered and the solvent was removed by evaporation then the crude material was purified by HPLC, eluting with 10%-98% acetonitrile in water (0.1% formic acid) over 20 minutes. The fractions containing the desired product were evaporated to give the title compound as a gum (0.15 g). LCMS m/z 322.19 [M+H]$^+$ R.T.=11.14 min (Analytical Method 2).

Synthesis 76

(2-Chloro-5-phenyl-thiophen-3-yl)-(4,4-difluoro-azepan-1-yl)-methanone (AA-43)

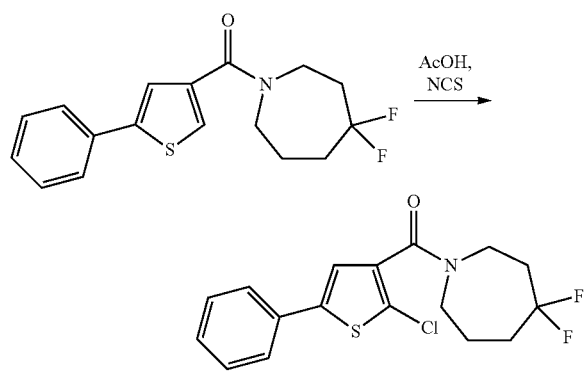

(4,4-Difluoro-azepan-1-yl)-(5-phenyl-thiophen-3-yl)-methanone (0.104 g, 0.33 mmol) and N-chlorosuccinimide (0.445 g, 0.33 mmol) in acetic acid (2 mL) were heated by microwave irradiation to 140° C. for 4 minutes. The mixture was diluted with acetonitrile and water and purified by HPLC, eluting with 10%-98% acetonitrile in water (0.1% formic acid). The fractions containing the desired product were evaporated to give the title compound as a gum (0.03 g). LCMS m/z 356.13 [M+H]+ R.T.=12.26 min (Analytical Method 2).

Synthesis 77

5-Oxazol-4-yl-thiophene-3-carboxylic acid

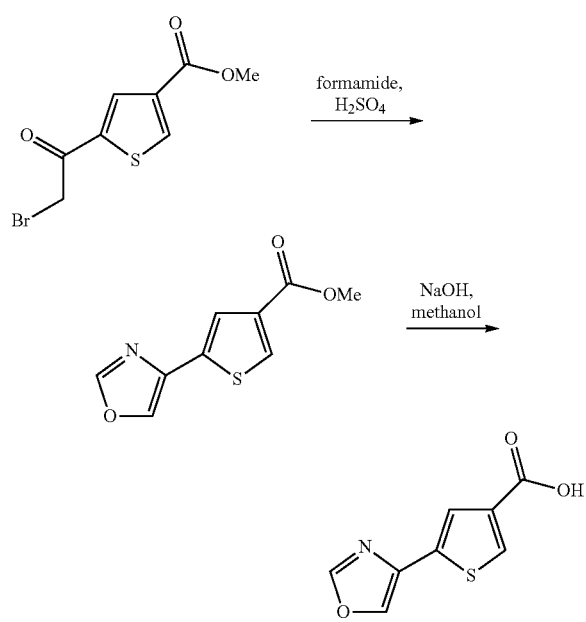

5-(2-Bromo-acetyl)-thiophene-3-carboxylic acid methyl ester (0.60 g, 2.28 mmol) was suspended in formamide (10 mL) then sulfuric acid (1 mL) was added and the tube purged with nitrogen then sealed. The mixture was heated at 150° C. by microwave irradiation for 15 minutes. The resultant solution was diluted with HCl (1 N) and water and extracted with ethyl acetate (×3). The organic phase was dried over sodium sulfate and evaporated then purified by chromatography on a silica II cartridge, eluting with 1:1 DCM: cyclohexane to afford 5-oxazol-4-yl-thiophene-3-carboxylic acid methyl ester as a pale yellow solid (0.197 g). LCMS m/z 210.14 [M+H]+ R.T.=3.64 min (Analytical Method 9).

5-Oxazol-4-yl-thiophene-3-carboxylic acid methyl ester (0.338 g, 1.62 mmol) was dissolved in methanol (3 mL) and sodium hydroxide (1 N, 2.1 mL) was added. The mixture was stirred at room temperature for 2 hours then a further amount of sodium hydroxide (1 N, 1 mL) was added and stirring continued overnight. The mixture was concentrated and the residue treated with HCl (1 N, 3.5 mL). The resultant precipitate was collected by filtration to give the title compound as a tan/off-white solid (0.158 g). The filtrate was passed through an SCX-2 cartridge (20 g) and concentrated to give a further amount of the title compound as a tan solid (0.078 g). LCMS m/z 196.13 [M+H]+ R. T.=3.22 min (Analytical Method 9).

Synthesis 78

(4,4-Difluoro-azepan-1-yl)-(5-oxazol-4-yl-thiophen-3-yl)-methanone (EE-61)

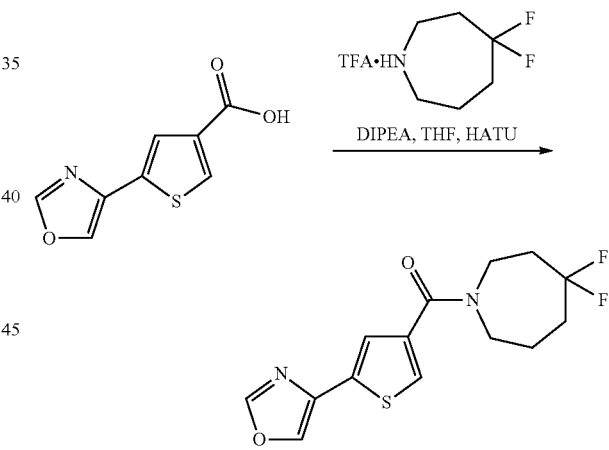

4,4-Difluoro-azepane trifluoroacetate (Synthesis 47, 0.113 g, 0.45 mmol) was dissolved in THF (1 mL) and added to 5-oxazol-4-yl-thiophene-3-carboxylic acid (0.059 g, 0.30 mmol). DIPEA (0.154 mL, 0.90 mmol) was added followed by HATU (0.125 g, 0.33 mmol) and the reaction mixture was then stirred at room temperature overnight. The mixture was diluted with DCM then washed with aqueous sodium carbonate solution. The organics were dried over sodium sulfate, filtered and evaporated. The crude material was purified by HPLC, eluting with 5%-98% methanol in water (0.1% formic acid). The fractions containing the desired product were freeze-dried to give the title compound (0.029 g). LCMS m/z 313.15 [M+H]+ R.T.=8.31 min (Analytical Method 10).

The following compounds were prepared using analogous methods.

| Code No. | Structure | ¹H NMR | Analytical Method | R.T. (min) | MS [m/z] |
|---|---|---|---|---|---|
| EE-62 | 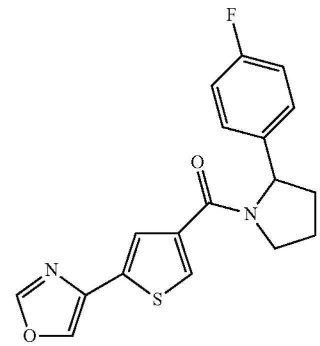 | — | 10 | 9.79 | 343.14 |
| EE-63 | 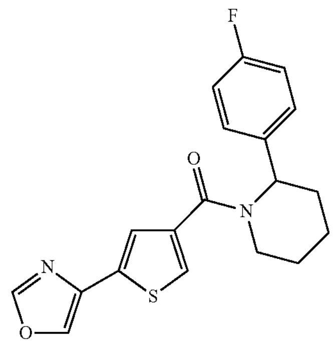 | — | 10 | 10.86 | 357.15 |

Biological Methods

Cellular In Vitro 11β-HSD1 Enzyme Inhibition Assay

Compounds were assessed by a Scintillation Proximity Assay (SPA) performed according to the following protocol:

HEK293 cells were stably transfected with a construct containing the full-length gene coding for the human 11β-HSD1 enzyme to create HEK293/11β-HSD1 cells. Cells were routinely cultured in DMEM containing 10% calf foetal serum, 1% glutamine, and 1% penicillin and streptomycin. Prior to assay, cells were plated at $2\times10^4$ cells/well in 96-well poly-D-Lys coated flat-bottomed microplates and incubated in 5% $CO_2$, 95% $O_2$ at 37° C. for 24 hours. The media in each well was removed immediately before assay.

Compounds to be tested were dissolved in DMSO at 10 mM and serially diluted into water containing 10% DMSO. Diluted compounds at a volume of 10 μL were added to wells of a 96-well V-bottomed microplate. A solution of DMEM, 1% glutamine, 1% penicillin and streptomycin, and 22 nM tritiated cortisone was prepared and 90 μL added to each well of the assay plate. This solution (100 pL/well) was transferred to the plate containing the cells. The plate was then incubated in 5% $CO_2$, 95% $O_2$ at 37° C. for 2 hours.

Following this incubation, 50 μL of the assay solution was transferred to each well of a 96-well scintillation microplate. A mixture consisting of anti-mouse YSi SPA beads, pre-mixed with anti-cortisol antibody in assay buffer (50 mM Tris.HCl, pH 7.0; 300 mM NaCl; 1 mM EDTA, 5% glycerol) was prepared and 50 μL added to each well of the scintillation microplate. An adhesive strip was applied to the microplate and the plate gently shaken for at least 2 hours at room temperature, and then spun briefly on a low speed centrifuge. The plate was read on a scintillation counter suitable for 96-well microplates. For the calculation of percentage inhibition, a series of wells were added to the plate that represented the assay maximum and the assay minimum: one set that contained substrate without cells (mimimum) and another set that contained substrate and cells without any compound (maximum).

The calculation of median inhibitory concentration ($IC_{50}$) values for the compounds was performed using GraphPad Prism® software. Dose-response curves for each compound were plotted as fractional inhibition and data fitted to the four parameter logistic equation.

Cellular In Vitro 11β-HSD2 Enzyme Inhibition Assay

For measurement of inhibition of 11β-HSD2, CHO cells stably transfected with the full-length gene coding for human 11β-HSD2 were used. Assays were carried out in 96-well microplates containing $1\times10^5$ cells/well. Controls and compounds were plated as above, so that the final DMSO concentration in each well was 1%. To initiate the assay, 90 μL of a solution of HAMS F-12 medium containing 1% glutamine, 1% penicillin and streptomycin, and 22 nM tritiated cortisol was added to each well of the assay plate. The plate was then incubated in 5% $CO_2$, 95% $O_2$ at 37° C. for 16 hours.

The assay solutions were transferred to glass tubes and 20 μL ethyl acetate added to each tube. Each tube was vortexed thoroughly and the upper layer containing the tritiated steroid transferred to a fresh glass tube. The solvent was evaporated by placing the tubes in a heating block at 65° C. under a stream of Nitrogen gas. 20 μL ethanol was added to each of the dried samples and vortexed briefly. Each sample was applied to a silica TLC plate and the plate dried. The plate was placed vertically in a glass tank containing 92% chloroform:8% ethanol and the solvent allowed to rise up the plate. The plate was dried, placed in an imaging cassette, and overlayed with a tritium imaging plate for 1-2 days. The amount of enzyme inhibition in each sample was determined by measuring the intensity of the substrate and product spots using a phosphoimager.

IC$_{50}$ values for inhibitors were determined as described for 11β-HSD1.

Biological Data

Cellular In Vitro Enzyme Inhibition Data

The following compounds were tested using the cellular in vitro enzyme inhibition assays described above: AA-01 through AA-51; BB-01 through BB-07; CC-01 through CC-02; DD-01; EE-001 through EE-64; FF-001 through FF-30; and GG-01 through GG-04.

All of the compounds tested have an IC$_{50}$ of less than about 35 μM, often less than about 10 μM, and in many cases less than about 1 μM. Generally, the IC$_{50}$ ratio for 11β-HSD2 to 11β-HSD1 is at least about five or greater, and in many cases ten or greater. For example, data for some of the compounds is shown in the following table.

TABLE 1

In vitro Enzyme Inhibition Data

| Code No. | IC$_{50}$ for 11β-HSD1 (HEK293) | IC$_{50}$ for 11β-HSD2 (CHO) |
| --- | --- | --- |
| AA-30 | 130 nM | >10,000 nM |
| BB-03 | 513 nM | >10,000 nM |
| CC-02 | 1,400 nM | >10,000 nM |
| EE-12 | 799 nM | >10,000 nM |
| FF-06 | 463 nM | >10,000 nM |
| GG-01 | 339 nM | >10,000 nM |

The following compounds have an IC$_{50}$ for 11β-HSD1 (HEK293) of less than or equal to 1000 nM (1 μM): AA-21, AA-28, AA-29, AA-30, AA-32, AA-33, AA-35, AA-37, AA-39, AA-42, AA-46, AA-51, BB-03, BB-04, BB-05, EE-07, EE-12, EE-13, EE-14, EE-16, EE-18, EE-19, EE-23, EE-24, EE-25, EE-26, EE-27, EE-31, EE-32, EE-33, EE-34, EE-36, EE-37, EE-38, EE-39, EE-40, EE-41, EE-42, EE-43, EE-46, EE-47, EE-48, EE-49, EE-52, EE-53, EE-54, EE-55, EE-56, EE-57, EE-58, EE-59, EE-60, EE-61, EE-62, EE-63, EE-64, FF-01, FF-06, FF-08, FF-09, FF-10, FF-11, FF-12, FF-15, FF-16, FF-17, FF-18, FF-19, FF-20, FF-22, FF-23, FF-25, FF-26, FF-29, GG-01, GG-02, GG-03, GG-04.

The following compounds have an IC$_{50}$ for 11β-HSD1 (HEK293) of more than 1000 nM (1.0 μM) and less than or equal to 30 μM: AA-01, AA-02, AA-03, AA-04, AA-05, AA-06, AA-07, AA-08, AA-09, AA-10, AA-11, AA-12, AA-13, AA-14, AA-15, AA-16, AA-17, AA-18, AA-19, AA-20, AA-22, AA-23, AA-24, AA-25, AA-26, AA-27, AA-31, AA-34, AA-36, AA-38, AA-40, AA-41, AA-43, AA-44, AA-45, AA-47, AA-48, AA-49, AA-50, BB-01, BB-02, BB-06, BB-07, CC-01, CC-02, DD-01, EE-01, EE-02, EE-03, EE-04, EE-05, EE-06, EE-08, EE-09, EE-10, EE-11, EE-15, EE-17, EE-20, EE-21, EE-22, EE-28, EE-29, EE-30, EE-35, EE-44, EE-45, EE-50, EE-51, FF-02, FF-03, FF-04, FF-05, FF-07, FF-13, FF-14, FF-21, FF-24, FF-27, FF-28, FF-30.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Andrews, R. C., et al., 2003, "Effects of the 11beta-hydroxysteroid dehydrogenase inhibitor carbenoxolone on insulin sensitivity in men with type 2 diabetes," *J. Clin. Endocrinol. Metab.*, Vol. 88, pp. 285-291.

Arnold, W. D., et al., 2007, "Pyrimidinyl-Thiophene Kinase Modulators", international patent publication number WO 2007/053776 A1 published 10 May 2007.

Bao, J., et al., 2000, "3-Thienyl and 3-Furanyl Pyrrolidine Modulators of Chemokine Receptor Activity", international patent publication number WO 00/51608 A1 published 8 Sep. 2000.

Christy, C., et al., 2003, "Glucocorticoid action in mouse aorta; localisation of 11β-hydroxysteroid dehydrogenase type 2 and effects on responses to glucocorticoids in vitro," *Hypertension*, Vol. 42, pp. 580-587.

Cooper, M. S., et al., 2000, "Expression and functional consequences of 11β-hydroxysteroid dehydrogenase activity in human bone," *Bone*, Vol. 27, pp. 375-381.

Ernst, G., et al., 2004, "Biaryl Diazabicycloalkane Amides as Nicotinic Acetylcholine Agonists", international patent publication number WO 2004/016617 A1 published 26 Feb. 2004.

Hadoke, P. W. F., et al., 2001, "Endothelial cell dysfunction in mice after transgenic knockout of type 2, but not type 1, 11β-hydroxysteroid dehydrogenase," *Circulation*, Vol. 104, pp. 2832-2837.

Hwang et al., 2001, "4-Hydroxy-6-oxo-6,7-dihydro-thieno [2,3-b]pyrimidine derivatives: synthesis and their biological evaluation for the glycine site acting on the N-methyl-D-aspartate (NMDA) receptor", *Archives of Pharmacol. Research*, Vol. 24, No. 4, pp. 270-275.

Kotelevtsev, Y. V., et al., 1997, "11β-Hydroxysteroid dehydrogenase type 1 knockout mice show attenuated glucocorticoid inducible responses and resist hyperglycaemia on obesity and stress," *Proc. Natl. Acad. Sci.*, Vol. 94, pp. 14924-14929

Masuzaki, H., et al., 2001, "A Transgenic Model of Visceral Obesity and the Metabolic Syndrome," *Science*, Vol. 294, pp. 2166-2170.

Moisan, M. P., et al., 1990, "11 beta-hydroxysteroid dehydrogenase bioactivity and messenger RNA expression in rat forebrain: localization in hypothalamus, hippocampus, and cortex," *Endocrinology*, Vol. 127, pp. 1450-1455.

Morton, N. M., et al., 2001, "Improved lipid and lipoprotein profile, hepatic insulin sensitivity, and glucose tolerance in 11β-hydroxysteroid dehydrogenase type 1 null mice," *J. Biol. Chem.*, Vol. 276, pp. 41293-41300.

Morton, N. M., et al., 2004, "Novel adipose tissue-mediated resistance to diet-induced visceral obesity in 11β-hydroxysteroid dehydrogenase type 1 deficient mice," *Diabetes*, Vol. 53, pp. 931-938.

Paterson, J. M., et al., 2004, "Metabolic syndrome without obesity: hepatic overexpression of 11β-hydroxysteroid dehydrogenase type 1 in transgenic mice," *Proc. Natl. Acad. Sci.*, Vol. 101, pp. 7088-7093).

Rask, E., et al., 2001, "Tissue-specific dysregulation of cortisol metabolism in human obesity," *J. Clin. Endocrinol. Metab.*, Vol. 86, pp. 1418-1421.

Rauz, S., et al., 2001, "Expression and putative role of 11 beta-hydroxysteroid dehydrogenase isozymes within the human eye," *Investigative Opthalmology & Visual Science*, Vol. 42, pp. 2037-2042.

Sandeep, T. C., et al., 2004, "11β-hydroxysteroid dehydrogenase inhibition improves cognitive function in healthy elderly men and type 2 diabetics," *Proc. Natl. Acad. Sci. Vol.* 101, pp. 6734-6739.

Seckl, J. R., Walker, B. R., 2001, "11β-Hydroxysteroid dehydrogenase type 1—a tissue-specific amplifier of glucocorticoid action," *Endocrinology*, Vol. 142, pp. 1371-1376.

Small, G. R., et al., 2005, "Preventing local regeneration of glucocorticoids by 11β-hydroxysteroid dehydrogenase type 1 enhances angiogenesis," *Proc. Natl. Acad. Sci.*, Vol. 102, pp. 12165-12170.

Walker, B. R., et al., 1991, "11β-Hydroxysteroid dehydrogenase in vascular smooth muscle and heart: implications for cardiovascular responses to glucocorticoids," *Endocrinology*, Vol. 129, pp. 3305-3312.

Walker, B. R., et al., 1995, "Carbenoxolone increases hepatic insulin sensitivity in man: a novel role for 11-oxosteroid reductase in enhancing glucocorticoid receptor activation," *J. Clin. Endocrinol. Metab.*, Vol. 80, pp. 3155-3139.

Yau, J. L. W., et al., 2001, "Lack of tissue glucocorticoid reactivation in 11β-hydroxysteroid dehydrogenase type 1 knockout mice ameliorates age-related learning impairments," *Proc. Natl. Acad. Sci.*, Vol. 98, pp. 4716-4721.

The invention claimed is:

1. A compound selected from compounds of the following formula, and pharmaceutically acceptable salts thereof:

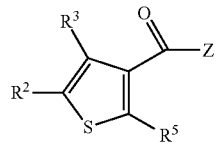

wherein:
—$R^2$ is independently —$R^{2B}$;
—$R^3$ is independently —H;
—$R^5$ is independently —H; and
-Z is independently -$J^1$ or $J^2$;
wherein:
—$R^{2B}$ is independently pyrazolyl, and is optionally substituted with one or more substituents independently selected from: —$R^{X1}$, —F, —Cl, —Br, —OH, O$R^{X1}$, —CN, —$NH_2$, —NH$R^{X1}$, or —N$R^{X1}{}_2$; wherein each —$R^{X1}$ is independently saturated aliphatic $C_{1-4}$alkyl;
wherein:
-$J^1$ is independently a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, and wherein said non-aromatic heterocyclyl group is optionally substituted; and
-$J^2$ is independently a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, and wherein said fused bicyclic non-aromatic heterocyclyl group is optionally substituted;

wherein:
each of -$J^1$ and $J^2$ is optionally substituted with one or more substituents independently selected from:
substituents on carbon, independently selected from: —$R^Q$, —$R^R$, $R^LR^R$, F, —Cl, —Br, —OH, —$R^L$—OH, —O$R^P$, —$R^L$—O$R^P$, —$NH_2$, —NH$R^P$, —N$R^P{}_2$, and —CN; and
substituents on nitrogen, if present, independently selected from: —$R^Q$, —$R^R$, —$R^L$—$R^R$, and —S(=O)$_2R^P$, wherein:
each —$R^P$ is independently —Re, —$R^R$, or —$R^L$—$R^R$;
each —$R^Q$ is independently saturated aliphatic $C_{1-4}$alkyl, and is optionally substituted with one or more fluorine atoms;
each —$R^R$ is independently phenyl, furanyl, thienyl, pyrrolyl, imidazolyl, pyrazolyl, triazolyl, tetrazolyl, oxazolyl, isoxazolyl, thiazolyl, isothiazolyl, pyridyl, pyrimidinyl, or pyridazinyl, and is optionally substituted with one or more substituents independently selected from:
—F, —Cl, —Br,
—$R^{K1}$, —$CF_3$,
—OH, —$OCF_3$,
—$NH_2$, —NH$R^{K1}$, —N$R^K{}_{12}$, and
—CN;
wherein each —$R^{K1}$ is independently saturated aliphatic $C_{1-4}$alkyl; and
each —$R^L$— is independently saturated aliphatic $C_{1-4}$alkylene.

2. A compound according to claim 1, wherein -Z is independently -$J^1$.

3. A compound according to claim 1, wherein -Z is independently -$J^2$.

4. A compound according to claim 1, wherein —$R^{2B}$ is independently pyrazol-4-yl, and is optionally substituted with one or more substituents independently selected from: —$R^{X1}$, —F, —Cl, —Br, —OH, —O$R^{X1}$, —CN, —$NH_2$, —NH$R^{X1}$, or —N$R^{X1}{}_2$; wherein each —$R^{X1}$ is independently saturated aliphatic $C_{1-4}$alkyl.

5. A compound according to claim 2, wherein —$R^{2B}$ is independently pyrazol-4-yl, and is optionally substituted with one or more substituents independently selected from: —$R^{X1}$, —F, —Cl, —Br, —OH, —O$R^{X1}$, —CN, —$NH_2$, —NH$R^{X1}$, or —N$R^{X1}{}_2$; wherein each —$R^{X1}$ is independently saturated aliphatic $C_{1-4}$alkyl.

6. A compound according to claim 3, wherein —$R^{2B}$ is independently pyrazol-4-yl, and is optionally substituted with one or more substituents independently selected from: —$R^{X1}$, —F, —Cl, —Br, —OH, —O$R^{X1}$, —CN, —NH$R^{X1}$, or —N$R^{X1}{}_2$; wherein each —$R^{X1}$ is independently saturated aliphatic $C_{1-4}$alkyl.

7. A compound according to claim 2, wherein -$J^1$ is independently selected from the following groups and is optionally substituted with one or more substituents independently selected from —$R^Q$, —$R^R$, —$R^L$—$R^R$, —F, —Br, —OH, —$R^L$—OH, —O$R^P$, —$R^L$—O$R^P$, —$NH_2$, —NH$R^P$, —N$R^P{}_2$, and —CN:

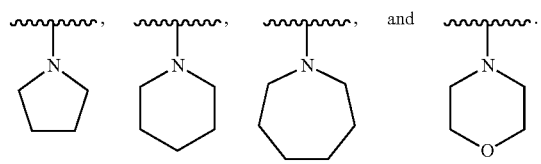

8. A compound according to claim 2, wherein -J¹ is independently the following group and is optionally substituted with one or more substituents independently selected from —R$^Q$, —R$^R$, R$^L$—R$^R$, F, —Cl, —Br, —OH, —R$^L$—OH, —OR$^P$, —R$^L$—OR$^P$, —NH$_2$, —NHR$^P$, —NR$^P_2$, and —CN:

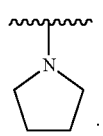

9. A compound according to claim 2, wherein -J¹ is independently the following group and is optionally substituted with one or more substituents independently selected from —R$^Q$, —R$^R$, R$^L$—R$^R$, F, —Br, —OH, —R$^L$—OH, —OR$^P$, —R$^L$—OR$^P$, —NH$_2$, —NHR$^P$, —NR$^P_2$, and —CN:

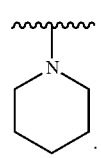

10. A compound according to claim 2, wherein -J¹ is independently the following group and is optionally substituted with one or more substituents independently selected from —R$^Q$, —R$^R$, R$^L$—R$^R$, F, —Cl, —Br, —OH, —R$^L$—OH, —OR$^P$, —R$^L$—OR$^P$, —NH$_2$, —NHR$^P$, —NR$^P_2$, and —CN:

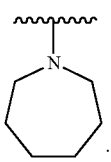

11. A compound according to claim 2, wherein -J¹ is independently the following group and is optionally substituted with one or more substituents independently selected from —R$^Q$, —R$^R$, —R$^L$—R$^R$, —F, —Cl, —Br, —OH, —R$^L$—OH, —OR$^P$, —R$^L$—OR$^P$, —NH$_2$, —NHR$^P$, —NR$^P_2$, and —CN:

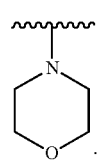

12. A compound according to claim 2, wherein -J¹ is independently selected from the following groups:

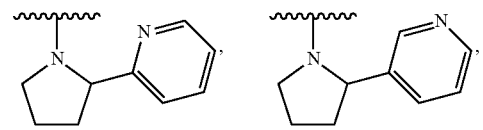

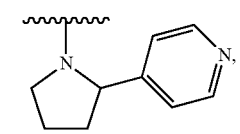

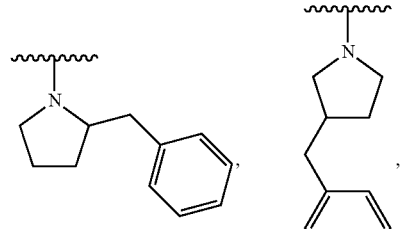

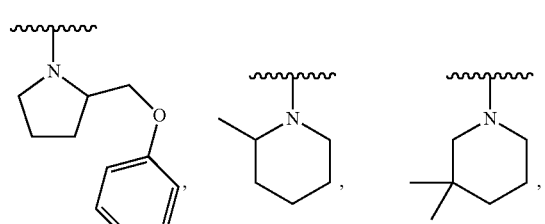

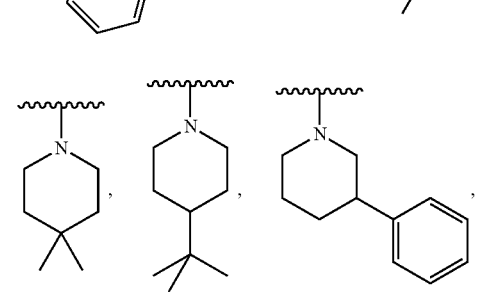

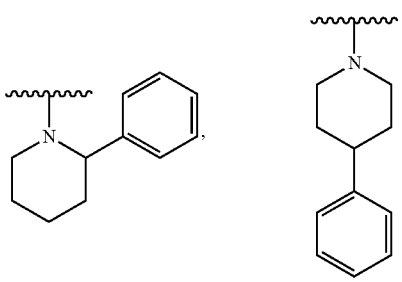

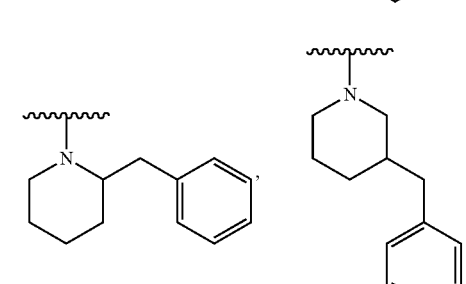

-continued

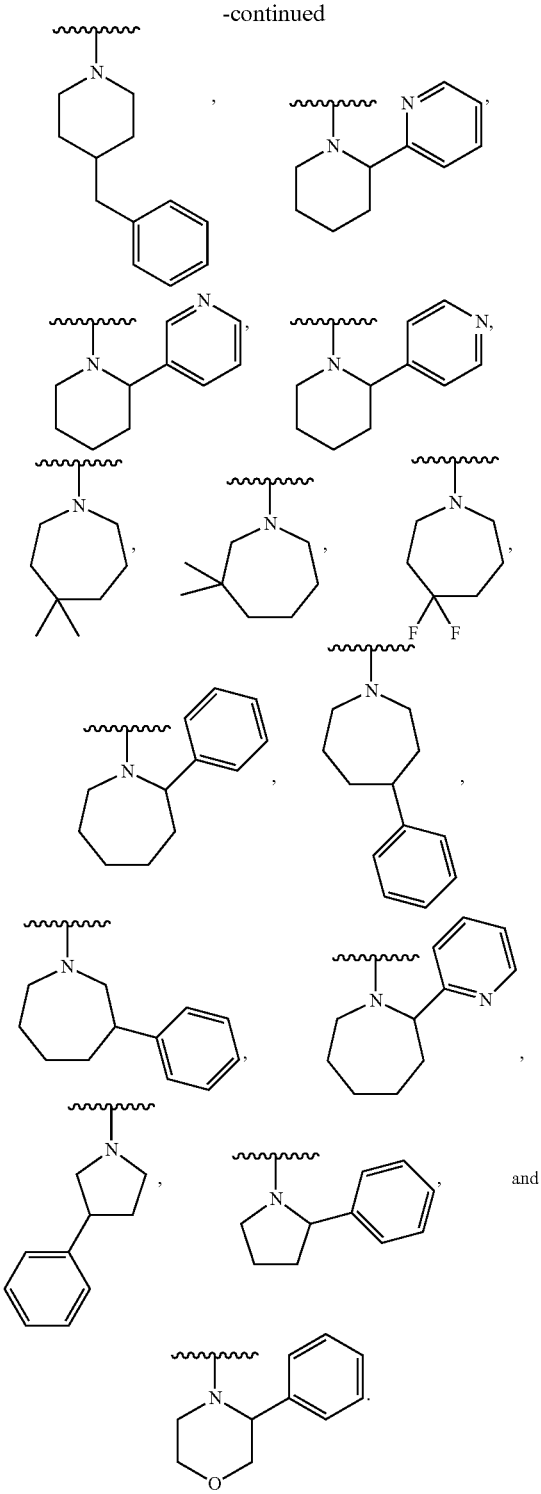

13. A compound according to claim 3, wherein exactly 1 of said -J² ring atoms is a ring heteroatom, and is N.

14. A compound according to claim 3, wherein said -J² is a fused bicyclic non-aromatic heterocyclyl group having 10 ring atoms.

15. A compound according to claim 3, wherein -J² is independently the following group and is optionally substituted with one or more substituents independently selected from —R$^Q$, —R$^R$, R$^L$—R$^R$, F, —Cl, —Br, —OH, —R$^L$—OH, —OR$^P$, —R$^L$—OR$^P$, —NH$_2$, —NHR$^P$, —NR$^P_2$, and —CN:

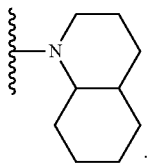

16. A compound according to claim 3, wherein -J² is independently the following group and is unsubstituted:

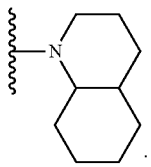

17. A compound according to claim 3, wherein -J² is independently selected from the following groups and is unsubstituted:

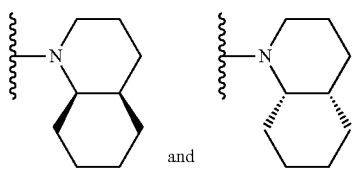

and

18. A compound according to claim 2, selected from the following compounds, and pharmaceutically acceptable salts thereof:

(EE-08)

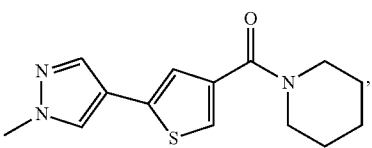

(EE-16)

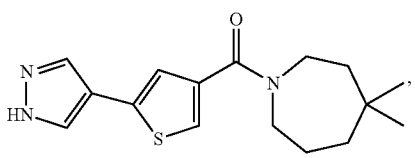

(EE-17)

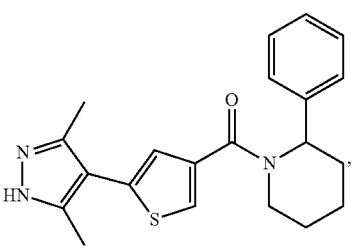

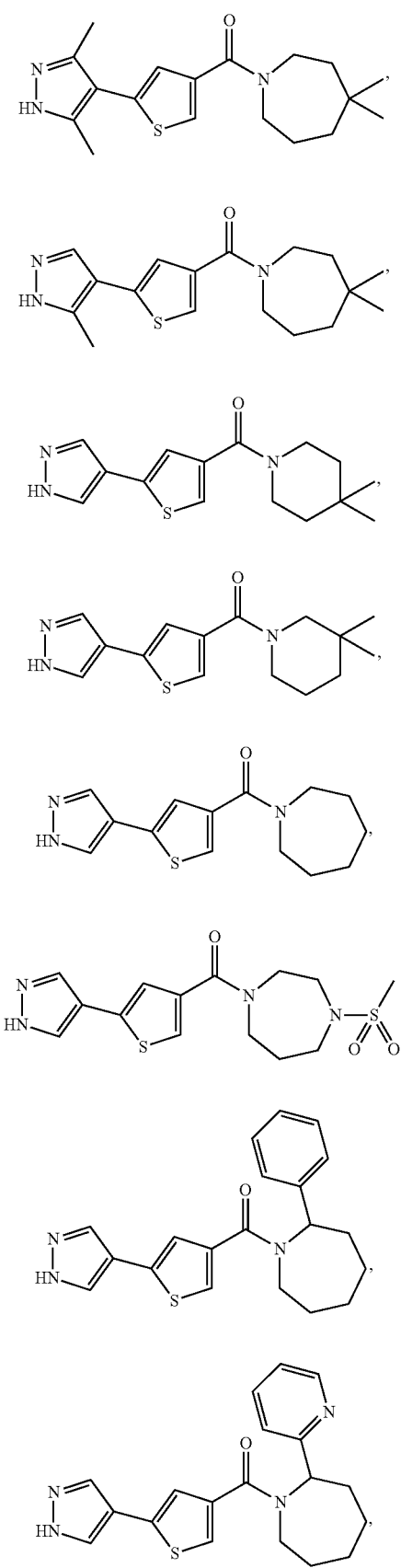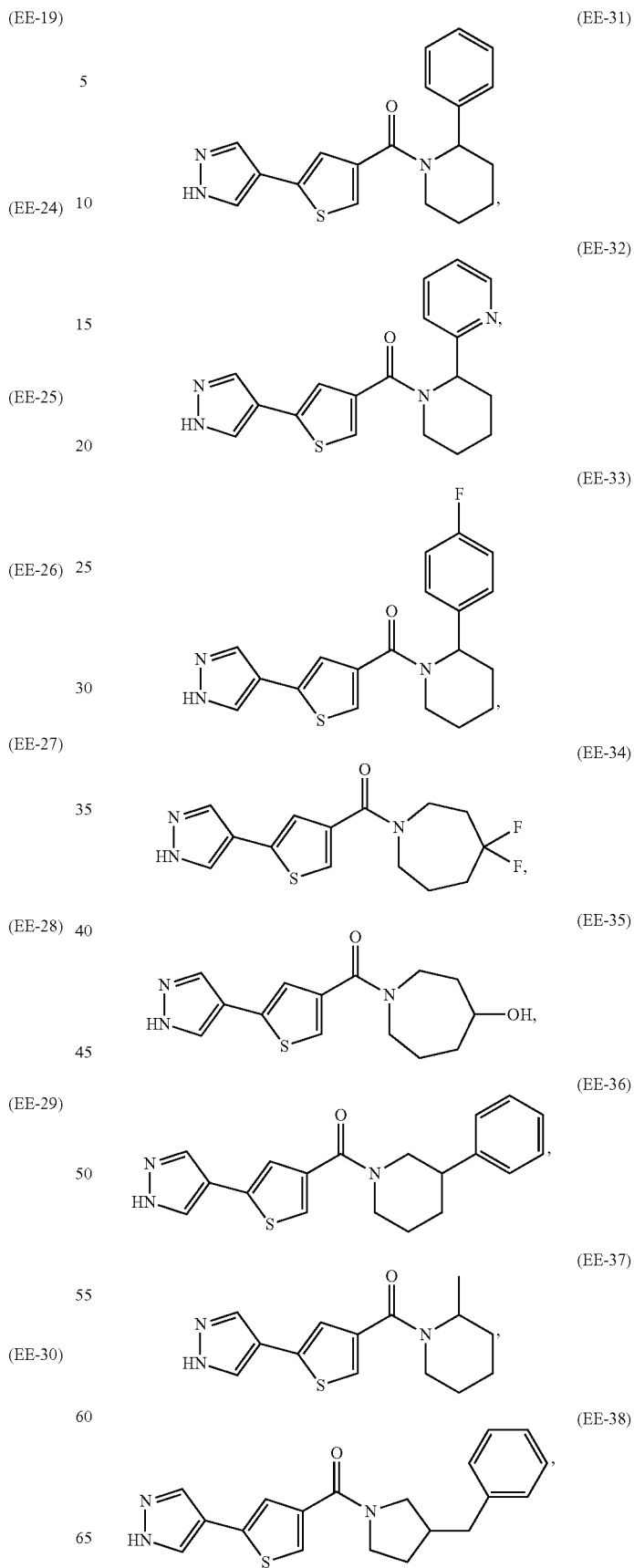

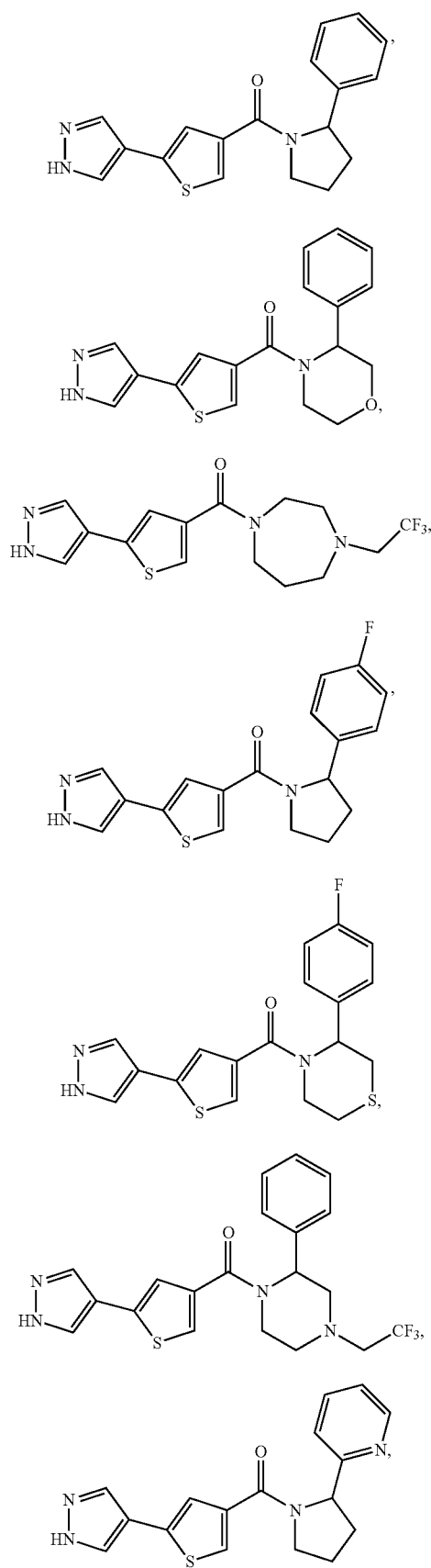
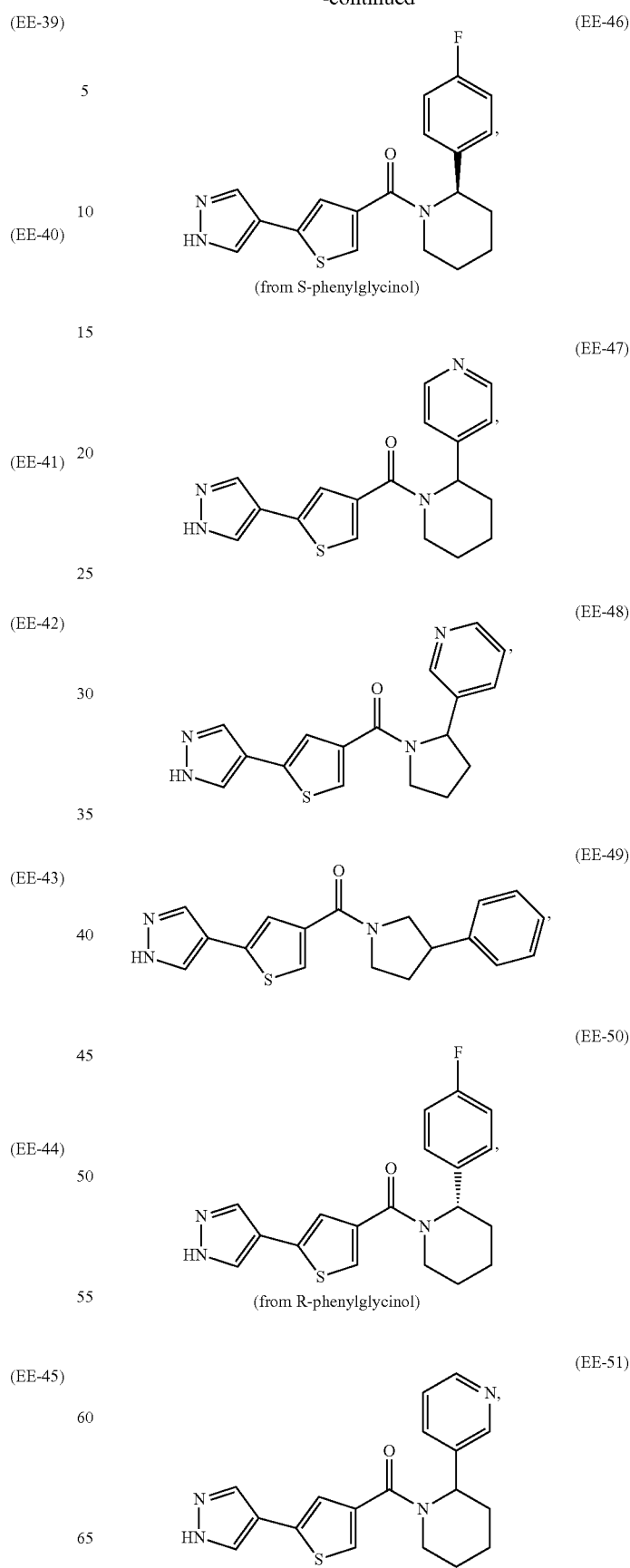

19. A compound according to claim 3, selected from the following compounds, and pharmaceutically acceptable salts thereof:

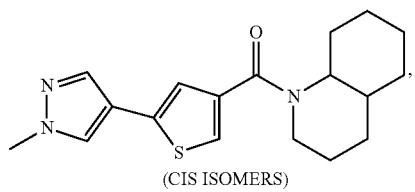
(FF-10)
(CIS ISOMERS)
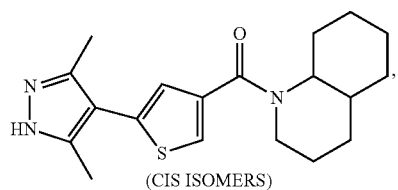
(FF-11)
(CIS ISOMERS)
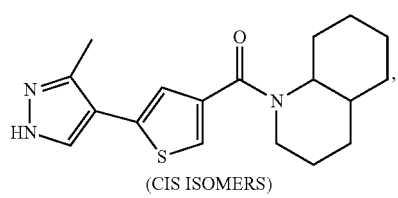
(FF-15)
(CIS ISOMERS)
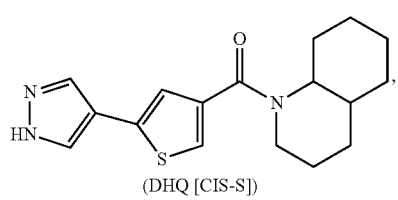
(FF-16)
(DHQ [CIS-S])
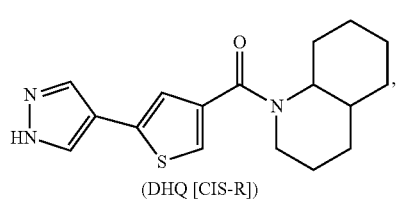
(FF-17)
(DHQ [CIS-R])
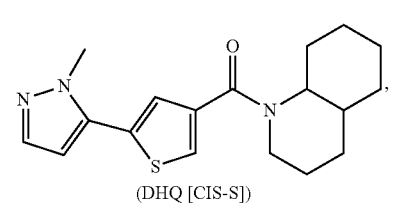
(FF-18)
(DHQ [CIS-S])
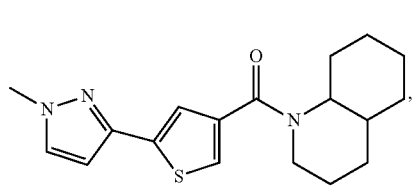
(FF-20)
(DHQ [CIS-S])
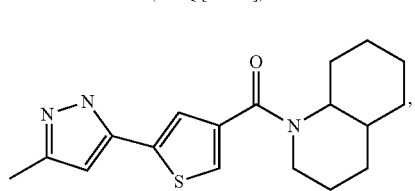
(FF-21)
(DHQ [CIS-S])
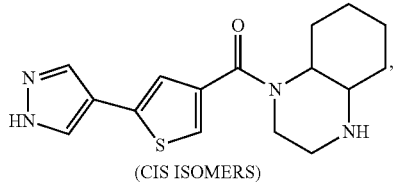
(FF-24)
(CIS ISOMERS)
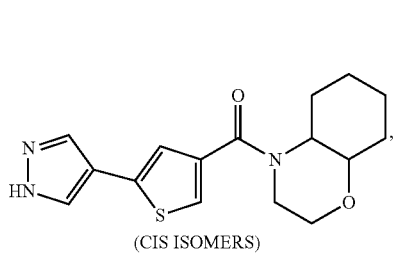
(FF-25)
(CIS ISOMERS)
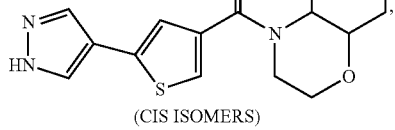
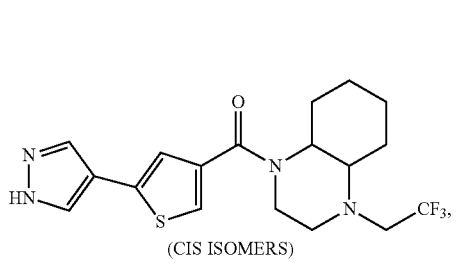
(FF-26)
(CIS ISOMERS)
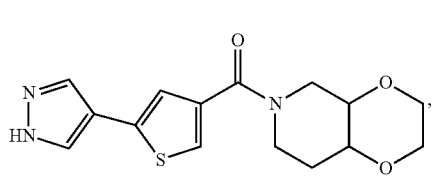
(FF-27)
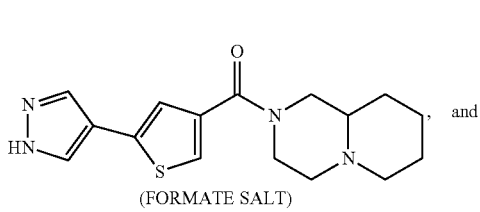
(FF-28)
(FORMATE SALT)
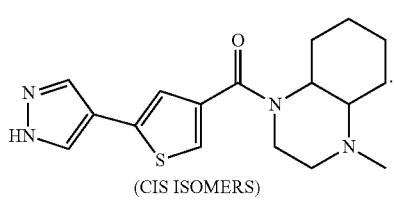
(FF-30)
(CIS ISOMERS)
and
20. A pharmaceutical composition comprising a compound according to claim 1, and a pharmaceutically acceptable carrier or diluent.

21. A pharmaceutical composition comprising a compound according to claim 2, and a pharmaceutically acceptable carrier or diluent.

22. A pharmaceutical composition comprising a compound according to claim 3, and a pharmaceutically acceptable carrier or diluent.

23. A pharmaceutical composition comprising a compound according to claim 4, and a pharmaceutically acceptable carrier or diluent.

24. A pharmaceutical composition comprising a compound according to claim 5, and a pharmaceutically acceptable carrier or diluent.

25. A pharmaceutical composition comprising a compound according to claim 6, and a pharmaceutically acceptable carrier or diluent.

26. A pharmaceutical composition comprising a compound according to claim 7, and a pharmaceutically acceptable carrier or diluent.

27. A pharmaceutical composition comprising a compound according to claim 15, and a pharmaceutically acceptable carrier or diluent.

28. A pharmaceutical composition comprising a compound according to claim 16, and a pharmaceutically acceptable carrier or diluent.

29. A pharmaceutical composition comprising a compound according to claim 17, and a pharmaceutically acceptable carrier or diluent.

* * * * *